United States Patent
Koepke et al.

(10) Patent No.: US 9,834,795 B2
(45) Date of Patent: *Dec. 5, 2017

(54) RECOMBINANT MICROORGANISMS AND USES THEREFOR

(71) Applicant: LanzaTech New Zealand Limited, Skokie, IL (US)

(72) Inventors: Michael Koepke, Skokie, IL (US); Sean Simpson, Skokie, IL (US); Fungmin Liew, Skokie, IL (US); Wendy Yiting Chen, Sydney (AU)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,891

(22) Filed: Jul. 8, 2016

(65) Prior Publication Data

US 2016/0376615 A1  Dec. 29, 2016

Related U.S. Application Data

(63) Continuation of application No. 13/403,972, filed on Feb. 23, 2012, now Pat. No. 9,410,130.

(60) Provisional application No. 61/446,832, filed on Feb. 25, 2011.

(51) Int. Cl.
| | |
|---|---|
| C12P 7/30 | (2006.01) |
| C12N 15/74 | (2006.01) |
| C12N 9/10 | (2006.01) |
| C12N 9/88 | (2006.01) |
| C12N 9/04 | (2006.01) |
| C12N 15/52 | (2006.01) |
| C12P 7/04 | (2006.01) |
| C12P 7/28 | (2006.01) |

(52) U.S. Cl.
CPC .............. *C12P 7/30* (2013.01); *C12N 9/0006* (2013.01); *C12N 9/1029* (2013.01); *C12N 9/13* (2013.01); *C12N 9/88* (2013.01); *C12N 15/52* (2013.01); *C12N 15/74* (2013.01); *C12P 7/04* (2013.01); *C12P 7/28* (2013.01); *C12Y 101/01001* (2013.01); *C12Y 203/01009* (2013.01); *C12Y 208/03009* (2013.01); *C12Y 401/01004* (2013.01); *Y02P 20/52* (2015.11)

(58) Field of Classification Search
None
See application file for complete search history.

(56) References Cited

U.S. PATENT DOCUMENTS

| | | |
|---|---|---|
| 2008/0293125 A1 | 11/2008 | Subbian et al. |
| 2009/0203100 A1 | 8/2009 | Simpson et al. |
| 2009/0246842 A1 | 10/2009 | Hawkins et al. |
| 2010/0304453 A1 | 12/2010 | Trawick et al. |
| 2012/0101304 A1 | 4/2012 | Becker et al. |

FOREIGN PATENT DOCUMENTS

| | | |
|---|---|---|
| WO | 2009113878 A1 | 9/2009 |
| WO | 2009131040 A1 | 10/2009 |
| WO | 2010121849 A1 | 10/2010 |
| WO | 2011022651 A1 | 2/2011 |

OTHER PUBLICATIONS

Banerjee, Lactose-inducible system for metabolic engineering of Clostridium ljungdahlii, 80: 2410-2416, 2014.
Bertsch, Bioenergetic constraints for conversion of syngas to biofuels in acetogenic bacteria, Biotechnol Biofuels, 8: 210, 2015.
Burk, Biotechnology for chemical production: challenges and opportunities, Trends Biotechnol, 34: 187-190, 2016.
Durre, Metabolic engineering of solventogenic Clostridia, Handbook on Clostridia, CRC Press, pp. 813-814, 2005.
Durre, New insights and novel developments in clostridial acetone/butanol/isopropanol fermentation, Appl Microbial Biotechnol, 49: 639-648, 1998.
Heap, A modular system for Clostridium shuttle plasmids, J Microbiol Methods, 78: 79-85, 2009.
Hill, Functional analysis of conserved histidines in ADP-glucose pyrophosphorylase from *Escherichia coli*, Biochem Biophys Res Comm, 244: 573-577, 1998.
Jojima, Production of isopropanol by metabolically engineered *Escherichia coli*, Appl Microbiol Biotechnol, 77: 1219-1224, 2008.
Jones, Acetone-butanol fermentation revisited, Microbiol Rev, 50: 484-524, 1986.
Kopke, Clostridium ljungdahlii represents a microbial production platform based on syngas, PNAS USA, 107: 13087-13092, 2010.
Lazar, Transforming growth factor alpha: mutation of aspartic acid 47 and leucine 48 results in different biological activities, Mol Cell Biol, 8: 1247-1252, 1988.
Nielsen, Engineering alternative butanol production platforms in heterologous bacteria, Metabol Eng, 11: 262-273, 2009.
Ramachandriya, Reduction of acetone to isopropanol using producer gas fermenting microbes, Biotechnol Bioeng, 108: 2330-2338, 2011.
Schiel-Bengelsdorf, Pathway engineering and synthetic biology using acetogens, FEBS Lett, 586: 2191-2198, 2012.
UniProKB—0716S7 & 0716S6, 2004.
Wang, Markerless chromosomal gene deletion in Clostridium beijerinckii using CRISPR/Cas9 system, J Biotechnol, 200: 1-5, 2015.
Wang, NADP-specific electron bifurcating [FeFe]-hydrogenase in a functional complex with formate dehydrogenase in Clostridium autoethanogenum grown on CO, J Bacteriol, 195: 4373-4386, 2013.
Communication pursuant to Article 94(3) in European Patent Application 12749472.2, European Patent Office, Feb. 6, 2017.
Mehta et al., Enzyme activities in Clostridia producing ethanol from carbon monoxide, 104th General Meeting of the American Society for Microbiology, Abstract O-081, p. 474, May 26, 2004.

*Primary Examiner* — Yong D Pak
(74) *Attorney, Agent, or Firm* — Andrea Schoen

(57) ABSTRACT

The invention provides recombinant microorganisms and methods for the production of acetone from gaseous substrates. For example, the recombinant microorganism may be modified to express an exogenous thiolase, an exogenous CoA transferase, and an exogenous decarboxylase.

14 Claims, 59 Drawing Sheets

MKGFAMLGINKLGWIEKKNPVPGPYDAIVHPLAVSPCTSDIHTVFEGALGNRENMILGHEAVGEIAEVGSEVKDFKVG
DRVIVPCTTPDWRSLEVQAGFQQHSNGMLAGWKFSNFKDGVFADYFHVNDADMNLAILPDEIPLESAVMMTDMM
TTGFHGAELADIKMGSSVVVIGIGAVGLMGIAGSKLRGAGRIIGVGSRPVCVETAKFYGATDIVNYKNGDIVEQIMDLT
HGKGVDRVIMAGGGAETLAQAVTMVKPGGVISNINYHGSGDTLPIPRVQWGCGMAHKTIRGGLCPGGRLRMEMLR
DLVLYKRVDLSKLVTHVFDGAENIEKALLLMKNKPKDLIKSVVTF*

FIG 14

ATGAAAGGTTTTGCAATGTTAGGTATTAACAAATTAGGATGGATTGAAAAGAAAAACCCAGTGCCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGCCATGAAGCTGTAGGTGAAATAGCCGAAGTTGGCAGCGAAGTTAAAGATTTTAA
AGTTGGCGATAGAGTTATCGTACCATGCACAACACCTGACTGGAGATCTTTAGAAGTCCAAGCTGGTTTTCAGCAG
CATTCAAACGGTATGCTTGCAGGATGGAAGTTTTCCAATTTTAAAGACGGTGTATTTGCAGATTACTTTCATGTAAA
CGATGCAGATATGAATCTTGCCATACTCCCAGATGAAATACCTTTAGAAAGTGCAGTTATGATGACAGACATGATG
ACTACTGGTTTTCATGGAGCAGAACTTGCAGACATAAAAATGGGCTCCAGCGTTGTAGTAATTGGTATAGGAGCT
GTTGGATTAATGGGAATAGCCGGTTCCAAACTTCGAGGAGCAGGCAGAATTATCGGTGTTGGAAGCAGACCTGTT
TGTGTTGAAACAGCTAAATTTTATGGAGCAACTGATATTGTAAATTATAAAAATGGTGATATAGTTGAACAAATCA
TGGACTTAACTCATGGTAAAGGTGTAGACCGTGTAATCATGGCAGGCGGTGGTGCTGAAACACTAGCACAAGCAG
TAACTATGGTTAAACCTGGCGGCGTAAATTCTAACATCAACTACCATGGAAGCGGTGATACTTTACCAATACCTCGT
GTTCAATGGGGCTGCGGCATGGCTCACAAAACTATAAGAGGAGGATTATGCCCCGGCGGACGTCTTAGAATGGA
AATGCTAAGAGATCTTGTTCTATATAAACGTGTTGATTTGAGTAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA

FIG 15

ATGAAAGGTTTTGCAATGTTAGGTATTAACAAATTAGGATGGATTGAAAAGAAAAACCCAGTGCCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGCCATGAAGCTGTAGGTGAAATAGCCGAAGTTGGCAGCGAAGTTAAAGATTTTAA
AGTTGGCGATAGAGTTATCGTACCATGCACAACACCTGACTGGAGATCTTTAGAAGTCCAAGCTGGTTTTCAGCAG
CATTCAAACGGTATGCTTGCAGGATGGAAGTTTTCCAATTTTAAAGATGGTGTATTTGCAGATTACTTTCATGTAAA
CGATGCAGATATGAATCTTGCCATACTCCCAGATGAAATACCTTTAGAAAGTGCAGTTATGATGACAGACATGATG
ACTACTGGTTTTCATGGAGCAGAACTTGCAGACATAAAAATGGGCTCCAGCGTTGTAGTAATTGGTATAGGAGCT
GTTGGATTAATGGGAATAGCCGGTTCCAAACTTCGAGGAGCAGGCAGAATTATCGGTGTTGGAAGCAGACCTGTT
TGTGTTGAAACAGCTAAATTTTATGGAGCAACTGATATTGTAAATTATAAAAATGGTGATATAGTTGAACAAATCA
TGGACTTAACTCATGGTAAAGGTGTAGACCGTGTAATCATGGCAGGCGGTGGTGCTGAAACACTAGCACAAGCAG
TAACTATGGTTAAACCTGGCGGCGTAAATTCTAACATCAACTACCATGGAAGCGGTGATACTTTACCAATACCTCGT
GTTCAATGGGCTGCGGCATGGCTCACAAAACTATAAGAGGAGGATTATGCCCCGGCGGACGTCTTAGAATGGA
AATGCTAAGAGATCTTGTTCTATATAAACGTGTTGATTTGAGTAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA

FIG 16

```
ATGAAAGGTTTTGCAATGTTAGGTATTAACAAGTTAGGATGGATTGAAAAGAAAAACCCAGTACCAGGTCCTTAT
GATGCGATTGTACATCCTCTAGCTGTATCCCCATGTACATCAGATATACATACGGTTTTTGAAGGAGCACTTGGTAA
TAGGGAAAATATGATTTTAGGTCACGAAGCTGTAGGTGAAATAGCTGAAGTTGGCAGTGAAGTTAAAGATTTTAA
AGTTGGCGATAGAGTTATCGTACCATGCACAACACCTGACTGGAGATCCTTAGAAGTCCAAGCTGGTTTTCAACAG
CATTCAAACGGTATGCTTGCAGGATGGAAGTTTTCCAATTTTAAAGACGGTGTATTTGCAGATTACTTTCATGTAAA
CGATGCAGATATGAATCTTGCAATACTTCCAGATGAAATACCTTTAGAAAGTGCAGTTATGATGACAGACATGATG
ACTACTGGTTTTCATGGGGCAGAACTTGCTGACATAAAAATGGGTTCCAGTGTTGTCGTAATTGGTATAGGAGCTG
TTGGATTAATGGGAATAGCCGGTTCCAAACTTCGAGGAGCAGGTAGAATTATCGGTGTTGGAAGCAGACCCGTTT
GTGTTGAAACAGCTAAATTTTATGGAGCAACTGATATTGTAAATTATAAAAATGGTGATATAGTTGAACAAATAAT
GGACTTAACTCATGGTAAAGGTGTAGACCGTGTAATCATGGCAGGCGGTGGTGCTGAAACACTAGCACAAGCAGT
AACTATGGTTAAACCTGGCGGCGTAATTTCTAACATCAACTACCATGGAAGCGGTGATACTTTGCCAATACCTCGT
GTTCAATGGGGCTGCGGCATGGCTCACAAAACTATAAGAGGAGGGTTATGTCCCGGCGGACGTCTTAGAATGGA
AATGCTAAGAGACCTTGTTCTATATAAACGTGTTGATTTGAGCAAACTTGTTACTCATGTATTTGATGGTGCAGAAA
ATATTGAAAAGGCCCTTTTGCTTATGAAAAATAAGCCAAAAGATTTAATTAAATCAGTAGTTACATTCTAA
```

FIG 17

```
ATGAAAGAAGTTGTAATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCAGAGGATGTTAATGA
AGTCATTTTAGGAAATGTTCTTCAAGCAGGTTTAGGACAGAATCCAGCAAGACAGGCATCTTTTAAAGCAGGATTA
CCAGTTGAAATTCCAGCTATGACTATTAATAAGGTTTGTGGTTCAGGACTTAGAACAGTTAGCTTAGCAGCACAAA
TTATAAAAGCAGGAGATGCTGACGTAATAATAGCAGGTGGTATGGAAAATATGTCTAGAGCTCCTTACTTAGCGA
ATAACGCTAGATGGGGATATAGAATGGGAAACGCTAAATTTGTTGATGAAATGATCACTGACGGATTGTGGGATG
CATTTAATGATTACCACATGGGAATAACAGCAGAAAACATAGCTGAGAGATGGAACATTTCAAGAGAAGAACAAG
ATGAGTTTGCTCTTGCATCACAAAAAAAGCTGAAGAAGCTATAAAATCAGGTCAATTTAAAGATGAAATAGTTCC
TGTAGTAATTAAAGGCAGAAAGGGAGAAACTGTAGTTGATACAGATGAGCACCCTAGATTTGGATCAACTATAGA
AGGACTTGCAAAATTAAAACCTGCCTTCAAAAAAGATGGAACAGTTACAGCTGGTAATGCATCAGGATTAAATGA
CTGTGCAGCAGTACTTGTAATCATGAGTGCAGAAAAAGCTAAAGAGCTTGGAGTAAAACCACTTGCTAAGATAGT
TTCTTATGGTTCAGCAGGAGTTGACCCAGCAATAATGGGATATGGACCTTTCTATGCAACAAAAGCAGCTATTGAA
AAAGCAGGTTGGACAGTTGATGAATTAGATTTAATAGAATCAAATGAAGCTTTTGCAGCTCAAAGTTTAGCAGTAG
CAAAAGATTTAAAATTTGATATGAATAAAGTAAATGTAAATGGAGGAGCTATTGCCCTTGGTCATCCAATTGGAGC
ATCAGGTGCAAGAATACTCGTTACTCTTGTACACGCAATGCAAAAAGAGATGCAAAAAAGGCTTAGCAACTTTA
TGTATAGGTGGCGGACAAGGAACAGCAATATTGCTAGAAAAGTGCTAG
```

FIG 18

```
ATGAATAAATTAGTAAAATTAACAGATTTAAAGCGCATTTTCAAAGATGGCATGACAATTATGGTTGGGGGTTTTT
TAGATTGTGGAACTCCTGAAAATATTATAGATATGCTAGTTGATTTAAATATAAAAAATCTGACTATTATAAGCAAT
GATACAGCTTTTCCTAATAAAGGAATAGGAAAACTTATTGTAAATGGTCAAGTTTCTAAAGTAATTGCTTCACATAT
TGGAACTAATCCTGAAACTGGAAAAAAAATGAGCTCTGGAGAACTTAAAGTTGAGCTTTCCCCACAAGGAACACT
GATTGAAAGAATTCGTGCAGCTGGATCTGGACTCGGAGGTGTATTAACTCCAACTGGACTTGGAACTATCGTTGA
AGAAGGTAAGAAAAAGTTACTATCGATGGCAAAGAATATCTATTAGAACTTCCTTTATCTGCTGATGTTTCATTAA
TAAAAGGTAGCATTGTAGATGAATTTGGAAATACCTTCTATAGGGCTGCTACTAAAAATTTCAATCCATATATGGC
AATGGCTGCAAAAACAGTTATAGTTGAAGCAGAAATTTAGTTAAATGTGAAGATTTAAAAAGAGATGCCATAAT
GACTCCTGGCGTATTAGTAGATTATATCGTTAAGGAGGCGGCTTAA
```

FIG 19

TTGATTGTAGATAAAGTTTTAGCAAAAGAGATAATTGCCAAAAGAGTTGCAAAAGAACTAAAAAAAGACCAACTC
GTAAACCTTGGAATAGGACTTCCAACTTTAGTAGCAAATTATGTACCAAAAGAAATGAACATTACTTTTGAATCAG
AAAATGGCATGGTTGGTATGGCACAAATGGCATCATCAGGTGAAAATGACCCAGATATAATAAATGCTGGCGGG
GAATATGTAACATTATTACCTCAAGGTTCATTTTTTGATAGTTCAATGTCTTTCGCACTAATACGAGGAGGACATGT
TGATGTTGCTGTTCTTGGTGCTCTAGAAGTTGATGAAAAAGGTAATTTAGCTAACTGGATTGTTCCAAATAAAATT
GTCCCAGGTATGGGTGGCGCTATGGATTTAGCAATAGGCGCAAAAAAAATAATAGTGGCAATGCAACATACAGG
AAAAAGTAAACCTAAAATCGTTAAAAAATGTACTCTCCCACTTACTGCTAAGGCTCAAGTGGATTTAATTGTCACAG
AACTTTGTGTAATTGATGTAACAAATGACGGCTTACTTTTAAAAGAAATTCATAAAGATACAACTATTGATGAAATT
AAATTTTTAACAGATGCAGATTTAATTATTCCAGATAACTTAAAGATTATGGATATATGA

FIG 20

ATGTTAGAAAGTGAAGTATCTAAACAAATTACAACTCCACTTGCTGCTCCAGCGTTTCCTAGAGGACCATATAGGT
TTCACAATAGAGAATATCTAAACATTATTTATCGAACTGATTTAGATGCTCTTCGAAAAATAGTACCAGAGCCACTT
GAATTAGATAGAGCATATGTTAGATTTGAAATGATGGCTATGCCTGATACAACCGGACTAGGCTCATATACAGAAT
GTGGTCAAGCTATTCCAGTAAAATATAATGGTGTTAAGGGTGACTACTTGCATATGATGTATCTAGATAATGAACC
TGCTATTGCTGTTGGAAGAGAAAGTAGCGCTTATCCAAAAAAGCTTGGCTATCCAAAGCTATTTGTTGATTCAGAT
ACTTTAGTTGGGACACTTAAATATGGTACATTACCAGTAGCTACTGCAACAATGGGATATAAGCACGAGCCTCTAG
ATCTTAAAGAAGCCTATGCTCAAATTGCAAGACCCAATTTTATGCTAAAAATCATTCAAGGTTACGATGGTAAGCC
AAGAATTTGTGAACTAATATGTGCAGAAAATACTGATATAACTATTCACGGTGCTTGGACTGGAAGTGCACGTCTA
CAATTATTTAGCCATGCACTAGCTCCTCTTGCTGATTTACCTGTATTAGAGATTGTATCAGCATCTCATATCCTCACA
GATTTAACTCTTGGAACACCTAAGGTTGTACATGATTATCTTTCAGTAAAATAA

FIG 21

AGATAGTCATAATAGTTCCAGAATAGTTCAATTTAGAAATTAGACTAAACTTCAAAATGTTTGTTAAATATATACCA
AACTAGTATAGATATTTTTTAAATACTGGACTTAAACAGTAGTAATTTGCCTAAAAAATTTTTTCAATTTTTTTTAAA
AAATCCTTTTCAAGTTGTACATTGTTATGGTAATATGTAATTGAAGAAGTTATGTAGTAATATTGTAAACGTTTCTT
GATTTTTTTACATCCATGTAGTGCTTAAAAAACCAAAATATGTCACATGCAATTGTATATTTCAAATAACAATATTTA
TTTTCTCGTTAAATTCACAAATAATTTATTAATAATATCAATAACCAAGATTATACTTAAATGGATGTTTATTTTTTAA
CACTTTTATAGTAAATATATTTATTTTATGTAGTAAAAAGGTTATAATTATAATTGTATTTATTACAATTAATTAAAAT
AAAAAAATAGGGTTTTAGGTAAAATTAAGTTATTTTAAGAAGTAATTACAATAAAAATTGAAGTTATTTCTTTAAGGA
GGGAATTATTAAA

FIG 22

MFPCNAYIEYGDKNMNSFIEDVEQIYNFIKKNIDVEEKMHFIETYKQKSNMKKEISFSEEYYKQKIMNGKNGVVYTPPE
MAAFMVKNLINVNDVIGNPFIKIIDPSCGSGNLICKCFLYLNRIFIKNIEVINSKNNLNLKLEDISYHIVRNNLFGFDIDETAI
KVLKIDLFLISNQFSEKNFQVKDFLVENIDRKYDVFIGNPPYIGHKSVDSSYSYVLRKIYGSIYRDKGDISYCFFQKSLKCLKE
GGKLVFVTSRYFCESCSGKELRKFLIENTSIYKIIDFYGIRPFKRVGIDPMIIFLVRTKNWNNNIEIIRPNKIEKNEKNKFLDSL
FLDKSEKCKKFSISQKSINNDGWVFVDEVEKNIIDKIKEKSKFILKDICHSCQGIITGCDRAFIVDRDIINSRKIELRLIKPWIKS
SHIRKNEVIKGEKFIIYSNLIENETECPNAIKYIEQYKKRLMERRECKKGTRKWYELQWGRKPEIFEEKKIVFPYKSCDNRFA
LDKGSYFSADIYSLVLKKNVPFTYEILLNILNSPLYEFYFKTFAKKLGENLYEYYPNNLMKLCIPSIDFGGENNIEKKLYDFFGL
TDKEIEIVEKIKDNC*

FIG 23

```
ATGTTTCCGTGCAATGCCTATATCGAATATGGTGATAAAAATATGAACAGCTTTATCGAAGATGTGGAACAGATCT
ACAACTTCATTAAAAAGAACATTGATGTGGAAGAAAAGATGCATTTCATTGAAACCTATAAACAGAAAAGCAACAT
GAAGAAAGAGATTAGCTTTAGCGAAGAATACTATAAACAGAAGATTATGAACGGCAAAAATGGCGTTGTGTACAC
CCCGCCGGAAATGGCGGCCTTTATGGTTAAAAATCTGATCAACGTTAACGATGTTATTGGCAATCCGTTTATTAAA
ATCATTGACCCGAGCTGCGGTAGCGGCAATCTGATTTGCAAATGTTTTCTGTATCTGAATCGCATCTTTATTAAGAA
CATTGAGGTGATTAACAGCAAAAATAACCTGAATCTGAAACTGGAAGACATCAGCTACCACATCGTTCGCAACAAT
CTGTTTGGCTTCGATATTGACGAAACCGCGATCAAAGTGCTGAAAATTGATCTGTTTCTGATCAGCAACCAATTTAG
CGAGAAAAATTTCCAGGTTAAAGACTTTCTGGTGGAAAATATTGATCGCAAATATGACGTGTTCATTGGTAATCCG
CCGTATATCGGTCACAAAAGCGTGGACAGCAGCTACAGCTACGTGCTGCGCAAAATCTACGGCAGCATCTACCGC
GACAAAGGCGATATCAGCTATTGTTTCTTTCAGAAGAGCCTGAAATGTCTGAAGGAAGGTGGCAAACTGGTGTTT
GTGACCAGCCGCTACTTCTGCGAGAGCTGCAGCGGTAAAGAACTGCGTAAATTCCTGATCGAAAACACGAGCATT
TACAAGATCATTGATTTTTACGGCATCCGCCCGTTCAAACGCGTGGGTATCGATCCGATGATTATTTTTCTGGTTCG
TACGAAGAACTGGAACAATAACATTGAAATTATTCGCCCGAACAAGATTGAAAAGAACGAAAAGAACAAATTCCT
GGATAGCCTGTTCCTGGACAAAAGCGAAAAGTGTAAAAAGTTTAGCATTAGCCAGAAAAGCATTAATAACGATGG
CTGGGTTTTCGTGGACGAAGTGGAGAAAAACATTATCGACAAAATCAAAGAGAAAAGCAAGTTCATTCTGAAAGA
TATTTGCCATAGCTGTCAAGGCATTATCACCGGTTGTGATCGCGCCTTTATTGTGGACCGTGATATCATCAATAGCC
GTAAGATCGAACTGCGTCTGATTAAACCGTGGATTAAAAGCAGCCATATCCGTAAGAATGAAGTTATTAAGGGCG
AAAAATTCATCATCTATAGCAACCTGATTGAGAATGAAACCGAGTGTCCGAATGCGATTAAATATATCGAACAGTA
CAAGAAACGTCTGATGGAGCGCCGCGAATGCAAAAAGGGCACGCGTAAGTGGTATGAACTGCAATGGGGCCGTA
AACCGGAAATCTTCGAAGAAAAGAAAATTGTTTTCCCGTATAAAAGCTGTGACAATCGTTTTGCACTGGATAAGGG
TAGCTATTTTAGCGCAGACATTTATAGCCTGGTTCTGAAGAAAAATGTGCCGTTCACCTATGAGATCCTGCTGAATA
TCCTGAATAGCCCGCTGTACGAGTTTTACTTTAAGACCTTCGCGAAAAAGCTGGGCGAGAATCTGTACGAGTACTA
TCCGAACAACCTGATGAAGCTGTGCATCCCGAGCATCGATTTCGGCGGTGAGAACAATATTGAGAAAAAGCTGTA
TGATTTCTTTGGTCTGACGGATAAAGAAATTGAGATTGTGGAGAAGATCAAAGATAACTGCTAA
```

FIG 24

```
MKGFAMLGINKLGWIEKERPVAGSYDAIVRPLAVSPCTSDIHTVFEGALGDRKNMILGHEAVGEVVEVGSEVKDFKPG
DRVIVPCTTPDWRSLEVQAGFQQHSNGMLAGWKFSNFKDGVFGEYFHVNDADMNLAILPKDMPLENAVMITDMM
TTGFHGAELADIQMGSSVVVIGIGAVGLMGIAGAKLRGAGRIIGVGSRPICVEAAKFYGATDILNYKNGHIVDQVMKLT
NGKGVDRVIMAGGGSETLSQAVSMVKPGGIISNINYHGSGDALLIPRVEWGCGMAHKTIKGGLCPGGRLRAEMLRD
MVVYNRVDLSKLVTHVYHGFDHIEEALLLMKDKPKDLIKAVVIL
```

FIG 25

```
ATGAAAGGTTTTGCAATGCTAGGTATTAATAAGTTAGGATGGATCGAAAAAGAAAGGCCAGTTGCGGGTTCATAT
GATGCTATTGTACGCCCATTAGCAGTATCTCCGTGTACATCAGATATACATACTGTTTTTGAGGGAGCTCTTGGAGA
TAGGAAGAATATGATTTTAGGGCATGAAGCTGTAGGTGAAGTTGTTGAAGTAGGAAGTGAAGTGAAGGATTTTA
AACCTGGTGACAGAGTTATAGTTCCTTGTACAACTCCAGATTGGAGATCTTTGGAAGTTCAAGCTGGTTTTCAACA
GCACTCAAACGGTATGCTCGCAGGATGGAAATTTTCAAATTTCAAGGATGGAGTTTTTGGTGAATATTTTCATGTA
AATGATGCGGATATGAATCTTGCGATTCTACCTAAAGACATGCCATTAGAAAATGCTGTTATGATAACAGATATGA
TGACTACTGGATTTCATGGAGCAGAACTTGCAGATATTCAAATGGGTTCAAGTGTTGTGGTAATTGGCATTGGAGC
TGTTGGCTTAATGGGAATAGCAGGTGCTAAATTACGTGGAGCAGGTAGAATAATTGGAGTGGGGAGCAGGCCGA
TTTGTGTTGAGGCTGCAAAATTTATGGAGCAACAGATATTCTAAATTATAAAAATGGTCATATAGTTGATCAAGTT
ATGAAATTAACGAATGGAAAAGGCGTTGACCGCGTAATTATGGCAGGCGGTGGTTCTGAAACATTATCCCAAGCA
GTATCTATGGTTAAACCAGGAGGAATAATTTCTAATATAAATTATCATGGAAGTGGAGATGCTTTACTAATACCAC
GTGTAGAATGGGGATGTGGAATGGCTCACAAGACTATAAAAGGAGGTCTTTGTCCTGGGGGACGTTTGAGAGCA
GAAATGTTAAGAGATATGGTAGTATATAATCGTGTTGATCTAAGTAAATTAGTTACACATGTATATCATGGATTTG
ATCACATAGAAGAAGCACTGTTATTAATGAAAGACAAGCCAAAAGACTTAATTAAAGCAGTAGTTATATTATAA
```

FIG 26

MKGFAMLSIGKVGWIEKEKPAPGPFDAIVRPLAVAPCTSDIHTVFEGAIGERHNMILGHEAVGEVVEVGSEVKDFKPG
DRVVVPAITPDWRTSEVQRGYHQHSGGMLAGWKFSNVKDGVFGEFFHVNDADMNLAHLPKEIPLEAAVMIPDMM
TTGFHGAELADIELGATVAVLGIGPVGLMAVAGAKLRGAGRIIAVGSRPVCVDAAKYYGATDIVNYKDGPIESQIMNLT
EGKGVDAAIIAGGNADIMATAVKIVKPGGTIANVNYFGEGEVLPVPRLEWGCGMAHKTIKGGLCPGGRLRMERLIDLV
FYKRVDPSKLVTHVFRGFDNIEKAFMLMKDKPKDLIKPVVILA

FIG 27

ATGAAAGGTTTTGCAATGCTAGGTATTAATAAGTTAGGATGGATCGAAAAAGAAAGGCCAGTTGCGGGTTCATAT
GATGCTATTGTACGCCCATTAGCAGTATCTCCGTGTACATCAGATATACATACTGTTTTTGAGGGAGCTCTTGGAGA
TAGGAAGAATATGATTTTAGGGCATGAAGCTGTAGGTGAAGTTGTTGAAGTAGGAAGTGAAGTGAAGGATTTTA
AACCTGGTGACAGAGTTATAGTTCCTTGTACAACTCCAGATTGGAGATCTTTGGAAGTTCAAGCTGGTTTTCAACA
GCACTCAAACGGTATGCTCGCAGGATGGAAATTTTCAAATTTCAAGGATGGAGTTTTTGGTGAATATTTTCATGTA
AATGATGCGGATATGAATCTTGCGATTCTACCTAAAGACATGCCATTAGAAAATGCTGTTATGATAACAGATATGA
TGACTACTGGATTTCATGGAGCAGAACTTGCAGATATTCAAATGGGTTCAAGTGTTGTGGTAATTGGCATTGGAGC
TGTTGGCTTAATGGGAATAGCAGGTGCTAAATTACGTGGAGCAGGTAGAATAATTGGAGTGGGGAGCAGGCCGA
TTTGTGTTGAGGCTGCAAAATTTTATGGAGCAACAGATATTCTAAATTATAAAAATGGTCATATAGTTGATCAAGTT
ATGAAATTAACGAATGGAAAAGGCGTTGACCGCGTAATTATGGCAGGCGGTGGTTCTGAAACATTATCCCAAGCA
GTATCTATGGTTAAACCAGGAGGAATAATTTCTAATATAAATTATCATGGAAGTGGAGATGCTTTACTAATACCAC
GTGTAGAATGGGGATGTGGAATGGCTCACAAGACTATAAAAGGAGGTCTTTGTCCTGGGGGACGTTTGAGAGCA
GAAATGTTAAGAGATATGGTAGTATATAATCGTGTTGATCAAGTAAATTAGTTACACATGTATATCATGGATTTG
ATCACATAGAAGAAGCACTGTTATTAATGAAAGACAAGCCAAAAGACTTAATTAAAGCAGTAGTTATATTATAA

FIG 28

MKEVVIASAVRTAIGSYGKSLKDVPAVDLGATAIKEAVKKAGIKPEDVNEVILGNVLQAGLGQNPARQASFKAGLPVEIP
AMTINKVCGSGLRTVSLAAQIIKAGDADVIIAGGMENMSRAPYLANNARWGYRMGNAKFVDEMITDGLWDAFNDY
HMGITAENIAERWNISREEQDEFALASQKKAEEAIKSGQFKDEIVPVVIKGRKGETVVDTDEHPRFGSTIEGLAKLKPAFK
KDGTVTAGNASGLNDCAAVLVIMSAEKAKELGVKPLAKIVSYGSAGVDPAIMGYGPFYATKAAIEKAGWTVDELDLIES
NEAFAAQSLAVAKDLKFDMNKVNVNGGAIALGHPIGASGARILVTLVHAMQKRDAKKGLATLCIGGGQGTAILLEKC*

FIG 29

MNKLVKLTDLKRIFKDGMTIMVGGFLDCGTPENIIDMLVDLNIKNLTIISNDTAFPNKGIGKLIVNGQVSKVIASHIGTNP
ETGKKMSSGELKVELSPQGTLIERIRAAGSGLGGVLTPTGLGTIVEEGKKKVTIDGKEYLLELPLSADVSLIKGSIVDEFGNT
FYRAATKNFNPYMAMAAKTVIVEAENLVKCEDLKRDAIMTPGVLVDYIVKEAA*

FIG 30

LIVDKVLAKEIIAKRVAKELKKDQLVNLGIGLPTLVANYVPKEMNITFESENGMVGMAQMASSGENDPDIINAGGEYVT
LLPQGSFFDSSMSFALIRGGHVDVAVLGALEVDEKGNLANWIVPNKIVPGMGGAMDLAIGAKKIIVAMQHTGKSKPKI
VKKCTLPLTAKAQVDLIVTELCVIDVTNDGLLLKEIHKDTTIDEIKFLTDADLIIPDNLKIMDI*

FIG 31

MLESEVSKQITTPLAAPAFPRGPYRFHNREYLNIIYRTDLDALRKIVPEPLELDRAYVRFEMMAMPDTTGLGSYTECGQA
IPVKYNGVKGDYLHMMYLDNEPAIAVGRESSAYPKKLGYPKLFVDSDTLVGTLKYGTLPVATATMGYKHEPLDLKEAYA
QIARPNFMLKIIQGYDGKPRICELICAENTDITIHGAWTGSARLQLFSHALAPLADLPVLEIVSASHILTDLTLGTPKVVHDY
LSVK*

FIG 32

TGAAAGAAAGATATGGAACAGTCTATAAAGGCTCTCAGAGGCTCATAGACGAAGAAAGTGGAGAAGTCATAGAG
GTAGACAAGTTATACCGTAAACAAACGTCTGGTAACTTCGTAAAGGCATATATAGTGCAATTAATAAGTATGTTAG
ATATGATTGGCGGAAAAAAACTTAAAATCGTTAACTATATCCTAGATAATGTCCACTTAAGTAACAATACAATGAT
AGCTACAACAAGAGAAATAGCAAAAGCTACAGGAACAAGTCTACAAACAGTAATAACAACACTTAAAATCTTAGA
AGAAGGAAATATTATAAAAAGAAAAACTGGAGTATTAATGTTAAACCCTGAACTACTAATGAGAGGCGACGACCA
AAAACAAAAATACCTCTTACTCGAATTTGGGAACTTTGAGCAAGAGGCAAATGAAATAGATTGACCTCCCAATAAC
ACCACGTAGTTATTGGGAGGTCAATCTATGAAATGCGATTAAGGGCCGGCCAGTGGGCAAGTTGAAAAATTCACA
AAAATGTGGTATAATATCTTTGTTCATTAGAGCGATAAACTTGAATTTGAGAGGGAACTTAGATGGTATTTGAAAA
AATTGATAAAAATAGTTGGAACAGAAAAGAGTATTTTGACCACTACTTTGCAAGTGTACCTTGTACCTACAGCATG
ACCGTTAAAGTGGATATCACACAAATAAAGGAAAAGGGAATGAAACTATATCCTGCAATGCTTTATTATATTGCAA
TGATTGTAAACCGCCATTCAGAGTTTAGGACGGCAATCAATCAAGATGGTGAATTGGGGATATATGATGAGATGA
TACCAAGCTATACAATATTTCACAATGATACTGAAACATTTTCCAGCCTTTGGACTGAGTGTAAGTCTGACTTTAAA
TCATTTTTAGCAGATTATGAAAGTGATACGCAACGGTATGGAAACAATCATAGAATGGAAGGAAAGCCAAATGCT
CCGGAAAACATTTTTAATGTATCTATGATACCGTGGTCAACCTTCGATGGCTTTAATCTGAATTTGCAGAAAGGATA
TGATTATTTGATTCCTATTTTTACTATGGGGAAATATTATAAAGAAGATAACAAAATTATACTTCCTTTGGCAATTCA
AGTTCATCACGCAGTATGTGACGGATTTCACATTTGCCGTTTTGTAAACGAATTGCAGGAATTGATAAATAGTTAA
CTTCAGGTTTGTCTGTAACTAAAAACAAGTATTTAAGCAAAAACATCGTAGAAATACGGTGTTTTTTGTTACCCTAA
GTTTAAACTCCTTTTTGATAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAAACGCCTGGTATC
TTTATAGTCCTGTCGGGTTTCGCCACCTCTGACTTGAGCGTCGATTTTTGTGATGCTCGTCAGGGGGCGGAGCCT
ATGGAAAAACGCCAGCAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCAGGGCCCCCTGCAGGATAAAAAAA
TTGTAGATAAATTTTATAAAATAGTTTTATCTACAATTTTTTTATCAGGAAACAGCTATGACCGCGGCCGCAGATAG
TCATAATAGTTCCAGAATAGTTCAATTTAGAAATTAGACTAAACTTCAAAATGTTTGTTAAATATATACCAAACTAG
TATAGATATTTTTTAAATACTGGACTTAAACAGTAGTAATTTGCCTAAAAAATTTTTTCAATTTTTTTTAAAAAATCCT
TTTCAAGTTGTACATTGTTATGGTAATATGTAATTGAAGAAGTTATGTAGTAATATTGTAAACGTTTCTTGATTTTTT
TACATCCATGTAGTGCTTAAAAAACCAAAATATGTCACATGCAATTGTATATTTCAAATAACAATATTTATTTTCTCG
TTAAATTCACAAATAATTTATTAATAATATCAATAACCAAGATTATACTTAAATGGATGTTTATTTTTTAACACTTTTA
TAGTAAATATATTTATTTTATGTAGTAAAAAGGTTATAATTATAATTGTATTTATTACAATTAATTAAAATAAAAAAT
AGGGTTTTAGGTAAAATTAAGTTATTTTAAGAAGTAATTACAATAAAAATTGAAGTTATTTCTTTAAGGAGGGAAT
TATTCATATGAAAGAAGTTGTAATAGCTAGTGCAGTAAGAACAGCGATTGGATCTTATGGAAAGTCTCTTAAGGAT
GTACCAGCAGTAGATTTAGGAGCTACAGCTATAAAGGAAGCAGTTAAAAAAGCAGGAATAAAACCAGAGGATGT
TAATGAAGTCATTTTAGGAAATGTTCTTCAAGCAGGTTTAGGACAGAATCCAGCAAGACAGGCATCTTTTAAAGCA
GGATTACCAGTTGAAATTCCAGCTATGACTATTAATAAGGTTTGTGGTTCAGGACTTAGAACAGTTAGCTTAGCAG
CACAAATTATAAAAGCAGGAGATGCTGACGTAATAATAGCAGGTGGTATGGAAAATATGTCTAGAGCTCCTTACTT
AGCGAATAACGCTAGATGGGGATATAGAATGGGAAACGCTAAATTTGTTGATGAAATGATCACTGACGGATTGTG
GGATGCATTTAATGATTACCACATGGGAATAACAGCAGAAAACATAGCTGAGAGATGGAACATTTCAAGAGAAGA
ACAAGATGAGTTTGCTCTTGCATCACAAAAAAAGCTGAAGAAGCTATAAAATCAGGTCAATTTAAAGATGAAAT

AGTTCCTGTAGTAATTAAAGGCAGAAAGGGAGAAACTGTAGTTGATACAGATGAGCACCCTAGATTTGGATCAAC
TATAGAAGGACTTGCAAAATTAAAACCTGCCTTCAAAAAAGATGGAACAGTTACAGCTGGTAATGC
ATCAGGATTAAATGACTGTGCAGCAGTACTTGTAATCATGAGTGCAGAAAAAGCTAAAGAGCTTGGAGTAAAACC
ACTTGCTAAGATAGTTTCTTATGGTTCAGCAGGAGTTGACCCAGCAATAATGGGATATGGACCTTTCTATGCAACA
AAAGCAGCTATTGAAAAAGCAGGTTGGACAGTTGATGAATTAGATTTAATAGAATCAAATGAAGCTTTTGCAGCTC
AAAGTTTAGCAGTAGCAAAAGATTTAAAATTTGATATGAATAAAGTAAATGTAAATGGAGGAGCTATTGCCCTTG
GTCATCCAATTGGAGCATCAGGTGCAAGAATACTCGTTACTCTTGTACACGCAATGCAAAAAGAGATGCAAAAA
AAGGCTTAGCAACTTTATGTATAGGTGGCGGACAAGGAACAGCAATATTGCTAGAAAAGTGCTAGGAATTCGAGC
TCGGTACCAGGGAGATATTAAAATGAATAAATTAGTAAAATTAACAGATTTAAAGCGCATTTTCAAAGATGGCATG
ACAATTATGGTTGGGGGTTTTTTAGATTGTGGAACTCCTGAAAATATTATAGATATGCTAGTTGATTTAAATATAAA
AAATCTGACTATTATAAGCAATGATACAGCTTTTCCTAATAAAGGAATAGGAAAACTTATTGTAAATGGTCAAGTTT
CTAAAGTAATTGCTTCACATATTGGAACTAATCCTGAAACTGGAAAAAAAATGAGCTCTGGAGAACTTAAAGTTGA
GCTTTCCCCACAAGGAACACTGATTGAAAGAATTCGTGCAGCTGGATCTGGACTCGGAGGTGTATTAACTCCAACT
GGACTTGGAACTATCGTTGAAGAAGGTAAGAAAAAAGTTACTATCGATGGCAAAGAATATCTATTAGAACTTCCTT
TATCTGCTGATGTTTCATTAATAAAAGGTAGCATTGTAGATGAATTTGGAAATACCTTCTATAGGGCTGCTACTAAA
AATTTCAATCCATATATGGCAATGGCTGCAAAAACAGTTATAGTTGAAGCAGAAAATTTAGTTAAATGTGAAGATT
TAAAAAGAGATGCCATAATGACTCCTGGCGTATTAGTAGATTATATCGTTAAGGAGGCGGCTTAATTGATTGTAGA
TAAAGTTTTAGCAAAAGAGATAATTGCCAAAAGAGTTGCAAAAGAACTAAAAAAAGACCAACTCGTAAACCTTGG
AATAGGACTTCCAACTTTAGTAGCAAATTATGTACCAAAAGAAATGAACATTACTTTTGAATCAGAAAATGGCATG
GTTGGTATGGCACAAATGGCATCATCAGGTGAAAATGACCCAGATATAATAAATGCTGGCGGGGAATATGTAACA
TTATTACCTCAAGGTTCATTTTTTGATAGTTCAATGTCTTTCGCACTAATACGAGGAGGACATGTTGATGTTGCTGTT
CTTGGTGCTCTAGAAGTTGATGAAAAAGGTAATTTAGCTAACTGGATTGTTCCAAATAAAATTGTCCCAGGTATGG
GTGGCGCTATGGATTTAGCAATAGGCGCAAAAAAAATAATAGTGGCAATGCAACATACAGGAAAAAGTAAACCTA
AAATCGTTAAAAAATGTACTCTCCCACTTACTGCTAAGGCTCAAGTGGATTTAATTGTCACAGAACTTTGTGTAATT
GATGTAACAAATGACGGCTTACTTTTAAAAGAAATTCATAAAGATACAACTATTGATGAAATTAAATTTTTAACAGA
TGCAGATTTAATTATTCCAGATAACTTAAAGATTATGGATATATGAATCATTCTATTTTAAATATATAACTTTAAAAA
TCTTATGTATTAAAAACTAAGAAAAGAGGTTGATTGTTTTATGTTAGAAAGTGAAGTATCTAAACAAATTACAACTC
CACTTGCTGCTCCAGCGTTTCCTAGAGGACCATATAGGTTTCACAATAGAGAATATCTAAACATTATTTATCGAACT
GATTTAGATGCTCTTCGAAAAATAGTACCAGAGCCACTTGAATTAGATAGAGCATATGTTAGATTTGAAATGATGG
CTATGCCTGATACAACCGGACTAGGCTCATATACAGAATGTGGTCAAGCTATTCCAGTAAAATATAATGGTGTTAA
GGGTGACTACTTGCATATGATGTATCTAGATAATGAACCTGCTATTGCTGTTGGAAGAGAAAGTAGCGCTTATCCA
AAAAAGCTTGGCTATCCAAAGCTATTTGTTGATTCAGATACTTTAGTTGGGACACTTAAATATGGTACATTACCAGT
AGCTACTGCAACAATGGGATATAAGCACGAGCCTCTAGATCTTAAAGAAGCCTATGCTCAAATTGCAAGACCCAAT
TTTATGCTAAAAATCATTCAAGGTTACGATGGTAAGCCAAGAATTTGTGAACTAATATGTGCAGAAATACTGATA
TAACTATTCACGGTGCTTGGACTGGAAGTGCACGTCTACAATTATTTAGCCATGCACTAGCTCCTCTTGCTGATTTA
CCTGTATTAGAGATTGTATCAGCATCTCATATCCTCACAGATTTAACTCTTGGAACACCTAAGGTTGTACATGATTA
TCTTTCAGTAAAATAAAAGCAATATAGAGGATCCTCTAGAGTCGACGTCACGCGTCCATGGAGATCTCGAGGCCTG
CAGACATGCAAGCTTGGCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGATCGCCCTTCCCAACAGT
TGCGCAGCCTGAATGGCGAATGGCGCTAGCATAAAAATAAGAAGCCTGCATTTGCAGGCTTCTTATTTTTATGGCG
CGCCGCATTCACTTCTTTTCTATATAAATATGAGCGAAGCGAATAAGCGTCGGAAAAGCAGCAAAAAGTTTCCTTT
TTGCTGTTGGAGCATGGGGGTTCAGGGGTGCAGTATCTGACGTCAATGCCGAGCGAAAGCGAGCCGAAGGGTA
GCATTTACGTTAGATAACCCCCTGATATGCTCCGACGCTTTATATAGAAAGAAGATTCAACTAGGTAAAATCTTAA
TATAGGTTGAGATGATAAGGTTTATAAGGAATTTGTTTGTTCTAATTTTTCACTCATTTTGTTCTAATTTCTTTTAACA
AATGTTCTTTTTTTTTTAGAACAGTTATGATATAGTTAGAATAGTTTAAAATAAGGAGTGAGAAAAAG

FIG 33 (continued)

```
ATGAATAAATTAGTAAAATTAACAGATTTAAAGCGCATTTTCAAAGATGGCATGACAATTATGGTTGGGGGTTTTT
TAGATTGTGGAACTCCTGAAAATATTATAGATATGCTAGTTGATTTAAATATAAAAAATCTGACTATTATAAGCAAT
GATACAGCTTTTCCTAATAAAGGAATAGGAAAACTTATTGTAAATGGTCAAGTTTCTAAAGTAATTGCTTCACATAT
TGGAACTAATCCTGAAACTGGAAAAAAAATGAGCTCTGGAGAACTTAAAGTTGAGCTTTCCCCACAAGGAACACT
GATTGAAAGAATTCGTGCAGCTGGATCTGGACTCGGAGGTGTATTAACTCCAACTGGACTTGGAACTATCGTTGA
AGAAGGTAAGAAAAAAGTTACTATCGATGGCAAAGAATATCTATTAGAACTTCCTTTATCTGCTGATGTTTCATTAA
TAAAAGGTAGCATTGTAGATGAATTTGGAAATACCTTCTATAGGGCTGCTACTAAAAATTTCAATCCATATATGGC
AATGGCTGCAAAAACAGTTATAGTTGAAGCAGAAAATTTAGTTAAATGTGAAGATTTAAAAAGAGATGCCATAAT
GACTCCTGGCGTATTAGTAGATTATATCGTTAAGGAGGCGGCTTAATTGATTGTAGATAAAGTTTTAGCAAAAGAG
ATAATTGCCAAAAGAGTTGCAAAAGAACTAAAAAAAGACCAACTCGTAAACCTTGGAATAGGACTTCCAACTTTAG
TAGCAAATTATGTACCAAAAGAAATGAACATTACTTTTGAATCAGAAAATGGCATGGTTGGTATGGCACAAATGGC
ATCATCAGGTGAAAATGACCCAGATATAATAAATGCTGGCGGGGAATATGTAACATTATTACCTCAAGGTTCATTT
TTTGATAGTTCAATGTCTTTCGCACTAATACGAGGAGGACATGTTGATGTTGCTGTTCTTGGTGCTCTAGAAGTTGA
TGAAAAAGGTAATTTAGCTAACTGGATTGTTCCAAATAAAATTGTCCCAGGTATGGGTGGCGCTATGGATTTAGCA
ATAGGCGCAAAAAAAATAATAGTGGCAATGCAACATACAGGAAAAAGTAAACCTAAAATCGTTAAAAAATGTACT
CTCCCACTTACTGCTAAGGCTCAAGTGGATTTAATTGTCACAGAACTTTGTGTAATTGATGTAACAAATGACGGCTT
ACTTTTAAAAGAAATTCATAAAGATACAACTATTGATGAAATTAAATTTTTAACAGATGCAGATTTAATTATTCCAG
ATAACTTAAAGATTATGGATATATGAATCATTCTATTTTAAATATATAACTTTAAAAATCTTATGTATTAAAAACTAA
GAAAAGAGGTTGATTGTTTTATGTTAGAAAGTGAAGTATCTAAACAAATTACAACTCCACTTGCTGCTCCAGCGTTT
CCTAGAGGACCATATAGGTTTCACAATAGAGAATATCTAAACATTATTTATCGAACTGATTTAGATGCTCTTCGAAA
AATAGTACCAGAGCCACTTGAATTAGATAGAGCATATGTTAGATTTGAAATGATGGCTATGCCTGATACAACCGGA
CTAGGCTCATATACAGAATGTGGTCAAGCTATTCCAGTAAAATATAATGGTGTTAAGGGTGACTACTTGCATATGA
TGTATCTAGATAATGAACCTGCTATTGCTGTTGGAAGAGAAAGTAGCGCTTATCCAAAAAAGCTTGGCTATCCAAA
GCTATTTGTTGATTCAGATACTTTAGTTGGGACACTTAAATATGGTACATTACCAGTAGCTACTGCAACAATGGGAT
ATAAGCACGAGCCTCTAGATCTTAAAGAAGCCTATGCTCAAATTGCAAGACCCAATTTTATGCTAAAAATCATTCAA
GGTTACGATGGTAAGCCAAGAATTTGTGAACTAATATGTGCAGAAAATACTGATATAACTATTCACGGTGCTTGGA
CTGGAAGTGCACGTCTACAATTATTTAGCCATGCACTAGCTCCTCTTGCTGATTTACCTGTATTAGAGATTGTATCA
GCATCTCATATCCTCACAGATTTAACTCTTGGAACACCTAAGGTTGTACATGATTATCTTTCAGTAAAATAA
```

FIG 34

```
ATGAAAGAAAGATATGGAACAGTCTATAAAGGCTCTCAGAGGCTCATAGACGAAGAAAGTGGAGAAGTCATAGA
GGTAGACAAGTTATACCGTAAACAAACGTCTGGTAACTTCGTAAAGGCATATATAGTGCAATTAATAAGTATGTTA
GATATGATTGGCGGAAAAAAACTTAAATCGTTAACTATATCCTAGATAATGTCCACTTAAGTAACAATACAATGA
TAGCTACAACAAGAGAAATAGCAAAAGCTACAGGAACAAGTCTACAAACAGTAATAACAACACTTAAAATCTTAG
AAGAAGGAAATATTATAAAAAGAAAAACTGGAGTATTAATGTTAAACCCTGAACTACTAATGAGAGGCGACGACC
AAAAACAAAATACCTCTTACTCGAATTTGGGAACTTTGAGCAAGAGGCAAATGAAATAGATTGACCTCCCAATAA
CACCACGTAGTTATTGGGAGGTCAATCTATGAAATGCGATTAAGGGCCGGCCAGTGGGCAAGTTGAAAAATTCAC
AAAAAATGTGGTATAATATCTTTGTTCATTAGAGCGATAAACTTGAATTTGAGAGGGAACTTAGATGGTATTTGAAA
AAATTGATAAAAATAGTTGGAACAGAAAAGAGTATTTTGACCACTACTTTGCAAGTGTACCTTGTACCTACAGCAT
GACCGTTAAAGTGGATATCACACAAATAAAGGAAAAGGGAATGAAACTATATCCTGCAATGCTTTATTATATTGCA
ATGATTGTAAACCGCCATTCAGAGTTTAGGACGGCAATCAATCAAGATGGTGAATTGGGGATATATGATGAGATG
ATACCAAGCTATACAATATTTCACAATGATACTGAAACATTTTCCAGCCTTTGGACTGAGTGTAAGTCTGACTTTAA
ATCATTTTTAGCAGATTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCTGAATTTGCAGAAAGGAT
ATGATTATTTGATTCCTATTTTTACTATGGGGAAATATTATAAAGAAGATAACAAAATTATACTTCCTTTGGCAATTC
AAGTTCATCACGCAGTATGTGACGGATTTCACATTTGCCGTTTTGTAAACGAATTGCAGGAATTGATAAAT
```

FIG 35

```
AGTTAACTTCAGGTTTGTCTGTAACTAAAAACAAGTATTTAAGCAAAAACATCGTAGAAATACGGTGTTTTTTGTTA
CCCTAAGTTTAAACTCCTTTTTGATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTTCCGAAGGTAACTGGCTTCAGCAG
AGCGCAGATACCAAATACTGTTCTTCTAGTGTAGCCGTAGTTAGGCCACCACTTCAAGAACTCTGTAGCACCGCCT
ACATACCTCGCTCTGCTAATCCTGTTACCAGTGGCTGCTGCCAGTGGCGATAAGTCGTGTCTTACCGGGTTGGACT
CAAGACGATAGTTACCGGATAAGGCGCAGCGGTCGGGCTGAACGGGGGGTTCGTGCACACAGCCCAGCTTGGAG
CGAACGACCTACACCGAACTGAGATACCTACAGCGTGAGCTATGAGAAAGCGCCACGCTTCCCGAAGGGAGAAA
GGCGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTGTGATGCTCGTCAGGGGGGC
GGAGCCTATGGAAAAACGCCAGCAACGCGGCCTTTTTACGGTTCCTGGCCTTTTGCTGGCCTTTTGCTCACATGTTC
TTTCCTGCGTTATCCCCTGATTCTGTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAATACGCAGGGCCCCCTGCAGGATA
AAAAAATTGTAGATAAATTTTATAAAATAGTTTTATCTACAATTTTTTTATCAGGAAACAGCTATGACCGCGGCCGC
AGATAGTCATAATAGTTCCAGAATAGTTCAATTTAGAAATTAGACTAAACTTCAAAATGTTTGTTAAATATATACCA
AACTAGTATAGATATTTTTTAAATACTGGACTTAAACAGTAGTAATTTGCCTAAAAAATTTTTTCAATTTTTTTTAAA
AAATCCTTTTCAAGTTGTACATTGTTATGGTAATATGTAATTGAAGAAGTTATGTAGTAATATTGTAAACGTTTCTT
GATTTTTTTACATCCATGTAGTGCTTAAAAAACCAAAATATGTCACATGCAATTGTATATTTCAAATAACAATATTTA
TTTTCTCGTTAAATTCACAAATAATTTATTAATAATATCAATAACCAAGATTATACTTAAATGGATGTTTATTTTTTAA
CACTTTTATAGTAAATATATTTATTTTATGTAGTAAAAAGGTTATAATTATAATTGTATTTATTACAATTAATTAAAAT
AAAAAATAGGGTTTTAGGTAAAATTAAGTTATTTTAAGAAGTAATTACAATAAAAATTGAAGTTATTTCTTTAAGGA
GGGAATTATTCATATGAAAGAAGTTGTAATAGCTAGTGCAGTAAGAACAGCGATTGGATCTTATGGAAAGTCTCTT
AAGGATGTACCAGCAGTAGATTTAGGAGCTACAGCTATAAAGGAAGCAGTTAAAAAAGCAGGAATAAAACCAGA
GGATGTTAATGAAGTCATTTTAGGAAATGTTCTTCAAGCAGGTTTAGGACAGAATCCAGCAAGACAGGCATCTTTT
AAAGCAGGATTACCAGTTGAAATTCCAGCTATGACTATTAATAAGGTTTGTGGTTCAGGACTTAGAACAGTTAGCT
TAGCAGCACAAATTATAAAAGCAGGAGATGCTGACGTAATAATAGCAGGTGGTATGGAAAATATGTCTAGAGCTC
CTTACTTAGCGAATAACGCTAGATGGGGATATAGAATGGGAAACGCTAAATTTGTTGATGAAATGATCACTGACG
GATTGTGGGATGCATTTAATGATTACCACATGGGAATAACAGCAGAAAACATAGCTGAGAGATGGAACATTTCAA
GAGAAGAACAAGATGAGTTTGCTCTTGCATCACAAAAAAAAGCTGAAGAAGCTATAAAATCAGGTCAATTTAAAG
ATGAAATAGTTCCTGTAGTAATTAAAGGCAGAAAGGGAGAAACTGTAGTTGATACAGATGAGCACCCTAGATTTG
GATCAACTATAGAAGGACTTGCAAAATTAAAACCTGCCTTCAAAAAAGATGGAACAGTTACAGCTGGTAATGCATC
AGGATTAAATGACTGTGCAGCAGTACTTGTAATCATGAGTGCAGAAAAAGCTAAAGAGCTTGGAGTAAAACCACT
TGCTAAGATAGTTTCTTATGGTTCAGCAGGAGTTGACCCAGCAATAATGGGATATGGACCTTTCTATGCAACAAAA
GCAGCTATTGAAAAAGCAGGTTGGACAGTTGATGAATTAGATTTAATAGAATCAAATGAAGCTTTTGCAGCTCAAA
GTTTAGCAGTAGCAAAAGATTTAAAATTTGATATGAATAAAGTAAATGTAAATGGAGGAGCTATTGCCCTTGGTCA
TCCAATTGGAGCATCAGGTGCAAGAATACTCGTTACTCTTGTACACGCAATGCAAAAAGAGATGCAAAAAAAGG
CTTAGCAACTTTATGTATAGGTGGCGGACAAGGAACAGCAATATTGCTAGAAAAGTGCTAGGAATTCGAGCTCGG
TACCAGGGAGATATTAAAATGAATAAATTAGTAAAATTAACAGATTTAAAGCGCATTTTCAAAGATGGCATGACAA
TTATGGTTGGGGGTTTTTTAGATTGTGGAACTCCTGAAAATATTATAGATATGCTAGTTGATTTAAATATAAAAAT
CTGACTATTATAAGCAATGATACAGCTTTTCCTAATAAAGGAATAGGAAAACTTATTGTAAATGGTCAAGTTTCTAA
AGTAATTGCTTCACATATTGGAACTAATCCTGAAACTGGAAAAAAAATGAGCTCTGGAGAACTTAAAGTTGAGCTT
TCCCCACAAGGAACACTGATTGAAAGAATTCGTGCAGCTGGATCTGGACTCGGAGGTGTATTAACTCCAACTGGA
CTTGGAACTATCGTTGAAGAAGGTAAGAAAAAGTTACTATCGATGGCAAAGAATATCTATTAGAACTTCCTTTAT
CTGCTGATGTTTCATTAATAAAAGGTAGCATTGTAGATGAATTTGGAAATACCTTCTATAGGGCTGCTACTAAAAAT
TTCAATCCATATATGGCAATGGCTGCAAAAACAGTTATAGTTGAAGCAGAAAATTTAGTTAAATGTGAAGATTTAA
AAAGAGATGCCATAATGACTCCTGGCGTATTAGTAGATTATATCGTTAAGGAGGCGGCTTAATTGATTGTAGATAA
AGTTTTAGCAAAAGAGATAATTGCCAAAAGAGTTGCAAAAGAACTAAAAAAAGACCAACTCGTAAAC
```

FIG 35 (continued)

```
CTTGGAATAGGACTTCCAACTTTAGTAGCAAATTATGTACCAAAAGAAATGAACATTACTTTTGAATCAGAAAATG
GCATGGTTGGTATGGCACAAATGGCATCATCAGGTGAAAATGACCCAGATATAATAAATGCTGGCGGGGAATATG
TAACATTATTACCTCAAGGTTCATTTTTTGATAGTTCAATGTCTTTCGCACTAATACGAGGAGGACATGTTGATGTT
GCTGTTCTTGGTGCTCTAGAAGTTGATGAAAAAGGTAATTTAGCTAACTGGATTGTTCCAAATAAAATTGTCCCAG
GTATGGGTGGCGCTATGGATTTAGCAATAGGCGCAAAAAAAATAATAGTGGCAATGCAACATACAGGAAAAAGT
AAACCTAAAATCGTTAAAAAATGTACTCTCCCACTTACTGCTAAGGCTCAAGTGGATTTAATTGTCACAGAACTTTG
TGTAATTGATGTAACAAATGACGGCTTACTTTTAAAAGAAATTCATAAAGATACAACTATTGATGAAATTAAATTTT
TAACAGATGCAGATTTAATTATTCCAGATAACTTAAAGATTATGGATATATGAATCATTCTATTTTAAATATATAACT
TTAAAAATCTTATGTATTAAAAACTAAGAAAAGAGGTTGATTGTTTTATGTTAGAAAGTGAAGTATCTAAACAAATT
ACAACTCCACTTGCTGCTCCAGCGTTTCCTAGAGGACCATATAGGTTTCACAATAGAGAATATCTAAACATTATTTA
TCGAACTGATTTAGATGCTCTTCGAAAAATAGTACCAGAGCCACTTGAATTAGATAGAGCATATGTTAGATTTGAA
ATGATGGCTATGCCTGATACAACCGGACTAGGCTCATATACAGAATGTGGTCAAGCTATTCCAGTAAAATATAATG
GTGTTAAGGGTGACTACTTGCATATGATGTATCTAGATAATGAACCTGCTATTGCTGTTGGAAGAGAAAGTAGCGC
TTATCCAAAAAAGCTTGGCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCTATGCTCAAATTGCAAG
ACCCAATTTTATGCTAAAAATCATTCAAGGTTACGATGGTAAGCCAAGAATTTGTGAACTAATATGTGCAGAAAAT
ACTGATATAACTATTCACGGTGCTTGGACTGGAAGTGCACGTCTACAATTATTTAGCCATGCACTAGCTCCTCTTGC
TGATTTACCTGTATTAGAGATTGTATCAGCATCTCATATCCTCACAGATTTAACTCTTGGAACACCTAAGGTTGTAC
ATGATTATCTTTCAGTAAAATAAAAGCAATATAGAGGATCCTCTAGAGTCGACTTAGGAGGTTCTATTATGAAAGG
TTTTGCAATGTTAGGTATTAACAAATTAGGATGGATTGAAAAGAAAAACCCAGTGCCAGGTCCTTATGATGCGATT
GTACATCCTCTAGCTGTATCCCCATGTACATCAGATATACATACGGTTTTTGAAGGAGCACTTGGTAATAGGGAAA
ATATGATTTTAGGCCATGAAGCTGTAGGTGAAATAGCCGAAGTTGGCAGCGAAGTTAAAGATTTTAAAGTTGGCG
ATAGAGTTATCGTACCATGCACAACACCTGACTGGAGATCTTTAGAAGTCCAAGCTGGTTTTCAGCAGCATTCAAA
CGGTATGCTTGCAGGATGGAAGTTTTCCAATTTTAAAGATGGTGTATTTGCAGATTACTTTCATGTAAACGATGCA
GATATGAATCTTGCCATACTCCCAGATGAAATACCTTTAGAAAGTGCAGTTATGATGACAGACATGATGACTACTG
GTTTTCATGGAGCAGAACTTGCAGACATAAAAATGGGCTCCAGCGTTGTAGTAATTGGTATAGGAGCTGTTGGAT
TAATGGGAATAGCCGGTTCCAAACTTCGAGGAGCAGGCAGAATTATCGGTGTTGGAAGCAGACCTGTTTGTGTTG
AAACAGCTAAATTTTATGGAGCAACTGATATTGTAAATTATAAAAATGGTGATATAGTTGAACAAATCATGGACTT
AACTCATGGTAAAGGTGTAGACCGTGTAATCATGGCAGGCGGTGGTGCTGAAACACTAGCACAAGCAGTAACTAT
GGTTAAACCTGGCGGCGTAAATTCTAACATCAACTACCATGGAAGCGGTGATACTTTACCAATACCTCGTGTTCAAT
GGGGCTGCGGCATGGCTCACAAAACTATAAGAGGAGGATTATGCCCCGGCGGACGTCTTAGAATGGAAATGCTA
AGAGATCTTGTTCTATATAAACGTGTTGATTTGAGTAAACTTGTTACTCATGTATTTGATGGTGCAGAAAATATTGA
AAAGGCCCTTTTGCTTATGAAAAATAAGCCAAAAGATTTAATTAAATCAGTAGTTACATTCTAAAAATTCATATAAA
AAAACTGTCGCATTAAAAAAATGTCTCGAGGCCTGCAGACATGCAAGCTTGGCACTGGCCGTCGTTTTACAACGTC
GTGACTGGGAAAACCCTGGCGTTACCCAACTTAATCGCCTTGCAGCACATCCCCCTTTCGCCAGCTGGCGTAATAG
CGAAGAGGCCCGCACCGATCGCCCTTCCCAACAGTTGCGCAGCCTGAATGGCGAATGGCGCTAGCATAAAAATAA
GAAGCCTGCATTTGCAGGCTTCTTATTTTTATGGCGCGCCGCATTCACTTCTTTTCTATATAAATATGAGCGAAGCG
AATAAGCGTCGGAAAAGCAGCAAAAAGTTTCCTTTTTGCTGTTGGAGCATGGGGGTTCAGGGGGTGCAGTATCTG
ACGTCAATGCCGAGCGAAAGCGAGCCGAAGGGTAGCATTTACGTTAGATAACCCCCTGATATGCTCCGACGCTTT
ATATAGAAAGAAGATTCAACTAGGTAAAATCTTAATATAGGTTGAGATGATAAGGTTTATAAGGAATTTGTTTGT
TCTAATTTTTCACTCATTTTGTTCTAATTTCTTTTAACAAATGTTCTTTTTTTTTAGAACAGTTATGATATAGTTAGAA
TAGTTTAAAATAAGGAGTGAGAAAAAG
```

FIG 35 (continued)

```
GTTTGCCACCTGACGTCTAAGAAAAGGAATATTCAGCAATTTGCCCGTGCCGAAGAAAGGCCCACCCGTGAAGGT
GAGCCAGTGAGTTGATTGCTACGTAATTAGTTAGTTAGCCCTTAGTGACTCGTAATACGACTCACTATAGGGCTCG
AGGCGGCCGCGCAACGCAATTAATGTGAGTTAGCTCACTCATTAGGCACCCCAGGCTTTACACTTTATGCTTCCGG
CTCGTATGTTGTGTGGAATTGTGAGCGGATAACAATTTCACACAGGAAACACATATGTTTCCGTGCAATGCCTATA
TCGAATATGGTGATAAAAATATGAACAGCTTTATCGAAGATGTGGAACAGATCTACAACTTCATTAAAAAGAACAT
TGATGTGGAAGAAAAGATGCATTTCATTGAAACCTATAAACAGAAAAGCAACATGAAGAAAGAGATTAGCTTTAG
CGAAGAATACTATAAACAGAAGATTATGAACGGCAAAAATGGCGTTGTGTACACCCCGCCGGAAATGGCGGCCTT
TATGGTTAAAAATCTGATCAACGTTAACGATGTTATTGGCAATCCGTTTATTAAAATCATTGACCCGAGCTGCGGTA
GCGGCAATCTGATTTGCAAATGTTTTCTGTATCTGAATCGCATCTTTATTAAGAACATTGAGGTGATTAACAGCAAA
AATAACCTGAATCTGAAACTGGAAGACATCAGCTACCACATCGTTCGCAACAATCTGTTTGGCTTCGATATTGACG
AAACCGCGATCAAAGTGCTGAAAATTGATCTGTTTCTGATCAGCAACCAATTTAGCGAGAAAAATTTCCAGGTTAA
AGACTTTCTGGTGGAAAATATTGATCGCAAATATGACGTGTTCATTGGTAATCCGCCGTATATCGGTCACAAAAGC
GTGGACAGCAGCTACAGCTACGTGCTGCGCAAAATCTACGGCAGCATCTACCGCGACAAAGGCGATATCAGCTAT
TGTTTCTTTCAGAAGAGCCTGAAATGTCTGAAGGAAGGTGGCAAACTGGTGTTTGTGACCAGCCGCTACTTCTGCG
AGAGCTGCAGCGGTAAAGAACTGCGTAAATTCCTGATCGAAAACACGAGCATTTACAAGATCATTGATTTTTACGG
CATCCGCCCGTTCAAACGCGTGGGTATCGATCCGATGATTATTTTTCTGGTTCGTACGAAGAACTGGAACAATAAC
ATTGAAATTATTCGCCCGAACAAGATTGAAAAGAACGAAAAGAACAAATTCCTGGATAGCCTGTTCCTGGACAAA
AGCGAAAAGTGTAAAAAGTTTAGCATTAGCCAGAAAAGCATTAATAACGATGGCTGGGTTTCGTGGACGAAGTG
GAGAAAAACATTATCGACAAAATCAAAGAGAAAAGCAAGTTCATTCTGAAAGATATTTGCCATAGCTGTCAAGGC
ATTATCACCGGTTGTGATCGCGCCTTTATTGTGGACCGTGATATCATCAATAGCCGTAAGATCGAACTGCGTCTGAT
TAAACCGTGGATTAAAAGCAGCCATATCCGTAAGAATGAAGTTATTAAGGGCGAAAAATTCATCATCTATAGCAAC
CTGATTGAGAATGAAACCGAGTGTCCGAATGCGATTAAATATATCGAACAGTACAAGAAACGTCTGATGGAGCGC
CGCGAATGCAAAAAGGGCACGCGTAAGTGGTATGAACTGCAATGGGGCCGTAAACCGGAAATCTTCGAAGAAAA
GAAAATTGTTTTCCCGTATAAAAGCTGTGACAATCGTTTTGCACTGGATAAGGGTAGCTATTTTAGCGCAGACATTT
ATAGCCTGGTTCTGAAGAAAAATGTGCCGTTCACCTATGAGATCCTGCTGAATATCCTGAATAGCCCGCTGTACGA
GTTTTACTTTAAGACCTTCGCGAAAAAGCTGGGCGAGAATCTGTACGAGTACATCCGAACAACCTGATGAAGCTG
TGCATCCCGAGCATCGATTTCGGCGGTGAGAACAATATTGAGAAAAAGCTGTATGATTTCTTTGGTCTGACGGATA
AAGAAATTGAGATTGTGGAGAAGATCAAAGATAACTGCTAAGAATTCGATATCACCCGGGAACTAGTCTGCAGCC
CTTTAGTGAGGGTTAATTGGAGTCACTAAGGGTTAGTTAGTTAGATTAGCAGAAAGTCAAAAGCCTCCGACCGGA
GGCTTTTGACTAAAACTTCCCTTGGGGTTATCATTGGGGCTCACTCAAAGGCGGTAATCAGATAAAAAAAATCCTT
AGCTTTCGCTAAGGATGATTTCTGCTAGAGATGGAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTTTTGATAATCTCATG
ACCAAAATCCCTTAACGTGAGTTTTCGTTCCACTGAGCGTCAGACCCCTTAATAAGATGATCTTCTTGAGATCGTTT
TGGTCTGCGCGTAATCTCTTGCTCTGAAAACGAAAAAACCGCCTTGCAGGGCGGTTTTTCGAAGGTTCTCTGAGCT
ACCAACTCTTTGAACCGAGGTAACTGGCTTGGAGGAGCGCAGTCACCAAAACTTGTCCTTTCAGTTTAGCCTTAAC
CGGCGCATGACTTCAAGACTAACTCCTCTAAATCAATTACCAGTGGCTGCTGCCAGTGGTGCTTTTGCATGTCTTTC
CGGGTTGGACTCAAGACGATAGTTACCGGATAAGGCGCAGCGGTCGGACTGAACGGGGGGTTCGTGCATACAGT
CCAGCTTGGAGCGAACTGCCTACCCGGAACTGAGTGTCAGGCGTGGAATGAGACAAACGCGGCCATAACAGCGG
AATGACACCGGTAAACCGAAAGGCAGGAACAGGAGAGCGCACGAGGGAGCCGCCAGGGGAAACGCCTGGTATC
TTTATAGTCCTGTCGGGTTTCGCCACCACTGATTTGAGCGTCAGATTTCGTGATGCTTGTCAGGGGGCGGAGCCT
ATGGAAAAACGGCTTTGCCGCGGCCCTCTCACTTCCCTGTTAAGTATCTTCCTGGCATCTTCCAGGAAATCTCCGCC
CCGTTCGTAAGCCATTTCCGCTCGCCGCAGTCGAACGACCGAGCGTAGCGAGTCAGTGAGCGAGGAAGCGGAAT
ATATCCTGTATCACATATTCTGCTGACGCACCGGTGCAGCCTTTTTCTCCTGCCACATGAAGCACTTCACTGACACC
CTCATCAGTGCCAACATAGTAAGCCAGTATACACTCCGCTAGCGCTGAGGTCTGCCTCGTGAAG
```

FIG 36

AAGGTGTTGCTGACTCATACCAGGCCTGAATCGCCCCATCATCCAGCCAGAAAGTGAGGGAGCCACGGTTGATGA
GAGCTTTGTTGTAGGTGGACCAGTTGGTGATTTTGAACTTTTGCTTTGCCACGGAACGGTCTGCGTTGTCGGGAAG
ATGCGTGATCTGATCCTTCAACTCAGCAAAAGTTCGATTTATTCAACAAAGCCACGTTGTGTCTCAAAATCTCTGAT
GTTACATTGCACAAGATAAAAATATATCATCATGAACAATAAAACTGTCTGCTTACATAAACAGTAATACAAGGGG
TGTTTACTAGAGGTTGATCGGGCACGTAAGAGGTTCCAACTTTCACCATAATGAAATAAGATCACTACCGGGCGTA
TTTTTTGAGTTATCGAGATTTTCAGGAGCTAAGGAAGCTAAAATGGAGAAAAAAATCACGGGATATACCACCGTTG
ATATATCCCAATGGCATCGTAAAGAACATTTTGAGGCATTTCAGTCAGTTGCTCAATGTACCTATAACCAGACCGTT
CAGCTGGATATTACGGCCTTTTTAAAGACCGTAAAGAAAAATAAGCACAAGTTTTATCCGGCCTTTATTCACATTCT
TGCCCGCCTGATGAACGCTCACCCGGAGTTTCGTATGGCCATGAAAGACGGTGAGCTGGTGATCTGGGATAGTGT
TCACCCTTGTTACACCGTTTTCCATGAGCAAACTGAAACGTTTTCGTCCCTCTGGAGTGAATACCACGACGATTTCC
GGCAGTTTCTCCACATATATTCGCAAGATGTGGCGTGTTACGGTGAAAACCTGGCCTATTTCCCTAAAGGGTTTATT
GAGAATATGTTTTTTGTCTCAGCCAATCCCTGGGTGAGTTTCACCAGTTTTGATTTAAACGTGGCCAATATGGACAA
CTTCTTCGCCCCCGTTTTCACGATGGGCAAATATTATACGCAAGGCGACAAGGTGCTGATGCCGCTGGCGATCCAG
GTTCATCATGCCGTTTGTGATGGCTTCCATGTCGGCCGCATGCTTAATGAATTACAACAGTACTGTGATGAGTGGC
AGGGCGGGGCGTAATAATACTAGCTCCGGCAAAAAAACGGGCAAGGTGTCACCACCCTGCCCTTTTTCTTTAAAA
CCGAAAAGATTACTTCGC

FIG 36 (continued)

GCGGCCGCGCAACGCAATTAATGTGAGTTAGCTCACTCATTAGGCACCCCAGGCTTTACACTTTATGCTTCCGGCTC
GTATGTTGTGTGGAATTGTGAGCGGATAACAATTTCACACAGGAAACACAT

FIG 37

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTCAATTTTCATTCTTTTTAAAGGAGATTAGCATACATTTTATCATAATTATACAGACAATATAGTAATATA
TGATGTTAAAATATCAATATATGGTTAAAAATCTGTATATTTTTTCCCATTTTAATTATTTGTACTATAATATTACACT
GAGTGTATTGTATATTTAAAAAATATTTGGTACAATTAGTTAGTTAAATAAATTCTAAATTGTAAATTATCAGAATC
CTTATTAAGGAAATACATAGATTTAAGGAGAAATCATAAAAAGGTGTAATATAAACTGGCTAAAATTGAGCAAAA
ATTGAGCAATTAAGACTTTTTGATTGTATCTTTTTATATATTTAAGGTATATAATCTTATTTATATTGGGGGAACTTG
ATGAATAAACATATTCTAGAC

FIG 38

TAATTTTTTGTGTCAATAATTTTTGTTATATTATTTTAATTAAATTTTTCACATGTATAATTAAAAGTAAGATAGATAT
TCTAATGTACTTACTTAGGTAGAAAAACATGTATACAAAATTAAAAAACTATTATAACACATAGTATCAATATTGAA
GGTAATACTGTTCAATATCGATACAGATAAAAAAATATATAATACAGAAGAAAAAATTATAAATTTGTGGTATAAT
ATAAAGTATAGTAATTTAAGTTTAAACCTCGTGAAAACGCTAACAAATAATAGGAGGTGTATTAT

FIG 39

ATAGTATAACTTTAAAAAACTGTCTTAAAAAGTTGTTATATAAAAAATGTTGACAATTAAACAGCTATTTAGTGCAA
AACAACCATAAAAATTTAAAAAATACCATAAATTACTTGAAAAATAGTTGATAATAATGTAGAGTTATAAACAAAG
GTGAAAAGCATTACTTGTATTCTTTTTATATATTATTATAAATTAAAATGAAGCTGTATTAGAAAAAATACACACCT
GTAATATAAAATTTTAAATTAATTTTTAATTTTTTCAAATGTATTTTACATGTTTAGAATTTTGATGTATATTAAAT
AGTAGAATACATAAGATACTTAATTTAATTAAAGATAGTTAAGTACTTTTCAATGTGCTTTTTTAGATGTTTAATACA
AATCTTTAATTGTAAAAGAAATGCTGTACTATTTACTGTACTAGTGACGGGATTAAACTGTATTAATTATAAATAAA
AAATAAGTACAGTTGTTTAAAATTATATTTTGTATTAAATCTAATAGTACGATGTAAGTTATTTTATACTATTGCTAG
TTTAATAAAAAGATTTAATTATATACTTGAAAAGGAGAGGAATTTTTATGCGTAAA

FIG 40

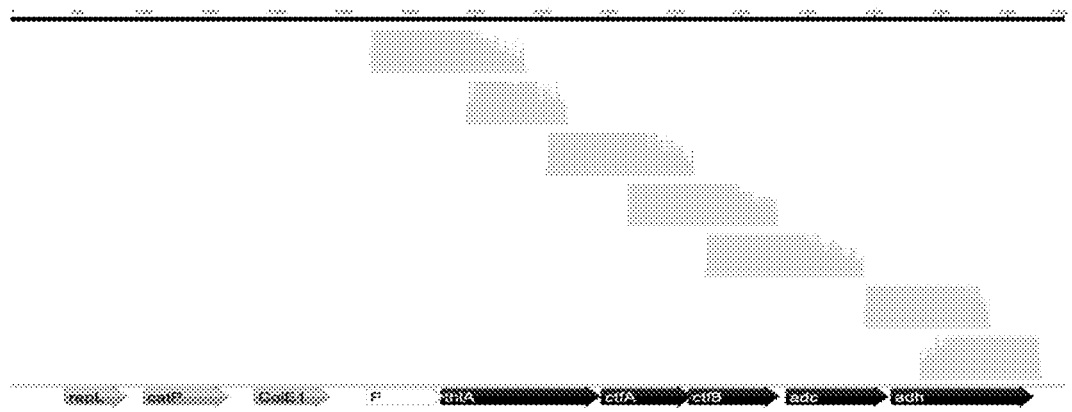
FIG 41
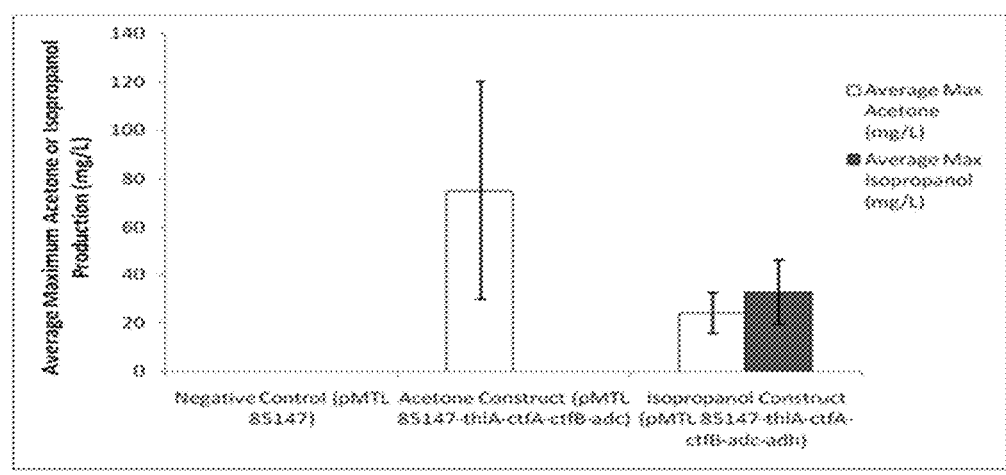
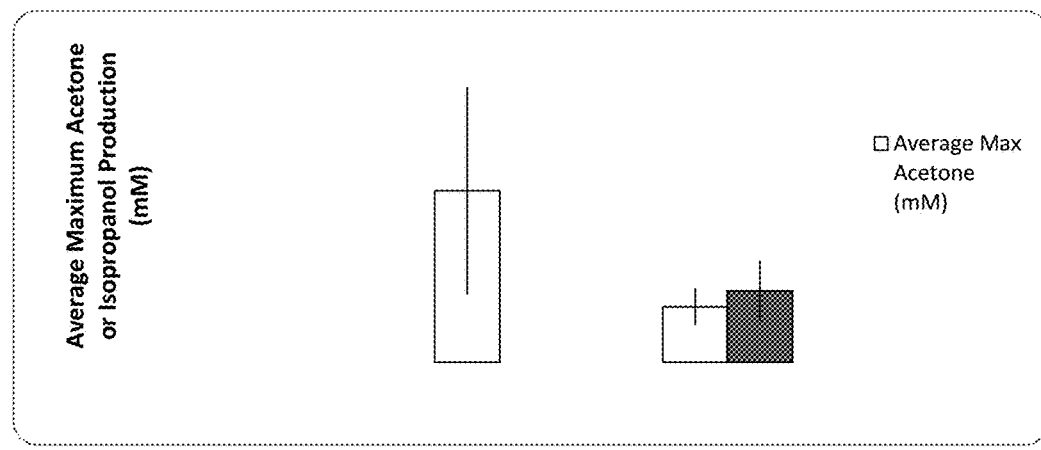
FIG 42

AGATAGTCATAATAGTTCCAGAATAGTTTAATTTAGCATTTGGATTAAATTCCCATATGTTTGTTAAATATATACCAA
ACTAGTATAGATATTTTTAAAATACTGTACTTAAACAGTAGTAATTTACGTAAAAAAATTTTTTGATTTTTTTAAAAA
AGTCCTTTTCAAGTTGTACATTATTATGGTAATATGTAATTGAAGAAGTTGTGTAGTAATATTGTAAACGTTTCTTA
ATTTATTTTCATCCATGTAGTGCTTAAAAAACCAAAATATGTCACACGCAATTGCATATTTCAAACAATAATATTTAT
TTTCTCGTTAAATTCACAAATAATTTATTAATAATATCAATAACCAAGATTATACTTAAATGGATGTTTATTTTTTAAC
ATTTTTTATAGTAAATATATTTATTTTATGTAGTAAAAAGGTTATAATTATAATTGTATTTATTACAATTAATTAAAAT
AAAAAAATAGGGTTTTAGGTAAAATTAAGTTATTTTAAGAAGTAATTACAACAAAAATTGAAGTTATTTCTTTAAG
GAGGGAATTATTAAA

FIG 44

AGATAGTCATAATAGTTCCAGAATAGTTTAATTTTGAAATTGGAGTAAACTTCCAAATGTTTGTTAAATATATACCA
AACTAGTATAGATATTTTTAAATACTAGACTTAAACAGTAGAAATTTGCCTAAAAAATTTTTAGTTTTTTAAAAAA
ATCCTTTTCAAGTTGTACGTTATTATGGTAATATGTAATTGAAGAAGTTATGTAATAATATTGTAAACGTTTCTTAAT
TTTTTTACATCCATGTAATGCTTAAAAGACCAAAATATGTCACATGTAATTGTATATTTCACATAATAATATTTATTTT
CTTATTAAATTCACAAATAATTTATTAATAATATCAATAACCAAGATTATACTTAAATGGATGTTTATTTTTTAACATT
TTTTATGGTAAATATATTTATTTTATGTAGTAAAAAGGTTATAATTATAATTGTATTTATTACAATTAATTAAAATAA
AAAATAGGGTTTTAGGTAAAATTAAGTTATTTTAAGAAGTAATTACAACAAAAATTGAAGTTATTTCTTTAAGGAG
GGAATTATTAAA

FIG 45

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTCAATTTTCATTCTTTTTAAAGGAGATTAGCATACATTTTATCATAATTATACAGACAATATAGTAATATA
TGATGTTAAAATATCAATATATGGTTAAAAATCTGTATATTTTTTCCCATTTTAATTATTTGTACTATAATATTACACT
GAGTGTATTGTATATTTAAAAAATATTTGGTACAATTAGTTAGTTAAATAAATTCTAAATTGTAAATTATCAGAATC
CTTATTAAGGAAATACATAGATTTAAGGAGAAATCATAAAAAGGTGTAATATAAACTGGCTAAAATTGAGCAAAA
ATTGAGCAATTAAGACTTTTTGATTGTATCTTTTTATATATTTAAGGTATATAATCTTATTTATATTGGGGGAAC

FIG 46

TTATAAGAAATCCTAAGGAATATGATGTAATGAGTAAAGCTATAAATCCTTATGGAGATGGCAAGGCAGCTTATA
GAATAACAGAAGCTATTTTACAATATTTTGATTTAGCAAAAGGTACATATAGTGAGTTTAAATCAAATTAAAAAGTT
ATAATTTTGAATTTTCATTCTTTTTAAAGGAGATTAGCATACATTTTATCATAATTATACAGACAATATAGTAATATA
TGATGTTAAAATATCAATATATGGTTAAAAAACTGTATATTTTTTCCCATTTTAATTATTTGTACTATAATATTACACT
GAGTGTATTGTATATTTAAAAAATATTTGGTACAATTAGTTAGTTAAATAAATTCTAAATTATAAATTATCAGAAAC
CTTATTAAGGAAATACATAGATTTAGGGAGAAATAATAAAAAGGTGTAATATAAACTGGCTAAAGTTGAGTAATT
AAGACTTTTAGGTTGTATCTTTTTATATATTTAAGGTATATAATCTTAGTTATATAGGGGGAACTTGATGAATAAAC
ATATTCTAGAC

FIG 47

TAATTTTTTGTGTCAATAATTTTTGTTATATTATTTTAATTAAATTTTTCACATGTATAATTAAAAGTAAGATAGATAT
TCTAATGTACTTACTTAGGTAGAAAAACATGTATACAAAATTAAAAAACTATTATAACACATAGTATCAATATTGAA
GGTAATACTGTTCAATATCGATACAGATAAAAAAAATATATAATACAGAAGAAAAAATTATAAATTTGTGGTATAA
TATAAAGTATAGTAATTTAAGTTTAAACCTCGTGAAAACGCTAACAAATAATAGGAGGTGTATTAT

FIG 48

TAATTTTTTATATCAATAATTTTTATTATATTATTTTAATTAAATTTTTCACATGTATAATTAAAAGTAAGATAGAGAT
AGTTAGGATATTTTAGTGCATTTATTTAGATAAAAAATATGTATACAAGATTAGAAAAAAATTATAACACATAATAG
TTGCATTGAAGGTAATACTGTTCAATATCGATACAGATAAAAAAATTTATAATACAGAAGAAAAAAATATAAATTT
GTGGTATAATATAAAATATAATAATTTAGATTTACACCCCGTGAAAACGCTAACAAATAAATAGGGAG

FIG 49

ATAGTATAACTTTAAAAAAACTGTCTTAAAAAGTTGTTATATAAAAAATGTTGACAATTAAACAGCTATTTAGTGCAA
AACAACCATAAAAATTTAAAAAAATACCATAAATTACTTGAAAAATAGTTGATAATAATGTAGAGTTATAAACAAAG
GTGAAAAGCATTACTTGTATTCTTTTTTATATATTATTATAAATTAAAATGAAGCTGTATTAGAAAAAATACACACCT
GTAATATAAAATTTTAAATTAATTTTTAATTTTTTCAAAATGTATTTTACATGTTTAGAATTTTGATGTATATTAAAAT
AGTAGAATACATAAGATACTTAATTTAATTAAAGATAGTTAAGTACTTTTCAATGTGCTTTTTAGATGTTTAATACA
AATCTTTAATTGTAAAAGAAATGCTGTACTATTTACTGTACTAGTGACGGGATTAAACTGTATTAATTATAAATAAA
AAATAAGTACAGTTGTTTAAAATTATATTTTGTATTAAATCTAATAGTACGATGTAAGTTATTTTATACTATTGCTAG
TTTAATAAAAAGATTTAATTATATACTTGAAAAGGAGAGGAATTTTT

FIG 50

ATAGAATAACTTAAAAAAACTGTCTTAAAAAGCTGTTATATAAAAAAATGTTAACAATTAAACAGCTATTTAGTGCA
AAACAACCATAAAAATTTAAAAAAATACCATAAATTACTTGAAAAATAGTAGAGAATAATGTAGAGTTATAAACGAA
GGTGAAAAGCATTACTTGTATTCCTTTTTACAGACTATTATAAATTAAGATAAAGCTGTATTAGGAAAAATGCACAC
CTGTAATATAAGGTTTTAAATTAATTTTTAATTTTCCCAAAATGTATTTTACATGTTTAGAATTTTGATGTATATTAAA
ATAGTAGAATACATAAGATACTTAATTTAATAAAGATAGTTAAGTACTTTTCAATGTACTTTTTTAGATATTTAATAC
AAGTTTTTAATTGTAAAAAAATGCTGTGCTATTTACTGTACTAATGGTAGTACTATATCTGTATTAATTGTATGTAAA
AAGTAAGTATAGTTATTTAAGATTATGTTTTGTATTAAATCTAAATAGTACAATGTAGGTTATGTTATACTATTGCTA
GTTTAATAAAAAGATTTAATTATATACTTGAAAAGGAGAGGAATTTTTATGCGTAAA

FIG 51

SEQ ID NO: 72
ATGTATACAGTAGGAGATTACCTATTAGACCGATTACACGAGTTAGGAATTGAAGAAATTTTTGGAGTCCCTGGAG
ACTATAACTTACAATTTTTAGATCAAATTATTTCCCACAAGGATATGAAATGGGTCGGAAATGCTAATGAATTAAAT
GCTTCATATATGGCTGATGGCTATGCTCGTACTAAAAAAGCTGCCGCATTTCTTACAACCTTTGGAGTAGGTGAATT
GAGTGCAGTTAATGGATTAGCAGGAAGTTACGCCGAAAATTTACCAGTAGTAGAAATAGTGGGATCACCTACATC
AAAAGTTCAAAATGAAGGAAAATTTGTTCATCATACGCTGGCTGACGGTGATTTTAAACACTTTATGAAAATGCAC
GAACCTGTTACAGCAGCTCGAACTTTACTGACAGCAGAAAATGCAACCGTTGAAATTGACCGAGTACTTTCTGCAC
TATTAAAAGAAAGAAAACCTGTCTATATCAACTTACCAGTTGATGTTGCTGCTGCAAAAGCAGAGAAACCCTCACT
CCCTTTGAAAAAGGAAAACTCAACTTCAAATACAAGTGACCAAGAAATTTTGAACAAAATTCAAGAAAGCTTGAAA
AATGCCAAAAAACCAATCGTGATTACAGGACATGAAATAATTAGTTTTGGCTTAGAAAAAACAGTCACTCAATTTA
TTTCAAAGACAAAACTACCTATTACGACATTAAACTTTGGTAAAAGTTCAGTTGATGAAGCCCTCCCTTCATTTTA
GGAATCTATAATGGTACACTCTCAGAGCCTAATCTTAAAGAATTCGTGGAATCAGCCGACTTCATCTTGATGCTTG
GAGTTAAACTCACAGACTCTTCAACAGGAGCCTTCACTCATCATTTAAATGAAAATAAAATGATTTCACTGAATATA
GATGAAGGAAAAATATTTAACGAAAGAATCCAAAATTTTGATTTTGAATCCCTCATCTCCTCTCTCTTAGACCTAAG
CGAAATAGAATACAAAGGAAAATATATCGATAAAAAGCAAGAAGACTTTGTTCCATCAAATGCGCTTTTATCACAA
GACCGCCTATGGCAAGCAGTTGAAAACCTAACTCAAAGCAATGAAACAATCGTTGCTGAACAAGGGACATCATTC
TTTGGCGCTTCATCAATTTTCTTAAAATCAAAGAGTCATTTTATTGGTCAACCCTTATGGGGATCAATTGGATATAC
ATTCCCAGCAGCATTAGGAAGCCAAATTGCAGATAAAGAAAGCAGACACCTTTTATTTATTGGTGATGGTTCACTT
CAACTTACAGTGCAAGAATTAGGATTAGCAATCAGAGAAAAAATTAATCCAATTTGCTTTATTATCAATAATGATG
GTTATACAGTCGAAAGAGAAATTCATGGACCAAATCAAAGCTACAATGATATTCCAATGTGGAATTACTCAAAATT
ACCAGAATCGTTTGGAGCAACAGAAGATCGAGTAGTCTCAAAAATCGTTAGAACTGAAAATGAATTTGTGTCTGTC
ATGAAAGAAGCTCAAGCAGATCCAAATAGAATGTACTGGATTGAGTTAATTTTGGCAAAAGAAGGTGCACCAAAA
GTACTGAAAAAAATGGGCAAACTATTTGCTGAACAAAATAAATCATAA

SEQ ID NO: 73
MYTVGDYLLDRLHELGIEEIFGVPGDYNLQFLDQIISHKDMKWVGNANELNASYMADGYARTKKAAAFLTTFGVGELS
AVNGLAGSYAENLPVVEIVGSPTSKVQNEGKFVHHTLADGDFKHFMKMHEPVTAARTLLTAENATVEIDRVLSALLKER
KPVYINLPVDVAAAKAEKPSLPLKKENSTSNTSDQEILNKIQESLKNAKKPIVITGHEIISFGLEKTVTQFISKTKLPITTLNFG
KSSVDEALPSFLGIYNGTLSEPNLKEFVESADFILMLGVKLTDSSTGAFTHHLNENKMISLNIDEGKIFNERIQNFDFESLIS
SLLDLSEIEYKGKYIDKKQEDFVPSNALLSQDRLWQAVENLTQSNETIVAEQGTSFFGASSIFLKSKSHFIGQPLWGSIGYT
FPAALGSQIADKESRHLLFIGDGSLQLTVQELGLAIREKINPICFIINNDGYTVEREIHGPNQSYNDIPMWNYSKLPESFGA
TEDRVVSKIVRTENEFVSVMKEAQADPNRMYWIELILAKEGAPKVLKKMGKLFAEQNKS*

FIG 54

SEQ ID NO: 74
ATGTCTATTCCAGAAACTCAAAAAGCCATTATCTTCTACGAATCCAACGGCAAGTTGGAGCATAAGGATATCCCAG
TTCCAAAGCCAAAGCCCAACGAATTGTTAATCAACGTCAAGTACTCTGGTGTCTGCCACACCGATTTGCACGCTTG
GCATGGTGACTGGCCATTGCCAACTAAGTTACCATTAGTTGGTGGTCACGAAGGTGCCGGTGTCGTTGTCGGCAT
GGGTGAAAACGTTAAGGGCTGGAAGATCGGTGACTACGCCGGTATCAAATGGTTGAACGGTTCTTGTATGGCCTG
TGAATACTGTGAATTGGGTAACGAATCCAACTGTCCTCACGCTGACTTGTCTGGTTACACCCACGACGGTTCTTTCC
AAGAATACGCTACCGCTGACGCTGTTCAAGCCGCTCACATTCCTCAAGGTACTGACTTGGCTGAAGTCGCGCCAAT
CTTGTGTGCTGGTATCACCGTATACAAGGCTTTGAAGTCTGCCAACTTGAGAGCAGGCCACTGGGCGGCCATTTCT
GGTGCTGCTGGTGGTCTAGGTTCTTTGGCTGTTCAATATGCTAAGGCGATGGGTTACAGAGTCTTAGGTATTGATG
GTGGTCCAGGAAAGGAAGAATTGTTTACCTCGCTCGGTGGTGAAGTATTCATCGACTTCACCAAAGAGAAGGACA
TTGTTAGCGCAGTCGTTAAGGCTACCAACGGCGGTGCCCACGGTATCATCAATGTTTCCGTTTCCGAAGCCGCTAT
CGAAGCTTCTACCAGATACTGTAGGGCGAACGGTACTGTTGTCTTGGTTGGTTTGCCAGCCGGTGCAAAGTGCTCC
TCTGATGTCTTCAACCACGTT
GTCAAGTCTATCTCCATTGTCGGCTCTTACGTGGGGAACAGAGCTGATACCAGAGAAGCCTTAGATTTCTTTGCCA
GAGGTCTAGTCAAGTCTCCAATAAAGGTAGTTGGCTTATCCAGTTTACCAGAAATTTACGAAAAGATGGAGAAGG
GCCAAATTGCTGGTAGATACGTTGTTGACACTTCTAAATAA

SEQ ID NO: 75
MSIPETQKAIIFYESNGKLEHKDIPVPKPKPNELLINVKYSGVCHTDLHAWHGDWPLPTKLPLVGGHEGAGVVVGMGE
NVKGWKIGDYAGIKWLNGSCMACEYCELGNESNCPHADLSGYTHDGSFQEYATADAVQAAHIPQGTDLAEVAPILCA
GITVYKALKSANLRAGHWAAISGAAGGLGSLAVQYAKAMGYRVLGIDGGPGKEELFTSLGGEVFIDFTKEKDIVSAVVK
ATNGGAHGIINVSVSEAAIEASTRYCRANGTVVLVGLPAGAKCSSDVFNHVVKSISIVGSYVGNRADTREALDFFARGLV
KSPIKVVGLSSLPEIYEKMEKGQIAGRYVVDTSK*

SEQ ID NO: 76
CATATGTATACAGTAGGAGATTACCTATTAGACCGATTACACGAGTTAGGAATTGAAGAAATTTTTGGAGTCCCTG
GAGACTATAACTTACAATTTTTAGATCAAATTATTTCCCACAAGGATATGAAATGGGTCGGAAATGCTAATGAATT
AAATGCTTCATATATGGCTGATGGCTATGCTCGTACTAAAAAAGCTGCCGCATTTCTTACAACCTTTGGAGTAGGT
GAATTGAGTGCAGTTAATGGATTAGCAGGAAGTTACGCCGAAAATTTACCAGTAGTAGAAATAGTGGGATCACCT
ACATCAAAAGTTCAAAATGAAGGAAAATTTGTTCATCATACGCTGGCTGACGGTGATTTTAAACACTTTATGAAAA
TGCACGAACCTGTTACAGCAGCTCGAACTTTACTGACAGCAGAAAATGCAACCGTTGAAATTGACCGAGTACTTTC
TGCACTATTAAAAGAAAGAAAACCTGTCTATATCAACTTACCAGTTGATGTTGCTGCTGCAAAAGCAGAGAAACCC
TCACTCCCTTTGAAAAAGGAAAACTCAACTTCAAATACAAGTGACCAAGAAATTTTGAACAAAATTCAAGAAAGCT
TGAAAAATGCCAAAAAACCAATCGTGATTACAGGACATGAAATAATTAGTTTTGGCTTAGAAAAAACAGTCACTCA
ATTTATTTCAAAGACAAAACTACCTATTACGACATTAAACTTTGGTAAAAGTTCAGTTGATGAAGCCCTCCCTTCATT
TTTAGGAATCTATAATGGTACACTCTCAGAGCCTAATCTTAAAGAATTCGTGGAATCAGCCGACTTCATCTTGATGC
TTGGAGTTAAACTCACAGACTCTTCAACAGGAGCCTTCACTCATCATTTAAATGAAAATAAAATGATTTCACTGAAT
ATAGATGAAGGAAAAATATTTAACGAAAGAATCCAAAATTTTGATTTTGAATCCCTCATCTCCTCTCTCTTAGACCT
AAGCGAAATAGAATACAAAGGAAAATATATCGATAAAAAGCAAGAAGACTTTGTTCCATCAAATGCGCTTTTATCA
CAAGACCGCCTATGGCAAGCAGTTGAAAACCTAACTCAAAGCAATGAAACAATCGTTGCTGAACAAGGGACATCA
TTCTTTGGCGCTTCATCAATTTTCTTAAAATCAAAGAGTCATTTTATTGGTCAACCCTTATGGGGATCAATTGGATAT
ACATTCCCAGCAGCATTAGGAAGCCAAATTGCAGATAAAGAAAGCAGACACCTTTTATTTATTGGTGATGGTTCAC
TTCAACTTACAGTGCAAGAATTAGGATTAGCAATCAGAGAAAAAATTAATCCAATTTGCTTTATTATCAATAATGAT
GGTTATACAGTCGAAAGAGAAATTCATGGACCAAATCAAAGCTACAATGATATTCCAATGTGGAATTACTCAAAAT
TACCAGAATCGTTTGGAGCAACAGAAGATCGAGTAGTCTCAAAAATCGTTAGAACTGAAAATGAATTTGTGTCTGT
CATGAAAGAAGCTCAAGCAGATCCAAATAGAATGTACTGGATTGAGTTAATTTTGGCAAAAGAAGGTGCACCAAA
AGTACTGAAAAAAATGGGCAAACTATTTGCTGAACAAAATAAATCATAA

FIG 55

SEQ ID NO: 77
ATGTCTATTCCAGAAACTCAAAAAGCCATTATCTTCTACGAATCCAACGGCAAGTTGGAGCATAAGGATATCCCAG
TTCCAAAGCCAAAGCCCAACGAATTGTTAATCAACGTCAAGTACTCTGGTGTCTGCCACACCGATTTGCACGCTTG
GCATGGTGACTGGCCATTGCCAACTAAGTTACCATTAGTTGGTGGTCACGAAGGTGCCGGTGTCGTTGTCGGCAT
GGGTGAAAACGTTAAGGGCTGGAAGATCGGTGACTACGCCGGTATCAAATGGTTGAACGGTTCTTGTATGGCCTG
TGAATACTGTGAATTGGGTAACGAATCCAACTGTCCTCACGCTGACTTGTCTGGTTACACCCACGACGGTTCTTTCC
AAGAATACGCTACCGCTGACGCTGTTCAAGCCGCTCACATTCCTCAAGGTACTGACTTGGCTGAAGTCGCGCCAAT
CTTGTGTGCTGGTATCACCGTATACAAGGCTTTGAAGTCTGCCAACTTGAGAGCAGGCCACTGGGCGGCCATTTCT
GGTGCTGCTGGTGGTCTAGGTTCTTTGGCTGTTCAATATGCTAAGGCGATGGGTTACAGAGTCTTAGGTATTGATG
GTGGTCCAGGAAAGGAAGAATTGTTTACCTCGCTCGGTGGTGAAGTATTCATCGACTTCACCAAAGAGAAGGACA
TTGTTAGCGCAGTCGTTAAGGCTACCAACGGCGGTGCCCACGGTATCATCAATGTTTCCGTTCCGAAGCCGCTAT
CGAAGCTTCTACCAGATACTGTAGGGCGAACGGTACTGTTGTCTTGGTTGGTTGCCAGCCGGTGCAAAGTGCTCC
TCTGATGTCTTCAACCACGTTGTCAAGTCTATCTCCATTGTCGGCTCTTACGTGGGGAACAGAGCTGATACCAGAG
AAGCCTTAGATTTCTTTGCCAGAGGTCTAGTCAAGTCTCCAATAAAGGTAGTTGGCTTATCCAGTTTACCAGAAATT
TACGAAAAGATGGAGAAGGGCCAAATTGCTGGTAGATACGTTGTTGACACTTCTAAATAA

SEQ ID NO: 78
CATATGTATACAGTAGGAGATTACCTATTAGACCGATTACACGAGTTAGGAATTGAAGAAATTTTTGGAGTCCCTG
GAGACTATAACTTACAATTTTTAGATCAAATTATTTCCCACAAGGATATGAAATGGGTCGGAAATGCTAATGAATT
AAATGCTTCATATATGGCTGATGGCTATGCTCGTACTAAAAAAGCTGCCGCATTTCTTACAACCTTTGGAGTAGGT
GAATTGAGTGCAGTTAATGGATTAGCAGGAAGTTACGCCGAAAATTTACCAGTAGTAGAAATAGTGGGATCACCT
ACATCAAAAGTTCAAAATGAAGGAAAATTTGTTCATCATACGCTGGCTGACGGTGATTTTAAACACTTTATGAAAA
TGCACGAACCTGTTACAGCAGCTCGAACTTTACTGACAGCAGAAAATGCAACCGTTGAAATTGACCGAGTACTTTC
TGCACTATTAAAAGAAAGAAAACCTGTCTATATCAACTTACCAGTTGATGTTGCTGCTGCAAAAGCAGAGAAACCC
TCACTCCCTTTGAAAAAGGAAAACTCAACTTCAAATACAAGTGACCAAGAAATTTTGAACAAAATTCAAGAAAGCT
TGAAAAATGCCAAAAAACCAATCGTGATTACAGGACATGAAATAATTAGTTTTGGCTTAGAAAAAACAGTCACTCA
ATTTATTTCAAAGACAAAACTACCTATTACGACATTAAACTTTGGTAAAAGTTCAGTTGATGAAGCCCTCCCTTCATT
TTTAGGAATCTATAATGGTACACTCTCAGAGCCTAATCTTAAAGAATTCGTGGAATCAGCCGACTTCATCTTGATGC
TTGGAGTTAAACTCACAGACTCTTCAACAGGAGCCTTCACTCATCATTTAAATGAAAATAAAATGATTTCACTGAAT
ATAGATGAAGGAAAAATATTTAACGAAAGAATCCAAAATTTTGATTTTGAATCCCTCATCTCCTCTCTCTTAGACCT
AAGCGAAATAGAATACAAAGGAAAATATATCGATAAAAAGCAAGAAGACTTTGTTCCATCAAATGCGCTTTTATCA
CAAGACCGCCTATGGCAAGCAGTTGAAAACCTAACTCAAAGCAATGAAACAATCGTTGCTGAACAAGGGACATCA
TTCTTTGGCGCTTCATCAATTTTCTTAAAATCAAAGAGTCATTTTATTGGTCAACCCTTATGGGGATCAATTGGATAT
ACATTCCCAGCAGCATTAGGAAGCCAAATTGCAGATAAAGAAAGCAGACACCTTTTATTTATTGGTGATGGTTCAC
TTCAACTTACAGTGCAAGAATTAGGATTAGCAATCAGAGAAAAAATTAATCCAATTTGCTTTATTATCAATAATGAT
GGTTATACAGTCGAAAGAGAAATTCATGGACCAAATCAAAGCTACAATGATATTCCAATGTGGAATTACTCAAAAT
TACCAGAATCGTTTGGAGCAACAGAAGATCGAGTAGTCTCAAAAATCGTTAGAACTGAAAATGAATTTGTGTCTGT
CATGAAAGAAGCTCAAGCAGATCCAAATAGAATGTACTGGATTGAGTTAATTTTGGCAAAAGAAGGTGCACCAAA
AGTACTGAAAAAATGGGCAAACTATTTGCTGAACAAAATAAATCATAAGAATTCAAAAAAAAAAAAAAAAAAA
AAAAAAAAAAAAAAATGTCTATTCCAGAAACTCAAAAAGCCATTATCTTCTACGAATCCAACGGCAAGTTGGAGC
ATAAGGATATCCCAGTTCCAAAGCCAAAGCCCAACGAATTGTTAATCAACGTCAAGTACTCTGGTGTCTGCCACAC
CGATTTGCACGCTTGGCATGGTGACTGGCCATTGCCAACTAAGTTACCATTAGTTGGTGGTCACGAAGGTGCCGGT
GTCGTTGTCGGCATGGGTGAAAACGTTAAGGGCTGGAAGATCGGTGACTACGCCGGTATCAAATGGTTGAACGG
TTCTTGTATGGCCTGTGAATACTGTGAATTGGGTAACGAATCCAACTGTCCTCACGCTGACTTGTCTGGTTACACCC
ACGACGGTTCTTTCCAAGAATACGCTACCGCTGACGCT
GTTCAAGCCGCTCACATTCCTCAAGGTACTGACTTGGCTGAAGTCGCGCCAATCTTGTGTGCTGGTATCACCGTATA
CAAGGCTTTGAAGTCTGCCAACTTGAGAGCAGGCCACTGGGCGGCCATTTCTGGTGCTGCTGGTGGTCTAGGTTC
TTTGGCTGTTCAATATGCTAAGGCGATGGGTTACAGAGTCTTAGGTATTGATGGTGGTCCAGGAAAGGAAGAATT
GTTTACCTCGCTCGGTGGTGAAGTATTCATCGACTTCACCAAAGAGAAGGACATTGTTAGCGCAGTCGTTAAGGCT
ACCAACGGCGGTGCCCACGGTATCATCAATGTTTCCGTTCCGAAGCCGCTATCGAAGCTTCTACCAGATACTGTA
GGGCGAACGGTACTGTTGTCTTGGTTGGTTGCCAGCCGGTGCAAAGTGCTCCTCTGATGTCTTCAACCACGTTGT
CAAGTCTATCTCCATTGTCGGCTCTTACGTGGGGAACAGAGCTGATACCAGAGAAGCCTTAGATTTCTTTGCCAGA
GGTCTAGTCAAGTCTCCAATAAAGGTAGTTGGCTTATCCAGTTTACCAGAAATTTACGAAAAGATGGAGAAGGGC
CAAATTGCTGGTAGATACGTTGTTGACACTTCTAAATAAGGTACC

FIG 56

SEQ ID NO: 79
AATATGATATTTATGTCCATTGTGAAAGGGATTATATTCAACTATTATTCCAGTTACGTTCATAGAAATTTTCCTTTC
TAAAATATTTTATTCCATGTCAAGAACTCTGTTTATTTCATTAAAGAACTATAAGTACAAAGTATAAGGCATTTGAA
AAAATAGGCTAGTATATTGATTGATTATTTATTTTAAAATGCCTAAGTGAAATATATACATATTATAACAATAAAAT
AAGTATTAGTGTAGGATTTTTAAATAGAGTATCTATTTTCAGATTAAATTTTTGATTATTTGATTTAC
ATTATATAATATTGAGTAAAGTATTGACTAGCAAAATTTTTTGATACTTTAATTTGTGAAATTTCTTATCAAAAGTTA
TATTTTTGAATAATTTTTATTGAAAAATACAACTAAAAAGGATTATAGTATAAGTGTGTGTAATTTTGTGTTAAATTT
AAAGGGAGGAAATGAACATGAAA

SEQ ID NO: 82
AAACTCCTTTTTGATAATCTCATGACCAAAATCCCTTAACGTGAGTTTTCGTTCCACTGAGCGTCAGACCCCGTAGA
AAAGATCAAAGGATCTTCTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCTTCAGCAGAGCGCAGAT
ACCAAATACTGTTCTTCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGAAACGCCTGGTATCTTTA
TAGTCCTGTCGGGTTTCGCCACCTCTGACTTGAGCGTCGATTTTGTGATGCTCGTCAGGGGGGCGGAGCCTATGG
AAAAACGCCAGCAACGCGGCCTTTTTACGGTTCCTGGCCTTTTGCTGGCCTTTTGCTCACATGTTCTTTCCTGCGTTA
TCCCCTGATTCTGTGGATAACCGTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAGGGCCCCTGCAGGATAAAAAAATTGTA
GATAAATTTTATAAAATAGTTTTATCTACAATTTTTTTATCAGGAAACAGCTATGACCGCGGCCGCAATATGATATT
TATGTCCATTGTGAAAGGGATTATATTCAACTATTATTCCAGTTACGTTCATAGAAATTTTCCTTTCTAAAATATTTT
ATTCCATGTCAAGAACTCTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAATAAAATAAGTATTAGTGT
AGGATTTTTAAATAGAGTATCTATTTTCAGATTAAATTTTTGATTATTTGATTTACATTATATAATATTGAGTAAAGT
ATTGACTAGCAAAATTTTTTGATACTTTAATTTGTGAAATTTCTTATCAAAAGTTATATTTTTGAATAATTTTTATTGA
AAAATACAACTAAAAAGGATTATAGTATAAGTGTGTGTAATTTTGTGTTAAATTTAAAGGGAGGAAATGAACATG
AAACATATGGTGACCATGATTACGAATTCGAGCTCGGTACCCGGGGATCCTCTAGAGTCGACGTCACGCGTCCAT
GGAGATCTCGAGGCCTGCAGACATGCAAGCTTGGCACTGGCCGTCGTTTTACAACGTCGTGACTGGGAAAACCCT
GGCGTTACCCAACTTAATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGCGCTAGCATAAAAATAAGAAGCCTGCATTTGCAG
GCTTCTTATTTTTATGGCGCGCCGCATTCACTTCT

FIG 57

```
TTTCTATATAAATATGAGCGAAGCGAATAAGCGTCGGAAAAGCAGCAAAAAGTTTCCTTTTTGCTGTTGGAGCATG
GGGGTTCAGGGGGTGCAGTATCTGACGTCAATGCCGAGCGAAAGCGAGCCGAAGGGTAGCATTTACGTTAGATA
ACCCCCTGATATGCTCCGACGCTTTATATAGAAAAGAAGATTCAACTAGGTAAAATCTTAATATAGGTTGAGATGA
TAAGGTTTATAAGGAATTTGTTTGTTCTAATTTTTCACTCATTTTGTTCTAATTTCTTTTAACAAATGTTCTTTTTTTTT
TAGAACAGTTATGATATAGTTAGAATAGTTTAAAATAAGGAGTGAGAAAAAGATGAAAGAAAGATATGGAACAG
TCTATAAAGGCTCTCAGAGGCTCATAGACGAAGAAAGTGGAGAAGTCATAGAGGTAGACAAGTTATACCGTAAAC
AAACGTCTGGTAACTTCGTAAAGGCATATATAGTGCAATTAATAAGTATGTTAGATATGATTGGCGGAAAAAAACT
TAAAATCGTTAACTATATCCTAGATAATGTCCACTTAAGTAACAATACAATGATAGCTACAACAAGAGAAATAGCA
AAAGCTACAGGAACAAGTCTACAAACAGTAATAACAACACTTAAAATCTTAGAAGAAGGAAATATTATAAAAGA
AAAACTGGAGTATTAATGTTAAACCCTGAACTACTAATGAGAGGCGACGACCAAAAACAAAAATACCTCTTACTCG
AATTTGGGAACTTTGAGCAAGAGGCAAATGAAATAGATTGACCTCCCAATAACACCACGTAGTTATTGGGAGGTC
AATCTATGAAATGCGATTAAGGGCCGGCCGAAGCAAACTTAAGAGTGTGTTGATAGTGCAGTATCTTAAAATTTTG
TATAATAGGAATTGAAGTTAAATTAGATGCTAAAAATTTGTAATTAAGAAGGAGTGATTACATGAACAAAAATATA
AAATATTCTCAAAACTTTTTAACGAGTGAAAAAGTACTCAACCAAATAATAAAACAATTGAATTTAAAAGAAACCG
ATACCGTTTACGAAATTGGAACAGGTAAAGGGCATTTAACGACGAAACTGGCTAAAATAAGTAAACAGGTAACGT
CTATTGAATTAGACAGTCATCTATTCAACTTATCGTCAGAAAAATTAAAACTGAATACTCGTGTCACTTTAATTCACC
AAGATATTCTACAGTTTCAATTCCCTAACAAACAGAGGTATAAAATTGTTGGGAGTATTCCTTACCATTTAAGCACA
CAAATTATTAAAAAAGTGGTTTTTGAAAGCCATGCGTCTGACATCTATCTGATTGTTGAAGAAGGATTCTACAAGC
GTACCTTGGATATTCACCGAACACTAGGGTTGCTCTTGCACACTCAAGTCTCGATTCAGCAATTGCTTAAGCTGCCA
GCGGAATGCTTTCATCCTAAACCAAAAGTAAACAGTGTCTTAATAAAACTTACCCGCCATACCACAGATGTTCCAG
ATAAATATTGGAAGCTATATACGTACTTTGTTTCAAAATGGGTCAATCGAGAATATCGTCAACTGTTTACTAAAAAT
CAGTTTCATCAAGCAATGAAACACGCCAAAGTAAACAATTTAAGTACCGTTACTTATGAGCAAGTATTGTCTATTTT
TAATAGTTATCTATTATTTAACGGGAGGAAATAATTCTATGAGTCGCTTTTGTAAATTTGGAAAGTTACACGTTACT
AAAGGGAATGTGTTT
```

FIG 57 (continued)

SEQ ID NO: 83

```
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCCTGCAGGATAAAA
AAATTGTAGATAAATTTTATAAAATAGTTTTATCTACAATTTTTTTATCAGGAAACAGCT
ATGACCGCGGCCGCAATATGATATTTATGTCCATTGTGAAAGGGATTATATTCAACTATT
ATTCCAGTTACGTTCATAGAAATTTTCCTTTCTAAAATATTTTATTCCATGTCAAGAACT
CTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAA
TAAAATAAGTATTAGTGTAGGATTTTTAAATAGAGTATCTATTTTCAGATTAAATTTTTG
ATTATTTGATTTACATTATATAATATTGAGTAAAGTATTGACTAGCAAAATTTTTTGATA
CTTTAATTTGTGAAATTTCTTATCAAAAGTTATATTTTTGAATAATTTTTTATTGAAAAAT
ACAACTAAAAAGGATTATAGTATAAGTGTGTGTAATTTTGTGTTAAATTTAAAGGGAGGA
AATGAACATGAAACATATGTATACAGTTGGTGATTATTTACTTGATAGATTACATGAACT
TGGAATAGAAGAAATTTTTGGTGTACCAGGTGATTACAATCTTCAATTCTTAGATCAAAT
AATATCACATAAGGATATGAAATGGGTTGGTAATGCTAATGAATTAAATGCATCATATAT
GGCAGACGGATATGCAAGAACTAAAAAGGCAGCAGCATTTCTTACTACATTTGGTGTTGG
TGAATTAAGTGCAGTAAATGGATTAGCTGGAAGTTACGCAGAAAACTTACCAGTTGTTGA
AATAGTTGGATCTCCTACTAGTAAAGTACAAAATGAAGGTAAATTTGTACATCACACTCT
TGCAGATGGTGATTTTAAGCATTTTATGAAAATGCATGAACCTGTTACAGCTGCAAGAAC
ACTTCTTACAGCTGAAAACGCTACTGTAGAAATTGATAGAGTTTTATCTGCTTTACTTAA
AGAAAGAAAGCCAGTATATATTAACCTTCCAGTAGATGTAGCAGCAGCAAAAGCTGAGAA
ACCTTCATTACCACTTAAAAAGGAAAATTCAACATCAAATACATCTGATCAAGAGATATT
AAATAAAATTCAGGAAAGTCTTAAAAATGCAAAGAAACCTATAGTAATAACTGGACATGA
AATAATTAGTTTTGGATTAGAAAAGACAGTTACACAGTTTATAAGTAAAACTAAGCTTCC
AATTACAACTTTAAATTTTGGAAAGAGTTCAGTAGATGAGGCACTTCCATCATTCTTAGG
AATTTATAATGGAACATTATCTGAACCTAATCTTAAAGAATTTGTAGAGAGTGCTGATTT
TATATTAATGTTAGGTGTAAAACTTACTGATAGTAGTACTGGTGCATTTACTCATCATCT
TAACGAAAATAAGATGATATCATTAAATATAGACGAAGGTAAAATATTCAATGAAAGAAT
ACAGAACTTTGATTTTGAATCACTTATATCATCATTACTTGATTTATCAGAGATAGAATA
CAAAGGAAAATATATAGATAAAAAGCAAGAAGATTTTGTTCCATCTAATGCTCTTCTTTC
TCAAGATAGACTTTGGCAAGCAGTTGAGAATCTTACACAGTCTAATGAAACTATAGTTGC
TGAGCAAGGAACATCATTTTTCGGTGCATCAAGTATATTTTTAAAATCTAAAAGTCACTT
TATTGGACAACCTCTTTGGGGTTCTATTGGATATACTTTTCCAGCAGCTTTAGGAAGTCA
AATAGCTGATAAAGAAAGTAGACATTTATTATTTATTGGTGACGGTTCACTTCAGCTTAC
AGTACAAGAATTAGGATTAGCTATAAGAGAGAAGATAAATCCTATTTGTTTCATAATAAA
CAATGATGGATATACTGTAGAAAGAGAAATTCACGGACCAAATCAGTCATATAATGATAT
```

FIG 58

```
TCCAATGTGGAATTATTCAAAGTTACCTGAATCTTTCGGTGCTACTGAAGATAGAGTAGT
TTCTAAAATTGTTAGAACAGAGAACGAATTTGTATCTGTTATGAAAGAAGCTCAGGCTGA
CCCTAATAGAATGTATTGGATTGAATTAATTTTAGCAAAAGAAGGTGCTCCTAAAGTACT
TAAGAAAATGGGAAAATTATTTGCAGAACAAAATAAGTCATAAGAATTCCCATAATAAAG
AAAGAATTTTAAATAAAGGAGGAACAAAGATGAGTATACCAGAAACACAAAAAGCAATTA
TATTTTATGAGTCAAATGGAAAATTAGAGCATAAAGATATACCTGTACCAAAACCAAAAC
CAAACGAACTTCTTATAAATGTTAAGTATTCTGGTGTTTGTCATACTGATCTTCATGCAT
GGCATGGTGATTGGCCTCTTCCAACTAAATTACCTCTTGTAGGTGGTCATGAAGGTGCTG
GTGTAGTTGTAGGTATGGGTGAAAATGTTAAAGGTTGGAAAATAGGTGATTATGCTGGAA
TTAAATGGCTTAATGGATCTTGTATGGCATGCGAGTATTGTGAATTAGGAAATGAAAGTA
ATTGTCCACATGCTGACTTAAGTGGTTATACTCATGATGGATCTTTTCAAGAATATGCTA
CTGCAGATGCAGTTCAGGCTGCACACATTCCACAGGGAACTGATCTTGCTGAAGTAGCTC
CTATATTATGCGCTGGAATTACAGTATACAAAGCATTAAAAAGTGCTAATCTTAGAGCAG
GACACTGGGCAGCTATAAGTGGTGCTGCAGGTGGTTAGGATCTTTAGCAGTTCAATATG
CTAAAGCTATGGGATATAGAGTATTAGGAATAGACGGTGGTCCAGGAAAAGAAGAGTTAT
TTACATCATTAGGTGGTGAAGTTTTTATAGATTTCACAAAGGAAAAAGATATTGTTTCAG
CTGTAGTAAAGGCAACTAATGGTGGTGCACACGGAATTATAAATGTTTCAGTATCTGAAG
CAGCAATAGAAGCAAGTACTAGATATTGTAGAGCAAACGGAACAGTAGTTTTAGTTGGAC
TTCCAGCTGGTGCAAAGTGTTCATCTGACGTATTTAACCATGTAGTAAAGAGTATTTCAA
TAGTTGGATCTTACGTAGGTAATAGAGCTGATACAAGAGAAGCTTTAGATTTCTTTGCAA
GAGGTTTAGTTAAGAGTCCTATAAAAGTAGTAGGACTTTCATCACTTCCTGAAATTTATG
AAAAGATGGAAAAGGGACAAATAGCTGGTAGATATGTTGTAGATACAAGTAAATAAGGTA
CCCGGGGATCCTCTAGAGTCGACGTCACGCGTCCATGGAGATCTCGAGGCCTGCAGACAT
GCAAGCTTGGCACTGGCCGTCGTTTTACAACGTCGTGACTGGGAAAACCCTGGCGTTACC
CAACTTAATCGCCTTGCAGCACATCCCCCTTTCGCCAGCTGGCGTAATAGCGAAGAGGCC
CGCACCGATCGCCCTTCCCAACAGTTGCGCAGCCTGAATGGCGAATGGCGCTAGCATAAA
AATAAGAAGCCTGCATTTGCAGGCTTCTTATTTTTATGGCGCGCCGCATTCACTTCTTTT
CTATATAAATATGAGCGAAGCGAATAAGCGTCGGAAAAGCAGCAAAAAGTTTCCTTTTTG
CTGTTGGAGCATGGGGGTTCAGGGGGTGCAGTATCTGACGTCAATGCCGAGCGAAAGCGA
GCCGAAGGGTAGCATTTACGTTAGATAACCCCCTGATATGCTCCGACGCTTTATATAGAA
AAGAAGATTCAACTAGGTAAAATCTTAATATAGGTTGAGATGATAAGGTTTATAAGGAAT
TTGTTTGTTCTAATTTTTCACTCATTTTGTTCTAATTTCTTTTAACAAATGTTCTTTTTT
TTTTAGAACAGTTATGATATAGTTAGAATAGTTTAAAATAAGGAGTGAGAAAAAGATGAA
AGAAAGATATGGAACAGTCTATAAAGGCTCTCAGAGGCTCATAGACGAAGAAAGTGGAGA
AGTCATAGAGGTAGACAAGTTATACCGTAAACAAACGTCTGGTAACTTCGTAAAGGCATA
TATAGTGCAATTAATAAGTATGTTAGATATGATTGGCGGAAAAAAACTTAAAATCGTTAA
CTATATCCTAGATAATGTCCACTTAAGTAACAATACAATGATAGCTACAACAAGAGAAAT
AGCAAAAGCTACAGGAACAAGTCTACAAACAGTAATAACAACACTTAAAATCTTAGAAGA
AGGAAATATTATAAAAGAAAAACTGGAGTATTAATGTTAAACCCTGAACTACTAATGAG
AGGCGACGACCAAAAACAAAATACCTCTTACTCGAATTTGGGAACTTTGAGCAAGAGGC
AAATGAAATAGATTGACCTCCCAATAACACCACGTAGTTATTGGGAGGTCAATCTATGAA
ATGCGATTAAGGGCCGGCCGAAGCAAACTTAAGAGTGTGTTGATAGTGCAGTATCTTAAA
ATTTTGTATAATAGGAATTGAAGTTAAATTAGATGCTAAAAATTTGTAATTAAGAAGGAG
TGATTACATGAACAAAAATATAAAATATTCTCAAAACTTTTTAACGAGTGAAAAAGTACT
CAACCAAATAATAAAACAATTGAATTTAAAAGAAACCGATACCGTTTACGAAATTGGAAC
AGGTAAAGGGCATTTAACGACGAAACTGGCTAAAATAAGTAAACAGGTAACGTCTATTGA
ATTAGACAGTCATCTATTCAACTTATCGTCAGAAAAATTAAAACTGAATACTCGTGTCAC
TTTAATTCACCAAGATATTCTACAGTTTCAATTCCCTAACAAACAGAGGTATAAAATTGT
```

FIG 58 (continued)

TGGGAGTATTCCTTACCATTTAAGCACACAAATTATTAAAAAAGTGGTTTTTGAAAGCCA
TGCGTCTGACATCTATCTGATTGTTGAAGAAGGATTCTACAAGCGTACCTTGGATATTCA
CCGAACACTAGGGTTGCTCTTGCACACTCAAGTCTCGATTCAGCAATTGCTTAAGCTGCC
AGCGGAATGCTTTCATCCTAAACCAAAAGTAAACAGTGTCTTAATAAAACTTACCCGCCA
TACCACAGATGTTCCAGATAAATATTGGAAGCTATATACGTACTTTGTTTCAAAATGGGT
CAATCGAGAATATCGTCAACTGTTTACTAAAAATCAGTTTCATCAAGCAATGAAACACGC
CAAAGTAAACAATTTAAGTACCGTTACTTATGAGCAAGTATTGTCTATTTTTAATAGTTA
TCTATTATTTAACGGGAGGAAATAATTCTATGAGTCGCTTTTGTAAATTTGGAAAGTTAC
ACGTTACTAAAGGGAATGTGTTT

FIG 58 (continued)

SEQ ID NO: 84
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCCTGCAGGATAAAA
AAATTGTAGATAAATTTTATAAAATAGTTTTATCTACAATTTTTTTATCAGGAAACAGCT
ATGACCGCGGCCGCAATATGATATTTATGTCCATTGTGAAAGGGATTATATTCAACTATT
ATTCCAGTTACGTTCATAGAAATTTTCCTTTCTAAAATATTTTATTCCATGTCAAGAACT
CTGTTTATTTCATTAAAGAACTATAAGTACAAAGTATAAGGCATTTGAAAAAATAGGCTA
GTATATTGATTGATTATTTATTTTAAAATGCCTAAGTGAAATATATACATATTATAACAA
TAAAATAAGTATTAGTGTAGGATTTTTAAATAGAGTATCTATTTTCAGATTAAATTTTTG
ATTATTTGATTTACATTATATAATATTGAGTAAAGTATTGACTAGCAAAATTTTTTGATA
CTTTAATTTGTGAAATTTCTTATCAAAAGTTATATTTTGAATAATTTTTATTGAAAAAT
ACAACTAAAAAGGATTATAGTATAAGTGTGTGTAATTTTGTGTTAAATTTAAAGGGAGGA
AATGAACATGAAACATATGTATACAGTTGGTGATTATTTACTTGATAGATTACATGAACT
TGGAATAGAAGAAATTTTTGGTGTACCAGGTGATTACAATCTTCAATTCTTAGATCAAAT
AATATCACATAAGGATATGAAATGGGTTGGTAATGCTAATGAATTAAATGCATCATATAT
GGCAGACGGATATGCAAGAACTAAAAAGGCAGCAGCATTTCTTACTACATTGGTGTTGG
TGAATTAAGTGCAGTAAATGGATTAGCTGGAAGTTACGCAGAAAACTTACCAGTTGTTGA
AATAGTTGGATCTCCTACTAGTAAAGTACAAAATGAAGGTAAATTTGTACATCACACTCT
TGCAGATGGTGATTTTAAGCATTTTATGAAAATGCATGAACCTGTTACAGCTGCAAGAAC
ACTTCTTACAGCTGAAAACGCTACTGTAGAAATTGATAGAGTTTTATCTGCTTTACTTAA
AGAAAGAAAGCCAGTATATATTAACCTTCCAGTAGATGTAGCAGCAGCAAAAGCTGAGAA
ACCTTCATTACCACTTAAAAAGGAAAATTCAACATCAAATACATCTGATCAAGAGATATT
AAATAAAATTCAGGAAAGTCTTAAAAATGCAAAGAAACCTATAGTAATAACTGGACATGA

FIG 59

```
AATAATTAGTTTTGGATTAGAAAAGACAGTTACACAGTTTATAAGTAAAACTAAGCTTCC
AATTACAACTTTAAATTTTGGAAAGAGTTCAGTAGATGAGGCACTTCCATCATTCTTAGG
AATTTATAATGGAACATTATCTGAACCTAATCTTAAAGAATTTGTAGAGAGTGCTGATTT
TATATTAATGTTAGGTGTAAAACTTACTGATAGTAGTACTGGTGCATTTACTCATCATCT
TAACGAAAATAAGATGATATCATTAAATATAGACGAAGGTAAAATATTCAATGAAAGAAT
ACAGAACTTTGATTTTGAATCACTTATATCATCATTACTTGATTTATCAGAGATAGAATA
CAAAGGAAAATATATAGATAAAAAGCAAGAAGATTTTGTTCCATCTAATGCTCTTCTTTC
TCAAGATAGACTTTGGCAAGCAGTTGAGAATCTTACACAGTCTAATGAAACTATAGTTGC
TGAGCAAGGAACATCATTTTTCGGTGCATCAAGTATATTTTTAAAATCTAAAAGTCACTT
TATTGGACAACCTCTTTGGGGTTCTATTGGATATACTTTTCCAGCAGCTTTAGGAAGTCA
AATAGCTGATAAAGAAAGTAGACATTTATTATTTATTGGTGACGGTTCACTTCAGCTTAC
AGTACAAGAATTAGGATTAGCTATAAGAGAGAAGATAAATCCTATTTGTTTCATAATAAA
CAATGATGGATATACTGTAGAAAGAGAAATTCACGGACCAAATCAGTCATATAATGATAT
TCCAATGTGGAATTATTCAAAGTTACCTGAATCTTTCGGTGCTACTGAAGATAGAGTAGT
TTCTAAAATTGTTAGAACAGAGAACGAATTTGTATCTGTTATGAAAGAAGCTCAGGCTGA
CCCTAATAGAATGTATTGGATTGAATTAATTTTAGCAAAAGAAGGTGCTCCTAAAGTACT
TAAGAAAATGGGAAAATTATTTGCAGAACAAAATAAGTCATAAGAATTTGTTTGTTCTAA
TTTTTCACTCATTTTGTTCTAATTTCTTTTAACAAATGTTCTTTTTTTTTTAGAACAGTT
ATGATATAGTTAGAATAGTTTAAAATAAGGAGTGAGAAAAAGATGAAAGAAAGATATGGA
ACAGTCTATAAAGGCTCTCAGAGGCTCATAGACGAAGAAAGTGGAGAAGTCATAGAGGTA
GACAAGTTATACCGTAAACAAACGTCTGGTAACTTCGTAAAGGCATATATAGTGCAATTA
ATAAGTATGTTAGATATGATTGGCGGAAAAAAACTTAAAATCGTTAACTATATCCTAGAT
AATGTCCACTTAAGTAACAATACAATGATAGCTACAACAAGAGAAATAGCAAAAGCTACA
GGAACAAGTCTACAAACAGTAATAACAACACTTAAAATCTTAGAAGAAGGAAATATTATA
AAAAGAAAAACTGGAGTATTAATGTTAAACCCTGAACTACTAATGAGAGGCGACGACCAA
AAACAAAAATACCTCTTACTCGAATTTGGGAACTTTGAGCAAGAGGCAAATGAAATAGAT
TGACCTCCCAATAACACCACGTAGTTATTGGGAGGTCAATCTATGAAATGCGATTAAGGG
CCGGCCGAAGCAAACTTAAGAGTGTGTTGATAGTGCAGTATCTTAAAATTTTGTATAATA
GGAATTGAAGTTAAATTAGATGCTAAAAATTTGTAATTAAGAAGGAGTGATTACATGAAC
AAAAATATAAAATATTCTCAAAACTTTTTAACGAGTGAAAAAGTACTCAACCAAATAATA
AAACAATTGAATTTAAAAGAAACCGATACCGTTTACGAAATTGGAACAGGTAAAGGGCAT
TTAACGACGAAACTGGCTAAAATAAGTAAACAGGTAACGTCTATTGAATTAGACAGTCAT
CTATTCAACTTATCGTCAGAAAAATTAAAACTGAATACTCGTGTCACTTTAATTCACCAA
GATATTCTACAGTTTCAATTCCCTAACAAACAGAGGTATAAAATTGTTGGGAGTATTCCT
TACCATTTAAGCACACAAATTATTAAAAAAGTGGTTTTTGAAAGCCATGCGTCTGACATC
TATCTGATTGTTGAAGAAGGATTCTACAAGCGTACCTTGGATATTCACCGAACACTAGGG
TTGCTCTTGCACACTCAAGTCTCGATTCAGCAATTGCTTAAGCTGCCAGCGGAATGCTTT
CATCCTAAACCAAAAGTAAACAGTGTCTTAATAAAACTTACCCGCCATACCACAGATGTT
CCAGATAAATATTGGAAGCTATATACGTACTTTGTTTCAAAATGGGTCAATCGAGAATAT
CGTCAACTGTTTACTAAAAATCAGTTTCATCAAGCAATGAAACACGCCAAAGTAAACAAT
TTAAGTACCGTTACTTATGAGCAAGTATTGTCTATTTTTAATAGTTATCTATTATTTAAC
GGGAGGAAATAATTCTATGAGTCGCTTTTGTAAATTTGGAAAGTTACACGTTACTAAAGG
GAATGTGTTT
```

FIG 59 (continued)

SEQ ID NO: 95
AAACTCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACT
GTTCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTT
ACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGATAAC
CGTATTACCGCCTTTGAGTGAGCTGATACCGCTCGCCGCAGCCGAACGACCGAGCGCAGC
GAGTCAGTGAGCGAGGAAGCGGAAGAGCGCCCAATACGCAGGGCCCCTGCAGGGCCGCA
GATAGTCATAATAGTTCCAGAATAGTTCAATTTAGAAATTAGACTAAACTTCAAAATGTT
TGTTAAATATATACCAAACTAGTATAGATATTTTTTAAATACTGGACTTAAACAGTAGTA
ATTTGCCTAAAAAATTTTTTCAATTTTTTTTAAAAAATCCTTTTCAAGTTGTACATTGTT
ATGGTAATATGTAATTGAAGAAGTTATGTAGTAATATTGTAAACGTTTCTTGATTTTTTT
ACATCCATGTAGTGCTTAAAAAACCAAAATATGTCACATGCAATTGTATATTTCAAATAA
CAATATTTATTTTCTCGTTAAATTCACAAATAATTTATTAATAATATCAATAACCAAGAT
TATACTTAAATGGATGTTTATTTTTTAACACTTTTATAGTAAATATATTTATTTTATGTA
GTAAAAAGGTTATAATTATAATTGTATTTATTACAATTAATTAAAATAAAAAATAGGGTT
TTAGGTAAAATTAAGTTATTTTAAGAAGTAATTACAATAAAAATTGAAGTTATTTCTTTA
AGGAGGGAATTATTCATATGAAAGAAGTTGTAATAGCTAGTGCAGTAAGAACAGCGATTG
GATCTTATGGAAAGTCTCTTAAGGATGTACCAGCAGTAGATTTAGGAGCTACAGCTATAA
AGGAAGCAGTTAAAAAAGCAGGAATAAAACCAGAGGATGTTAATGAAGTCATTTTAGGAA
ATGTTCTTCAAGCAGGTTTAGGACAGAATCCAGCAAGACAGGCATCTTTTAAAGCAGGAT
TACCAGTTGAAATTCCAGCTATGACTATTAATAAGGTTTGTGGTTCAGGACTTAGAACAG
TTAGCTTAGCAGCACAAATTATAAAAGCAGGAGATGCTGACGTAATAATAGCAGGTGGTA
TGGAAAATATGTCTAGAGCTCCTTACTTAGCGAATAACGCTAGATGGGGATATAGAATGG
GAAACGCTAAATTTGTTGATGAAATGATCACTGACGGATTGTGGGATGCATTTAATGATT
ACCACATGGGAATAACAGCAGAAAACATAGCTGAGAGATGGAACATTTCAAGAGAAGAAC
AAGATGAGTTTGCTCTTGCATCACAAAAAAAAGCTGAAGAAGCTATAAAATCAGGTCAAT
TTAAAGATGAAATAGTTCCTGTAGTAATTAAAGGCAGAAAGGGAGAAACTGTAGTTGATA
CAGATGAGCACCCTAGATTTGGATCAACTATAGAAGGACTTGCAAAATTAAAACCTGCCT
TCAAAAAAGATGGAACAGTTACAGCTGGTAATGCATCAGGATTAAATGACTGTGCAGCAG
TACTTGTAATCATGAGTGCAGAAAAAGCTAAAGAGCTTGGAGTAAAACCACTTGCTAAGA
TAGTTTCTTATGGTTCAGCAGGAGTTGACCCAGCAATAATGGGATATGGACCTTTCTATG
CAACAAAAGCAGCTATTGAAAAGCAGGTTGGACAGTTGATGAATTAGATTTAATAGAAT
CAAATGAAGCTTTTGCAGCTCAAAGTTTAGCAGTAGCAAAAGATTTAAAATTTGATATGA
ATAAAGTAAATGTAAATGGAGGAGCTATTGCCCTTGGTCATCCAATTGGAGCATCAGGTG
CAAGAATACTCGTTACTCTTGTACACGCAATGCAAAAAGAGATGCAAAAAAGGCTTAG
CAACTTTATGTATAGGTGGCGGACAAGGAACAGCAATATTGCTAGAAAGTGCTAGGAAT
TCGAGCTCGGTACCAGGGAGATATTAAAATGAATAAATTAGTAAAATTAACAGATTTAAA
GCGCATTTTCAAAGATGGCATGACAATTATGGTTGGGGGTTTTTTAGATTGTGGAACTCC
TGAAAATATTATAGATATGCTAGTTGATTTAAATATAAAAAATCTGACTATTATAAGCAA
TGATACAGCTTTTCCTAATAAAGGAATAGGAAAACTTATTGTAAATGGTCAAGTTTCTAA

FIG 60

```
AGTAATTGCTTCACATATTGGAACTAATCCTGAAACTGGAAAAAAAATGAGCTCTGGAGA
ACTTAAAGTTGAGCTTTCCCCACAAGGAACACTGATTGAAAGAATTCGTGCAGCTGGATC
TGGACTCGGAGGTGTATTAACTCCAACTGGACTTGGAACTATCGTTGAAGAAGGTAAGAA
AAAAGTTACTATCGATGGCAAAGAATATCTATTAGAACTTCCTTTATCTGCTGATGTTTC
ATTAATAAAAGGTAGCATTGTAGATGAATTTGGAAATACCTTCTATAGGGCTGCTACTAA
AAATTTCAATCCATATATGGCAATGGCTGCAAAAACAGTTATAGTTGAAGCAGAAAATTT
AGTTAAATGTGAAGATTTAAAAAGAGATGCCATAATGACTCCTGGCGTATTAGTAGATTA
TATCGTTAAGGAGGCGGCTTAATTGATTGTAGATAAAGTTTTAGCAAAAGAGATAATTGC
CAAAAGAGTTGCAAAAGAACTAAAAAAAGACCAACTCGTAAACCTTGGAATAGGACTTCC
AACTTTAGTAGCAAATTATGTACCAAAAGAAATGAACATTACTTTTGAATCAGAAAATGG
CATGGTTGGTATGGCACAAATGGCATCATCAGGTGAAAATGACCCAGATATAATAAATGC
TGGCGGGGAATATGTAACATTATTACCTCAAGGTTCATTTTTTGATAGTTCAATGTCTTT
CGCACTAATACGAGGAGGACATGTTGATGTTGCTGTTCTTGGTGCTCTAGAAGTTGATGA
AAAAGGTAATTTAGCTAACTGGATTGTTCCAAATAAAATTGTCCCAGGTATGGGTGGCGC
TATGGATTTAGCAATAGGCGCAAAAAAAATAATAGTGGCAATGCAACATACAGGAAAAAG
TAAACCTAAAATCGTTAAAAAATGTACTCTCCCACTTACTGCTAAGGCTCAAGTGGATTT
AATTGTCACAGAACTTTGTGTAATTGATGTAACAAATGACGGCTTACTTTTAAAAGAAAT
TCATAAAGATACAACTATTGATGAAATTAAATTTTTAACAGATGCAGATTTAATTATTCC
AGATAACTTAAAGATTATGGATATATGAATCGCGGCCGCAATATGATATTTATGTCCATT
GTGAAAGGGATTATATTCAACTATTATTCCAGTTACGTTCATAGAAATTTTCCTTTCTAA
AATATTTTATTCCATGTCAAGAACTCTGTTTATTTCATTAAAGAACTATAAGTACAAAGT
ATAAGGCATTTGAAAAAATAGGCTAGTATATTGATTGATTATTTATTTTAAAATGCCTAA
GTGAAATATACATATTATAACAATAAAATAAGTATTAGTGTAGGATTTTTAAATAGAG
TATCTATTTTCAGATTAAATTTTTGATTATTTGATTTACATTATATAATATTGAGTAAAG
TATTGACTAGCAAAATTTTTTGATACTTTAATTTGTGAAATTTCTTATCAAAGTTATAT
TTTTGAATAATTTTTATTGAAAAATACAACTAAAAAGGATTATAGTATAAGTGTGTGTAA
TTTTGTGTTAAATTTAAAGGGAGGAAATGAACATGAAACATATGTATACAGTTGGTGATT
ATTTACTTGATAGATTACATGAACTTGGAATAGAAGAAATTTTTGGTGTACCAGGTGATT
ACAATCTTCAATTCTTAGATCAAATAATATCACATAAGGATATGAAATGGGTTGGTAATG
CTAATGAATTAAATGCATCATATATGGCAGACGGATATGCAAGAACTAAAAAGGCAGCAG
CATTTCTTACTACATTTGGTGTTGGTGAATTAAGTGCAGTAAATGGATTAGCTGGAAGTT
ACGCAGAAAAACTTACCAGTTGTTGAAATAGTTGGATCTCCTACTAGTAAAGTACAAAATG
AAGGTAAATTTGTACATCACACTCTTGCAGATGGTGATTTTAAGCATTTTATGAAAATGC
ATGAACCTGTTACAGCTGCAAGAACACTTCTTACAGCTGAAAACGCTACTGTAGAAATTG
ATAGAGTTTTATCTGCTTTACTTAAAGAAAGAAAGCCAGTATATATTAACCTTCCAGTAG
ATGTAGCAGCAGCAAAAGCTGAGAAACCTTCATTACCACTTAAAAAGGAAAATTCAACAT
CAAATACATCTGATCAAGAGATATTAAATAAAATTCAGGAAAGTCTTAAAAATGCAAAGA
AACCTATAGTAATAACTGGACATGAAATAATTAGTTTTGGATTAGAAAAGACAGTTACAC
AGTTTATAAGTAAAACTAAGCTTCCAATTACAACTTTAAATTTTGGAAAGAGTTCAGTAG
ATGAGGCACTTCCATCATTCTTAGGAATTTATAATGGAACATTATCTGAACCTAATCTTA
AAGAATTTGTAGAGAGTGCTGATTTTATATTAATGTTAGGTGTAAAACTTACTGATAGTA
GTACTGGTGCATTTACTCATCATCTTAACGAAAATAAGATGATATCATTAAATATAGACG
AAGGTAAAATATTCAATGAAAGAATACAGAACTTTGATTTTGAATCACTTATATCATCAT
TACTTGATTTATCAGAGATAGAATACAAAGGAAAATATATAGATAAAAAGCAAGAAGATT
TTGTTCCATCTAATGCTCTTCTTTCTCAAGATAGACTTTGGCAAGCAGTTGAGAATCTTA
CACAGTCTAATGAAACTATAGTTGCTGAGCAAGGAACATCATTTTTCGGTGCATCAAGTA
TATTTTTAAAATCTAAAAGTCACTTTATTGGACAACCTCTTTGGGGTTCTATTGGATATA
CTTTTCCAGCAGCTTTAGGAAGTCAAATAGCTGATAAAGAAAGTAGACATTTATTATTTA
```

FIG 60 (continued)

```
TTGGTGACGGTTCACTTCAGCTTACAGTACAAGAATTAGGATTAGCTATAAGAGAGAAGA
TAAATCCTATTTGTTTCATAATAAACAATGATGGATATACTGTAGAAAGAGAAATTCACG
GACCAAATCAGTCATATAATGATATTCCAATGTGGAATTATTCAAAGTTACCTGAATCTT
TCGGTGCTACTGAAGATAGAGTAGTTTCTAAAATTGTTAGAACAGAGAACGAATTTGTAT
CTGTTATGAAAGAAGCTCAGGCTGACCCTAATAGAATGTATTGGATTGAATTAATTTTAG
CAAAAGAAGGTGCTCCTAAAGTACTTAAGAAAATGGGAAAATTATTTGCAGAACAAAATA
AGTCATAAGAATTTGTTTGTTCTAATTTTTCACTCATTTTGTTCTAATTTCTTTTAACAA
ATGTTCTTTTTTTTTAGAACAGTTATGATATAGTTAGAATAGTTTAAAATAAGGAGTGA
GAAAAAGATGAAAGAAAGATATGGAACAGTCTATAAAGGCTCTCAGAGGCTCATAGACGA
AGAAAGTGGAGAAGTCATAGAGGTAGACAAGTTATACCGTAAACAAACGTCTGGTAACTT
CGTAAAGGCATATATAGTGCAATTAATAAGTATGTTAGATATGATTGGCGGAAAAAAACT
TAAAATCGTTAACTATATCCTAGATAATGTCCACTTAAGTAACAATACAATGATAGCTAC
AACAAGAGAAATAGCAAAAGCTACAGGAACAAGTCTACAAACAGTAATAACAACACTTAA
AATCTTAGAAGAAGGAAATATTATAAAAAGAAAACTGGAGTATTAATGTTAAACCCTGA
ACTACTAATGAGAGGCGACGACCAAAAACAAAAATACCTCTTACTCGAATTTGGGAACTT
TGAGCAAGAGGCAAATGAAATAGATTGACCTCCCAATAACACCACGTAGTTATTGGGAGG
TCAATCTATGAAATGCGATTAAGGGCCGGCCGAAGCAAACTTAAGAGTGTGTTGATAGTG
CAGTATCTTAAAATTTTGTATAATAGGAATTGAAGTTAAATTAGATGCTAAAAATTTGTA
ATTAAGAAGGAGTGATTACATGAACAAAAATATAAAATATTCTCAAAACTTTTTAACGAG
TGAAAAAGTACTCAACCAAATAATAAAACAATTGAATTTAAAAGAAACCGATACCGTTTA
CGAAATTGGAACAGGTAAAGGGCATTTAACGACGAAACTGGCTAAAATAAGTAAACAGGT
AACGTCTATTGAATTAGACAGTCATCTATTCAACTTATCGTCAGAAAAATTAAAACTGAA
TACTCGTGTCACTTTAATTCACCAAGATATTCTACAGTTTCAATTCCCTAACAAACAGAG
GTATAAAATTGTTGGGAGTATTCCTTACCATTTAAGCACACAAATTATTAAAAAAGTGGT
TTTTGAAAGCCATGCGTCTGACATCTATCTGATTGTTGAAGAAGGATTCTACAAGCGTAC
CTTGGATATTCACCGAACACTAGGGTTGCTCTTGCACACTCAAGTCTCGATTCAGCAATT
GCTTAAGCTGCCAGCGGAATGCTTTCATCCTAAACCAAAAGTAAACAGTGTCTTAATAAA
ACTTACCCGCCATACCACAGATGTTCCAGATAAATATTGGAAGCTATATACGTACTTTGT
TTCAAAATGGGTCAATCGAGAATATCGTCAACTGTTTACTAAAAATCAGTTTCATCAAGC
AATGAAACACGCCAAAGTAAACAATTTAAGTACCGTTACTTATGAGCAAGTATTGTCTAT
TTTTAATAGTTATCTATTATTTAACGGGAGGAAATAATTCTATGAGTCGCTTTTGTAAAT
TTGGAAAGTTACACGTTACTAAAGGGAATGTGTTT
```

FIG 60 (continued)

SEQ ID NO: 98
CCAGTGGGCAAGTTGAAAAATTCACAAAAATGTGGTATAATATCTTTGTTCATTAGAGCG
ATAAACTTGAATTTGAGAGGGAACTTAGATGGTATTTGAAAAAATTGATAAAAATAGTTG
GAACAGAAAAGAGTATTTTGACCACTACTTTGCAAGTGTACCTTGTACCTACAGCATGAC
CGTTAAAGTGGATATCACACAAATAAAGGAAAAGGGAATGAAACTATATCCTGCAATGCT
TTATTATATTGCAATGATTGTAAACCGCCATTCAGAGTTTAGGACGGCAATCAATCAAGA
TGGTGAATTGGGGATATATGATGAGATGATACCAAGCTATACAATATTTCACAATGATAC
TGAAACATTTTCCAGCCTTTGGACTGAGTGTAAGTCTGACTTTAAATCATTTTTAGCAGA
TTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCT
GAATTTGCAGAAAGGATATGATTATTTGATTCCTATTTTTACTATGGGGAAATATTATAA
AGAAGATAACAAAATTATACTTCCTTTGGCAATTCAAGTTCATCACGCAGTATGTGACGG
ATTTCACATTTGCCGTTTTGTAAACGAATTGCAGGAATTGATAAATAGTTAACTTCAGGT
TTGTCTGTAACTAAAAACAAGTATTTAAGCAAAAACATCGTAGAAATACGGTGTTTTTTG
TTACCCTAAGTTTAAACTCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGTTTG
TTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTTT
ACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCCAATACGCAGGGCCCC
CTGCAGGATAAAAAAATTGTAGATAAATTTTATAAAATAGTTTTATCTACAATTTTTTTA
TCAGGAAACAGCTATGACCGCGGCCGCAGATAGTCATAATAGTTCCAGAATAGTTCAATT
TAGAAATTAGACTAAACTTCAAAATGTTTGTTAAATATATACCAAACTAGTATAGATATT
TTTTAAATACTGGACTTAAACAGTAGTAATTTGCCTAAAAAATTTTTTCAATTTTTTTTA
AAAAATCCTTTTCAAGTTGTACATTGTTATGGTAATATGTAATTGAAGAAGTTATGTAGT
AATATTGTAAACGTTTCTTGATTTTTTTACATCCATGTAGTGCTTAAAAAACCAAAATAT
GTCACATGCAATTGTATATTTCAAATAACAATATTTATTTTCTCGTTAAATTCACAAATA
ATTTATTAATAATATCAATAACCAAGATTATACTTAAATGGATGTTTATTTTTTAACACT
TTTATAGTAAATATATTTATTTTATGTAGTAAAAAGGTTATAATTATAATTGTATTTATT
ACAATTAATTAAAATAAAAAATAGGGTTTTAGGTAAAATTAAGTTATTTTAAGAAGTAAT
TACAATAAAAATTGAAGTTATTTCTTTAAGGAGGGAATTATTCATATGAAAGAAGTTGTA
ATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCA
GAGGATGTTAATGAAGTCATTTTAGGAAATGTTCTTCAAGCAGGTTTAGGACAGAATCCA
GCAAGACAGGCATCTTTTAAAGCAGGATTACCAGTTGAAATTCCAGCTATGACTATTAAT
AAGGTTTGTGGTTCAGGACTTAGAACAGTTAGCTTAGCAGCACAAATTATAAAAGCAGGA
GATGCTGACGTAATAATAGCAGGTGGTATGGAAAATATGTCTAGAGCTCCTTACTTAGCG
AATAACGCTAGATGGGGATATAGAATGGGAAACGCTAAATTTGTTGATGAAATGATCACT
GACGGATTGTGGGATGCATTTAATGATTACCACATGGGAATAACAGCAGAAAACATAGCT
GAGAGATGGAACATTTCAAGAGAAGAACAAGATGAGTTTGCTCTTGCATCACAAAAAAAA
GCTGAAGAAGCTATAAAATCAGGTCAATTTAAAGATGAAATAGTTCCTGTAGTAATTAAA
GGCAGAAAGGGAGAAACTGTAGTTGATACAGATGAGCACCCTAGATTTGGATCAACTATA
GAAGGACTTGCAAAATTAAAACCTGCCTTCAAAAAAGATGGAACAGTTACAGCTGGTAAT

FIG 61

```
GCATCAGGATTAAATGACTGTGCAGCAGTACTTGTAATCATGAGTGCAGAAAAAGCTAAA
GAGCTTGGAGTAAAACCACTTGCTAAGATAGTTTCTTATGGTTCAGCAGGAGTTGACCCA
GCAATAATGGGATATGGACCTTTCTATGCAACAAAAGCAGCTATTGAAAAGCAGGTTGG
ACAGTTGATGAATTAGATTTAATAGAATCAAATGAAGCTTTTGCAGCTCAAAGTTTAGCA
GTAGCAAAAGATTTAAAATTTGATATGAATAAAGTAAATGTAAATGGAGGAGCTATTGCC
CTTGGTCATCCAATTGGAGCATCAGGTGCAAGAATACTCGTTACTCTTGTACACGCAATG
CAAAAAAGAGATGCAAAAAAAGGCTTAGCAACTTTATGTATAGGTGGCGGACAAGGAACA
GCAATATTGCTAGAAAAGTGCTAGGAATTCGAGCTCGGTACCAGGGAGATATTAAAATGA
ATAAATTAGTAAAATTAACAGATTTAAAGCGCATTTTCAAAGATGGCATGACAATTATGG
TTGGGGGTTTTTTAGATTGTGGAACTCCTGAAAATATTATAGATATGCTAGTTGATTTAA
ATATAAAAAATCTGACTATTATAAGCAATGATACAGCTTTTCCTAATAAAGGAATAGGAA
AACTTATTGTAAATGGTCAAGTTTCTAAAGTAATTGCTTCACATATTGGAACTAATCCTG
AAACTGGAAAAAAAATGAGCTCTGGAGAACTTAAAGTTGAGCTTTCCCCACAAGGAACAC
TGATTGAAAGAATTCGTGCAGCTGGATCTGGACTCGGAGGTGTATTAACTCCAACTGGAC
TTGGAACTATCGTTGAAGAAGGTAAGAAAAAGTTACTATCGATGGCAAGAATATCTAT
TAGAACTTCCTTTATCTGCTGATGTTTCATTAATAAAAGGTAGCATTGTAGATGAATTTG
GAAATACCTTCTATAGGGCTGCTACTAAAAATTTCAATCCATATATGGCAATGGCTGCAA
AAACAGTTATAGTTGAAGCAGAAAATTTAGTTAAATGTGAAGATTTAAAAAGAGATGCCA
TAATGACTCCTGGCGTATTAGTAGATTATATCGTTAAGGAGGCGGCTTAATTGATTGTAG
ATAAAGTTTTAGCAAAAGAGATAATTGCCAAAAGAGTTGCAAAAGAACTAAAAAAAGACC
AACTCGTAAACCTTGGAATAGGACTTCCAACTTTAGTAGCAAATTATGTACCAAAAGAAA
TGAACATTACTTTTGAATCAGAAAATGGCATGGTTGGTATGGCACAAATGGCATCATCAG
GTGAAAATGACCCAGATATAATAAATGCTGGCGGGGAATATGTAACATTATTACCTCAAG
GTTCATTTTTTGATAGTTCAATGTCTTTCGCACTAATACGAGGAGGACATGTTGATGTTG
CTGTTCTTGGTGCTCTAGAAGTTGATGAAAAAGGTAATTTAGCTAACTGGATTGTTCCAA
ATAAAATTGTCCCAGGTATGGGTGGCGCTATGGATTTAGCAATAGGCGCAAAAAAAATAA
TAGTGGCAATGCAACATACAGGAAAAAGTAAACCTAAAATCGTTAAAAAATGTACTCTCC
CACTTACTGCTAAGGCTCAAGTGGATTTAATTGTCACAGAACTTTGTGTAATTGATGTAA
CAAATGACGGCTTACTTTTAAAAGAAATTCATAAAGATACAACTATTGATGAAATTAAAT
TTTTAACAGATGCAGATTTAATTATTCCAGATAACTTAAAGATTATGGATATATGAATCA
TTCTATTTTAAATATATAACTTTAAAAATCTTATGTATTAAAAACTAAGAAAAGAGGTTG
ATTGTTTTATGTTAGAAAGTGAAGTATCTAAACAAATTACAACTCCACTTGCTGCTCCAG
CGTTTCCTAGAGGACCATATAGGTTTCACAATAGAGAATATCTAAACATTATTTATCGAA
CTGATTTAGATGCTCTTCGAAAAATAGTACCAGAGCCACTTGAATTAGATAGAGCATATG
TTAGATTTGAAATGATGGCTATGCCTGATACAACCGGACTAGGCTCATATACAGAATGTG
GTCAAGCTATTCCAGTAAAATATAATGGTGTTAAGGGTGACTACTTGCATATGATGTATC
TAGATAATGAACCTGCTATTGCTGTTGGAAGAGAAAGTAGCGCTTATCCAAAAAAGCTTG
GCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCT
ATGCTCAAATTGCAAGACCCAATTTTATGCTAAAAATCATTCAAGGTTACGATGGTAAGC
CAAGAATTTGTGAACTAATATGTGCAGAAAATACTGATATAACTATTCACGGTGCTTGGA
CTGGAAGTGCACGTCTACAATTATTTAGCCATGCACTAGCTCCTCTTGCTGATTTACCTG
TATTAGAGATTGTATCAGCATCTCATATCCTCACAGATTTAACTCTTGGAACACCTAAGG
TTGTACATGATTATCTTTCAGTAAAATAAAAGCAATATAGAGGATCCAGGAGGAACAAAG
ATGAGTATACCAGAAACACAAAAAGCAATTATATTTTATGAGTCAAATGGAAAATTAGAG
CATAAAGATATACCTGTACCAAAACCAAAACCAAACGAACTTCTTATAAATGTTAAGTAT
TCTGGTGTTTGTCATACTGATCTTCATGCATGGCATGGTGATTGGCCTCTTCCAACTAAA
```

FIG 61 (continued)

```
TTACCTCTTGTAGGTGGTCATGAAGGTGCTGGTGTAGTTGTAGGTATGGGTGAAAATGTT
AAAGGTTGGAAAATAGGTGATTATGCTGGAATTAAATGGCTTAATGGATCTTGTATGGCA
TGCGAGTATTGTGAATTAGGAAATGAAAGTAATTGTCCACATGCTGACTTAAGTGGTTAT
ACTCATGATGGATCTTTTCAAGAATATGCTACTGCAGATGCAGTTCAGGCTGCACACATT
CCACAGGGAACTGATCTTGCTGAAGTAGCTCCTATATTATGCGCTGGAATTACAGTATAC
AAAGCATTAAAAAGTGCTAATCTTAGAGCAGGACACTGGGCAGCTATAAGTGGTGCTGCA
GGTGGTTTAGGATCTTTAGCAGTTCAATATGCTAAAGCTATGGGATATAGAGTATTAGGA
ATAGACGGTGGTCCAGGAAAAGAAGAGTTATTTACATCATTAGGTGGTGAAGTTTTTATA
GATTTCACAAAGGAAAAAGATATTGTTTCAGCTGTAGTAAAGGCAACTAATGGTGGTGCA
CACGGAATTATAAATGTTTCAGTATCTGAAGCAGCAATAGAAGCAAGTACTAGATATTGT
AGAGCAAACGGAACAGTAGTTTTAGTTGGACTTCCAGCTGGTGCAAAGTGTTCATCTGAC
GTATTTAACCATGTAGTAAAGAGTATTTCAATAGTTGGATCTTACGTAGGTAATAGAGCT
GATACAAGAGAAGCTTTAGATTTCTTTGCAAGAGGTTTAGTTAAGAGTCCTATAAAAGTA
GTAGGACTTTCATCACTTCCTGAAATTTATGAAAAGATGGAAAAGGGACAAATAGCTGGT
AGATATGTTGTAGATACAAGTAAATAAGGCCATGGAGATCTCGAGGCCTGCAGACATGCA
AGCTTGGCACTGGCCGTCGTTTTACAACGTCGTGACTGGGAAAACCCTGGCGTTACCCAA
CTTAATCGCCTTGCAGCACATCCCCCTTTCGCCAGCTGGCGTAATAGCGAAGAGGCCCGC
ACCGATCGCCCTTCCCAACAGTTGCGCAGCCTGAATGGCGAATGGCGCTAGCATAAAAAT
AAGAAGCCTGCATTTGCAGGCTTCTTATTTTTATGGCGCGCCGCCATTATTTTTTTGAAC
AATTGACAATTCATTTCTTATTTTTTATTAAGTGATAGTCAAAAGGCATAACAGTGCTGA
ATAGAAAGAAATTTACAGAAAAGAAAATTATAGAATTTAGTATGATTAATTATACTCATT
TATGAATGTTTAATTGAATACAAAAAAAAATACTTGTTATGTATTCAATTACGGGTTAAA
ATATAGACAAGTTGAAAAATTTAATAAAAAAATAAGTCCTCAGCTCTTATATATTAAGCT
ACCAACTTAGTATATAAGCCAAAACTTAAATGTGCTACCAACACATCAAGCCGTTAGAGA
ACTCTATCTATAGCAATATTTCAAATGTACCGACATACAAGAGAAACATTAACTATATAT
ATTCAATTTATGAGATTATCTTAACAGATATAAATGTAAATTGCAATAAGTAAGATTTAG
AAGTTTATAGCCTTTGTGTATTGGAAGCAGTACGCAAAGGCTTTTTTATTTGATAAAAAT
TAGAAGTATATTTATTTTTTCATAATTAATTTATGAAAATGAAAGGGGGTGAGCAAAGTG
ACAGAGGAAAGCAGTATCTTATCAAATAACAAGGTATTAGCAATATCATTATTGACTTTA
GCAGTAAACATTATGACTTTTATAGTGCTTGTAGCTAAGTAGTACGAAAGGGGGAGCTTT
AAAAAGCTCCTTGGAATACATAGAATTCATAAATTAATTTATGAAAAGAAGGGCGTATAT
GAAAACTTGTAAAAATTGCAAAGAGTTTATTAAAGATACTGAAATATGCAAAATACATTC
GTTGATGATTCATGATAAAACAGTAGCAACCTATTGCAGTAAATACAATGAGTCAAGATG
TTTACATAAAGGGAAAGTCCAATGTATTAATTGTTCAAAGATGAACCGATATGGATGGTG
TGCCATAAAAATGAGATGTTTTACAGAGGAAGAACAGAAAAAAGAACGTACATGCATTAA
ATATTATGCAAGGAGCTTTAAAAAAGCTCATGTAAAGAAGAGTAAAAAGAAAAAATAATT
TATTTATTAATTTAATATTGAGAGTGCCGACACAGTATGCACTAAAAAATATATCTGTGG
TGTAGTGAGCCGATACAAAAGGATAGTCACTCGCATTTTCATAATACATCTTATGTTATG
ATTATGTGTCGGTGGGACTTCACGACGAAAACCCACAATAAAAAAAGAGTTCGGGGTAGG
GTTAAGCATAGTTGAGGCAACTAAACAATCAAGCTAGGATATGCAGTAGCAGACCGTAAG
GTCGTTGTTTAGGTGTGTTGTAATACATACGCTATTAAGATGTAAAAATACGGATACCAA
TGAAGGGAAAGTATAATTTTTGGATGTAGTTTGTTTGTTCATCTATGGGCAAACTACGT
CCAAAGCCGTTTCCAAATCTGCTAAAAGTATATCCTTTCTAAAATCAAAGTCAAGTATG
AAATCATAAATAAAGTTTAATTTTGAAGTTATTATGATATTATGTTTTTCTATTAAAATA
AATTAAGTATATAGAATAGTTTAATAATAGTATATACTTAATGTGATAAGTGTCTGACAG
TGTCACAGAAAGGATGATTGTTATGGATTATAAGCGGCCGG
```

FIG 61 (continued)

SEQ ID NO: 101
CCAGTGGGCAAGTTGAAAAATTCACAAAAATGTGGTATAATATCTTTGTTCATTAGAGCG
ATAAACTTGAATTTGAGAGGGAACTTAGATGGTATTTGAAAAAATTGATAAAAATAGTTG
GAACAGAAAAGAGTATTTTGACCACTACTTTGCAAGTGTACCTTGTACCTACAGCATGAC
CGTTAAAGTGGATATCACACAAATAAAGGAAAAGGGAATGAAACTATATCCTGCAATGCT
TTATTATATTGCAATGATTGTAAACCGCCATTCAGAGTTTAGGACGGCAATCAATCAAGA
TGGTGAATTGGGGATATATGATGAGATGATACCAAGCTATACAATATTTCACAATGATAC
TGAAACATTTTCCAGCCTTTGGACTGAGTGTAAGTCTGACTTTAAATCATTTTTAGCAGA
TTATGAAAGTGATACGCAACGGTATGGAAACAATCATAGAATGGAAGGAAAGCCAAATGC
TCCGGAAAACATTTTTAATGTATCTATGATACCGTGGTCAACCTTCGATGGCTTTAATCT
GAATTTGCAGAAAGGATATGATTATTTGATTCCTATTTTTACTATGGGGAAATATTATAA
AGAAGATAACAAAATTATACTTCCTTTGGCAATTCAAGTTCATCACGCAGTATGTGACGG
ATTTCACATTTGCCGTTTTGTAAACGAATTGCAGGAATTGATAAATAGTTAACTTCAGGT
TTGTCTGTAACTAAAAACAAGTATTTAAGCAAAAACATCGTAGAAATACGGTGTTTTTTG
TTACCCTAAGTTTAAACTCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGTTTG
TTTGCCGGATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGA
CAGGTATCCGGTAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTTT
ACGGTTCCTGGCCTTTTGCTGGCCTTTTGCTCACATGTTCTTTCCTGCGTTATCCCCTGA
TTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCCAATACGCAGGGCCCC
CTGCAGGATAAAAAAATTGTAGATAAATTTTATAAAATAGTTTTATCTACAATTTTTTTA
TCAGGAAACAGCTATGACCGCGGCCGCAGATAGTCATAATAGTTCCAGAATAGTTCAATT
TAGAAATTAGACTAAACTTCAAAATGTTTGTTAAATATATACCAAACTAGTATAGATATT
TTTTAAATACTGGACTTAAACAGTAGTAATTTGCCTAAAAAATTTTTTCAATTTTTTTTA
AAAAATCCTTTTCAAGTTGTACATTGTTATGGTAATATGTAATTGAAGAAGTTATGTAGT
AATATTGTAAACGTTTCTTGATTTTTTTACATCCATGTAGTGCTTAAAAAACCAAAATAT
GTCACATGCAATTGTATATTTCAAATAACAATATTTATTTTCTCGTTAAATTCACAAATA
ATTTATTAATAATATCAATAACCAAGATTATACTTAAATGGATGTTTATTTTTTAACACT
TTTATAGTAAATATATTTATTTTATGTAGTAAAAAGGTTATAATTATAATTGTATTTATT
ACAATTAATTAAAATAAAAAATAGGGTTTTAGGTAAAATTAAGTTATTTTAAGAAGTAAT
TACAATAAAAATTGAAGTTATTTCTTTAAGGAGGGAATTATTCATATGAAAGAAGTTGTA
ATAGCTAGTGCAGTAAGAACAGCGATTGGATCTTATGGAAAGTCTCTTAAGGATGTACCA
GCAGTAGATTTAGGAGCTACAGCTATAAAGGAAGCAGTTAAAAAAGCAGGAATAAAACCA
GAGGATGTTAATGAAGTCATTTTAGGAAATGTTCTTCAAGCAGGTTTAGGACAGAATCCA
GCAAGACAGGCATCTTTTAAAGCAGGATTACCAGTTGAAATTCCAGCTATGACTATTAAT
AAGGTTTGTGGTTCAGGACTTAGAACAGTTAGCTTAGCAGCACAAATTATAAAAGCAGGA
GATGCTGACGTAATAATAGCAGGTGGTATGGAAAATATGTCTAGAGCTCCTTACTTAGCG

FIG 62

```
AATAACGCTAGATGGGGATATAGAATGGGAAACGCTAAATTTGTTGATGAAATGATCACT
GACGGATTGTGGGATGCATTTAATGATTACCACATGGGAATAACAGCAGAAAACATAGCT
GAGAGATGGAACATTTCAAGAGAAGAACAAGATGAGTTTGCTCTTGCATCACAAAAAAAA
GCTGAAGAAGCTATAAAATCAGGTCAATTTAAAGATGAAATAGTTCCTGTAGTAATTAAA
GGCAGAAAGGGAGAAACTGTAGTTGATACAGATGAGCACCCTAGATTTGGATCAACTATA
GAAGGACTTGCAAAATTAAAACCTGCCTTCAAAAAAGATGGAACAGTTACAGCTGGTAAT
GCATCAGGATTAAATGACTGTGCAGCAGTACTTGTAATCATGAGTGCAGAAAAAGCTAAA
GAGCTTGGAGTAAAACCACTTGCTAAGATAGTTTCTTATGGTTCAGCAGGAGTTGACCCA
GCAATAATGGGATATGGACCTTTCTATGCAACAAAAGCAGCTATTGAAAAGCAGGTTGG
ACAGTTGATGAATTAGATTTAATAGAATCAAATGAAGCTTTTGCAGCTCAAAGTTTAGCA
GTAGCAAAAGATTTAAAATTTGATATGAATAAAGTAAATGTAAATGGAGGAGCTATTGCC
CTTGGTCATCCAATTGGAGCATCAGGTGCAAGAATACTCGTTACTCTTGTACACGCAATG
CAAAAAAGAGATGCAAAAAAAGGCTTAGCAACTTTATGTATAGGTGGCGGACAAGGAACA
GCAATATTGCTAGAAAAGTGCTAGGAATTCGAGCTCGGTACCAGGGAGATATTAAAATGA
ATAAATTAGTAAAATTAACAGATTTAAAGCGCATTTTCAAAGATGGCATGACAATTATGG
TTGGGGGTTTTTTAGATTGTGGAACTCCTGAAAATATTATAGATATGCTAGTTGATTTAA
ATATAAAAAATCTGACTATTATAAGCAATGATACAGCTTTTCCTAATAAAGGAATAGGAA
AACTTATTGTAAATGGTCAAGTTTCTAAAGTAATTGCTTCACATATTGGAACTAATCCTG
AAACTGGAAAAAAAATGAGCTCTGGAGAACTTAAAGTTGAGCTTTCCCCACAAGGAACAC
TGATTGAAAGAATTCGTGCAGCTGGATCTGGACTCGGAGGTGTATTAACTCCAACTGGAC
TTGGAACTATCGTTGAAGAAGGTAAGAAAAAAGTTACTATCGATGGCAAAGAATATCTAT
TAGAACTTCCTTTATCTGCTGATGTTTCATTAATAAAAGGTAGCATTGTAGATGAATTTG
GAAATACCTTCTATAGGGCTGCTACTAAAAATTTCAATCCATATATGGCAATGGCTGCAA
AAACAGTTATAGTTGAAGCAGAAAATTTAGTTAAATGTGAAGATTTAAAAAGAGATGCCA
TAATGACTCCTGGCGTATTAGTAGATTATATCGTTAAGGAGGCGGCTTAATTGATTGTAG
ATAAAGTTTTAGCAAAAGAGATAATTGCCAAAAGAGTTGCAAAAGAACTAAAAAAAGACC
AACTCGTAAACCTTGGAATAGGACTTCCAACTTTAGTAGCAAATTATGTACCAAAAGAAA
TGAACATTACTTTTGAATCAGAAAATGGCATGGTTGGTATGGCACAAATGGCATCATCAG
GTGAAAATGACCCAGATATAATAAATGCTGGCGGGGAATATGTAACATTATTACCTCAAG
GTTCATTTTTTGATAGTTCAATGTCTTTCGCACTAATACGAGGAGGACATGTTGATGTTG
CTGTTCTTGGTGCTCTAGAAGTTGATGAAAAAGGTAATTTAGCTAACTGGATTGTTCCAA
ATAAAATTGTCCCAGGTATGGGTGGCGCTATGGATTTAGCAATAGGCGCAAAAAAAATAA
TAGTGGCAATGCAACATACAGGAAAAAGTAAACCTAAAATCGTTAAAAAATGTACTCTCC
CACTTACTGCTAAGGCTCAAGTGGATTTAATTGTCACAGAACTTTGTGTAATTGATGTAA
CAAATGACGGCTTACTTTTAAAAGAAATTCATAAAGATACAACTATTGATGAAATTAAAT
TTTTAACAGATGCAGATTTAATTATTCCAGATAACTTAAAGATTATGGATATATGAATCA
TTCTATTTTAAATATATAACTTTAAAAATCTTATGTATTAAAAACTAAGAAAAGAGGTTG
ATTGTTTTATGTTAGAAAGTGAAGTATCTAAACAAATTACAACTCCACTTGCTGCTCCAG
CGTTTCCTAGAGGACCATATAGGTTTCACAATAGAGAATATCTAAACATTATTTATCGAA
CTGATTTAGATGCTCTTCGAAAAATAGTACCAGAGCCACTTGAATTAGATAGAGCATATG
TTAGATTTGAAATGATGGCTATGCCTGATACAACCGGACTAGGCTCATATACAGAATGTG
GTCAAGCTATTCCAGTAAAATATAATGGTGTTAAGGGTGACTACTTGCATATGATGTATC
TAGATAATGAACCTGCTATTGCTGTTGGAAGAGAAAGTAGCGCTTATCCAAAAAAGCTTG
GCTATCCAAAGCTATTTGTTGATTCAGATACTTTAGTTGGGACACTTAAATATGGTACAT
TACCAGTAGCTACTGCAACAATGGGATATAAGCACGAGCCTCTAGATCTTAAAGAAGCCT
ATGCTCAAATTGCAAGACCCAATTTTATGCTAAAAATCATTCAAGGTTACGATGGTAAGC
CAAGAATTTGTGAACTAATATGTGCAGAAAATACTGATATAACTATTCACGGTGCTTGGA
```

FIG 62 (continued)

```
CTGGAAGTGCACGTCTACAATTATTTAGCCATGCACTAGCTCCTCTTGCTGATTTACCTG
TATTAGAGATTGTATCAGCATCTCATATCCTCACAGATTTAACTCTTGGAACACCTAAGG
TTGTACATGATTATCTTTCAGTAAAATAAAAGCAATATAGAGGATCCACAGCTATGACCG
CGGCCGCAATATGATATTTATGTCCATTGTGAAAGGGATTATATTCAACTATTATTCCAG
TTACGTTCATAGAAATTTTCCTTTCTAAAATATTTTATTCCATGTCAAGAACTCTGTTTA
TTTCATTAAAGAACTATAAGTACAAAGTATAAGGCATTTGAAAAAATAGGCTAGTATATT
GATTGATTATTTATTTTAAAATGCCTAAGTGAAATATATACATATTATAACAATAAAATA
AGTATTAGTGTAGGATTTTTAAATAGAGTATCTATTTTCAGATTAAATTTTTGATTATTT
GATTTACATTATATAATATTGAGTAAAGTATTGACTAGCAAAATTTTTTGATACTTTAAT
TTGTGAAATTTCTTATCAAAAGTTATATTTTTGAATAATTTTTATTGAAAATACAACTA
AAAAGGATTATAGTATAAGTGTGTGTAATTTTGTGTTAAATTTAAAGGGAGGAAATGAAC
ATGAAACATATGTATACAGTTGGTGATTATTTACTTGATAGATTACATGAACTTGGAATA
GAAGAAATTTTGGTGTACCAGGTGATTACAATCTTCAATTCTTAGATCAAATAATATCA
CATAAGGATATGAAATGGGTTGGTAATGCTAATGAATTAAATGCATCATATATGGCAGAC
GGATATGCAAGAACTAAAAAGGCAGCAGCATTTCTTACTACATTTGGTGTTGGTGAATTA
AGTGCAGTAAATGGATTAGCTGGAAGTTACGCAGAAAACTTACCAGTTGTTGAAATAGTT
GGATCTCCTACTAGTAAAGTACAAAATGAAGGTAAATTTGTACATCACACTCTTGCAGAT
GGTGATTTTAAGCATTTTATGAAAATGCATGAACCTGTTACAGCTGCAAGAACACTTCTT
ACAGCTGAAAACGCTACTGTAGAAATTGATAGAGTTTTATCTGCTTTACTTAAAGAAAGA
AAGCCAGTATATATTAACCTTCCAGTAGATGTAGCAGCAGCAAAAGCTGAGAAACCTTCA
TTACCACTTAAAAAGGAAAATTCAACATCAAATACATCTGATCAAGAGATATTAAATAAA
ATTCAGGAAAGTCTTAAAAATGCAAAGAAACCTATAGTAATAACTGGACATGAAATAATT
AGTTTTGGATTAGAAAAGACAGTTACACAGTTTATAAGTAAAACTAAGCTTCCAATTACA
ACTTTAAATTTTGGAAAGAGTTCAGTAGATGAGGCACTTCCATCATTCTTAGGAATTTAT
AATGGAACATTATCTGAACCTAATCTTAAAGAATTTGTAGAGAGTGCTGATTTTATATTA
ATGTTAGGTGTAAAACTTACTGATAGTAGTACTGGTGCATTTACTCATCATCTTAACGAA
AATAAGATGATATCATTAAATATAGACGAAGGTAAAATATTCAATGAAAGAATACAGAAC
TTTGATTTTGAATCACTTATATCATCATTACTTGATTTATCAGAGATAGAATACAAAGGA
AAATATATAGATAAAAAGCAAGAAGATTTTGTTCCATCTAATGCTCTTCTTTCTCAAGAT
AGACTTTGGCAAGCAGTTGAGAATCTTACACAGTCTAATGAAACTATAGTTGCTGAGCAA
GGAACATCATTTTTCGGTGCATCAAGTATATTTTTAAAATCTAAAAGTCACTTTATTGGA
CAACCTCTTTGGGGTTCTATTGGATATACTTTTCCAGCAGCTTTAGGAAGTCAAATAGCT
GATAAAGAAAGTAGACATTTATTATTTATTGGTGACGGTTCACTTCAGCTTACAGTACAA
GAATTAGGATTAGCTATAAGAGAGAAGATAAATCCTATTTGTTTCATAATAAACAATGAT
GGATATACTGTAGAAAGAGAAATTCACGGACCAAATCAGTCATATAATGATATTCCAATG
TGGAATTATTCAAAGTTACCTGAATCTTTCGGTGCTACTGAAGATAGAGTAGTTTCTAAA
ATTGTTAGAACAGAGAACGAATTTGTATCTGTTATGAAAGAAGCTCAGGCTGACCCTAAT
AGAATGTATTGGATTGAATTAATTTTAGCAAAAGAAGGTGCTCCTAAAGTACTTAAGAAA
ATGGGAAAATTATTTGCAGAACAAAATAAGTCATAAGAATTCCCATAATAAAGAAAGAAT
TTTAAATAAAGGAGGAACAAAGATGAGTATACCAGAAACACAAAAAGCAATTATATTTTA
TGAGTCAAATGGAAAATTAGAGCATAAAGATATACCTGTACCAAAACCAAAACCAAACGA
ACTTCTTATAAATGTTAAGTATTCTGGTGTTTGTCATACTGATCTTCATGCATGGCATGG
TGATTGGCCTCTTCCAACTAAATTACCTCTTGTAGGTGGTCATGAAGGTGCTGGTGTAGT
TGTAGGTATGGGTGAAAATGTTAAAGGTTGGAAAATAGGTGATTATGCTGGAATTAAATG
GCTTAATGGATCTTGTATGGCATGCGAGTATTGTGAATTAGGAAATGAAAGTAATTGTCC
ACATGCTGACTTAAGTGGTTATACTCATGATGGATCTTTTCAAGAATATGCTACTGCAGA
TGCAGTTCAGGCTGCACACATTCCACAGGGAACTGATCTTGCTGAAGTAGCTCCTATATT
```

FIG 62 (continued)

```
ATGCGCTGGAATTACAGTATACAAAGCATTAAAAAGTGCTAATCTTAGAGCAGGACACTG
GGCAGCTATAAGTGGTGCTGCAGGTGGTTTAGGATCTTTAGCAGTTCAATATGCTAAAGC
TATGGGATATAGAGTATTAGGAATAGACGGTGGTCCAGGAAAAGAAGAGTTATTTACATC
ATTAGGTGGTGAAGTTTTTATAGATTTCACAAAGGAAAAAGATATTGTTTCAGCTGTAGT
AAAGGCAACTAATGGTGGTGCACACGGAATTATAAATGTTTCAGTATCTGAAGCAGCAAT
AGAAGCAAGTACTAGATATTGTAGAGCAAACGGAACAGTAGTTTTAGTTGGACTTCCAGC
TGGTGCAAAGTGTTCATCTGACGTATTTAACCATGTAGTAAAGAGTATTTCAATAGTTGG
ATCTTACGTAGGTAATAGAGCTGATACAAGAGAAGCTTTAGATTTCTTTGCAAGAGGTTT
AGTTAAGAGTCCTATAAAAGTAGTAGGACTTTCATCACTTCCTGAAATTTATGAAAAGAT
GGAAAAGGGACAAATAGCTGGTAGATATGTTGTAGATACAAGTAAATAAGGCCATGGAGA
TCTCGAGGCCTGCAGACATGCAAGCTTGGCACTGGCCGTCGTTTTACAACGTCGTGACTG
GGAAAACCCTGGCGTTACCCAACTTAATCGCCTTGCAGCACATCCCCCTTTCGCCAGCTG
GCGTAATAGCGAAGAGGCCCGCACCGATCGCCCTTCCCAACAGTTGCGCAGCCTGAATGG
CGAATGGCGCTAGCATAAAAATAAGAAGCCTGCATTTGCAGGCTTCTTATTTTTATGGCG
CGCCGCCATTATTTTTTTGAACAATTGACAATTCATTTCTTATTTTTTATTAAGTGATAG
TCAAAAGGCATAACAGTGCTGAATAGAAAGAAATTTACAGAAAAGAAAATTATAGAATTT
AGTATGATTAATTATACTCATTTATGAATGTTTAATTGAATACAAAAAAAAATACTTGTT
ATGTATTCAATTACGGGTTAAAATATAGACAAGTTGAAAAATTTAATAAAAAAATAAGTC
CTCAGCTCTTATATATTAAGCTACCAACTTAGTATATAAGCCAAAACTTAAATGTGCTAC
CAACACATCAAGCCGTTAGAGAACTCTATCTATAGCAATATTTCAAATGTACCGACATAC
AAGAGAAACATTAACTATATATATTCAATTTATGAGATTATCTTAACAGATATAAATGTA
AATTGCAATAAGTAAGATTTAGAAGTTTATAGCCTTTGTGTATTGGAAGCAGTACGCAAA
GGCTTTTTTATTTGATAAAAATTAGAAGTATATTTATTTTTTCATAATTAATTTATGAAA
ATGAAAGGGGGTGAGCAAAGTGACAGAGGAAAGCAGTATCTTATCAAATAACAAGGTATT
AGCAATATCATTATTGACTTTAGCAGTAAACATTATGACTTTTATAGTGCTTGTAGCTAA
GTAGTACGAAAGGGGGAGCTTTAAAAAGCTCCTTGGAATACATAGAATTCATAAATTAAT
TTATGAAAAGAAGGGCGTATATGAAAACTTGTAAAAATTGCAAAGAGTTTATTAAAGATA
CTGAAATATGCAAAATACATTCGTTGATGATTCATGATAAAACAGTAGCAACCTATTGCA
GTAAATACAATGAGTCAAGATGTTTACATAAAGGGAAAGTCCAATGTATTAATTGTTCAA
AGATGAACCGATATGGATGGTGTGCCATAAAAATGAGATGTTTTACAGAGGAAGAACAGA
AAAAAGAACGTACATGCATTAAATATTATGCAAGGAGCTTTAAAAAAGCTCATGTAAAGA
AGAGTAAAAAGAAAAAATAATTTATTTATTAATTTAATATTGAGAGTGCCGACACAGTAT
GCACTAAAAAATATATCTGTGGTGTAGTGAGCCGATACAAAAGGATAGTCACTCGCATTT
TCATAATACATCTTATGTTATGATTATGTGTCGGTGGGACTTCACGACGAAAACCCACAA
TAAAAAAAGAGTTCGGGGTAGGGTTAAGCATAGTTGAGGCAACTAAACAATCAAGCTAGG
ATATGCAGTAGCAGACCGTAAGGTCGTTGTTTAGGTGTGTTGTAATACATACGCTATTAA
GATGTAAAAATACGGATACCAATGAAGGGAAAAGTATAATTTTTGGATGTAGTTTGTTTG
TTCATCTATGGGCAAACTACGTCCAAAGCCGTTTCCAAATCTGCTAAAAAGTATATCCTT
TCTAAAATCAAAGTCAAGTATGAAATCATAAATAAAGTTTAATTTTGAAGTTATTATGAT
ATTATGTTTTTCTATTAAAATAAATTAAGTATATAGAATAGTTTAATAATAGTATATACT
TAATGTGATAAGTGTCTGACAGTGTCACAGAAAGGATGATTGTTATGGATTATAAGCGGC
CGG
```

FIG 62 (continued)

SEQUENCE LISTING

```
<160> NUMBER OF SEQ ID NOS: 101

<210> SEQ ID NO 1
<211> LENGTH: 351
<212> TYPE: PRT
<213> ORGANISM: Clostridium autoethanogenum

<400> SEQUENCE: 1

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95
```

-continued

```
Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350
```

<210> SEQ ID NO 2
<211> LENGTH: 1056
<212> TYPE: DNA
<213> ORGANISM: Clostridium autoethanogenum

<400> SEQUENCE: 2

```
atgaaaggtt ttgcaatgtt aggtattaac aaattaggat ggattgaaaa gaaaaaccca     60
gtgccaggtc cttatgatgc gattgtacat cctctagctg tatccccatg tacatcagat    120
atacatacgg tttttgaagg agcacttggt aatagggaaa atatgatttt aggccatgaa    180
gctgtaggtg aaatagccga agttggcagc gaagttaaag attttaaagt tggcgataga    240
gttatcgtac catgcacaac acctgactgg agatctttag aagtccaagc tggttttcag    300
cagcattcaa acggtatgct tgcaggatgg aagttttcca attttaaaga cggtgtattt    360
gcagattact ttcatgtaaa cgatgcagat atgaatcttg ccatactccc agatgaaata    420
cctttagaaa gtgcagttat gatgacagac atgatgacta ctggttttca tggagcagaa    480
cttgcagaca taaaaatggg ctccagcgtt gtagtaattg gtataggagc tgttggatta    540
atgggaatag ccggttccaa acttcgagga gcaggcagaa ttatcggtgt tggaagcaga    600
cctgtttgtg ttgaaacagc taaattttat ggagcaactg atattgtaaa ttataaaaat    660
```

```
ggtgatatag ttgaacaaat catggactta actcatggta aaggtgtaga ccgtgtaatc    720
atggcaggcg gtggtgctga acactagca caagcagtaa ctatggttaa acctggcggc    780
gtaatttcta acatcaacta ccatggaagc ggtgatactt taccaatacc tcgtgttcaa    840
tggggctgcg gcatggctca caaaactata agaggaggat tatgccccgg cggacgtctt    900
agaatggaaa tgctaagaga tcttgttcta tataaacgtg ttgatttgag taaacttgtt    960
actcatgtat ttgatggtgc agaaaatatt gaaaaggccc ttttgcttat gaaaaataag   1020
ccaaaagatt taattaaatc agtagttaca ttctaa                            1056

<210> SEQ ID NO 3
<211> LENGTH: 1056
<212> TYPE: DNA
<213> ORGANISM: Clostridium ljungdahlii

<400> SEQUENCE: 3
atgaaaggtt ttgcaatgtt aggtattaac aaattaggat ggattgaaaa gaaaaaccca     60
gtgccaggtc cttatgatgc gattgtacat cctctagctg tatccccatg tacatcagat    120
atacatacgg tttttgaagg agcacttggt aatagggaaa atatgatttt aggccatgaa    180
gctgtaggtg aaatagccga agttggcagc gaagttaaag attttaaagt tggcgataga    240
gttatcgtac catgcacaac acctgactgg agatctttag aagtccaagc tggttttcag    300
cagcattcaa acggtatgct tgcaggatgg aagttttcca attttaaaga tggtgtattt    360
gcagattact ttcatgtaaa cgatgcagat atgaatcttg ccatactccc agatgaaata    420
cctttagaaa gtgcagttat gatgacagac atgatgacta ctggttttca tggagcagaa    480
cttgcagaca taaaaatggg ctccagcgtt gtagtaattg gtataggagc tgttggatta    540
atgggaatag ccggttccaa acttcgagga gcaggcagaa ttatcggtgt tggaagcaga    600
cctgtttgtg ttgaaacagc taaatttttat ggagcaactg atattgtaaa ttataaaaat    660
ggtgatatag ttgaacaaat catggactta actcatggta aaggtgtaga ccgtgtaatc    720
atggcaggcg gtggtgctga acactagca caagcagtaa ctatggttaa acctggcggc    780
gtaatttcta acatcaacta ccatggaagc ggtgatactt taccaatacc tcgtgttcaa    840
tggggctgcg gcatggctca caaaactata agaggaggat tatgccccgg cggacgtctt    900
agaatggaaa tgctaagaga tcttgttcta tataaacgtg ttgatttgag taaacttgtt    960
actcatgtat ttgatggtgc agaaaatatt gaaaaggccc ttttgcttat gaaaaataag   1020
ccaaaagatt taattaaatc agtagttaca ttctaa                            1056

<210> SEQ ID NO 4
<211> LENGTH: 1056
<212> TYPE: DNA
<213> ORGANISM: Clostridium ragsdalei

<400> SEQUENCE: 4
atgaaaggtt ttgcaatgtt aggtattaac aagttaggat ggattgaaaa gaaaaaccca     60
gtaccaggtc cttatgatgc gattgtacat cctctagctg tatccccatg tacatcagat    120
atacatacgg tttttgaagg agcacttggt aatagggaaa atatgatttt aggtcacgaa    180
gctgtaggtg aaatagctga agttggcagt gaagttaaag attttaaagt tggcgataga    240
gttatcgtac catgcacaac acctgactgg agatccttag aagtccaagc tggttttcaa    300
cagcattcaa acggtatgct tgcaggatgg aagttttcca attttaaaga cggtgtattt    360
gcagattact ttcatgtaaa cgatgcagat atgaatcttg caatacttcc agatgaaata    420
```

-continued

```
cctttagaaa gtgcagttat gatgacagac atgatgacta ctggttttca tggggcagaa      480
cttgctgaca taaaaatggg ttccagtgtt gtcgtaattg gtataggagc tgttggatta      540
atgggaatag ccggttccaa acttcgagga gcaggtagaa ttatcggtgt tggaagcaga      600
cccgtttgtg ttgaaacagc taaattttat ggagcaactg atattgtaaa ttataaaaat      660
ggtgatatag ttgaacaaat aatggactta actcatggta aaggtgtaga ccgtgtaatc      720
atggcaggcg gtggtgctga aacactagca caagcagtaa ctatggttaa acctggcggc      780
gtaatttcta acatcaacta ccatggaagc ggtgatactt tgccaatacc tcgtgttcaa      840
tggggctgcg gcatggctca caaaactata agaggagggt tatgtcccgg cggacgtctt      900
agaatggaaa tgctaagaga ccttgttcta tataaacgtg ttgatttgag caaacttgtt      960
actcatgtat tgatggtgc agaaaatatt gaaaaggccc ttttgcttat gaaaaataag     1020
ccaaaagatt taattaaatc agtagttaca ttctaa                              1056
```

<210> SEQ ID NO 5
<211> LENGTH: 20
<212> TYPE: DNA
<213> ORGANISM: Artificial sequence
<220> FEATURE:
<223> OTHER INFORMATION: synthetic primer

<400> SEQUENCE: 5
tcaggacctt ctggaactgg          20

<210> SEQ ID NO 6
<211> LENGTH: 20
<212> TYPE: DNA
<213> ORGANISM: Artificial sequence
<220> FEATURE:
<223> OTHER INFORMATION: synthetic primer

<400> SEQUENCE: 6
acctcccctt ttcttggaga          20

<210> SEQ ID NO 7
<211> LENGTH: 20
<212> TYPE: DNA
<213> ORGANISM: Artificial sequence
<220> FEATURE:
<223> OTHER INFORMATION: synthetic primer

<400> SEQUENCE: 7
caggtttcgg tgctgaccta          20

<210> SEQ ID NO 8
<211> LENGTH: 20
<212> TYPE: DNA
<213> ORGANISM: Artificial sequence
<220> FEATURE:
<223> OTHER INFORMATION: synthetic primer

<400> SEQUENCE: 8
aactccgccg ttgtatttca          20

<210> SEQ ID NO 9
<211> LENGTH: 25
<212> TYPE: DNA
<213> ORGANISM: Artificial sequence
<220> FEATURE:
<223> OTHER INFORMATION: synthetic primer

<400> SEQUENCE: 9
acaagatggg gtcgaaacag tttgg                                     25

<210> SEQ ID NO 10
<211> LENGTH: 25
<212> TYPE: DNA
<213> ORGANISM: Artificial sequence
<220> FEATURE:
<223> OTHER INFORMATION: synthetic primer

<400> SEQUENCE: 10
tggcactgga cttactctac atggg                                     25

<210> SEQ ID NO 11
<211> LENGTH: 30
<212> TYPE: DNA
<213> ORGANISM: Artificial sequence
<220> FEATURE:
<223> OTHER INFORMATION: synthetic primer

<400> SEQUENCE: 11
tatttccgaa gatgatattg aattgtatgg                                30

<210> SEQ ID NO 12
<211> LENGTH: 24
<212> TYPE: DNA
<213> ORGANISM: Artificial sequence
<220> FEATURE:
<223> OTHER INFORMATION: synthetic primer

<400> SEQUENCE: 12
tccagcaggt gttgggttta tagc                                      24

<210> SEQ ID NO 13
<211> LENGTH: 22
<212> TYPE: DNA
<213> ORGANISM: Artificial sequence
<220> FEATURE:
<223> OTHER INFORMATION: synthetic primer

<400> SEQUENCE: 13
agctgcaact cctggtggag gc                                        22

<210> SEQ ID NO 14
<211> LENGTH: 27
<212> TYPE: DNA
<213> ORGANISM: Artificial sequence
<220> FEATURE:
<223> OTHER INFORMATION: synthetic primer

<400> SEQUENCE: 14
gccttttacc ttttcgtcat actgtgc                                   27

<210> SEQ ID NO 15
<211> LENGTH: 29
<212> TYPE: DNA
<213> ORGANISM: Artificial sequence
<220> FEATURE:
<223> OTHER INFORMATION: synthetic primer

<400> SEQUENCE: 15
gcttacatta gtaagagttg gagcaaacg                                 29

<210> SEQ ID NO 16
<211> LENGTH: 29

```
<212> TYPE: DNA
<213> ORGANISM: Artificial sequence
<220> FEATURE:
<223> OTHER INFORMATION: synthetic primer

<400> SEQUENCE: 16
acttgtcctg tgatatatct gctggtagc                                29

<210> SEQ ID NO 17
<211> LENGTH: 26
<212> TYPE: DNA
<213> ORGANISM: Artificial sequence
<220> FEATURE:
<223> OTHER INFORMATION: synthetic primer

<400> SEQUENCE: 17
ggtccttatg atgcgattgt acatcc                                   26

<210> SEQ ID NO 18
<211> LENGTH: 26
<212> TYPE: DNA
<213> ORGANISM: Artificial sequence
<220> FEATURE:
<223> OTHER INFORMATION: synthetic primer

<400> SEQUENCE: 18
gctatttcac ctacagcttc atggcc                                   26

<210> SEQ ID NO 19
<211> LENGTH: 654
<212> TYPE: DNA
<213> ORGANISM: Clostridium beijerinckii

<400> SEQUENCE: 19
atgaataaat tagtaaaatt aacagattta aagcgcattt tcaaagatgg catgacaatt    60
atggttgggg gttttttaga ttgtggaact cctgaaaata ttatagatat gctagttgat   120
ttaaatataa aaatctgac tattataagc aatgatacag cttttcctaa taaggaata    180 ggaaaactta ttgtaaatgg tcaagtttct aaagtaattg cttcacatat ggaactaat   240 cctgaaactg aaaaaaaat gagctctgga gaacttaaag ttgagctttc cccacaagga   300
acactgattg aaagaattcg tgcagctgga tctggactcg gaggtgtatt aactccaact   360
ggacttggaa ctatcgttga agaaggtaag aaaaaagtta ctatcgatgg caaagaatat   420
ctattagaac ttcctttatc tgctgatgtt tcattaataa aaggtagcat tgtagatgaa   480
tttggaaata ccttctatag ggctgctact aaaaatttca atccatatat ggcaatggct   540
gcaaaaacag ttatagttga agcagaaaat ttagttaaat gtgaagattt aaaaagagat   600
gccataatga ctcctggcgt attagtagat tatatcgtta aggaggcggc ttaa         654

<210> SEQ ID NO 20
<211> LENGTH: 666
<212> TYPE: DNA
<213> ORGANISM: Clostridium beijerinckii

<400> SEQUENCE: 20
ttgattgtag ataaagttttt agcaaaagag ataattgcca aaagagttgc aaaagaacta   60
aaaaaagacc aactcgtaaa ccttggaata ggacttccaa ctttagtagc aaattatgta   120
ccaaagaaaa tgaacattac ttttgaatca gaaaatggca tggttggtat ggcacaaatg   180
gcatcatcag gtgaaaatga cccagatata ataaatgctg gcggggaata tgtaacatta   240
```

-continued

```
ttacctcaag gttcattttt tgatagttca atgtctttcg cactaatacg aggaggacat    300
gttgatgttg ctgttcttgg tgctctagaa gttgatgaaa aaggtaattt agctaactgg    360
attgttccaa ataaaattgt cccaggtatg ggtggcgcta tggatttagc aataggcgca    420
aaaaaaataa tagtggcaat gcaacataca ggaaaaagta aacctaaaat cgttaaaaaa    480
tgtactctcc cacttactgc taaggctcaa gtggatttaa ttgtcacaga actttgtgta    540
attgatgtaa caaatgacgg cttactttta aaagaaattc ataaagatac aactattgat    600
gaaattaaat ttttaacaga tgcagattta attattccag ataacttaaa gattatggat    660
atatga                                                               666

<210> SEQ ID NO 21
<211> LENGTH: 741
<212> TYPE: DNA
<213> ORGANISM: Clostridium beijerinckii

<400> SEQUENCE: 21
atgttagaaa gtgaagtatc taaacaaatt acaactccac ttgctgctcc agcgtttcct     60
agaggaccat ataggtttca caatagagaa tatctaaaca ttatttatcg aactgattta    120
gatgctcttc gaaaaatagt accagagcca cttgaattag atagagcata tgttagattt    180
gaaatgatgg ctatgcctga tacaaccgga ctaggctcat atacagaatg tggtcaagct    240
attccagtaa aatataatgg tgttaagggt gactacttgc atatgatgta tctagataat    300
gaacctgcta ttgctgttgg aagagaaagt agcgcttatc caaaaaagct tggctatcca    360
aagctatttg ttgattcaga tactttagtt gggacactta aatatggtac attaccagta    420
gctactgcaa caatgggata taagcacgag cctctagatc ttaaagaagc ctatgctcaa    480
attgcaagac ccaattttat gctaaaaatc attcaaggtt acgatggtaa gccaagaatt    540
tgtgaactaa tatgtgcaga aaatactgat ataactattc acggtgcttg gactggaagt    600
gcacgtctac aattatttag ccatgcacta gctcctcttg ctgatttacc tgtattagag    660
attgtatcag catctcatat cctcacagat ttaactcttg gaacacctaa ggttgtacat    720
gattatcttt cagtaaaata a                                              741

<210> SEQ ID NO 22
<211> LENGTH: 558
<212> TYPE: DNA
<213> ORGANISM: Clostridium autoethanogenum

<400> SEQUENCE: 22
agatagtcat aatagttcca gaatagttca atttagaaat tagactaaac ttcaaaatgt     60
ttgttaaata tataccaaac tagtatagat attttttaaa tactggactt aaacagtagt    120
aatttgccta aaaaattttt tcaatttttt ttaaaaaatc cttttcaagt tgtacattgt    180
tatggtaata tgtaattgaa gaagttatgt agtaatattg taaacgtttc ttgatttttt    240
tacatccatg tagtgcttaa aaaaccaaaa tatgtcacat gcaattgtat atttcaaata    300
acaatattta ttttctcgtt aaattcacaa ataatttatt aataatatca ataaccaaga    360
ttatacttaa atggatgttt attttttaac acttttatag taaatatatt tattttatgt    420
agtaaaaagg ttataattat aattgtattt attacaatta attaaaataa aaaatagggt    480
tttaggtaaa attaagttat tttaagaagt aattacaata aaaattgaag ttatttcttt    540
aaggagggaa ttattaaa                                                  558
```

```
<210> SEQ ID NO 23
<211> LENGTH: 26
<212> TYPE: DNA
<213> ORGANISM: Artificial sequence
<220> FEATURE:
<223> OTHER INFORMATION: synthetic primer

<400> SEQUENCE: 23
gttcatatga aagaagttgt aatagc                                         26

<210> SEQ ID NO 24
<211> LENGTH: 25
<212> TYPE: DNA
<213> ORGANISM: Artificial sequence
<220> FEATURE:
<223> OTHER INFORMATION: synthetic primer

<400> SEQUENCE: 24
caagaattcc tagcactttt ctagc                                          25

<210> SEQ ID NO 25
<211> LENGTH: 26
<212> TYPE: DNA
<213> ORGANISM: Artificial sequence
<220> FEATURE:
<223> OTHER INFORMATION: synthetic primer

<400> SEQUENCE: 25
ctaggtacca gggagatatt aaaatg                                         26

<210> SEQ ID NO 26
<211> LENGTH: 26
<212> TYPE: DNA
<213> ORGANISM: Artificial sequence
<220> FEATURE:
<223> OTHER INFORMATION: synthetic primer

<400> SEQUENCE: 26
cgtggatcct ctatattgct tttatt                                         26

<210> SEQ ID NO 27
<211> LENGTH: 29
<212> TYPE: DNA
<213> ORGANISM: Artificial sequence
<220> FEATURE:
<223> OTHER INFORMATION: synthetic primer

<400> SEQUENCE: 27
aagcggccgc agatagtcat aatagttcc                                      29

<210> SEQ ID NO 28
<211> LENGTH: 29
<212> TYPE: DNA
<213> ORGANISM: Artificial sequence
<220> FEATURE:
<223> OTHER INFORMATION: synthetic primer

<400> SEQUENCE: 28
ttccatatga ataattccct ccttaaagc                                      29

<210> SEQ ID NO 29
<211> LENGTH: 20
<212> TYPE: DNA
<213> ORGANISM: Artificial sequence
<220> FEATURE:
<223> OTHER INFORMATION: synthetic primer
```

```
<400> SEQUENCE: 29
cagaggatgt taatgaagtc                                              20

<210> SEQ ID NO 30
<211> LENGTH: 18
<212> TYPE: DNA
<213> ORGANISM: Artificial sequence
<220> FEATURE:
<223> OTHER INFORMATION: synthetic primer

<400> SEQUENCE: 30
ctgtgcagca gtacttgt                                                18

<210> SEQ ID NO 31
<211> LENGTH: 15
<212> TYPE: DNA
<213> ORGANISM: Artificial sequence
<220> FEATURE:
<223> OTHER INFORMATION: synthetic primer

<400> SEQUENCE: 31
gcaatgatac agctt                                                   15

<210> SEQ ID NO 32
<211> LENGTH: 19
<212> TYPE: DNA
<213> ORGANISM: Artificial sequence
<220> FEATURE:
<223> OTHER INFORMATION: synthetic primer

<400> SEQUENCE: 32
aaccttggaa taggacttc                                               19

<210> SEQ ID NO 33
<211> LENGTH: 20
<212> TYPE: DNA
<213> ORGANISM: Artificial sequence
<220> FEATURE:
<223> OTHER INFORMATION: synthetic primer

<400> SEQUENCE: 33
tgtgaactaa tatgtgcaga                                              20

<210> SEQ ID NO 34
<211> LENGTH: 601
<212> TYPE: PRT
<213> ORGANISM: Artificial sequence
<220> FEATURE:
<223> OTHER INFORMATION: synthetic protein

<400> SEQUENCE: 34

Met Phe Pro Cys Asn Ala Tyr Ile Glu Tyr Gly Asp Lys Asn Met Asn
 1               5                  10                  15

Ser Phe Ile Glu Asp Val Glu Gln Ile Tyr Asn Phe Ile Lys Lys Asn
                20                  25                  30

Ile Asp Val Glu Glu Lys Met His Phe Ile Glu Thr Tyr Lys Gln Lys
            35                  40                  45

Ser Asn Met Lys Lys Glu Ile Ser Phe Ser Glu Glu Tyr Tyr Lys Gln
        50                  55                  60

Lys Ile Met Asn Gly Lys Asn Gly Val Val Tyr Thr Pro Pro Glu Met
    65                  70                  75                  80

Ala Ala Phe Met Val Lys Asn Leu Ile Asn Val Asn Asp Val Ile Gly
                85                  90                  95
```

-continued

```
Asn Pro Phe Ile Lys Ile Ile Asp Pro Ser Cys Gly Ser Gly Asn Leu
            100                 105                 110
Ile Cys Lys Cys Phe Leu Tyr Leu Asn Arg Ile Phe Ile Lys Asn Ile
        115                 120                 125
Glu Val Ile Asn Ser Lys Asn Leu Asn Leu Lys Leu Glu Asp Ile
130                 135                 140
Ser Tyr His Ile Val Arg Asn Asn Leu Phe Gly Phe Asp Ile Asp Glu
145                 150                 155                 160
Thr Ala Ile Lys Val Leu Lys Ile Asp Leu Phe Leu Ile Ser Asn Gln
                165                 170                 175
Phe Ser Glu Lys Asn Phe Gln Val Lys Asp Phe Leu Val Glu Asn Ile
            180                 185                 190
Asp Arg Lys Tyr Asp Val Phe Ile Gly Asn Pro Pro Tyr Ile Gly His
        195                 200                 205
Lys Ser Val Asp Ser Ser Tyr Ser Tyr Val Leu Arg Lys Ile Tyr Gly
    210                 215                 220
Ser Ile Tyr Arg Asp Lys Gly Asp Ile Ser Tyr Cys Phe Phe Gln Lys
225                 230                 235                 240
Ser Leu Lys Cys Leu Lys Glu Gly Gly Lys Leu Val Phe Val Thr Ser
                245                 250                 255
Arg Tyr Phe Cys Glu Ser Cys Ser Gly Lys Glu Leu Arg Lys Phe Leu
            260                 265                 270
Ile Glu Asn Thr Ser Ile Tyr Lys Ile Ile Asp Phe Tyr Gly Ile Arg
        275                 280                 285
Pro Phe Lys Arg Val Gly Ile Asp Pro Met Ile Ile Phe Leu Val Arg
    290                 295                 300
Thr Lys Asn Trp Asn Asn Asn Ile Glu Ile Ile Arg Pro Asn Lys Ile
305                 310                 315                 320
Glu Lys Asn Glu Lys Asn Lys Phe Leu Asp Ser Leu Phe Leu Asp Lys
                325                 330                 335
Ser Glu Lys Cys Lys Lys Phe Ser Ile Ser Gln Lys Ser Ile Asn Asn
            340                 345                 350
Asp Gly Trp Val Phe Val Asp Glu Val Glu Lys Asn Ile Ile Asp Lys
        355                 360                 365
Ile Lys Glu Lys Ser Lys Phe Ile Leu Lys Asp Ile Cys His Ser Cys
    370                 375                 380
Gln Gly Ile Ile Thr Gly Cys Asp Arg Ala Phe Ile Val Asp Arg Asp
385                 390                 395                 400
Ile Ile Asn Ser Arg Lys Ile Glu Leu Arg Leu Ile Lys Pro Trp Ile
                405                 410                 415
Lys Ser Ser His Ile Arg Lys Asn Glu Val Ile Lys Gly Glu Lys Phe
            420                 425                 430
Ile Ile Tyr Ser Asn Leu Ile Glu Asn Glu Thr Glu Cys Pro Asn Ala
        435                 440                 445
Ile Lys Tyr Ile Glu Gln Tyr Lys Lys Arg Leu Met Glu Arg Arg Glu
    450                 455                 460
Cys Lys Lys Gly Thr Arg Lys Trp Tyr Glu Leu Gln Trp Gly Arg Lys
465                 470                 475                 480
Pro Glu Ile Phe Glu Glu Lys Lys Ile Val Phe Pro Tyr Lys Ser Cys
                485                 490                 495
Asp Asn Arg Phe Ala Leu Asp Lys Gly Ser Tyr Phe Ala Asp Ile
            500                 505                 510
```

| | | | | | | | | | | | |
|---|---|---|---|---|---|---|---|---|---|---|---|
|Tyr|Ser|Leu|Val|Leu|Lys|Lys|Asn|Val|Pro|Phe|Thr|Tyr|Glu|Ile|Leu|
| | |515| | | |520| | | |525| |

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
                580                 585                 590

Ile Val Glu Lys Ile Lys Asp Asn Cys
                595                 600

<210> SEQ ID NO 35
<211> LENGTH: 1806
<212> TYPE: DNA
<213> ORGANISM: Artificial sequence
<220> FEATURE:
<223> OTHER INFORMATION: synthetic gene

<400> SEQUENCE: 35

```
atgtttccgt gcaatgccta tatcgaatat ggtgataaaa atatgaacag ctttatcgaa    60
gatgtggaac agatctacaa cttcattaaa aagaacattg atgtggaaga aaagatgcat   120
ttcattgaaa cctataaaca gaaaagcaac atgaagaaag agattagctt tagcgaagaa   180
tactataaac agaagattat gaacggcaaa aatggcgttg tgtacacccc gccggaaatg   240
gcggccttta tggttaaaaa tctgatcaac gttaacgatg ttattggcaa tccgtttatt   300
aaaatcattg acccgagctg cggtagcggc aatctgattt gcaaatgttt tctgtatctg   360
aatcgcatct ttattaagaa cattgaggtg attaacagca aaataaccct gaatctgaaa   420
ctggaagaca tcagctacca catcgttcgc aacaatctgt ttggcttcga tattgacgaa   480
accgcgatca aagtgctgaa aattgatctg tttctgatca gcaaccaatt tagcgagaaa   540
aatttccagg ttaaagactt tctggtggaa atattgatc gcaaatatga cgtgttcatt   600
ggtaatccgc gtatatcgg tcacaaaagc gtggacagca gctacagcta cgtgctgcgc   660
aaaatctacg gcagcatcta ccgcgacaaa ggcgatatca gctattgttt ctttcagaag   720
agcctgaaat gtctgaagga aggtggcaaa ctggtgtttg tgaccagccg ctacttctgc   780
gagagctgca gcggtaaaga actgcgtaaa ttcctgatcg aaaacacgag catttacaag   840
atcattgatt tttacggcat ccgcccgttc aaacgcgtgg gtatcgatcc gatgattatt   900
tttctggttc gtacgaagaa ctggaacaat aacattgaaa ttattcgccc gaacaagatt   960
gaaaagaacg aaaagaacaa attcctggat agcctgttcc tggacaaaag cgaaaagtgt  1020
aaaaagttta gcattagcca gaaaagcatt aataacgatg gctggttttt cgtggacgaa  1080
gtggagaaaa acattatcga caaaatcaaa gagaaaagca gttcattct gaaagatatt  1140
tgccatagct gtcaaggcat tatcaccggt tgtgatcgcg cctttattgt ggaccgtgat  1200
atcatcaata gccgtaagat cgaactgcgt ctgattaaac gtggattaa aagcagccat  1260
atccgtaaga tgaagttat taagggcgaa aaattcatca tctatagcaa cctgattgag  1320
aatgaaaccg agtgtccgaa tgcgattaaa tatatcgaac agtacaagaa acgtctgatg  1380
gagcgccgcg aatgcaaaaa gggcacgcgt aagtggtatg aactgcaatg gggccgtaaa  1440
ccggaaatct tcgaagaaaa gaaattgtt ttcccgtata aaagctgtga caatcgtttt  1500
gcactggata agggtagcta ttttagcgca gacatttata gcctggttct gaagaaaaat  1560
```

-continued

```
gtgccgttca cctatgagat cctgctgaat atcctgaata gcccgctgta cgagttttac    1620
tttaagacct tcgcgaaaaa gctgggcgag aatctgtacg agtactatcc gaacaacctg    1680
atgaagctgt gcatcccgag catcgatttc ggcggtgaga acaatattga gaaaaagctg    1740
tatgatttct ttggtctgac ggataaagaa attgagattg gagaagat caaagataac     1800 tgctaa                                                               1806
```

<210> SEQ ID NO 36
<211> LENGTH: 37
<212> TYPE: DNA
<213> ORGANISM: Artificial sequence
<220> FEATURE:
<223> OTHER INFORMATION: synthetic primer

<400> SEQUENCE: 36
ccgaattcgt cgacaacaga gtttgatcct ggctcag                              37

<210> SEQ ID NO 37
<211> LENGTH: 37
<212> TYPE: DNA
<213> ORGANISM: Artificial sequence
<220> FEATURE:
<223> OTHER INFORMATION: synthetic primer

<400> SEQUENCE: 37
cccgggatcc aagcttacgg ctaccttgtt acgactt                              37

<210> SEQ ID NO 38
<211> LENGTH: 351
<212> TYPE: PRT
<213> ORGANISM: Clostridium beijerinckii

<400> SEQUENCE: 38

Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

```
Arg Ile Ile Gly Val Gly Ser Arg Pro Ile Cys Val Glu Ala Ala Lys
            195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
                260                 265                 270

Ala Leu Leu Ile Pro Arg Val Glu Trp Gly Cys Gly Met Ala His Lys
            275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
                340                 345                 350

<210> SEQ ID NO 39
<211> LENGTH: 1056
<212> TYPE: DNA
<213> ORGANISM: Clostridium beijerinckii

<400> SEQUENCE: 39
atgaaaggtt ttgcaatgct aggtattaat aagttaggat ggatcgaaaa agaaaggcca     60
gttgcgggtt catatgatgc tattgtacgc ccattagcag tatctccgtg tacatcagat    120
atacatactg tttttgaggg agctcttgga gataggaaga atatgatttt agggcatgaa    180
gctgtaggta agttgttgaa gtaggaagt gaagtgaagg attttaaacc tggtgacaga    240
gttatagttc cttgtacaac tccagattgg agatctttgg aagttcaagc tggttttcaa    300
cagcactcaa acggtatgct cgcaggatgg aaattttcaa atttcaagga tggagttttt    360
ggtgaatatt ttcatgtaaa tgatgcggat atgaatcttg cgattctacc taaagacatg    420
ccattagaaa atgctgttat gataacagat atgatgacta ctggatttca tggagcagaa    480
cttgcagata ttcaaatggg ttcaagtgtt gtggtaattg cattggagc tgttggctta    540 atgggaatag caggtgctaa attacgtgga gcaggtagaa taattggagt ggggagcagg    600
ccgatttgtg ttgaggctgc aaaatttttat ggagcaacag atattctaaa ttataaaaat    660
ggtcatatag ttgatcaagt tatgaaatta acgaatggaa aaggcgttga ccgcgtaatt    720
atggcaggcg gtggttctga acattatcc caagcagtat ctatggttaa ccaggagga    780 ataatttcta atataaatta tcatggaagt ggagatgctt tactaatacc acgtgtagaa    840
tggggatgtg gaatggctca caagactata aaaggaggtc tttgtcctgg gggacgtttg    900
agagcagaaa tgttaagaga tatggtagta tataatcgtg ttgatctaag taaattagtt    960
acacatgtat atcatggatt tgatcacata gaagaagcac tgttattaat gaaagacaag   1020
ccaaaagact taattaaagc agtagttata ttataa                             1056

<210> SEQ ID NO 40
<211> LENGTH: 352
<212> TYPE: PRT
<213> ORGANISM: Thermoanaerobacter brockii
```

<400> SEQUENCE: 40

| | | | | | | | | | | | | | | |
|---|---|---|---|---|---|---|---|---|---|---|---|---|---|---|
| Met | Lys | Gly | Phe | Ala | Met | Leu | Ser | Ile | Gly | Lys | Val | Gly | Trp | Ile | Glu |
| 1 | | | | 5 | | | | | 10 | | | | | 15 | |
| Lys | Glu | Lys | Pro | Ala | Pro | Gly | Pro | Phe | Asp | Ala | Ile | Val | Arg | Pro | Leu |
| | | | 20 | | | | | 25 | | | | | 30 | | |
| Ala | Val | Ala | Pro | Cys | Thr | Ser | Asp | Ile | His | Thr | Val | Phe | Glu | Gly | Ala |
| | | 35 | | | | | 40 | | | | | 45 | | | |
| Ile | Gly | Glu | Arg | His | Asn | Met | Ile | Leu | Gly | His | Glu | Ala | Val | Gly | Glu |
| | 50 | | | | | 55 | | | | | 60 | | | | |
| Val | Val | Glu | Val | Gly | Ser | Glu | Val | Lys | Asp | Phe | Lys | Pro | Gly | Asp | Arg |
| 65 | | | | | 70 | | | | | 75 | | | | | 80 |
| Val | Val | Val | Pro | Ala | Ile | Thr | Pro | Asp | Trp | Arg | Thr | Ser | Glu | Val | Gln |
| | | | | 85 | | | | | 90 | | | | | 95 | |
| Arg | Gly | Tyr | His | Gln | His | Ser | Gly | Gly | Met | Leu | Ala | Gly | Trp | Lys | Phe |
| | | | 100 | | | | | 105 | | | | | 110 | | |
| Ser | Asn | Val | Lys | Asp | Gly | Val | Phe | Gly | Glu | Phe | Phe | His | Val | Asn | Asp |
| | | 115 | | | | | 120 | | | | | 125 | | | |
| Ala | Asp | Met | Asn | Leu | Ala | His | Leu | Pro | Lys | Glu | Ile | Pro | Leu | Glu | Ala |
| | 130 | | | | | 135 | | | | | 140 | | | | |
| Ala | Val | Met | Ile | Pro | Asp | Met | Met | Thr | Thr | Gly | Phe | His | Gly | Ala | Glu |
| 145 | | | | | 150 | | | | | 155 | | | | | 160 |
| Leu | Ala | Asp | Ile | Glu | Leu | Gly | Ala | Thr | Val | Ala | Val | Leu | Gly | Ile | Gly |
| | | | | 165 | | | | | 170 | | | | | 175 | |
| Pro | Val | Gly | Leu | Met | Ala | Val | Ala | Gly | Ala | Lys | Leu | Arg | Gly | Ala | Gly |
| | | | 180 | | | | | 185 | | | | | 190 | | |
| Arg | Ile | Ile | Ala | Val | Gly | Ser | Arg | Pro | Val | Cys | Val | Asp | Ala | Ala | Lys |
| | | 195 | | | | | 200 | | | | | 205 | | | |
| Tyr | Tyr | Gly | Ala | Thr | Asp | Ile | Val | Asn | Tyr | Lys | Asp | Gly | Pro | Ile | Glu |
| | 210 | | | | | 215 | | | | | 220 | | | | |
| Ser | Gln | Ile | Met | Asn | Leu | Thr | Glu | Gly | Lys | Gly | Val | Asp | Ala | Ala | Ile |
| 225 | | | | | 230 | | | | | 235 | | | | | 240 |
| Ile | Ala | Gly | Gly | Asn | Ala | Asp | Ile | Met | Ala | Thr | Ala | Val | Lys | Ile | Val |
| | | | | 245 | | | | | 250 | | | | | 255 | |
| Lys | Pro | Gly | Gly | Thr | Ile | Ala | Asn | Val | Asn | Tyr | Phe | Gly | Glu | Gly | Glu |
| | | | 260 | | | | | 265 | | | | | 270 | | |
| Val | Leu | Pro | Val | Pro | Arg | Leu | Glu | Trp | Gly | Cys | Gly | Met | Ala | His | Lys |
| | | 275 | | | | | 280 | | | | | 285 | | | |
| Thr | Ile | Lys | Gly | Gly | Leu | Cys | Pro | Gly | Gly | Arg | Leu | Arg | Met | Glu | Arg |
| | 290 | | | | | 295 | | | | | 300 | | | | |
| Leu | Ile | Asp | Leu | Val | Phe | Tyr | Lys | Arg | Val | Asp | Pro | Ser | Lys | Leu | Val |
| 305 | | | | | 310 | | | | | 315 | | | | | 320 |
| Thr | His | Val | Phe | Arg | Gly | Phe | Asp | Asn | Ile | Glu | Lys | Ala | Phe | Met | Leu |
| | | | | 325 | | | | | 330 | | | | | 335 | |
| Met | Lys | Asp | Lys | Pro | Lys | Asp | Leu | Ile | Lys | Pro | Val | Val | Ile | Leu | Ala |
| | | | 340 | | | | | 345 | | | | | 350 | | |

<210> SEQ ID NO 41
<211> LENGTH: 1056
<212> TYPE: DNA
<213> ORGANISM: Thermoanaerobacter brockii

<400> SEQUENCE: 41
atgaaaggtt ttgcaatgct aggtattaat aagttaggat ggatcgaaaa agaaaggcca    60

```
gttgcgggtt catatgatgc tattgtacgc ccattagcag tatctccgtg tacatcagat    120
atacatactg tttttgaggg agctcttgga gataggaaga atatgatttt agggcatgaa    180
gctgtaggtg aagttgttga agtaggaagt gaagtgaagg attttaaacc tggtgacaga    240
gttatagttc cttgtacaac tccagattgg agatctttgg aagttcaagc tggttttcaa    300
cagcactcaa acggtatgct cgcaggatgg aaattttcaa atttcaagga tggagttttt    360
ggtgaatatt ttcatgtaaa tgatgcggat atgaatcttg cgattctacc taaagacatg    420
ccattagaaa atgctgttat gataacagat atgatgacta ctggatttca tggagcagaa    480
cttgcagata ttcaaatggg ttcaagtgtt gtggtaattg cattggagc tgttggctta    540 atgggaatag caggtgctaa attacgtgga gcaggtagaa taattggagt ggggagcagg    600
ccgatttgtg ttgaggctgc aaaatttat ggagcaacag atattctaaa ttataaaaat    660
ggtcatatag ttgatcaagt tatgaaatta acgaatggaa aaggcgttga ccgcgtaatt    720
atggcaggcg gtggttctga acattatcc caagcagtat ctatggttaa accaggagga    780
ataatttcta atataaatta tcatggaagt ggagatgctt tactaatacc acgtgtagaa    840
tggggatgtg aatggctca caagactata aaaggaggtc tttgtcctgg gggacgtttg    900
agagcagaaa tgttaagaga tatggtagta tataatcgtg ttgatctaag taaattagtt    960
acacatgtat atcatggatt tgatcacata gaagaagcac tgttattaat gaaagacaag    1020
ccaaaagact taattaaagc agtagttata ttataa                              1056
```

<210> SEQ ID NO 42
<211> LENGTH: 392
<212> TYPE: PRT
<213> ORGANISM: Clostridium acetobutylicum

<400> SEQUENCE: 42

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
```

```
              195                 200                 205
Gly Glu Thr Val Val Asp Thr Asp Glu His Pro Arg Phe Gly Ser Thr
210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 43
<211> LENGTH: 217
<212> TYPE: PRT
<213> ORGANISM: Clostridium beijerinckii

<400> SEQUENCE: 43

Met Asn Lys Leu Val Lys Leu Thr Asp Leu Lys Arg Ile Phe Lys Asp
1               5                   10                  15

Gly Met Thr Ile Met Val Gly Gly Phe Leu Asp Cys Gly Thr Pro Glu
            20                  25                  30

Asn Ile Ile Asp Met Leu Val Asp Leu Asn Ile Lys Asn Leu Thr Ile
        35                  40                  45

Ile Ser Asn Asp Thr Ala Phe Pro Asn Lys Gly Ile Gly Lys Leu Ile
    50                  55                  60

Val Asn Gly Gln Val Ser Lys Val Ile Ala Ser His Ile Gly Thr Asn
65                  70                  75                  80

Pro Glu Thr Gly Lys Lys Met Ser Ser Gly Glu Leu Lys Val Glu Leu
                85                  90                  95

Ser Pro Gln Gly Thr Leu Ile Glu Arg Ile Arg Ala Ala Gly Ser Gly
            100                 105                 110

Leu Gly Gly Val Leu Thr Pro Thr Gly Leu Gly Thr Ile Val Glu Glu
        115                 120                 125

Gly Lys Lys Lys Val Thr Ile Asp Gly Lys Glu Tyr Leu Leu Glu Leu
    130                 135                 140

Pro Leu Ser Ala Asp Val Ser Leu Ile Lys Gly Ser Ile Val Asp Glu
145                 150                 155                 160

Phe Gly Asn Thr Phe Tyr Arg Ala Ala Thr Lys Asn Phe Asn Pro Tyr
                165                 170                 175
```

```
Met Ala Met Ala Ala Lys Thr Val Ile Val Glu Ala Glu Asn Leu Val
            180                 185                 190
Lys Cys Glu Asp Leu Lys Arg Asp Ala Ile Met Thr Pro Gly Val Leu
        195                 200                 205
Val Asp Tyr Ile Val Lys Glu Ala Ala
        210                 215

<210> SEQ ID NO 44
<211> LENGTH: 221
<212> TYPE: PRT
<213> ORGANISM: Clostridium beijerinckii

<400> SEQUENCE: 44

Leu Ile Val Asp Lys Val Leu Ala Lys Glu Ile Ile Ala Lys Arg Val
1               5                   10                  15
Ala Lys Glu Leu Lys Lys Asp Gln Leu Val Asn Leu Gly Ile Gly Leu
            20                  25                  30
Pro Thr Leu Val Ala Asn Tyr Val Pro Lys Glu Met Asn Ile Thr Phe
        35                  40                  45
Glu Ser Glu Asn Gly Met Val Gly Met Ala Gln Met Ala Ser Ser Gly
    50                  55                  60
Glu Asn Asp Pro Asp Ile Ile Asn Ala Gly Gly Glu Tyr Val Thr Leu
65                  70                  75                  80
Leu Pro Gln Gly Ser Phe Phe Asp Ser Ser Met Ser Phe Ala Leu Ile
                85                  90                  95
Arg Gly Gly His Val Asp Val Ala Val Leu Gly Ala Leu Glu Val Asp
            100                 105                 110
Glu Lys Gly Asn Leu Ala Asn Trp Ile Val Pro Asn Lys Ile Val Pro
        115                 120                 125
Gly Met Gly Gly Ala Met Asp Leu Ala Ile Gly Ala Lys Lys Ile Ile
    130                 135                 140
Val Ala Met Gln His Thr Gly Lys Ser Lys Pro Lys Ile Val Lys Lys
145                 150                 155                 160
Cys Thr Leu Pro Leu Thr Ala Lys Ala Gln Val Asp Leu Ile Val Thr
                165                 170                 175
Glu Leu Cys Val Ile Asp Val Thr Asn Asp Gly Leu Leu Leu Lys Glu
            180                 185                 190
Ile His Lys Asp Thr Thr Ile Asp Glu Ile Lys Phe Leu Thr Asp Ala
        195                 200                 205
Asp Leu Ile Ile Pro Asn Asn Leu Lys Ile Met Asp Ile
    210                 215                 220

<210> SEQ ID NO 45
<211> LENGTH: 246
<212> TYPE: PRT
<213> ORGANISM: Clostridium beijerinckii

<400> SEQUENCE: 45

Met Leu Glu Ser Glu Val Ser Lys Gln Ile Thr Thr Pro Leu Ala Ala
1               5                   10                  15
Pro Ala Phe Pro Arg Gly Pro Tyr Arg Phe His Asn Arg Glu Tyr Leu
            20                  25                  30
Asn Ile Ile Tyr Arg Thr Asp Leu Asp Ala Leu Arg Lys Ile Val Pro
        35                  40                  45
Glu Pro Leu Glu Leu Asp Arg Ala Tyr Val Arg Phe Glu Met Met Ala
    50                  55                  60
```

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245

<210> SEQ ID NO 46
<211> LENGTH: 6832
<212> TYPE: DNA
<213> ORGANISM: Artificial sequence
<220> FEATURE:
<223> OTHER INFORMATION: synthetic plasmid

<400> SEQUENCE: 46
tgaaagaaag atatggaaca gtctataaag gctctcagag gctcatagac gaagaaagtg        60
gagaagtcat agaggtagac aagttatacc gtaaacaaac gtctggtaac ttcgtaaagg       120
catatatagt gcaattaata agtatgttag atatgattgg cggaaaaaaa cttaaaatcg       180
ttaactatat cctagataat gtccacttaa gtaacaatac aatgatagct acaacaagag       240
aaatagcaaa agctacagga acaagtctac aaacagtaat aacaacactt aaaatcttag       300
aagaaggaaa tattataaaa agaaaaactg gagtattaat gttaaaccct gaactactaa       360
tgagaggcga cgaccaaaaa caaaaatacc tcttactcga atttgggaac tttgagcaag       420
aggcaaatga aatagattga cctcccaata acaccacgta gttattggga ggtcaatcta       480
tgaaatgcga ttaagggccg gccagtgggc aagttgaaaa attcacaaaa atgtggtata       540
atatctttgt tcattagagc gataaacttg aatttgagag ggaacttaga tggtatttga       600
aaaaattgat aaaaatagtt ggaacagaaa agagtatttt gaccactact ttgcaagtgt       660
accttgtacc tacagcatga ccgttaaagt ggatatcaca caaataaagg aaaagggaat       720
gaaactatat cctgcaatgc tttattatat tgcaatgatt gtaaaccgcc attcagagtt       780
taggacggca atcaatcaag atggtgaatt ggggatatat gatgagatga taccaagcta       840
tacaatattt cacaatgata ctgaaacatt ttccagcctt tggactgagt gtaagtctga       900
ctttaaatca tttttagcag attatgaaag tgatacgcaa cggtatggaa acaatcatag       960
aatggaagga aagccaaatg ctccggaaaa cattttttaat gtatctatga taccgtggtc      1020

```
aaccttcgat ggctttaatc tgaatttgca gaaaggatat gattatttga ttcctatttt    1080
tactatgggg aaatattata aagaagataa caaaattata cttcctttgg caattcaagt    1140
tcatcacgca gtatgtgacg gatttcacat ttgccgtttt gtaaacgaat tgcaggaatt    1200
gataaatagt taacttcagg tttgtctgta actaaaaaca agtatttaag caaaaacatc    1260
gtagaaatac ggtgtttttt gttaccctaa gtttaaactc cttttgata atctcatgac     1320 caaaatccct taacgtgagt tttcgttcca ctgagcgtca gaccccgtag aaagatcaa     1380 aggatcttct tgagatcctt ttttctgcg cgtaatctgc tgcttgcaaa caaaaaaacc     1440
accgctacca gcggtggttt gtttgccgga tcaagagcta ccaactcttt ttccgaaggt    1500
aactggcttc agcagagcgc agataccaaa tactgttctt ctagtgtagc cgtagttagg    1560
ccaccacttc aagaactctg tagcaccgcc tacatacctc gctctgctaa tcctgttacc    1620
agtggctgct gccagtggcg ataagtcgtg tcttaccggg ttggactcaa gacgatagtt    1680
accggataag gcgcagcggt cgggctgaac ggggggttcg tgcacacagc ccagcttgga    1740
gcgaacgacc tacaccgaac tgagatacct acagcgtgag ctatgagaaa gcgccacgct    1800
tcccgaaggg agaaaggcgg acaggtatcc ggtaagcggc agggtcggaa caggagagcg    1860
cacgagggag cttccagggg gaaacgcctg gtatctttat agtcctgtcg ggtttcgcca    1920
cctctgactt gagcgtcgat ttttgtgatg ctcgtcaggg gggcggagcc tatgaaaaa     1980 cgccagcaac gcggcctttt tacggttcct ggccttttgc tggccttttg ctcacatgtt    2040
ctttcctgcg ttatccctg attctgtgga taaccgtatt accgcctttg agtgagctga     2100
taccgctcgc cgcagccgaa cgaccgagcg cagcgagtca gtgagcgagg aagcggaaga    2160
gcgcccaata cgcagggccc cctgcaggat aaaaaaattg tagataaatt ttataaaata    2220
gttttatcta caatttttt atcaggaaac agctatgacc gcggccgcag atagtcataa     2280
tagttccaga atagttcaat ttagaaatta gactaaactt caaaatgttt gttaaatata    2340
taccaaacta gtatagatat ttttaaata ctggacttaa acagtagtaa tttgcctaaa     2400
aaattttttc aattttttt aaaaaatcct tttcaagttg tacattgtta tggtaatatg     2460
taattgaaga agttatgtag taatattgta acgttctt gatttttta catccatgta       2520 gtgcttaaaa aaccaaaata tgtcacatgc aattgtatat ttcaaataac aatatttatt    2580
ttctcgttaa attcacaaat aatttattaa taatatcaat aaccaagatt atacttaaat    2640
ggatgtttat tttttaacac ttttatagta aatatattta ttttatgtag taaaaaggtt    2700
ataattataa ttgtatttat tacaattaat taaaataaaa aatagggttt taggtaaaat    2760
taagttattt taagaagtaa ttacaataaa aattgaagtt atttctttaa ggagggaatt    2820
attcatatga aagaagttgt aatagctagt gcagtaagaa cagcgattgg atcttatgga    2880
aagtctctta aggatgtacc agcagtagat ttaggagcta cagctataaa ggaagcagtt    2940
aaaaaagcag gaataaaacc agaggatgtt aatgaagtca ttttaggaaa tgttcttcaa    3000
gcaggtttag gacagaatcc agcaagacag gcatctttta aagcaggatt accagttgaa    3060
attccagcta tgactattaa taaggtttgt ggttcaggac ttagaacagt tagcttagca    3120
gcacaaatta taaaagcagg agatgctgac gtaataatag caggtggtat ggaaaatatg    3180
tctagagctc cttacttagc gaataacgct agatggggat atagaatggg aaacgctaaa    3240
tttgttgatg aaatgatcac tgacggattg tgggatgcat ttaatgatta ccacatggga    3300
ataacagcag aaaacatagc tgagagatgg aacatttcaa gagaagaaca agatgagttt    3360
```

```
gctcttgcat cacaaaaaaa agctgaagaa gctataaaat caggtcaatt taaagatgaa    3420
atagttcctg tagtaattaa aggcagaaag ggagaaactg tagttgatac agatgagcac    3480
cctagatttg gatcaactat agaaggactt gcaaaattaa aacctgcctt caaaaaagat    3540
ggaacagtta cagctggtaa tgcatcagga ttaaatgact gtgcagcagt acttgtaatc    3600
atgagtgcag aaaaagctaa agagcttgga gtaaaaccac ttgctaagat agtttcttat    3660
ggttcagcag gagttgaccc agcaataatg ggatatggac ctttctatgc aacaaaagca    3720
gctattgaaa aagcaggttg gacagttgat gaattagatt taatagaatc aaatgaagct    3780
tttgcagctc aaagtttagc agtagcaaaa gatttaaaat ttgatatgaa taaagtaaat    3840
gtaaatggag gagctattgc ccttggtcat ccaattggag catcaggtgc aagaatactc    3900
gttactcttg tacacgcaat gcaaaaaaga gatgcaaaaa aaggcttagc aactttatgt    3960
ataggtggcg gacaaggaac agcaatattg ctagaaaagt gctaggaatt cgagctcggt    4020
accagggaga tattaaaatg aataaattag taaaattaac agatttaaag cgcattttca    4080
aagatggcat gacaattatg gttggggtt ttttagattg tggaactcct gaaaatatta    4140
tagatatgct agttgattta aatataaaaa atctgactat tataagcaat gatacagctt    4200
ttcctaataa aggaatagga aaacttattg taaatggtca agtttctaaa gtaattgctt    4260
cacatattgg aactaatcct gaaactggaa aaaaaatgag ctctggagaa cttaaagttg    4320
agctttcccc acaaggaaca ctgattgaaa gaattcgtgc agctggatct ggactcggag    4380
gtgtattaac tccaactgga cttggaacta tcgttgaaga aggtaagaaa aaagttacta    4440
tcgatggcaa agaatatcta ttagaacttc ctttatctgc tgatgtttca ttaataaaag    4500
gtagcattgt agatgaattt ggaaatacct tctatagggc tgctactaaa aatttcaatc    4560
catatatggc aatggctgca aaaacagtta tagttgaagc agaaaattta gttaaatgtg    4620
aagatttaaa aagagatgcc ataatgactc ctggcgtatt agtagattat atcgttaagg    4680
aggcggctta attgattgta gataaagttt tagcaaaaga gataattgcc aaaagagttg    4740
caaaagaact aaaaaaagac caactcgtaa accttggaat aggacttcca actttagtag    4800
caaattatgt accaaaagaa atgaacatta cttttgaatc agaaaatggc atggttggta    4860
tggcacaaat ggcatcatca ggtgaaaatg acccagatat aataaatgct ggcggggaat    4920
atgtaacatt attccctcaa ggttcatttt ttgatagttc aatgtctttc gcactaatac    4980
gaggaggaca tgttgatgtt gctgttcttg gtgctctaga agttgatgaa aaaggtaatt    5040
tagctaactg gattgttcca aataaaattg tcccaggtat gggtggcgct atggattttag    5100 caataggcgc aaaaaaaata atagtggcaa tgcaacatac aggaaaaagt aaacctaaaa    5160
tcgttaaaaa atgtactctc ccacttactg ctaaggctca agtggattta attgtcacag    5220
aactttgtgt aattgatgta acaaatgacg gcttactttt aaaagaaatt cataaagata    5280
caactattga tgaaattaaa tttttaacag atgcagattt aattattcca gataacttaa    5340
agattatgga tatatgaatc attctatttt aaatatataa ctttaaaaat cttatgtatt    5400
aaaaactaag aaaagaggtt gattgtttta tgttagaaag tgaagtatct aaacaaatta    5460
caactccact tgctgctcca gcgtttccta gaggaccata taggtttcac aatagagaat    5520
atctaaacat tatttatcga actgatttag atgctcttcg aaaaatagta ccagagccac    5580
ttgaattaga tagagcatat gttagattg aaatgatggc tatgcctgat acaaccggac    5640
taggctcata tacagaatgt ggtcaagcta ttccagtaaa atataatggt gttaagggtg    5700
actacttgca tatgatgtat ctagataatg aacctgctat tgctgttgga agagaaagta    5760
```

```
gcgcttatcc aaaaaagctt ggctatccaa agctatttgt tgattcagat actttagttg       5820
ggacacttaa atatggtaca ttaccagtag ctactgcaac aatgggatat aagcacgagc       5880
ctctagatct aaagaagcc tatgctcaaa ttgcaagacc caattttatg ctaaaaatca       5940
ttcaaggtta cgatggtaag ccaagaattt gtgaactaat atgtgcagaa atactgata       6000 taactattca cggtgcttgg actggaagtg cacgtctaca attatttagc catgcactag       6060
ctcctcttgc tgatttacct gtattagaga ttgtatcagc atctcatatc ctcacagatt       6120
taactcttgg aacacctaag gttgtacatg attatctttc agtaaaataa aagcaatata       6180
gaggatcctc tagagtcgac gtcacgcgtc catggagatc tcgaggcctg cagacatgca       6240
agcttggcac tggccgtcgt tttacaacgt cgtgactggg aaaaccctgg cgttacccaa       6300
cttaatcgcc ttgcagcaca tcccccttc gccagctggc gtaatagcga agaggcccgc       6360
accgatcgcc cttcccaaca gttgcgcagc ctgaatggcg aatggcgcta gcataaaaat       6420
aagaagcctg catttgcagg cttcttattt ttatggcgcg ccgcattcac ttctttctta       6480
tataaatatg agcgaagcga ataagcgtcg gaaaagcagc aaaagtttc ctttttgctg       6540 ttggagcatg ggggttcagg gggtgcagta tctgacgtca atgccgagcg aaagcgagcc       6600
gaagggtagc atttacgtta gataaccccc tgatatgctc cgacgcttta tatagaaaag       6660
aagattcaac taggtaaaat cttaatatag gttgagatga taaggtttat aaggaatttg       6720
tttgttctaa tttttcactc attttgttct aatttcttt aacaaatgtt ctttttttt       6780 tagaacagtt atgatatagt tagaatagtt taaaataagg agtgagaaaa ag              6832

<210> SEQ ID NO 47
<211> LENGTH: 2133
<212> TYPE: DNA
<213> ORGANISM: Clostridium beijerinckii

<400> SEQUENCE: 47
atgaataaat tagtaaaatt aacagattta aagcgcattt tcaaagatgg catgacaatt         60
atggttgggg gttttttaga ttgtggaact cctgaaaata ttatagatat gctagttgat        120
ttaaatataa aaatctgac tattataagc aatgatacag cttttcctaa taaggaata         180 ggaaaactta ttgtaaatgg tcaagttct aaagtaattg cttcacatat tggaactaat        240
cctgaaactg aaaaaaaat gagctctgga gaacttaaag ttgagctttc cccacaagga        300
acactgattg aaagaattcg tgcagctgga tctggactcg gaggtgtatt aactccaact        360
ggacttggaa ctatcgttga agaaggtaag aaaaagttta tctcgatgg caagaatat        420 ctattagaac ttcctttatc tgctgatgtt tcattaataa aaggtagcat tgtagatgaa        480
tttggaaata ccttctatag gctgctact aaaaatttca atccatatat ggcaatggct        540
gcaaaaacag ttatagttga agcagaaaat ttagttaaat gtgaagattt aaaaagagat        600
gccataatga ctcctggcgt attagtagat tatatcgtta aggaggcggc ttaattgatt        660
gtagataaag ttttagcaaa agagataatt gccaaaagag ttgcaaaaga actaaaaaaa        720
gaccaactcg taaaccttgg aataggactt ccaactttag tagcaaatta tgtaccaaaa        780
gaaatgaaca ttacttttga atcagaaaat ggcatggttg tatgcaca aatggcatca        840 tcaggtgaaa atgacccaga tataataaat gctggcgggg aatatgtaac attattacct        900
caaggttcat ttttgatag ttcaatgtct ttcgcactaa tacgaggagg acatgttgat        960
gttgctgttc ttggtgctct agaagttgat gaaaaaggta atttagctaa ctggattgtt       1020
```

```
ccaaataaaa ttgtcccagg tatgggtggc gctatggatt tagcaatagg cgcaaaaaaa    1080
ataatagtgg caatgcaaca tacaggaaaa agtaaaccta aaatcgttaa aaaatgtact    1140
ctcccactta ctgctaaggc tcaagtggat ttaattgtca cagaactttg tgtaattgat    1200
gtaacaaatg acggcttact tttaaaagaa attcataaag atacaactat tgatgaaatt    1260
aaatttttaa cagatgcaga tttaattatt ccagataact aaagattat ggatatatga    1320 atcattctat tttaaatata taactttaaa aatcttatgt attaaaaact aagaaaagag    1380
gttgattgtt ttatgttaga aagtgaagta tctaaacaaa ttacaactcc acttgctgct    1440
ccagcgtttc ctagaggacc ataggtttt cacaatagag aatatctaaa cattatttat     1500
cgaactgatt tagatgctct tcgaaaaata gtaccagagc cacttgaatt agatagagca    1560
tatgttagat ttgaaatgat ggctatgcct gatacaaccg gactaggctc atatacagaa    1620
tgtggtcaag ctattccagt aaaatataat ggtgttaagg gtgactactt gcatatgatg    1680
tatctagata tgaacctgc tattgctgtt ggaagagaaa gtagcgctta tccaaaaaag      1740
cttggctatc caaagctatt tgttgattca gatactttag ttgggacact aaatatggt      1800 acattaccag tagctactgc aacaatggga tataagcacg agcctctaga tcttaaagaa    1860
gcctatgctc aaattgcaag acccaatttt atgctaaaaa tcattcaagg ttacgatggt    1920
aagccaagaa tttgtgaact aatatgtgca gaaaatactg atataactat tcacggtgct    1980
tggactggaa gtgcacgtct acaattattt agccatgcac tagctcctct tgctgattta    2040
cctgtattag agattgtatc agcatctcat atcctcacag atttaactct tggaacacct    2100
aaggttgtac atgattatct ttcagtaaaa taa                                 2133

<210> SEQ ID NO 48
<211> LENGTH: 7922
<212> TYPE: DNA
<213> ORGANISM: Artificial sequence
<220> FEATURE:
<223> OTHER INFORMATION: synthetic plasmid

<400> SEQUENCE: 48
atgaaagaaa gatatggaac agtctataaa ggctctcaga ggctcataga cgaagaaagt      60
ggagaagtca tagaggtaga caagttatac cgtaaacaaa cgtctggtaa cttcgtaaag     120
gcatatatag tgcaattaat aagtatgtta gatatgattg gcggaaaaaa acttaaaatc     180
gttaactata tcctagataa tgtccactta agtaacaata caatgatagc tacaacaaga     240
gaaatagcaa aagctacagg aacaagtcta caaacagtaa taacaacact taaaatctta     300
gaagaaggaa atattataaa aagaaaaact ggagtattaa tgttaaaccc tgaactacta     360
atgagaggcg acgaccaaaa acaaaaatac ctcttactcg aatttgggaa cttttgagcaa    420 gaggcaaatg aaatagattg acctcccaat aacaccacgt agttattggg aggtcaatct     480
atgaaatgcg attaagggcc ggccagtggg caagttgaaa aattcacaaa atgtggtat      540 aatatctttg ttcattagag cgataaactt gaatttgaga gggaacttag atggtatttg     600
aaaaaattga taaaaatagt tggaacagaa aagagtattt tgaccactac tttgcaagtg     660
taccttgtac ctcagcatg accgttaaag tggatatcac acaaataaag gaaaagggaa      720
tgaaactata tcctgcaatg ctttattata ttgcaatgat tgtaaaccgc cattcagagt     780
ttaggacggc aatcaatcaa gatggtgaat tggggatata tgatgagatg ataccaagct     840
atacaatatt tcaatgtgat actgaaacat tttccagcct ttggactgag tgtaagtctg     900
actttaaatc atttttagca gattatgaaa gtgatacgca acggtatgga aacaatcata     960
```

```
gaatggaagg aaagccaaat gctccggaaa acattttaa tgtatctatg ataccgtggt    1020
caaccttcga tggctttaat ctgaatttgc agaaaggata tgattatttg attcctattt    1080
ttactatggg gaaatattat aaagaagata acaaaattat acttcctttg gcaattcaag    1140
ttcatcacgc agtatgtgac ggatttcaca tttgccgttt tgtaaacgaa ttgcaggaat    1200
tgataaatag ttaacttcag gtttgtctgt aactaaaaac aagtatttaa gcaaaaacat    1260
cgtagaaata cggtgttttt tgttacccta agtttaaact ccttttgat aatctcatga    1320 ccaaaatccc ttaacgtgag ttttcgttcc actgagcgtc agaccccgta gaaaagatca    1380
aaggatcttc ttgagatcct ttttttctgc gcgtaatctg ctgcttgcaa acaaaaaaac    1440
caccgctacc agcggtggtt tgtttgccgg atcaagagct accaactctt tttccgaagg    1500
taactggctt cagcagagcg cagataccaa atactgttct tctagtgtag ccgtagttag    1560
gccaccactt caagaactct gtagcaccgc ctacatacct cgctctgcta atcctgttac    1620
cagtggctgc tgccagtggc gataagtcgt gtcttaccgg gttggactca agacgatagt    1680
taccggataa ggcgcagcgg tcgggctgaa cggggggttc gtgcacacag cccagcttgg    1740
agcgaacgac ctacaccgaa ctgagatacc tacagcgtga gctatgagaa agcgccacgc    1800
ttcccgaagg gagaaaggcg gacaggtatc cggtaagcgg cagggtcgga acaggagagc    1860
gcacgaggga gcttccaggg ggaaacgcct ggtatcttta tagtcctgtc gggtttcgcc    1920
acctctgact tgagcgtcga tttttgtgat gctcgtcagg gggggggagc ctatggaaaa    1980
acgccagcaa cgcggccttt ttacggttcc tggccttttg ctggcctttt gctcacatgt    2040
tctttcctgc gttatcccct gattctgtgg ataaccgtat taccgccttt gagtgagctg    2100
ataccgctcg ccgcagccga acgaccgagc gcagcgagtc agtgagcgag gaagcggaag    2160
agcgcccaat acgcagggcc ccctgcagga taaaaaaatt gtagataaat tttataaaat    2220
agttttatct acaattttt tatcaggaaa cagctatgac cgcggccgca gatagtcata    2280
atagttccag aatagttcaa tttagaaatt agactaaact tcaaatgtt tgttaaatat    2340 ataccaaact agtatagata ttttttaaat actggactta aacagtagta atttgcctaa    2400 aaaattttt caatttttt taaaaaatcc ttttcaagtt gtacattgtt atggtaatat    2460
gtaattgaag aagttatgta gtaatattgt aaacgtttct tgattttttt acatccatgt    2520
agtgcttaaa aaaccaaaat atgtcacatg caattgtata tttcaaataa caatatttat    2580
tttctcgtta aattcacaaa taatttatta ataatatcaa taaccaagat tatacttaaa    2640
tggatgttta ttttttaaca cttttatagt aaatatattt attttatgta gtaaaaaggt    2700
tataattata attgtatttta ttacaattaa ttaaaataaaa aatagggtt ttaggtaaaa    2760 ttaagttatt ttaagaagta attacaataa aaattgaagt tatttctta aggagggaat    2820 tattcatatg aaagaagttg taatagctag tgcagtaaga acagcgattg gatcttatgg    2880
aaagtctctt aaggatgtac cagcagtaga tttaggagct acagctataa aggaagcagt    2940
taaaaaagca ggaataaaac cagaggatgt taatgaagtc attttaggaa atgttcttca    3000
agcaggttta ggacagaatc cagcaagaca ggcatctttt aaagcaggat taccagttga    3060
aattccagct atgactatta ataaggtttg tggttcagga cttagaacag ttagcttagc    3120
agcacaaatt ataaaagcag gagatgctga cgtaataata gcaggtggta tggaaaatat    3180
gtctagagct ccttacttag cgaataacgc tagatgggga tatagaatgg gaaacgctaa    3240
atttgttgat gaaatgatca ctgacggatt gtgggatgca tttaatgatt accacatggg    3300
```

```
aataacagca gaaaacatag ctgagagatg gaacatttca agagaagaac aagatgagtt    3360
tgctcttgca tcacaaaaaa aagctgaaga agctataaaa tcaggtcaat ttaaagatga    3420
aatagttcct gtagtaatta aaggcagaaa gggagaaact gtagttgata cagatgagca    3480
ccctagattt ggatcaacta tagaaggact tgcaaaatta aaacctgcct tcaaaaaaga    3540
tggaacagtt acagctggta atgcatcagg attaaatgac tgtgcagcag tacttgtaat    3600
catgagtgca gaaaaagcta aagagcttgg agtaaaacca cttgctaaga tagtttctta    3660
tggttcagca ggagttgacc cagcaataat gggatatgga cctttctatg caacaaaagc    3720
agctattgaa aaagcaggtt ggacagttga tgaattagat ttaatagaat caaatgaagc    3780
ttttgcagct caaagtttag cagtagcaaa agatttaaaa tttgatatga ataaagtaaa    3840
tgtaaatgga ggagctattg cccttggtca tccaattgga gcatcaggtg caagaatact    3900
cgttactctt gtacacgcaa tgcaaaaaag agatgcaaaa aaaggcttag aactttatg    3960 tataggtggc ggacaaggaa cagcaatatt gctagaaaag tgctaggaat tcgagctcgg    4020
taccagggag atattaaaat gaataaatta gtaaaattaa cagatttaaa gcgcattttc    4080
aaagatggca tgacaattat ggttgggggt ttttagatt gtggaactcc tgaaaatatt    4140
atagatatgc tagttgattt aaatataaaa aatctgacta ttataagcaa tgatacagct    4200
tttcctaata aaggaatagg aaaacttatt gtaaatggtc aagtttctaa agtaattgct    4260
tcacatattg gaactaatcc tgaaactgga aaaaaaatga gctctggaga acttaaagtt    4320
gagctttccc cacaaggaac actgattgaa agaattcgtg cagctggatc tggactcgga    4380
ggtgtattaa ctccaactgg acttggaact atcgttgaag aaggtaagaa aaaagttact    4440
atcgatggca aagaatatct attagaactt ccttatctg ctgatgtttc attaataaaa    4500
ggtagcattg tagatgaatt tggaaatacc ttctataggg ctgctactaa aaatttcaat    4560
ccatatatgg caatggctgc aaaaacagtt atagttgaag cagaaaattt agttaaatgt    4620
gaagatttaa aaagagatgc cataatgact cctggcgtat tagtagatta tatcgttaag    4680
gaggcggctt aattgattgt agataaagtt ttagcaaaag agataattgc caaaagagtt    4740
gcaaaagaac taaaaaaga ccaactcgta aaccttggaa taggacttcc aactttagta    4800
gcaaattatg taccaaaaga aatgaacatt acttttgaat cagaaaatgg catggttggt    4860
atggcacaaa tggcatcatc aggtgaaaat gacccagata taataaatgc tggcggggaa    4920
tatgtaacat tattacctca aggttcattt tttgatagtt caatgtcttt cgcactaata    4980
cgaggaggac atgttgatgt tgctgttctt ggtgctctag aagttgatga aaaaggtaat    5040
ttagctaact ggattgttcc aaataaaatt gtcccaggta tgggtggcgc tatggattta    5100
gcaataggcg caaaaaaaat aatagtggca atgcaacata caggaaaaag taaacctaaa    5160
atcgttaaaa aatgtactct cccacttact gctaaggctc aagtggattt aattgtcaca    5220
gaactttgtg taattgatgt aacaaatgac ggcttacttt taaagaaat tcataaagat    5280 acaactattg atgaaattaa attttaaca gatgcagatt taattattcc agataactta    5340
aagattatgg atatatgaat cattctattt taaatatata actttaaaaa tcttatgtat    5400
taaaaactaa gaaagaggt tgattgtttt atgttagaaa gtgaagtatc taaacaaatt    5460
acaactccac ttgctgctcc agcgtttcct agaggaccat ataggtttca aatagagaa    5520 tatctaaaca ttatttatcg aactgattta gatgctcttc gaaaaatagt accagagcca    5580
cttgaattag atagagcata tgttagattt gaaatgatgg ctatgcctga tacaaccgga    5640
ctaggctcat atacagaatg tggtcaagct attccagtaa aatataatgg tgttaagggt    5700
```

```
gactacttgc atatgatgta tctagataat gaacctgcta ttgctgttgg aagagaaagt      5760
agcgcttatc caaaaaagct tggctatcca aagctatttg ttgattcaga tactttagtt      5820
gggacactta aatatggtac attaccagta gctactgcaa caatgggata taagcacgag      5880
cctctagatc ttaaagaagc ctatgctcaa attgcaagac ccaattttat gctaaaaatc      5940
attcaaggtt acgatggtaa gccaagaatt tgtgaactaa tatgtgcaga aaatactgat      6000
ataactattc acggtgcttg gactggaagt gcacgtctac aattatttag ccatgcacta      6060
gctcctcttg ctgatttacc tgtattagag attgtatcag catctcatat cctcacagat      6120
ttaactcttg gaacacctaa ggttgtacat gattatcttt cagtaaaata aaagcaatat      6180
agaggatcct ctagagtcga cttaggaggt tctattatga aaggttttgc aatgttaggt      6240
attaacaaat taggatggat tgaaaagaaa aacccagtgc caggtcctta tgatgcgatt      6300
gtacatcctc tagctgtatc cccatgtaca tcagatatac atacggtttt tgaaggagca      6360
cttggtaata gggaaaatat gattttaggc catgaagctg taggtgaaat agccgaagtt      6420
ggcagcgaag ttaaagattt taaagttggc gatagagtta tcgtaccatg cacaacacct      6480
gactggagat ctttagaagt ccaagctggt tttcagcagc attcaaacgg tatgcttgca      6540
ggatggaagt tttccaattt taaagatggt gtatttgcag attactttca tgtaaacgat      6600
gcagatatga atcttgccat actcccagat gaaatacctt tagaaagtgc agttatgatg      6660
acagacatga tgactactgg ttttcatgga gcagaacttg cagacataaa aatgggctcc      6720
agcgttgtag taattggtat aggagctgtt ggattaatgg aatagccggt ttccaaactt      6780
cgaggagcag gcagaattat cggtgttgga agcagacctg tttgtgttga aacagctaaa      6840
ttttatggag caactgatat tgtaaattat aaaaatggtg atatagttga acaaatcatg      6900
gacttaactc atggtaaagg tgtagaccgt gtaatcatgg caggcggtgg tgctgaaaca      6960
ctagcacaag cagtaactat ggttaaacct ggcggcgtaa tttctaacat caactaccat      7020
ggaagcggtg atactttacc aatacctcgt gttcaatggg gctgcggcat ggctcacaaa      7080
actataagag gaggattatg ccccggcgga cgtcttagaa tggaaatgct aagagatctt      7140
gttctatata acgtgttga tttgagtaaa cttgttactc atgtatttga tggtgcagaa      7200
aatattgaaa aggcccttt gcttatgaaa aataagccaa aagatttaat taaatcagta      7260
gttacattct aaaaattcat ataaaaaaac tgtcgcatta aaaaaatgtc tcgaggcctg      7320
cagacatgca agcttggcac tggccgtcgt tttacaacgt cgtgactggg aaaaccctgg      7380
cgttacccaa cttaatcgcc ttgcagcaca tccccctttc gccagctggc gtaatagcga      7440
agaggcccgc accgatcgcc cttcccaaca gttgcgcagc ctgaatggcg aatggcgcta      7500
gcataaaaat aagaagcctg catttgcagg cttcttattt ttatggcgcg ccgcattcac      7560
ttcttttcta tataaatatg agcgaagcga ataagcgtcg gaaaagcagc aaaaagtttc      7620 cttttgctg ttggagcatg ggggttcagg gggtgcagta tctgacgtca atgccgagcg      7680
aaagcgagcc gaagggtagc atttacgtta gataaccccc tgatatgctc cgacgcttta      7740
tatagaaaag aagattcaac taggtaaaat cttaatatag gttgagatga taggttttat       7800
aaggaatttg tttgttctaa ttttttcactc attttgttct aatttcttt aacaaatgtt      7860 cttttttttt tagaacagtt atgatatagt tagaatagtt taaaataagg agtgagaaaa      7920
ag                                                                     7922

<210> SEQ ID NO 49
```

<211> LENGTH: 4709
<212> TYPE: DNA
<213> ORGANISM: Artificial sequence
<220> FEATURE:
<223> OTHER INFORMATION: synthetic plasmid

<400> SEQUENCE: 49

| | | | | | |
|---|---|---|---|---|---|
| gtttgccacc | tgacgtctaa | gaaaaggaat | attcagcaat | ttgcccgtgc | cgaagaaagg | 60 |
| cccacccgtg | aaggtgagcc | agtgagttga | ttgctacgta | attagttagt | tagcccttag | 120 |
| tgactcgtaa | tacgactcac | tatagggctc | gaggcggccg | cgcaacgcaa | ttaatgtgag | 180 |
| ttagctcact | cattaggcac | cccaggcttt | acactttatg | cttccggctc | gtatgttgtg | 240 |
| tggaattgtg | agcggataac | aatttcacac | aggaaacaca | tatgtttccg | tgcaatgcct | 300 |
| atatcgaata | tggtgataaa | aatatgaaca | gctttatcga | agatgtggaa | cagatctaca | 360 |
| acttcattaa | aaagaacatt | gatgtggaag | aaaagatgca | tttcattgaa | acctataaac | 420 |
| agaaaagcaa | catgaagaaa | gagattagct | ttagcgaaga | atactataaa | cagaagatta | 480 |
| tgaacggcaa | aaatggcgtt | gtgtacaccc | cgccggaaat | ggcggccttt | atggttaaaa | 540 |
| atctgatcaa | cgttaacgat | gttattggca | atccgtttat | taaaatcatt | gacccgagct | 600 |
| gcggtagcgg | caatctgatt | tgcaaatgtt | ttctgtatct | gaatcgcatc | tttattaaga | 660 |
| acattgaggt | gattaacagc | aaaaataacc | tgaatctgaa | actggaagac | atcagctacc | 720 |
| acatcgttcg | caacaatctg | tttggcttcg | atattgacga | aaccgcgatc | aaagtgctga | 780 |
| aaattgatct | gtttctgatc | agcaaccaat | ttagcgagaa | aaatttccag | gttaaagact | 840 |
| ttctggtgga | aaatattgat | cgcaaatatg | acgtgttcat | tggtaatccg | ccgtatatcg | 900 |
| gtcacaaaag | cgtggacagc | agctacagct | acgtgctgcg | caaaatctac | ggcagcatct | 960 |
| accgcgacaa | aggcgatatc | agctattgtt | tctttcagaa | gagcctgaaa | tgtctgaagg | 1020 |
| aaggtggcaa | actggtgttt | gtgaccagcc | gctacttctg | cgagagctgc | agcggtaaag | 1080 |
| aactgcgtaa | attcctgatc | gaaaacacga | gcatttacaa | gatcattgat | ttttacggca | 1140 |
| tccgcccgtt | caaacgcgtg | gtatcgatc | cgatgattat | ttttctggtt | cgtacgaaga | 1200 |
| actggaacaa | taacattgaa | attattcgcc | cgaacaagat | tgaaaagaac | gaaaagaaca | 1260 |
| aattcctgga | tagcctgttc | ctggacaaaa | gcgaaaagtg | taaaaagttt | agcattagcc | 1320 |
| agaaaagcat | taataacgat | ggctgggttt | tcgtggacga | agtggagaaa | aacattatcg | 1380 |
| acaaaatcaa | agagaaaagc | aagttcattc | tgaaagatat | ttgccatagc | tgtcaaggca | 1440 |
| ttatcaccgg | ttgtgatcgc | gccttttattg | tggaccgtga | tatcatcaat | agccgtaaga | 1500 |
| tcgaactgcg | tctgattaaa | ccgtggatta | aaagcagcca | tatccgtaag | aatgaagtta | 1560 |
| ttaagggcga | aaaattcatc | atctatagca | acctgattga | gaatgaaacc | gagtgtccga | 1620 |
| atgcgattaa | atatatcgaa | cagtacaaga | aacgtctgat | ggagcgccgc | gaatgcaaaa | 1680 |
| agggcacgcg | taagtggtat | gaactgcaat | ggggccgtaa | accggaaatc | ttcgaagaaa | 1740 |
| agaaaattgt | tttcccgtat | aaaagctgtg | acaatcgttt | tgcactggat | aagggtagct | 1800 |
| attttagcgc | agacatttat | agcctggttc | tgaagaaaaa | tgtgccgttc | acctatgaga | 1860 |
| tcctgctgaa | tatcctgaat | agcccgctgt | acgagtttta | ctttaagacc | ttcgcgaaaa | 1920 |
| agctgggcga | aatctgtac | gagtactatc | cgaacaacct | gatgaagctg | tgcatcccga | 1980 |
| gcatcgattt | cggcggtgag | aacaatattg | agaaaagct | gtatgatttc | tttggtctga | 2040 |
| cggataaaga | aattgagatt | gtggagaaga | tcaaagataa | ctgctaagaa | ttcgatatca | 2100 |
| cccgggaact | agtctgcagc | cctttagtga | gggttaattg | gagtcactaa | gggttagtta | 2160 |

```
gttagattag cagaaagtca aaagcctccg accggaggct tttgactaaa acttcccttg    2220
gggttatcat tggggctcac tcaaaggcgg taatcagata aaaaaaatcc ttagctttcg    2280
ctaaggatga tttctgctag agatggaata gactggatgg aggcggataa agttgcagga    2340
ccacttctgc gctcggccct tccggctggc tggtttattg ctgataaatc tggagccggt    2400
gagcgtgggt ctcgcggtat cattgcagca ctggggccag atggtaagcc ctcccgtatc    2460
gtagttatct acacgacggg gagtcaggca actatggatg aacgaaatag acagatcgct    2520
gagataggtg cctcactgat taagcattgg taactgtcag accaagttta ctcatatata    2580
ctttagattg atttaaaact tcattttaa tttaaaagga tctaggtgaa gatccttttt    2640
gataatctca tgaccaaaat cccttaacgt gagttttcgt tccactgagc gtcagacccc    2700
ttaataagat gatcttcttg agatcgtttt ggtctgcgcg taatctcttg ctctgaaaac    2760
gaaaaaaccg ccttgcaggg cggttttttcg aaggttctct gagctaccaa ctctttgaac    2820
cgaggtaact ggcttggagg agcgcagtca ccaaaacttg tcctttcagt ttagccttaa    2880
ccggcgcatg acttcaagac taactcctct aaatcaatta ccagtggctg ctgccagtgg    2940
tgcttttgca tgtctttccg ggttggactc aagacgatag ttaccggata aggcgcagcg    3000
gtcggactga acgggggggtt cgtgcataca gtccagcttg gagcgaactg cctacccgga    3060
actgagtgtc aggcgtggaa tgagacaaac gcggccataa cagcggaatg acaccggtaa    3120
accgaaaggc aggaacagga gagcgcacga gggagccgcc aggggaaacg cctggtatct    3180
ttatagtcct gtcgggtttc gccaccactg atttgagcgt cagatttcgt gatgcttgtc    3240
aggggggcgg agcctatgga aaaacggctt tgccgcggcc ctctcacttc cctgttaagt    3300
atcttcctgg catcttccag gaaatctccg cccgttcgt aagccatttc cgctcgccgc    3360
agtcgaacga ccgagcgtag cgagtcagtg agcgaggaag cggaatatat cctgtatcac    3420
atattctgct gacgcaccgg tgcagccttt tttctcctgc cacatgaagc acttcactga    3480
caccctcatc agtgccaaca tagtaagcca gtatacactc cgctagcgct gaggtctgcc    3540
tcgtgaagaa ggtgttgctg actcatacca ggcctgaatc gccccatcat ccagccagaa    3600
agtgagggag ccacggttga tgagagcttt gttgtaggtg gaccagttgg tgattttgaa    3660
cttttgcttt gccacggaac ggtctgcgtt gtcgggaaga tgcgtgatct gatccttcaa    3720
ctcagcaaaa gttcgattta ttcaacaaag ccacgttgtg tctcaaaatc tctgatgtta    3780
cattgcacaa gataaaaata tatcatcatg aacaataaaa ctgtctgctt acataaacag    3840
taatacaagg ggtgtttact agaggttgat cgggcacgta agaggttcca actttcacca    3900
taatgaaata agatcactac cgggcgtatt ttttgagtta tcgagatttt caggagctaa    3960
ggaagctaaa atggagaaaa aaatcacggg atataccacc gttgatatat cccaatggca    4020
tcgtaaagaa cattttgagg catttcagtc agttgctcaa tgtacctata accagaccgt    4080
tcagctggat attacggcct ttttaaagac cgtaaagaaa aataagcaca gttttatcc    4140 ggcctttatt cacattcttg cccgcctgat gaacgctcac ccggagtttc gtatggccat    4200
gaaagacggt gagctggtga tctgggatag tgttcaccct tgttacaccg ttttccatga    4260
gcaaactgaa acgttttcgt ccctctggag tgaataccac gacgatttcc ggcagtttct    4320
ccacatatat tcgcaagatg tggcgtgtta cggtgaaaac ctggcctatt tccctaaagg    4380
gtttattgag aatatgtttt ttgtctcagc caatccctgg gtgagtttca ccagttttga    4440
tttaaacgtg gccaatatgg acaacttctt cgccccccgtt ttcacgatgg gcaaatatta    4500
```

| | |
|---|---|
| tacgcaaggc gacaaggtgc tgatgccgct ggcgatccag gttcatcatg ccgtttgtga | 4560 |
| tggcttccat gtcggccgca tgcttaatga attacaacag tactgtgatg agtggcaggg | 4620 |
| cggggcgtaa taatactagc tccggcaaaa aaacgggcaa ggtgtcacca ccctgccctt | 4680 |
| tttctttaaa accgaaaaga ttacttcgc | 4709 |

<210> SEQ ID NO 50
<211> LENGTH: 128
<212> TYPE: DNA
<213> ORGANISM: Escherichia coli

<400> SEQUENCE: 50

| | |
|---|---|
| gcggccgcgc aacgcaatta atgtgagtta gctcactcat taggcacccc aggctttaca | 60 |
| ctttatgctt ccggctcgta tgttgtgtgg aattgtgagc ggataacaat ttcacacagg | 120 |
| aaacacat | 128 |

<210> SEQ ID NO 51
<211> LENGTH: 560
<212> TYPE: DNA
<213> ORGANISM: Clostridium autoethanogenum

<400> SEQUENCE: 51

| | |
|---|---|
| ttataagaaa tcctaaggaa tatgatgtaa tgagtaaagc tataaatcct tatggagatg | 60 |
| gcaaggcagc ttatagaata acagaagcta ttttacaata ttttgattta gcaaaaggta | 120 |
| catatagtga gtttaaatca aattaaaaag ttataatttt caattttcat tctttttaaa | 180 |
| ggagattagc atacatttta tcataattat acagacaata tagtaatata tgatgttaaa | 240 |
| atatcaatat atggttaaaa atctgtatat ttttccccat tttaattatt tgtactataa | 300 |
| tattcactg agtgtattgt atatttaaaa aatatttggt acaattagtt agttaaataa | 360 |
| attctaaatt gtaaattatc agaatcctta ttaaggaaat acatagattt aaggagaaat | 420 |
| cataaaaagg tgtaatataa actggctaaa attgagcaaa aattgagcaa ttaagacttt | 480 |
| ttgattgtat cttttatat atttaaggta tataatctta tttatattgg gggaacttga | 540 |
| tgaataaaca tattctagac | 560 |

<210> SEQ ID NO 52
<211> LENGTH: 297
<212> TYPE: DNA
<213> ORGANISM: Clostridium autoethanogenum

<400> SEQUENCE: 52

| | |
|---|---|
| taattttttg tgtcaataat ttttgttata ttatttaat taaattttc acatgtataa | 60 |
| ttaaagtaa gatagatatt ctaatgtact tacttaggta gaaaaacatg tatacaaaat | 120 |
| taaaaaacta ttataacaca tagtatcaat attgaaggta atactgttca atatcgatac | 180 |
| agataaaaaa atatataata cagaagaaaa aattataaat ttgtggtata atataaagta | 240 |
| tagtaattta agtttaaacc tcgtgaaaac gctaacaaat aataggaggt gtattat | 297 |

<210> SEQ ID NO 53
<211> LENGTH: 599
<212> TYPE: DNA
<213> ORGANISM: Clostridium autoethanogenum

<400> SEQUENCE: 53

| | |
|---|---|
| atagtataac tttaaaaaac tgtcttaaaa agttgttata taaaaaatgt tgacaattaa | 60 |
| acagctattt agtgcaaaac aaccataaaa atttaaaaaa taccataaat tacttgaaaa | 120 |

```
atagttgata ataatgtaga gttataaaca aaggtgaaaa gcattacttg tattcttttt    180
tatatattat tataaattaa aatgaagctg tattagaaaa aatacacacc tgtaatataa    240
aattttaaat taattttttaa ttttttcaaa atgtattta catgtttaga attttgatgt    300
atattaaaat agtagaatac ataagatact taatttaatt aaagatagtt aagtactttt    360
caatgtgctt ttttagatgt ttaatacaaa tctttaattg taaaagaaat gctgtactat    420
ttactgtact agtgacggga ttaaactgta ttaattataa ataaaaaata agtacagttg    480
tttaaaatta tattttgtat taaatctaat agtacgatgt aagttattt atactattgc    540 tagtttaata aaaagattta attatatact tgaaaggag aggaattttt atgcgtaaa    599
```

```
<210> SEQ ID NO 54
<211> LENGTH: 34
<212> TYPE: DNA
<213> ORGANISM: Clostridium autoethanogenum

<400> SEQUENCE: 54
tatttgtcga cttaggaggt tctattatga aagg                                34
```

```
<210> SEQ ID NO 55
<211> LENGTH: 30
<212> TYPE: DNA
<213> ORGANISM: Clostridium autoethanogenum

<400> SEQUENCE: 55
aaaactcgag acatttttt aatgcgacag                                      30
```

```
<210> SEQ ID NO 56
<211> LENGTH: 560
<212> TYPE: DNA
<213> ORGANISM: Clostridium ljungdahlii

<400> SEQUENCE: 56
agatagtcat aatagttcca gaatagttta atttagcatt tggattaaat tcccatatgt     60
ttgttaaata taccaaac tagtatagat attttttaaaa tactgtactt aaacagtagt    120
aatttacgta aaaaaatttt ttgattttt taaaaagtc cttttcaagt tgtacattat    180
tatggtaata tgtaattgaa gaagttgtgt agtaatattg taaacgtttc ttaatttatt    240
ttcatccatg tagtgcttaa aaaaccaaaa tatgtcacac gcaattgcat atttcaaaca    300
ataatattta ttttctcgtt aaattcacaa ataatttatt aataatatca ataaccaaga    360
ttatacttaa atggatgttt attttttaac attttttata gtaaatatat ttattttatg    420
tagtaaaaag gttataatta taattgtatt tattacaatt aattaaaata aaaaaatagg    480
gttttaggta aaattaagtt attttaagaa gtaattacaa caaaaattga agttatttct    540
ttaaggaggg aattattaaa                                                560
```

```
<210> SEQ ID NO 57
<211> LENGTH: 557
<212> TYPE: DNA
<213> ORGANISM: Clostridium ragsdalei

<400> SEQUENCE: 57
agatagtcat aatagttcca gaatagttta attttgaaat tggagtaaac ttccaaatgt     60
ttgttaaata taccaaac tagtatagat attttttaaaa tactagactt aaacagtaga    120
aatttgccta aaaaatttt tagtttttta aaaaaatcct tttcaagttg tacgttatta    180
```

```
tggtaatatg taattgaaga agttatgtaa taatattgta aacgtttctt aattttttta    240
catccatgta atgcttaaaa gaccaaaata tgtcacatgt aattgtatat ttcacataat    300
aatatttatt ttcttattaa attcacaaat aatttattaa taatatcaat aaccaagatt    360
atacttaaat ggatgtttat tttttaacat ttttttatggt aaatatattt attttatgta   420
gtaaaaaggt tataattata attgtattta ttacaattaa ttaaaataaa aaatagggtt    480
ttaggtaaaa ttaagttatt ttaagaagta attacaacaa aaattgaagt tatttctttta  540 aggagggaat tattaaa                                                   557

<210> SEQ ID NO 58
<211> LENGTH: 536
<212> TYPE: DNA
<213> ORGANISM: Clostridium ljungdahlii

<400> SEQUENCE: 58
ttataagaaa tcctaaggaa tatgatgtaa tgagtaaagc tataaatcct tatggagatg     60
gcaaggcagc ttatagaata acagaagcta ttttacaata ttttgattta gcaaaaggta    120
catatagtga gtttaaatca aattaaaaag ttataatttt caatttttcat tcttttttaaa  180 ggagattagc atacatttta tcataattat acagacaata tagtaatata tgatgttaaa    240
atatcaatat atggtaaaaa atctgtatat tttttcccat tttaattatt tgtactataa    300
tattacactg agtgtattgt atatttaaaa aatatttggt acaattagtt agttaaataa    360
attctaaatt gtaaattatc agaatcctta ttaaggaaat acatagattt aaggagaaat    420
cataaaaagg tgtaatataa actggctaaa attgagcaaa aattgagcaa ttaagacttt    480
ttgattgtat cttttttatat atttaaggta tataatctta tttatattgg gggaac       536

<210> SEQ ID NO 59
<211> LENGTH: 549
<212> TYPE: DNA
<213> ORGANISM: Clostridium ragsdalei

<400> SEQUENCE: 59
ttataagaaa tcctaaggaa tatgatgtaa tgagtaaagc tataaatcct tatggagatg     60
gcaaggcagc ttatagaata acagaagcta ttttacaata ttttgattta gcaaaaggta    120
catatagtga gtttaaatca aattaaaaag ttataatttt gaattttcat tcttttttaaa   180 ggagattagc atacatttta tcataattat acagacaata tagtaatata tgatgttaaa    240
atatcaatat atggtaaaaa aactgtatat tttttcccat tttaattatt tgtactataa    300
tattacactg agtgtattgt atatttaaaa aatatttggt acaattagtt agttaaataa    360
attctaaatt ataaattatc agaaccctta ttaaggaaat acatagattt agggagaaat    420
aataaaaagg tgtaatataa actggctaaa gttgagtaat taagactttt aggttgtatc    480
tttttatata tttaaggtat ataatcttag ttatataggg ggaacttgat gaataaacat    540
attctagac                                                           549

<210> SEQ ID NO 60
<211> LENGTH: 298
<212> TYPE: DNA
<213> ORGANISM: Clostridium ljungdahlii

<400> SEQUENCE: 60 taatttttttg tgtcaataat ttttgttata ttatttttaat taaattttttc acatgtataa   60 ttaaaagtaa gatagatatt ctaatgtact tacttaggta gaaaaacatg tatacaaaat    120
```

```
taaaaaacta ttataacaca tagtatcaat attgaaggta atactgttca atatcgatac    180
agataaaaaa aatatataat acagaagaaa aaattataaa tttgtggtat aatataaagt    240
atagtaattt aagtttaaac ctcgtgaaaa cgctaacaaa taataggagg tgtattat     298
```

<210> SEQ ID NO 61
<211> LENGTH: 300
<212> TYPE: DNA
<213> ORGANISM: Clostridium ragsdalei

<400> SEQUENCE: 61

```
taattttttta tatcaataat ttttattata ttatttaat taaattttttc acatgtataa    60 ttaaaagtaa gatagagata gttaggatat tttagtgcat ttatttagat aaaaaatatg   120
tatacaagat tagaaaaaaa ttaacacaca taatagttgc attgaaggta atactgttca   180
atatcgatac agataaaaaa atttataata cagaagaaaa aaatataaat ttgtggtata   240
atataaaata taataattta gatttacacc ccgtgaaaac gctaacaaat aaatagggag   300
```

<210> SEQ ID NO 62
<211> LENGTH: 590
<212> TYPE: DNA
<213> ORGANISM: Clostridium ljungdahlii

<400> SEQUENCE: 62

```
atagtataac tttaaaaaac tgtcttaaaa agttgttata taaaaaatgt tgacaattaa    60
acagctattt agtgcaaaac aaccataaaa atttaaaaaa taccataaat tacttgaaaa   120
atagttgata ataatgtaga gttataaaca aaggtgaaaa gcattacttg tattcttttt   180
tatatattat tataaattaa aatgaagctg tattagaaaa aatacacacc tgtaatataa   240 aatttttaaat taatttttaa ttttttcaaa atgtatttta catgtttaga attttgatgt   300
atattaaaat agtagaatac ataagatact taatttaatt aaagatagtt aagtactttt   360
caatgtgctt ttttagatgt ttaatacaaa tcttttaattg taaaagaaat gctgtactat   420
ttactgtact agtgacggga ttaaactgta ttaattataa ataaaaaata agtacagttg   480
tttaaaatta tattttgtat taaatctaat agtacgatgt aagttatttt atactattgc   540
tagtttaata aaaagattta attatatact tgaaaaggag aggaatttttt                590
```

<210> SEQ ID NO 63
<211> LENGTH: 600
<212> TYPE: DNA
<213> ORGANISM: Clostridium ragsdalei

<400> SEQUENCE: 63
atagaataac ttaaaaaaac tgtcttaaaa agctgttata taaaaaaatg ttaacaatta 60
aacagctatt tagtgcaaaa caaccataaa aatttaaaaa ataccataaa ttacttgaaa 120
aatagtagag aataatgtag agttataaac gaaggtgaaa agcattactt gtattccttt 180
ttacagacta ttataaatta agataaagct gtattaggaa aaatgcacac ctgtaatata 240
aggttttaaa ttaattttta attttcccaa aatgtatttt acatgtttag aattttgatg 300
tatattaaaa tagtagaata cataagatac ttaatttaat aaagatagtt aagtactttt 360
caatgtactt ttttagatat ttaatacaag tttttaattg taaaaaaatg ctgtgctatt 420
tactgtacta atggtagtac tatatctgta ttaattgtat gtaaaaagta agtatagtta 480
tttaagatta tgttttgtat taaatctaaa tagtacaatg taggttatgt tatactattg 540
ctagtttaat aaaaagattt aattatatac ttgaaaagga gaggaatttt tatgcgtaaa    600

<210> SEQ ID NO 64
<211> LENGTH: 25
<212> TYPE: DNA
<213> ORGANISM: Artificial sequence
<220> FEATURE:
<223> OTHER INFORMATION: synthetic primer

<400> SEQUENCE: 64
ttgatgaaat gatcactgac ggatt    25

<210> SEQ ID NO 65
<211> LENGTH: 25
<212> TYPE: DNA
<213> ORGANISM: Artificial sequence
<220> FEATURE:
<223> OTHER INFORMATION: synthetic primer

<400> SEQUENCE: 65
gaaatgttcc atctctcagc tatgt    25

<210> SEQ ID NO 66
<211> LENGTH: 25
<212> TYPE: DNA
<213> ORGANISM: Artificial sequence
<220> FEATURE:
<223> OTHER INFORMATION: synthetic primer

<400> SEQUENCE: 66
ctaatacgag gaggacatgt tgatg    25

<210> SEQ ID NO 67
<211> LENGTH: 25
<212> TYPE: DNA
<213> ORGANISM: Artificial sequence
<220> FEATURE:
<223> OTHER INFORMATION: synthetic primer

<400> SEQUENCE: 67
cacccatacc tgggacaatt ttatt    25

<210> SEQ ID NO 68
<211> LENGTH: 25
<212> TYPE: DNA
<213> ORGANISM: Artificial sequence
<220> FEATURE:
<223> OTHER INFORMATION: synthetic primer

<400> SEQUENCE: 68
gggctgctac taaaaatttc aatcc    25

<210> SEQ ID NO 69
<211> LENGTH: 25
<212> TYPE: DNA
<213> ORGANISM: Artificial sequence
<220> FEATURE:
<223> OTHER INFORMATION: synthetic primer

<400> SEQUENCE: 69
caggagtcat tatggcatct cttttt    25

<210> SEQ ID NO 70
<211> LENGTH: 25
<212> TYPE: DNA
<213> ORGANISM: Artificial sequence

```
<220> FEATURE:
<223> OTHER INFORMATION: synthetic primer

<400> SEQUENCE: 70
tagtaccaga gccacttgaa ttaga                                           25

<210> SEQ ID NO 71
<211> LENGTH: 25
<212> TYPE: DNA
<213> ORGANISM: Artificial sequence
<220> FEATURE:
<223> OTHER INFORMATION: synthetic primer

<400> SEQUENCE: 71
ggaatagctt gaccacattc tgtat                                           25

<210> SEQ ID NO 72
<211> LENGTH: 1647
<212> TYPE: DNA
<213> ORGANISM: Lactococcus lactis

<400> SEQUENCE: 72
atgtatacag taggagatta cctattagac cgattacacg agttaggaat tgaagaaatt     60
tttggagtcc ctggagacta aacttacaa tttttagatc aaattatttc ccacaaggat    120
atgaaatggg tcggaaatgc taatgaatta aatgcttcat atatggctga tggctatgct    180
cgtactaaaa aagctgccgc atttcttaca acctttggag taggtgaatt gagtgcagtt    240
aatggattag caggaagtta cgccgaaaat ttaccagtag tagaaatagt gggatcacct    300
acatcaaaag ttcaaaatga aggaaaattt gttcatcata cgctggctga cggtgatttt    360 aaacactta tgaaaatgca cgaacctgtt acagcagctc gaactttact gacagcagaa    420
aatgcaaccg ttgaaattga ccgagtactt tctgcactat aaaagaaag aaaacctgtc    480 tatatcaact taccagttga tgttgctgct gcaaaagcag agaaaccctc actccctttg    540
aaaaaggaaa actcaacttc aaatacaagt gaccaagaaa ttttgaacaa aattcaagaa    600
agcttgaaaa atgccaaaaa accaatcgtg attacaggac atgaataat tagttttggc    660 ttagaaaaaa cagtcactca atttatttca aagacaaaac tacctattac gacattaaac    720
tttggtaaaa gttcagttga tgaagccctc ccttcatttt taggaatcta taatggtaca    780
ctctcagagc ctaatcttaa agaattcgtg gaatcagccg acttcatctt gatgcttgga    840
gttaaactca cagactcttc aacaggagcc ttcactcatc atttaaatga aaataaaatg    900
atttcactga atatagatga aggaaaaata tttaacgaaa gaatccaaaa ttttgatttt    960
gaatccctca tctcctctct cttagaccta agcgaaatag aatacaaagg aaaatatatc   1020
gataaaaagc aagaagactt tgttccatca aatgcgcttt tatcacaaga ccgcctatgg   1080
caagcagttg aaaacctaac tcaaagcaat gaaacaatcg ttgctgaaca agggacatca   1140
ttctttggcg cttcatcaat tttcttaaaa tcaaagagtc atttttattgg tcaacccta   1200 tggggatcaa ttggatatac attcccagca gcattaggaa gccaaattgc agataaagaa   1260
agcagacacc ttttatttat tggtgatggt tcacttcaac ttacagtgca agaattagga   1320
ttagcaatca gagaaaaaat taatccaatt tgctttatta tcaataatga tggttataca   1380
gtcgaaagag aaattcatgg accaaatcaa agctacaatg atattccaat gtggaattac   1440
tcaaaattac cagaatcgtt tggagcaaca gaagatcgag tagtctcaaa aatcgttaga   1500
actgaaaatg aatttgtgtc tgtcatgaaa gaagctcaag cagatccaaa tagaatgtac   1560
```

```
tggattgagt taattttggc aaaagaaggt gcaccaaaag tactgaaaaa aatgggcaaa      1620
ctatttgctg aacaaaataa atcataa                                         1647
```

<210> SEQ ID NO 73
<211> LENGTH: 548
<212> TYPE: PRT
<213> ORGANISM: Lactococcus lactis

<400> SEQUENCE: 73

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
```

|  |  | 355 |  |  |  | 360 |  |  |  | 365 |  |
| --- | --- | --- | --- | --- | --- | --- | --- | --- | --- | --- | --- |
| Ser | Asn | Glu | Thr | Ile | Val | Ala | Glu | Gln | Gly | Thr | Ser | Phe | Phe | Gly | Ala |
|  | 370 |  |  |  | 375 |  |  |  | 380 |  |  |

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
            485                 490                 495

Lys Ile Val Arg Thr Glu Asn Glu Phe Val Ser Val Met Lys Glu Ala
        500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 74
<211> LENGTH: 2094
<212> TYPE: DNA
<213> ORGANISM: Saccharomyces cerevisiae

<400> SEQUENCE: 74

| atgtctattc cagaaactca aaaagccatt atcttctacg aatccaacgg caagttggag | 60 |
| cataaggata tcccagttcc aaagccaaag cccaacgaat tgttaatcaa cgtcaagtac | 120 |
| tctggtgtct gccacaccga tttgcacgct tggcatggtg actggccatt gccaactaag | 180 |
| ttaccattag ttggtggtca cgaaggtgcc ggtgtcgttg tcggcatggg tgaaaacgtt | 240 |
| aagggctgga gatcggtga ctacgccggt atcaaatggt tgaacggttc ttgtatggcc | 300 |
| tgtgaatact gtgaattggg taacgaatcc aactgtcctc acgctgactt gtctggttac | 360 |
| acccacgacg gttctttcca agaatacgct accgctgacg ctgttcaagc cgctcacatt | 420 |
| cctcaaggta ctgacttggc tgaagtcgcg ccaatcttgt gtgctggtat caccgtatac | 480 |
| aaggctttga gtctgccaa cttgagagca ggccactggg cggccatttc tggtgctgct | 540 |
| ggtggtctag ttctttggc tgttcaatat gctaaggcga tgggttacag agtcttaggt | 600 |
| attgatggtg gtccaggaaa ggaagaattg tttacctcgc tcggtggtga agtattcatc | 660 |
| gacttcacca agagaagga cattgttagc gcagtcgtta aggctaccaa cggcggtgcc | 720 |
| cacggtatca tcaatgtttc cgtttccgaa gccgctatcg aagcttctac cagatactgt | 780 |
| agggcgaacg gtactgttgt cttggttggt ttgccagccg gtgcaaagtg ctcctctgat | 840 |
| gtcttcaacc acgttgtcaa gtctatctcc attgtcggct cttacgtggg gaacagagct | 900 |
| gataccagag aagcccttaga tttctttgcc agaggtctag tcaagtctcc aataaaggta | 960 |
| gttggcttat ccagtttacc agaaatttac gaaaagatgg agaagggcca aattgctggt | 1020 |

```
agatacgttg ttgacacttc taaataaatg tctattccag aaactcaaaa agccattatc    1080
ttctacgaat ccaacggcaa gttggagcat aaggatatcc cagttccaaa gccaaagccc    1140
aacgaattgt taatcaacgt caagtactct ggtgtctgcc acaccgattt gcacgcttgg    1200
catggtgact ggccattgcc aactaagtta ccattagttg gtggtcacga aggtgccggt    1260
gtcgttgtcg gcatgggtga aaacgttaag ggctggaaga tcggtgacta cgccggtatc    1320
aaatggttga acggttcttg tatggcctgt gaatactgtg aattgggtaa cgaatccaac    1380
tgtcctcacg ctgacttgtc tggttacacc cacgacggtt cttttccaaga atacgctacc    1440 gctgacgctg ttcaagccgc tcacattcct caaggtactg acttggctga agtcgcgcca    1500
atcttgtgtg ctggtatcac cgtatacaag gctttgaagt ctgccaactt gagagcaggc    1560
cactgggcgg ccatttctgg tgctgctggt ggtctaggtt ctttggctgt tcaatatgct    1620
aaggcgatgg gttacagagt cttaggtatt gatggtggtc aggaaaagga agaattgttt    1680
acctcgctcg gtggtgaagt attcatcgac ttcaccaaag agaaggacat tgttagcgca    1740
gtcgttaagg ctaccaacgg cggtgcccac ggtatcatca atgtttccgt ttccgaagcc    1800
gctatcgaag cttctaccag atactgtagg gcgaacggta ctgttgtctt ggttggtttg    1860
ccagccggtg caaagtgctc ctctgatgtc ttcaaccacg ttgtcaagtc tatctccatt    1920
gtcggctctt acgtggggaa cagagctgat accagaaag ccttagattt ctttgccaga     1980
ggtctagtca agtctccaat aaaggtagtt ggcttatcca gtttaccaga aatttacgaa    2040
aagatggaga agggccaaat tgctggtaga tacgttgttg acacttctaa ataa          2094
```

<210> SEQ ID NO 75
<211> LENGTH: 348
<212> TYPE: PRT
<213> ORGANISM: Saccharomyces cerevisiae

<400> SEQUENCE: 75

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
```

```
                180              185              190
Ala Met Gly Tyr Arg Val Leu Gly Ile Asp Gly Gly Pro Gly Lys Glu
            195              200              205

Glu Leu Phe Thr Ser Leu Gly Gly Glu Val Phe Ile Asp Phe Thr Lys
        210              215              220

Glu Lys Asp Ile Val Ser Ala Val Val Lys Ala Thr Asn Gly Gly Ala
225              230              235              240

His Gly Ile Ile Asn Val Ser Val Ser Glu Ala Ile Glu Ala Ser
            245              250              255

Thr Arg Tyr Cys Arg Ala Asn Gly Thr Val Val Leu Val Gly Leu Pro
            260              265              270

Ala Gly Ala Lys Cys Ser Ser Asp Val Phe Asn His Val Val Lys Ser
        275              280              285

Ile Ser Ile Val Gly Ser Tyr Val Gly Asn Arg Ala Asp Thr Arg Glu
            290              295              300

Ala Leu Asp Phe Phe Ala Arg Gly Leu Val Lys Ser Pro Ile Lys Val
305              310              315              320

Val Gly Leu Ser Ser Leu Pro Glu Ile Tyr Glu Lys Met Glu Lys Gly
                325              330              335

Gln Ile Ala Gly Arg Tyr Val Val Asp Thr Ser Lys
            340              345
```

<210> SEQ ID NO 76
<211> LENGTH: 1650
<212> TYPE: DNA
<213> ORGANISM: Lactococcus lactis

<400> SEQUENCE: 76

```
catatgtata cagtaggaga ttacctatta gaccgattac acgagttagg aattgaagaa    60
attttggag  tccctggaga ctataactta caattttag  atcaaattat tcccacaag    120
gatatgaaat gggtcggaaa tgctaatgaa ttaaatgctt catatatggc tgatggctat   180
gctcgtacta aaaagctgc  cgcatttctt acaacctttg gagtaggtga attgagtgca   240
gttaatggat tagcaggaag ttacgccgaa aatttaccag tagtagaaat agtgggatca   300
cctacatcaa aagttcaaaa tgaaggaaaa tttgttcatc atacgctggc tgacggtgat   360
tttaaacact ttatgaaaat gcacgaacct gttacagcag ctcgaacttt actgacagca   420
gaaaatgcaa ccgttgaaat tgaccgagta ctttctgcac tattaaaaga agaaaaacct   480
gtctatatca acttaccagt tgatgttgct gctgcaaaag cagagaaacc ctcactccct   540
ttgaaaaagg aaaactcaac ttcaaataca agtgaccaag aaattttgaa caaaattcaa   600
gaaagcttga aaaatgccaa aaaccaatc  gtgattacag acatgaaat  aattagtttt   660
ggcttagaaa aaacagtcac tcaatttatt tcaaagacaa aactacctat tacgacatta   720
aactttggta aaagttcagt tgatgaagcc ctcccttcat ttttaggaat ctataatggt   780
acactctcag agcctaatct taaagaattc gtggaatcag ccgacttcat cttgatgctt   840
ggagttaaac tcacagactc ttcaacagga gccttcactc atcatttaaa tgaaaataaa   900
atgatttcac tgaatataga tgaaggaaaa atatttaacg aaagaatcca aaattttgat   960
tttgaatccc tcatctcctc tctcttagac ctaagcgaaa tagaatacaa aggaaaatat  1020
atcgataaaa agcaagaaga ctttgttcca tcaaatgcgc ttttatcaca agaccgccta  1080
tggcaagcag ttgaaaacct aactcaaagc aatgaaacaa tcgttgctga acaagggaca  1140
tcattctttg gcgcttcatc aatttttctta aaatcaaaga gtcatttat  tggtcaaccc  1200
```

```
ttatggggat caattggata tacattccca gcagcattag gaagccaaat tgcagataaa    1260
gaaagcagac acctttatt tattggtgat ggttcacttc aacttacagt gcaagaatta    1320
ggattagcaa tcagagaaaa aattaatcca atttgcttta ttatcaataa tgatggttat    1380
acagtcgaaa gagaaattca tggaccaaat caaagctaca atgatattcc aatgtggaat    1440
tactcaaaat taccagaatc gtttggagca acagaagatc gagtagtctc aaaaatcgtt    1500
agaactgaaa atgaatttgt gtctgtcatg aaagaagctc aagcagatcc aaatagaatg    1560
tactggattg agttaatttt ggcaaaagaa ggtgcaccaa aagtactgaa aaaaatgggc    1620
aaactatttg ctgaacaaaa taaatcataa                                    1650
```

<210> SEQ ID NO 77
<211> LENGTH: 1047
<212> TYPE: DNA
<213> ORGANISM: Saccharomyces cerevisiae

<400> SEQUENCE: 77

```
atgtctattc cagaaactca aaaagccatt atcttctacg aatccaacgg caagttggag     60
cataaggata tcccagttcc aaagccaaag cccaacgaat tgttaatcaa cgtcaagtac    120
tctggtgtct gccacaccga tttgcacgct tggcatggtg actggccatt gccaactaag    180
ttaccattag ttggtggtca cgaaggtgcc ggtgtcgttg tcggcatggg tgaaaacgtt    240
aagggctgga agatcggtga ctacgccggt atcaaatggt tgaacggttc ttgtatggcc    300
tgtgaatact gtgaattggg taacgaatcc aactgtcctc acgctgactt gtctggttac    360
acccacgacg gttctttcca agaatacgct accgctgacg ctgttcaagc cgctcacatt    420
cctcaaggta ctgacttggc tgaagtcgcg ccaatcttgt gtgctggtat caccgtatac    480
aaggctttga gtctgccaa cttgagagca ggccactggg cggccatttc tggtgctgct    540
ggtggtctag gttctttggc tgttcaatat gctaaggcga tgggttacag agtcttaggt    600
attgatggtg gtccaggaaa ggaagaattg tttacctcgc tcggtggtga agtattcatc    660
gacttcacca agagaaggga cattgttagc gcagtcgtta aggctaccaa cggcggtgcc    720
cacggtatca tcaatgtttc cgtttccgaa gccgctatcg aagcttctac cagatactgt    780
agggcgaacg gtactgttgt cttggttggt ttgccagccg gtgcaaagtg ctcctctgat    840
gtcttcaacc acgttgtcaa gtctatctcc attgtcggct cttacgtggg gaacagagct    900
gataccagag aagccttaga tttctttgcc agaggtctag tcaagtctcc aataaaggta    960
gttggcttat ccagtttacc agaaatttac gaaaagatgg agaagggcca aattgctggt   1020
agatacgttg ttgacacttc taaataa                                       1047
```

<210> SEQ ID NO 78
<211> LENGTH: 2744
<212> TYPE: DNA
<213> ORGANISM: Artificial sequence
<220> FEATURE:
<223> OTHER INFORMATION: Synthetic operon

<400> SEQUENCE: 78

```
catatgtata cagtaggaga ttacctatta gaccgattac acgagttagg aattgaagaa     60 attttggag tccctggaga ctataactta caatttttag atcaaattat tcccacaag    120 gatatgaaat gggtcggaaa tgctaatgaa ttaaatgctt catatatggc tgatggctat    180
gctcgtacta aaaaagctgc cgcatttctt acaacctttg gagtaggtga attgagtgca    240
```

```
gttaatggat tagcaggaag ttacgccgaa aatttaccag tagtagaaat agtgggatca    300
cctacatcaa aagttcaaaa tgaaggaaaa tttgttcatc atacgctggc tgacggtgat    360
tttaaacact ttatgaaaat gcacgaacct gttacagcag ctcgaacttt actgacagca    420
gaaaatgcaa ccgttgaaat tgaccgagta ctttctgcac tattaaaaga agaaaaacct    480
gtctatatca acttaccagt tgatgttgct gctgcaaaag cagagaaacc ctcactccct    540
ttgaaaaagg aaaactcaac ttcaaataca agtgaccaag aaattttgaa caaaattcaa    600
gaaagcttga aaaatgccaa aaaccaatc gtgattacag gacatgaaat aattagtttt     660
ggcttagaaa aaacagtcac tcaatttatt tcaaagacaa aactacctat tacgacatta    720
aactttggta aagttcagt tgatgaagcc ctcccttcat ttttaggaat ctataatggt     780
acactctcag agcctaatct taaagaattc gtggaatcag ccgacttcat cttgatgctt    840
ggagttaaac tcacagactc ttcaacagga gccttcactc atcatttaaa tgaaaataaa    900
atgatttcac tgaatataga tgaaggaaaa atatttaacg aaagaatcca aaattttgat    960
tttgaatccc tcatctcctc tctcttagac ctaagcgaaa tagaatacaa aggaaaatat    1020
atcgataaaa agcaagaaga cttttgttcca tcaaatgcgc ttttatcaca agaccgccta   1080
tggcaagcag ttgaaaacct aactcaaagc aatgaaacaa tcgttgctga acaagggaca   1140
tcattctttg gcgcttcatc aattttctta aaatcaaaga gtcattttat tggtcaaccc    1200
ttatggggat caattggata tacattccca gcagcattag gaagccaaat tgcagataaa    1260
gaaagcagac cctttttatt tattggtgat ggttcacttc aacttacagt gcaagaatta    1320
ggattagcaa tcagagaaaa aattaatcca atttgcttta ttatcaataa tgatggttat    1380
acagtcgaaa gagaaattca tggaccaaat caaagctaca atgatattcc aatgtggaat    1440
tactcaaaat taccagaatc gtttggagca acagaagatc gagtagtctc aaaaatcgtt    1500
agaactgaaa atgaatttgt gtctgtcatg aaagaagctc aagcagatcc aaatagaatg    1560
tactggattg agttaatttt ggcaaaagaa ggtgcaccaa agtactgaa aaaaatgggc     1620
aaactatttg ctgaacaaaa taaatcataa gaattcaaaa aaaaaaaaa aaaaaaaaa      1680
aaaaaaaaa aatgtctatt ccagaaactc aaaaagccat tatcttctac gaatccaacg    1740
gcaagttgga gcataaggat atcccagttc aaagccaaa gcccaacgaa ttgttaatca     1800
acgtcaagta ctctggtgtc tgccacaccg atttgcacgc ttggcatggt gactggccat    1860
tgccaactaa gttaccatta gttggtggtc acgaaggtgc cggtgtcgtt gtcggcatgg    1920
gtgaaaacgt taagggctgg aagatcggtg actacgccgg tatcaaatgg ttgaacggtt    1980
cttgtatggc ctgtgaatac tgtgaattgg gtaacgaatc caactgtcct cacgctgact    2040
tgtctggtta cacccacgac ggttctttcc aagaatacgc taccgctgac gctgttcaag    2100
ccgctcacat tcctcaaggt actgacttgg ctgaagtcgc gccaatcttg tgtgctggta    2160
tcaccgtata caaggctttg aagtctgcca acttgagagc aggccactgg gcggccattt    2220
ctggtgctgc tggtggtcta ggttctttgg ctgttcaata tgctaaggcg atgggttaca    2280
gagtcttagg tattgatggt ggtccaggaa aggaagaatt gtttacctcg ctcggtggtg    2340
aagtattcat cgacttcacc aaagagaagg acattgttag cgcagtcgtt aaggctacca    2400
acggcggtgc ccacggtatc atcaatgttt ccgtttccga agccgctatc gaagcttcta    2460
ccagatactg tagggcgaac ggtactgttg tcttggttgg tttgccagcc ggtgcaaagt    2520
gctcctctga tgtcttcaac cacgttgtca agtctatctc cattgtcggc tcttacgtgg    2580
ggaacagagc tgataccaga gaagccttag atttctttgc cagaggtcta gtcaagtctc    2640
```

```
caataaaggt agttggctta tccagtttac cagaaattta cgaaaagatg gagaagggcc    2700
aaattgctgg tagatacgtt gttgacactt ctaaataagg tacc                    2744

<210> SEQ ID NO 79
<211> LENGTH: 479
<212> TYPE: DNA
<213> ORGANISM: Clostridium autoethanogenum

<400> SEQUENCE: 79
aatatgatat ttatgtccat tgtgaaaggg attatattca actattattc cagttacgtt     60
catagaaatt ttccttttcta aaatattta ttccatgtca agaactctgt ttatttcatt    120
aaagaactat aagtacaaag tataaggcat ttgaaaaaat aggctagtat attgattgat    180
tatttatttt aaaatgccta agtgaaatat atacatatta taacaataaa ataagtatta    240
gtgtaggatt tttaaataga gtatctattt tcagattaaa tttttgatta tttgatttac    300
attatataat attgagtaaa gtattgacta gcaaaatttt ttgatacttt aatttgtgaa    360
atttcttatc aaaagttata tttttgaata attttttattg aaaaatacaa ctaaaaagga   420
ttatagtata agtgtgtgta attttgtgtt aaatttaaag ggaggaaatg aacatgaaa     479

<210> SEQ ID NO 80
<211> LENGTH: 28
<212> TYPE: DNA
<213> ORGANISM: Artificial sequence
<220> FEATURE:
<223> OTHER INFORMATION: synthetic primer

<400> SEQUENCE: 80
gagcggccgc aatatgatat ttatgtcc                                        28

<210> SEQ ID NO 81
<211> LENGTH: 28
<212> TYPE: DNA
<213> ORGANISM: Artificial sequence
<220> FEATURE:
<223> OTHER INFORMATION: synthetic primer

<400> SEQUENCE: 81
ttccatatgt ttcatgttca tttcctcc                                        28

<210> SEQ ID NO 82
<211> LENGTH: 3552
<212> TYPE: DNA
<213> ORGANISM: Artificial sequence
<220> FEATURE:
<223> OTHER INFORMATION: synthetic plasmid

<400> SEQUENCE: 82
aaactccttt tgataatct catgaccaaa atcccttaac gtgagttttc gttccactga      60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
```

-continued

| | |
|---|---|
| cgtgagctat gagaaagcgc cacgcttccc gaagggagaa aggcggacag gtatccggta | 540 |
| agcggcaggg tcggaacagg agagcgcacg agggagcttc caggggggaaa cgcctggtat | 600 |
| ctttatagtc ctgtcgggtt tcgccacctc tgacttgagc gtcgatttt gtgatgctcg | 660 |
| tcagggggc ggagcctatg gaaaaacgcc agcaacgcgg cctttttacg gttcctggcc | 720 |
| ttttgctggc cttttgctca catgttcttt cctgcgttat ccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggcccctg caggataaaa | 900 |
| aaattgtaga taaattttat aaaatagttt tatctacaat tttttatca ggaaacagct | 960 |
| atgaccgcgg ccgcaatatg atatttatgt ccattgtgaa agggattata ttcaactatt | 1020 |
| attccagtta cgttcataga aattttcctt tctaaaatat tttattccat gtcaagaact | 1080 |
| ctgtttattt cattaaagaa ctataagtac aaagtataag gcatttgaaa aaataggcta | 1140 |
| gtatattgat tgattattta ttttaaaatg cctaagtgaa atatatacat attataacaa | 1200 |
| taaaataagt attagtgtag gattttaaa tagagtatct attttcagat taaattttg | 1260 |
| attatttgat ttacattata taatattgag taaagtattg actagcaaaa ttttttgata | 1320 |
| ctttaatttg tgaaatttct tatcaaaagt tatatttttg aataatttt attgaaaaat | 1380 |
| acaactaaaa aggattatag tataagtgtg tgtaatttg tgttaaattt aaagggagga | 1440 |
| aatgaacatg aaacatatgg tgaccatgat tacgaattcg agctcggtac ccggggatcc | 1500 |
| tctagagtcg acgtcacgcg tccatggaga tctcgaggcc tgcagacatg caagcttggc | 1560 |
| actggccgtc gttttacaac gtcgtgactg ggaaaaccct ggcgttaccc aacttaatcg | 1620 |
| ccttgcagca catccccctt tcgccagctg gcgtaatagc gaagaggccc gcaccgatcg | 1680 |
| cccttcccaa cagttgcgca gcctgaatgg cgaatgcgc tagcataaaa ataagaagcc | 1740 |
| tgcatttgca ggcttcttat ttttatggcg cgccgcattc acttcttttc tatataaata | 1800 |
| tgagcgaagc gaataagcgt cggaaaagca gcaaaaagtt tccttttgc tgttggagca | 1860 |
| tgggggttca gggggtgcag tatctgacgt caatgccgag cgaaagcgag ccgaagggta | 1920 |
| gcatttacgt tagataaccc cctgatatgc tccgacgctt tatatagaaa agaagattca | 1980 |
| actaggtaaa atcttaatat aggttgagat gataaggttt ataaggaatt tgtttgttct | 2040 |
| aattttttcac tcattttgtt ctaatttctt ttaacaaatg ttcttttttt tttagaacag | 2100 |
| ttatgatata gttagaatag tttaaaataa ggagtgagaa aaagatgaaa gaaagatatg | 2160 |
| gaacagtcta taaaggctct cagaggctca tagacgaaga aagtggagaa gtcatagagg | 2220 |
| tagacaagtt ataccgtaaa caaacgtctg gtaacttcgt aaaggcatat atagtgcaat | 2280 |
| taataagtat gttagatatg attggcggaa aaaaacttaa aatcgttaac tatatcctag | 2340 |
| ataatgtcca cttaagtaac aatacaatga tagctacaac aagagaaata gcaaaagcta | 2400 |
| caggaacaag tctacaaaca gtaataacaa cacttaaaat cttagaagaa ggaaatatta | 2460 |
| taaaaagaaa aactggagta ttaatgttaa accctgaact actaatgaga ggcgacgacc | 2520 |
| aaaaacaaaa atacctctta ctcgaatttg ggaactttga gcaagaggca aatgaaatag | 2580 |
| attgacctcc caataacacc acgtagttat tgggaggtca atctatgaaa tgcgattaag | 2640 |
| ggccggccga agcaaactta agagtgtgtt gatagtgcag tatcttaaaa ttttgtataa | 2700 |
| taggaattga agttaaatta gatgctaaaa atttgtaatt aagaaggagt gattacatga | 2760 |
| acaaaaatat aaaatattct caaaactttt taacagtgta aaaagtactc aaccaaataa | 2820 |
| taaaacaatt gaatttaaaa gaaaccgata ccgtttacga aattggaaca ggtaaagggc | 2880 |

```
atttaacgac gaaactggct aaaataagta acaggtaac gtctattgaa ttagacagtc    2940
atctattcaa cttatcgtca gaaaaattaa aactgaatac tcgtgtcact ttaattcacc    3000
aagatattct acagtttcaa ttccctaaca acagaggta taaaattgtt gggagtattc    3060
cttaccattt aagcacacaa attattaaaa aagtggtttt tgaaagccat gcgtctgaca    3120
tctatctgat tgttgaagaa ggattctaca agcgtacctt ggatattcac cgaacactag    3180
ggttgctctt gcacactcaa gtctcgattc agcaattgct taagctgcca gcggaatgct    3240
ttcatcctaa accaaaagta aacagtgtct taataaaact taccgccat accacagatg    3300 ttccagataa atattggaag ctatatacgt actttgtttc aaaatgggtc aatcgagaat    3360
atcgtcaact gtttactaaa aatcagtttc atcaagcaat gaaacacgcc aaagtaaaca    3420
atttaagtac cgttacttat gagcaagtat tgtctatttt taatagttat ctattattta    3480
acgggaggaa ataattctat gagtcgcttt tgtaaatttg gaaagttaca cgttactaaa    3540
gggaatgtgt tt                                                       3552

<210> SEQ ID NO 83
<211> LENGTH: 6263
<212> TYPE: DNA
<213> ORGANISM: Artificial sequence
<220> FEATURE:
<223> OTHER INFORMATION: synthetic plasmid

<400> SEQUENCE: 83
aaactccttt ttgataatct catgaccaaa atcccttaac gtgagttttc gttccactga      60
gcgtcagacc ccgtagaaaa gatcaaagga tcttcttgag atcctttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660 tcagggggggg ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat tttttttatca ggaaacagct    960 atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattatttta ttttaaaatg cctaagtgaa atatatacat attataacaa   1200
taaaataagt attagtgtag gatttttaaa tagagtatct attttcagat taaattttg    1260 attatttgat ttacattata taatattgag taaagtattg actagcaaaa ttttttgata   1320
```

```
ctttaatttg tgaaatttct tatcaaaagt tatattttg aataattttt attgaaaaat    1380
acaactaaaa aggattatag tataagtgtg tgtaattttg tgttaaattt aaagggagga   1440
aatgaacatg aaacatatgt atacagttgg tgattattta cttgatagat tacatgaact   1500
tggaatagaa gaattttttg gtgtaccagg tgattacaat cttcaattct tagatcaaat   1560
aatatcacat aaggatatga aatgggttgg taatgctaat gaattaaatg catcatatat   1620
ggcagacgga tatgcaagaa ctaaaaaggc agcagcattt cttactacat ttggtgttgg   1680
tgaattaagt gcagtaaatg gattagctgg aagttacgca gaaaacttac cagttgttga   1740
aatagttgga tctcctacta gtaaagtaca aaatgaaggt aaatttgtac atcacactct   1800
tgcagatggt gattttaagc attttatgaa aatgcatgaa cctgttacag ctgcaagaac   1860
acttcttaca gctgaaaacg ctactgtaga aattgataga gttttatctg ctttacttaa   1920
agaaagaaag ccagtatata ttaaccttcc agtagatgta gcagcagcaa aagctgagaa   1980
accttcatta ccacttaaaa aggaaaattc aacatcaaat acatctgatc aagagatatt   2040
aaataaaatt caggaaagtc ttaaaaatgc aaagaaacct atagtaataa ctggacatga   2100
ataattagt tttggattag aaaagacagt tacacagttt ataagtaaaa ctaagcttcc    2160
aattacaact ttaaattttg gaaagagttc agtagatgag gcacttccat cattcttagg   2220
aatttataat ggaacattat ctgaacctaa tcttaaagaa tttgtagaga gtgctgattt   2280
tatattaatg ttaggtgtaa aacttactga tagtagtact ggtgcattta ctcatcatct   2340
taacgaaaat aagatgatat cattaaatat agacgaaggt aaaatattca atgaaagaat   2400
acagaacttt gattttgaat cacttatatc atcattactt gatttatcag agatagaata   2460
caaaggaaaa tatatagata aaaagcaaga agattttgtt ccatctaatg ctcttctttc   2520
tcaagataga ctttggcaag cagttgagaa tcttacacag tctaatgaaa ctatagttgc   2580
tgagcaagga acatcatttt tcggtgcatc aagtatattt ttaaaatcta aaagtcactt   2640
tattggacaa cctctctttggg gttctattgg atatactttt ccagcagctt taggaagtca   2700
aatagctgat aaagaaagta gacatttatt atttattggt gacggttcac ttcagcttac   2760
agtacaagaa ttaggattag ctataagaga aagataaaat cctatttgtt tcataataaa   2820
caatgatgga tatactgtag aaagagaaat tcacggacca aatcagtcat ataatgatat   2880
tccaatgtgg aattattcaa agttacctga atctttcggt gctactgaag atagagtagt   2940
ttctaaaatt gttagaacag agaacgaatt tgtatctgtt atgaaagaag ctcaggctga   3000
ccctaataga atgtattgga ttgaattaat tttagcaaaa gaaggtgctc ctaaagtact   3060
taagaaaatg ggaaaattat tgcagaaaca aaataagtca taagaattcc cataataaag   3120
aaagaatttt aaataaagga ggaacaaaga tgagtatacc agaaacacaa aaagcaatta   3180
tattttatga gtcaaatgga aaattagagc ataaagatat acctgtacca aaaccaaaac   3240
caaacgaact tcttataaat gttaagtatt ctggtgtttg tcatactgat cttcatgcat   3300
ggcatggtga ttggcctctt ccaactaaat tacctcttgt aggtggtcat gaaggtgctg   3360
gtgtagttgt aggtatgggt gaaaatgtta aggttggaa ataggtgat tatgctggaa    3420
ttaaatggct taatggatct tgtatggcat gcgagtattg tgaattagga aatgaaagta   3480
attgtccaca tgctgactta agtggttata ctcatgatgg atcttttcaa gaatatgcta   3540
ctgcagatgc agttcaggct gcacacattc cacagggaac tgatcttgct gaagtagctc   3600
ctatattatg cgctggaatt acagtataca aagcattaaa aagtgctaat cttagagcag   3660
gacactgggc agctataagt ggtgctgcag gtggtttagg atctttagca gttcaatatg   3720
```

```
ctaaagctat gggatataga gtattaggaa tagacggtgg tccaggaaaa gaagagttat    3780
ttacatcatt aggtggtgaa gtttttatag atttcacaaa ggaaaaagat attgtttcag    3840
ctgtagtaaa ggcaactaat ggtggtgcac acggaattat aaatgtttca gtatctgaag    3900
cagcaataga agcaagtact agatattgta gagcaaacgg aacagtagtt ttagttggac    3960
ttccagctgg tgcaaagtgt tcatctgacg tatttaacca tgtagtaaag agtatttcaa    4020
tagttggatc ttacgtaggt aatagagctg atacaagaga agctttagat ttctttgcaa    4080
gaggtttagt taagagtcct ataaaagtag taggactttc atcacttcct gaaatttatg    4140
aaaagatgga aaagggacaa atagctggta gatatgttgt agatacaagt aaataaggta    4200
cccggggatc ctctagagtc gacgtcacgc gtccatggag atctcgaggc ctgcagacat    4260
gcaagcttgg cactggccgt cgttttacaa cgtcgtgact gggaaaaccc tggcgttacc    4320
caacttaatc gccttgcagc acatccccct ttcgccagct ggcgtaatag cgaagaggcc    4380
cgcaccgatc gcccttccca acagttgcgc agcctgaatg gcgaatggcg ctagcataaa    4440
aataagaagc ctgcatttgc aggcttctta ttttatggc gcgccgcatt cacttctttt    4500
ctatataaat atgagcgaag cgaataagcg tcggaaaagc agcaaaaagt ttcctttttg    4560
ctgttggagc atgggggttc aggggggtgca gtatctgacg tcaatgccga gcgaaagcga    4620
gccgaagggt agcatttacg ttagataacc ccctgatatg ctccgacgct ttatatagaa    4680
aagaagattc aactaggtaa aatcttaata taggttgaga tgataaggtt tataaggaat    4740
ttgtttgttc taattttca ctcatttgt tctaatttct tttaacaaat gttctttttt    4800
ttttagaaca gttatgatat agttagaata gtttaaaata aggagtgaga aaaagatgaa    4860
agaaagatat ggaacagtct ataaaggctc tcagaggctc atagacgaag aaagtggaga    4920
agtcatagag gtagacaagt tataccgtaa acaaacgtct ggtaacttcg taaaggcata    4980
tatagtgcaa ttaataagta tgttagatat gattggcgga aaaaaactta aaatcgttaa    5040
ctatatccta gataatgtcc acttaagtaa caatacaatg atagctacaa caagagaaat    5100
agcaaaagct acaggaacaa gtctacaaac agtaataaca acacttaaaa tcttagaaga    5160
aggaaatatt ataaaagaa aaactggagt attaatgtta aaccctgaac tactaatgag    5220
aggcgacgac caaaaacaaa aatacctctt actcgaattt gggaactttg agcaagaggc    5280
aaatgaaata gattgacctc ccaataacac cacgtagtta ttgggaggtc aatctatgaa    5340
atgcgattaa gggccggccg aagcaaactt aagagtgtgt tgatagtgca gtatcttaaa    5400
attttgtata ataggaattg aagttaaatt agatgctaaa aatttgtaat taagaaggag    5460
tgattacatg aacaaaaata taaatattc tcaaaacttt ttaacgagtg aaaaagtact    5520
caaccaaata ataaaacaat tgaatttaaa agaaaccgat accgtttacg aaattggaac    5580
aggtaaaggg catttaacga cgaaactggc taaataagt aaacaggtaa cgtctattga    5640
attagacagt catctattca acttatcgtc agaaaaatta aaactgaata ctcgtgtcac    5700
tttaattcac caagatattc tacagtttca attccctaac aaacagaggt ataaaattgt    5760
tgggagtatt ccttaccatt taagcacaca aattattaaa aaagtggttt ttgaaagcca    5820
tgcgtctgac atctatctga ttgttgaaga aggattctac aagcgtacct tggatattca    5880
ccgaacacta gggttgctct tgcacactca agtctcgatt cagcaattgc ttaagctgcc    5940
agcggaatgc tttcatccta aaccaaaagt aaacagtgtc ttaataaaac ttacccgcca    6000
taccacagat gttccagata aatattggaa gctatatacg tactttgttt caaaatgggt    6060
```

```
caatcgagaa tatcgtcaac tgtttactaa aaatcagttt catcaagcaa tgaaacacgc    6120
caaagtaaac aatttaagta ccgttactta tgagcaagta ttgtctattt ttaatagtta    6180
tctattattt aacgggagga ataattcta tgagtcgctt ttgtaaattt ggaaagttac     6240
acgttactaa agggaatgtg ttt                                            6263
```

<210> SEQ ID NO 84
<211> LENGTH: 4630
<212> TYPE: DNA
<213> ORGANISM: Artificial sequence
<220> FEATURE:
<223> OTHER INFORMATION: synthetic plasmid

<400> SEQUENCE: 84

```
aaactccttt ttgataatct catgaccaaa atcccttaac gtgagttttc gttccactga      60
gcgtcagacc ccgtagaaaa gatcaaagga tcttcttgag atcctttttt tctgcgcgta    120
atctgctgct tgcaaacaaa aaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggggaaa cgcctggtat    600 ctttatagtc ctgtcgggtt tcgccacctc tgacttgagc gtcgattttt gtgatgctcg    660 tcagggggg ggagcctatg gaaaaacgcc agcaacgcgg cctttttacg gttcctggcc    720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggcccctg caggataaaa    900 aaattgtaga taaattttat aaaatagttt tatctacaat ttttttatca ggaaacagct    960
atgaccgcgg ccgcaatatg atatttatgt ccattgtgaa agggattata ttcaactatt   1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gattttaaa tagagtatct attttcagat taaattttg    1260 attatttgat ttacattata taatattgag taaagtattg actagcaaaa ttttttgata   1320
ctttaatttg tgaaatttct tatcaaaagt tatattttg aataattttt attgaaaaat   1380
acaactaaaa aggattatag tataagtgtg tgtaattttg tgttaaattt aagggagga   1440 aatgaacatg aaacatatgt atacagttgg tgattattta cttgatagat tacatgaact   1500
tggaatagaa gaaattttg gtgtaccagg tgattacaat cttcaattct tagatcaaat   1560
aatatcacat aaggatatga atggggttgg taatgctaat gaattaaatg catcatatat   1620
ggcagacgga tatgcaagaa ctaaaaaggc agcagcattt cttactacat ttggtgttgg   1680
tgaattaagt gcagtaaatg gattagctgg aagttacgca gaaaacttac cagttgttga   1740
aatagttgga tctcctacta gtaaagtaca aaatgaaggt aaatttgtac atcacactct   1800
tgcagatggt gattttaagc attttatgaa aatgcatgaa cctgttacag ctgcaagaac   1860
```

```
acttcttaca gctgaaaacg ctactgtaga aattgataga gttttatctg ctttacttaa   1920
agaaagaaag ccagtatata ttaaccttcc agtagatgta gcagcagcaa aagctgagaa   1980
accttcatta ccacttaaaa aggaaaattc aacatcaaat acatctgatc aagagatatt   2040
aaataaaatt caggaaagtc ttaaaaatgc aaagaaacct atagtaataa ctggacatga   2100 ataattagt tttggattag aaaagacagt tacacagttt ataagtaaaa ctaagcttcc     2160
aattacaact ttaaattttg gaaagagttc agtagatgag gcacttccat cattcttagg   2220
aatttataat ggaacattat ctgaacctaa tcttaaagaa tttgtagaga gtgctgattt   2280
tatattaatg ttaggtgtaa aacttactga tagtagtact ggtgcattta ctcatcatct   2340
taacgaaaat aagatgatat cattaaatat agacgaaggt aaaatattca atgaaagaat   2400
acagaacttt gattttgaat cacttatatc atcattactt gatttatcag agatagaata   2460
caaaggaaaa tatatagata aaaagcaaga agattttgtt ccatctaatg ctcttctttc   2520
tcaagataga cttttggcaag cagttgagaa tcttacacag tctaatgaaa ctatagttgc   2580
tgagcaagga acatcatttt tcggtgcatc aagtatattt ttaaaatcta aaagtcactt   2640
tattggacaa cctctttggg gttctattgg atatactttt ccagcagctt taggaagtca   2700
aatagctgat aaagaaagta gacatttatt atttattggt gacggttcac ttcagcttac   2760
agtacaagaa ttaggattag ctataagaga gaagataaat cctatttgtt tcataataaa   2820
caatgatgga tatactgtag aaagagaaat tcacggacca aatcagtcat ataatgatat   2880
tccaatgtgg aattattcaa agttacctga atctttcggt gctactgaag atagagtagt   2940
ttctaaaatt gttagaacag agaacgaatt tgtatctgtt atgaaagaag ctcaggctga   3000
ccctaataga atgtattgga ttgaattaat tttagcaaaa gaaggtgctc ctaaagtact   3060
taagaaaatg ggaaaattat ttgcagaaca aaataagtca taagaatttg tttgttctaa   3120
tttttcactc attttgttct aatttctttt aacaaatgtt cttttttttt tagaacagtt   3180
atgatatagt tagaatagtt taaaataagg agtgagaaaa agatgaaaga aagatatgga   3240
acagtctata aaggctctca gaggctcata gacgaagaaa gtggagaagt catagaggta   3300
gacaagttat accgtaaaca aacgtctggt aacttcgtaa aggcatatat agtgcaatta   3360
ataagtatgt tagatatgat tggcggaaaa aaacttaaaa tcgttaacta tatcctagat   3420
aatgtccact taagtaacaa tacaatgata gctacaacaa gagaaatagc aaaagctaca   3480
ggaacaagtc tacaaacagt aataacaaca cttaaaatct tagaagaagg aaatattata   3540
aaaagaaaaa ctggagtatt aatgttaaac cctgaactac taatgagagg cgacgaccaa   3600
aaacaaaaat acctcttact cgaatttggg aactttgagc aagaggcaaa tgaaatagat   3660
tgacctccca ataacaccac gtagttattg ggaggtcaat ctatgaaatg cgattaaggg   3720
ccggccgaag caaacttaag agtgtgttga tagtgcagta tcttaaaatt ttgtataata   3780
ggaattgaag ttaaattaga tgctaaaaat ttgtaattaa gaaggagtga ttacatgaac   3840
aaaaatataa aatattctca aaacttttta acgagtgaaa aagtactcaa ccaaataata   3900
aaacaattga atttaaaaga aaccgatacc gtttacgaaa ttggaacagg taaagggcat   3960
ttaacgacga aactggctaa aataagtaaa caggtaacgt ctattgaatt agacagtcat   4020
ctattcaact tatcgtcaga aaaattaaaa ctgaatactc gtgtcacttt aattccacaa   4080
gatattctac agtttcaatt ccctaacaaa cagaggtata aaattgttgg gagtattcct   4140
taccatttaa gcacacaaat tattaaaaaa gtggtttttg aaagccatgc gtctgacatc   4200
```

```
tatctgattg ttgaagaagg attctacaag cgtaccttgg atattcaccg aacactaggg    4260
ttgctcttgc acactcaagt ctcgattcag caattgctta agctgccagc ggaatgcttt    4320
catcctaaac caaaagtaaa cagtgtctta ataaaactta cccgccatac cacagatgtt    4380
ccagataaat attggaagct atatacgtac tttgtttcaa aatgggtcaa tcgagaatat    4440
cgtcaactgt ttactaaaaa tcagtttcat caagcaatga aacacgccaa agtaaacaat    4500
ttaagtaccg ttacttatga gcaagtattg tctatttta atagttatct attatttaac    4560
gggaggaaat aattctatga gtcgcttttg taaatttgga aagttacacg ttactaaagg    4620
gaatgtgttt                                                          4630

<210> SEQ ID NO 85
<211> LENGTH: 23
<212> TYPE: DNA
<213> ORGANISM: Artificial sequence
<220> FEATURE:
<223> OTHER INFORMATION: synthetic primer

<400> SEQUENCE: 85
tcagttccct gtggaatgtg tgc                                             23

<210> SEQ ID NO 86
<211> LENGTH: 22
<212> TYPE: DNA
<213> ORGANISM: Artificial sequence
<220> FEATURE:
<223> OTHER INFORMATION: synthetic primer

<400> SEQUENCE: 86
tcagtagcac cgaaagattc ag                                              22

<210> SEQ ID NO 87
<211> LENGTH: 21
<212> TYPE: DNA
<213> ORGANISM: Artificial sequence
<220> FEATURE:
<223> OTHER INFORMATION: synthetic primer

<400> SEQUENCE: 87
agtgcctcat ctactgaact c                                               21

<210> SEQ ID NO 88
<211> LENGTH: 36
<212> TYPE: DNA
<213> ORGANISM: Artificial sequence
<220> FEATURE:
<223> OTHER INFORMATION: synthetic primer

<400> SEQUENCE: 88
attagtttaa acacgccagc aacgcggcct ttttac                               36

<210> SEQ ID NO 89
<211> LENGTH: 27
<212> TYPE: DNA
<213> ORGANISM: Artificial sequence
<220> FEATURE:
<223> OTHER INFORMATION: synthetic primer

<400> SEQUENCE: 89
tcctattcca aggtttacga gttggtc                                         27

<210> SEQ ID NO 90
<211> LENGTH: 27
```

```
<212> TYPE: DNA
<213> ORGANISM: Artificial sequence
<220> FEATURE:
<223> OTHER INFORMATION: synthetic primer

<400> SEQUENCE: 90 accccccaacc ataattgtca tgccatc                                              27

<210> SEQ ID NO 91
<211> LENGTH: 27
<212> TYPE: DNA
<213> ORGANISM: Artificial sequence
<220> FEATURE:
<223> OTHER INFORMATION: synthetic primer

<400> SEQUENCE: 91
tgcaagagca aactcatctt gttcttc                                               27

<210> SEQ ID NO 92
<211> LENGTH: 43
<212> TYPE: DNA
<213> ORGANISM: Artificial sequence
<220> FEATURE:
<223> OTHER INFORMATION: synthetic primer

<400> SEQUENCE: 92
agggtgcggc cgcgattcat atatccataa tctttaagtt atc                             43

<210> SEQ ID NO 93
<211> LENGTH: 38
<212> TYPE: DNA
<213> ORGANISM: Artificial sequence
<220> FEATURE:
<223> OTHER INFORMATION: synthetic primer

<400> SEQUENCE: 93
atcttctgca gggccgcaga tagtcataat agttccag                                   38

<210> SEQ ID NO 94
<211> LENGTH: 43
<212> TYPE: DNA
<213> ORGANISM: Artificial sequence
<220> FEATURE:
<223> OTHER INFORMATION: synthetic primer

<400> SEQUENCE: 94
agggtgcggc cgcgattcat atatccataa tctttaagtt atc                             43

<210> SEQ ID NO 95
<211> LENGTH: 7655
<212> TYPE: DNA
<213> ORGANISM: Artificial sequence
<220> FEATURE:
<223> OTHER INFORMATION: synthetic plasmid

<400> SEQUENCE: 95
aaactccttt ttgataatct catgaccaaa atcccttaac gtgagttttc gttccactga           60
gcgtcagacc ccgtagaaaa gatcaaagga tcttcttgag atccttttttt tctgcgcgta         120 atctgctgct tgcaaacaaa aaaaccaccg ctaccagcgg tggtttgttt gccggatcaa          180
gagctaccaa ctctttttcc gaaggtaact ggcttcagca gagcgcagat accaaatact          240
gttcttctag tgtagccgta gttaggccac cacttcaaga actctgtagc accgcctaca          300
tacctcgctc tgctaatcct gttaccagtg gctgctgcca gtggcgataa gtcgtgtctt          360
```

| | |
|---|---|
| accgggttgg actcaagacg atagttaccg gataaggcgc agcggtcggg ctgaacgggg | 420 |
| ggttcgtgca cacagcccag cttggagcga acgacctaca ccgaactgag atacctacag | 480 |
| cgtgagctat gagaaagcgc cacgcttccc gaagggagaa aggcggacag gtatccggta | 540 |
| agcggcaggg tcggaacagg agagcgcacg agggagcttc caggggaaa cgcctggtat | 600 |
| ctttatagtc ctgtcgggtt tcgccacctc tgacttgagc gtcgattttt gtgatgctcg | 660 |
| tcagggggc ggagcctatg gaaaaacgcc agcaacgcgg ccttttacg gttcctggcc | 720 |
| ttttgctggc cttttgctca catgttcttt cctgcgttat cccctgattc tgtggataac | 780 |
| cgtattaccg cctttgagtg agctgatacc gctcgccgca gccgaacgac cgagcgcagc | 840 |
| gagtcagtga gcgaggaagc ggaagagcgc ccaatacgca gggcccctg cagggccgca | 900 |
| gatagtcata atagttccag aatagttcaa tttagaaatt agactaaact tcaaaatgtt | 960 |
| tgttaaatat ataccaaact agtatagata tttttaaat actggactta aacagtagta | 1020 |
| atttgcctaa aaaatttttt cattttttt taaaaatcc ttttcaagtt gtacattgtt | 1080 |
| atggtaatat gtaattgaag aagttatgta gtaatattgt aaacgtttct tgattttttt | 1140 |
| acatccatgt agtgcttaaa aaccaaaat atgtcacatg caattgtata tttcaaataa | 1200 |
| caatatttat tttctcgtta aattcacaaa taatttatta ataatatcaa taaccaagat | 1260 |
| tatacttaaa tggatgttta ttttttaaca cttttatagt aaatatattt attttatgta | 1320 |
| gtaaaaaggt tataattata attgtattta ttacaattaa ttaaaataaa aatagggtt | 1380 |
| ttaggtaaaa ttaagttatt ttaagaagta attacaataa aaattgaagt tatttcttta | 1440 |
| aggagggaat tattcatatg aaagaagttg taatagctag tgcagtaaga acagcgattg | 1500 |
| gatcttatgg aaagtctctt aaggatgtac cagcagtaga tttaggagct acagctataa | 1560 |
| aggaagcagt taaaaagca ggaataaaac cagaggatgt taatgaagtc attttaggaa | 1620 |
| atgttcttca agcaggttta ggacagaatc cagcaagaca ggcatctttt aaagcaggat | 1680 |
| taccagttga aattccagct atgactatta ataaggtttg tggttcagga cttagaacag | 1740 |
| ttagcttagc agcacaaatt ataaaagcag gagatgctga cgtaataata gcaggtggta | 1800 |
| tggaaaatat gtctagagct ccttacttag cgaataacgc tagatgggga tatagaatgg | 1860 |
| gaaacgctaa atttgttgat gaaatgatca ctgacggatt gtgggatgca tttaatgatt | 1920 |
| accacatggg aataacagca gaaaacatag ctgagagatg gaacatttca agagaagaac | 1980 |
| aagatgagtt tgctcttgca tcacaaaaaa aagctgaaga agctataaaa tcaggtcaat | 2040 |
| ttaaagatga aatagttcct gtagtaatta aaggcagaaa gggagaaact gtagttgata | 2100 |
| cagatgagca ccctagattt ggatcaacta tagaaggact tgcaaaatta aaacctgcct | 2160 |
| tcaaaaaaga tggaacagtt acagctggta atgcatcagg attaaatgac tgtgcagcag | 2220 |
| tacttgtaat catgagtgca gaaaaagcta agagcttgg agtaaaacca cttgctaaga | 2280 |
| tagtttctta tggttcagca ggagttgacc cagcaataat gggatatgga ccttctatg | 2340 |
| caacaaaagc agctattgaa aaagcaggtt ggacagttga tgaattagat ttaatagaat | 2400 |
| caaatgaagc ttttgcagct caaagtttag cagtagcaaa agatttaaaa tttgatatga | 2460 |
| ataaagtaaa tgtaaatgga ggagctattg cccttggtca tccaattgga gcatcaggtg | 2520 |
| caagaatact cgttactctt gtacacgcaa tgcaaaaaag agatgcaaaa aaaggcttag | 2580 |
| caactttatg tataggtggc ggacaaggaa cagcaatatt gctagaaaag tgctaggaat | 2640 |
| tcgagctcgg taccagggag atattaaaat gaataaaatta gtaaaattaa cagatttaaa | 2700 |
| gcgcattttc aaagatggca tgacaattat ggttgggggt ttttagatt gtggaactcc | 2760 |

```
tgaaaatatt atagatatgc tagttgattt aaatataaaa aatctgacta ttataagcaa      2820
tgatacagct tttcctaata aaggaatagg aaaacttatt gtaaatggtc aagtttctaa      2880
agtaattgct tcacatattg gaactaatcc tgaaactgga aaaaaaatga gctctggaga      2940
acttaaagtt gagctttccc cacaaggaac actgattgaa agaattcgtg cagctggatc      3000
tggactcgga ggtgtattaa ctccaactgg acttggaact atcgttgaag aaggtaagaa      3060
aaaagttact atcgatggca agaatatct  attagaactt cctttatctg ctgatgtttc      3120
attaataaaa ggtagcattg tagatgaatt tggaaatacc ttctataggg ctgctactaa      3180
aaatttcaat ccatatatgg caatggctgc aaaaacagtt atagttgaag cagaaaattt      3240
agttaaatgt gaagatttaa aaagagatgc cataatgact cctggcgtat tagtagatta      3300
tatcgttaag gaggcggctt aattgattgt agataaagtt ttagcaaaag agataattgc      3360
caaaagagtt gcaaagaac  taaaaaaaga ccaactcgta aaccttggaa taggacttcc      3420
aactttagta gcaaattatg taccaaaaga aatgaacatt acttttgaat cagaaaatgg      3480
catggttggt atggcacaaa tggcatcatc aggtgaaaat gacccagata taataaatgc      3540
tggcggggaa tatgtaacat tattacctca aggttcattt tttgatagtt caatgtctt       3600 cgcactaata cgaggaggac atgttgatgt tgctgttctt ggtgctctag aagttgatga      3660
aaaaggtaat ttagctaact ggattgttcc aaataaaatt gtcccaggta tgggtggcgc      3720
tatggattta gcaataggcg caaaaaaat  aatagtggca atgcaacata caggaaaaag      3780
taaacctaaa atcgttaaaa aatgtactct cccacttact gctaaggctc aagtggattt      3840
aattgtcaca gaactttgtg taattgatgt aacaaatgac ggcttacttt taaaagaaat      3900
tcataaagat acaactattg atgaaattaa attttttaaca gatgcagatt taattattcc     3960
agataactta aagattatgg atatatgaat cgcggccgca atatgatatt tatgtccatt      4020
gtgaaaggga ttatattcaa ctattattcc agttacgttc atagaaattt tccttctaa       4080 aatatttat  tccatgtcaa gaactctgtt tatttcatta aagaactata agtacaaagt      4140
ataaggcatt tgaaaaaata ggctagtata ttgattgatt atttatttta aaatgcctaa      4200
gtgaaatata tacatattat aacaataaaa taagtattag tgtaggattt ttaaatagag      4260
tatctatttt cagattaaat ttttgattat ttgatttaca ttatataata ttgagtaaag      4320
tattgactag caaaattttt tgatacttta atttgtgaaa tttcttatca aaagttatat      4380
ttttgaataa tttttattga aaaatacaac taaaaaggat tatagtataa gtgtgtgtaa      4440
ttttgtgtta aatttaaagg gaggaaatga acatgaaaca tatgtataca gttggtgatt      4500
atttacttga tagattacat gaacttggaa tagaagaaat ttttggtgta ccaggtgatt      4560
acaatcttca attcttagat caaataatat cacataagga tatgaaatgg gttggtaatg      4620
ctaatgaatt aaatgcatca tatatggcag acggatatgc aagaactaaa aaggcagcag      4680
catttcttac tacatttggt gttggtgaat taagtgcagt aaatggatta gctggaagtt      4740
acgcagaaaa cttaccagtt gttgaaatag ttggatctcc tactagtaaa gtacaaaatg      4800
aaggtaaatt tgtacatcac actcttgcag atggtgattt taagcatttt atgaaaatgc      4860
atgaacctgt tacagctgca agaacacttc ttacagctga aaacgctact gtagaaattg      4920
atagagtttt atctgcttta cttaaagaaa gaaagccagt atatattaac cttccagtag      4980
atgtagcagc agcaaaagct gagaaacctt cattaccact taaaaaggaa aattcaacat      5040
caaatacatc tgatcaagag atattaaata aaattcagga aagtcttaaa aatgcaaaga      5100
```

```
aacctatagt aataactgga catgaaataa ttagttttgg attagaaaag acagttacac   5160
agtttataag taaaactaag cttccaatta caactttaaa ttttggaaag agttcagtag   5220
atgaggcact tccatcattc ttaggaattt ataatggaac attatctgaa cctaatctta   5280
aagaatttgt agagagtgct gattttatat taatgttagg tgtaaaactt actgatagta   5340
gtactggtgc atttactcat catcttaacg aaaataagat gatatcatta aatatagacg   5400
aaggtaaaat attcaatgaa agaatacaga actttgattt tgaatcactt atatcatcat   5460
tacttgattt atcagagata gaatacaaag gaaaatatat agataaaaag caagaagatt   5520
ttgttccatc taatgctctt ctttctcaag atagactttg gcaagcagtt gagaatctta   5580
cacagtctaa tgaaactata gttgctgagc aaggaacatc atttttcggt gcatcaagta   5640
tattttaaa atctaaaagt cactttattg acaacctct ttggggttct attggatata   5700
cttttccagc agctttagga agtcaaatag ctgataaaga aagtagacat ttattattta   5760
ttggtgacgg ttcacttcag cttacagtac aagaattagg attagctata agagagaaga   5820
taaatcctat ttgtttcata ataaacaatg atggatatac tgtagaaaga gaaattcacg   5880
gaccaaatca gtcatataat gatattccaa tgtggaatta ttcaaagtta cctgaatctt   5940
tcggtgctac tgaagataga gtagtttcta aaattgttag aacagagaac gaatttgtat   6000
ctgttatgaa agaagctcag gctgaccta tagaatgta ttggattgaa ttaattttag   6060
caaaagaagg tgctcctaaa gtacttaaga aaatgggaaa attatttgca gaacaaaata   6120
agtcataaga atttgtttgt tctaattttt cactcatttt gttctaattt cttttaacaa   6180
atgttctttt tttttagaa cagttatgat atagttagaa tagttaaaa taaggagtga   6240
gaaaagatg aaagaaagat atggaacagt ctataaaggc tctcagaggc tcatagacga   6300
agaaagtgga gaagtcatag aggtagacaa gttataccgt aaacaaacgt ctggtaactt   6360
cgtaaaggca tatatagtgc aattaataag tatgttagat atgattggcg aaaaaaact   6420
taaaatcgtt aactatatcc tagataatgt ccacttaagt aacaatacaa tgatagctac   6480
aacaagagaa atagcaaaag ctacaggaac aagtctacaa acagtaataa caacacttaa   6540
aatcttagaa gaaggaaata ttataaaaag aaaaactgga gtattaatgt taaaccctga   6600
actactaatg agaggcgacg accaaaaaca aaaatacctc ttactcgaat ttgggaactt   6660
tgagcaagag gcaaatgaaa tagattgacc tcccaataac accacgtagt tattgggagg   6720
tcaatctatg aaatgcgatt aagggccggc cgaagcaaac ttaagagtgt gttgatagtg   6780
cagtatctta aaattttgta taataggaat tgaagttaaa ttagatgcta aaaatttgta   6840
attaagaagg agtgattaca tgaacaaaaa tataaaatat tctcaaaact ttttaacgag   6900
tgaaaaagta ctcaaccaaa taataaaaca attgaatttta aaagaaaccg ataccgttta   6960
cgaaattgga acaggtaaag ggcatttaac gacgaaactg gctaaaataa gtaaacaggt   7020
aacgtctatt gaattagaca gtcatctatt caacttatcg tcagaaaaat taaaactgaa   7080
tactcgtgtc actttaattc accaagatat tctacagttt caattcccta caaacagag   7140
gtataaaatt gttgggagta ttccttacca tttaagcaca caaattatta aaaagtggt   7200
ttttgaaagc catgcgtctg acatctatct gattgttgaa gaaggattct acaagcgtac   7260
cttggatatt caccgaacac tagggttgct cttgcacact caagtctcga ttcagcaatt   7320
gcttaagctg ccagcggaat gctttcatcc taaaccaaaa gtaaacagtg tcttaataaa   7380
acttacccgc cataccacag atgttccaga taaaatttgg aagctatata cgtactttgt   7440
ttcaaaatgg gtcaatcgag aatatcgtca actgtttact aaaaatcagt ttcatcaagc   7500
```

```
aatgaaacac gccaaagtaa acaatttaag taccgttact tatgagcaag tattgtctat    7560
ttttaatagt tatctattat ttaacgggag gaaataattc tatgagtcgc ttttgtaaat    7620
ttggaaagtt acacgttact aaagggaatg tgttt                               7655

<210> SEQ ID NO 96
<211> LENGTH: 35
<212> TYPE: DNA
<213> ORGANISM: Artificial sequence
<220> FEATURE:
<223> OTHER INFORMATION: synthetic primer

<400> SEQUENCE: 96
acgttggatc caggaggaac aaagatgagt atacc                                 35

<210> SEQ ID NO 97
<211> LENGTH: 39
<212> TYPE: DNA
<213> ORGANISM: Artificial sequence
<220> FEATURE:
<223> OTHER INFORMATION: synthetic primer

<400> SEQUENCE: 97
agcgtccatg gccttattta cttgtatcta caacatatc                             39

<210> SEQ ID NO 98
<211> LENGTH: 8621
<212> TYPE: DNA
<213> ORGANISM: Artificial sequence
<220> FEATURE:
<223> OTHER INFORMATION: synthetic plasmid

<400> SEQUENCE: 98
ccagtgggca agttgaaaaa ttcacaaaaa tgtggtataa tatctttgtt cattagagcg      60
ataaacttga atttgagagg gaacttagat ggtatttgaa aaaattgata aaaatagttg     120
gaacagaaaa gagtattttg accactactt tgcaagtgta ccttgtacct acagcatgac     180
cgttaaagtg gatatcacac aaataaagga aagggaatg aaactatatc ctgcaatgct      240
ttattatatt gcaatgattg taaaccgcca ttcagagttt aggacggcaa tcaatcaaga     300
tggtgaattg gggatatatg atgagatgat accaagctat acaatatttc acaatgatac     360
tgaaacattt tccagccttt ggactgagtg taagtctgac tttaaatcat ttttagcaga     420
ttatgaaagt gatacgcaac ggtatggaaa caatcataga atggaaggaa agccaaatgc     480
tccgaaaaac atttttaatg tatctatgat accgtggtca accttcgatg ctttaatct      540 gaatttgcag aaaggatatg attatttgat tcctattttt actatgggga aatattataa     600
agaagataac aaaattatac ttcctttggc aattcaagtt catcacgcag tatgtgacgg     660
atttcacatt tgccgttttg taaacgaatt gcaggaattg ataaatagtt aacttcaggt     720
ttgtctgtaa ctaaaaacaa gtatttaagc aaaaacatcg tagaaatacg gtgttttttg     780
ttaccctaag tttaaactcc tttttgataa tctcatgacc aaaatccctt aacgtgagtt     840
ttcgttccac tgagcgtcag accccgtaga aagatcaaa ggatcttctt gagatccttt      900
ttttctgcgc gtaatctgct gcttgcaaac aaaaaaacca ccgctaccag cggtggtttg     960
tttgccggat caagagctac caactctttt tccgaaggta actggcttca gcagagcgca    1020
gataccaaat actgttcttc tagtgtagcc gtagttaggc caccacttca agaactctgt    1080
agcaccgcct acatacctcg ctctgctaat cctgttacca gtggctgctg ccagtggcga    1140
```

```
taagtcgtgt cttaccgggt tggactcaag acgatagtta ccggataagg cgcagcggtc    1200
gggctgaacg gggggttcgt gcacacagcc cagcttggag cgaacgacct acaccgaact    1260
gagataccta cagcgtgagc tatgagaaag cgccacgctt cccgaaggga gaaaggcgga    1320
caggtatccg gtaagcggca gggtcggaac aggagagcgc acgagggagc ttccaggggg    1380
aaacgcctgg tatctttata gtcctgtcgg gtttcgccac ctctgacttg agcgtcgatt    1440
tttgtgatgc tcgtcagggg ggcggagcct atggaaaaac gccagcaacg cggccttttt    1500
acggttcctg gccttttgct ggcttttgc tcacatgttc tttcctgcgt tatcccctga     1560
ttctgtggat aaccgtatta ccgcctttga gtgagctgat accgctcgcc gcagccgaac    1620
gaccgagcgc agcgagtcag tgagcgagga agcggaagag cgcccaatac gcagggcccc    1680
ctgcaggata aaaaaattgt agataaattt tataaaatag ttttatctac aattttttta    1740
tcaggaaaca gctatgaccg cggccgcaga tagtcataat agttccagaa tagttcaatt    1800
tagaaattag actaaacttc aaaatgtttg ttaaatatat accaaactag tatagatatt    1860
ttttaaatac tggacttaaa cagtagtaat ttgcctaaaa aattttttca atttttttta    1920
aaaaatcctt ttcaagttgt acattgttat ggtaatatgt aattgaagaa gttatgtagt    1980
aatattgtaa acgtttcttg attttttttac atccatgtag tgcttaaaaa accaaaatat    2040
gtcacatgca attgtatatt tcaaataaca atatttattt tctcgttaaa ttcacaaata    2100
atttattaat aatatcaata accaagatta tacttaaatg gatgtttatt ttttaacact    2160
tttatagtaa atatatttat tttatgtagt aaaaaggtta taattataat tgtatttatt    2220
acaattaatt aaaataaaaa atagggtttt aggtaaaatt aagttatttt aagaagtaat    2280
tacaataaaa attgaagtta tttctttaag gagggaatta ttcatatgaa agaagttgta    2340
atagctagtg cagtaagaac agcgattgga tcttatggaa agtctcttaa ggatgtacca    2400
gcagtagatt taggagctac agctataaag gaagcagtta aaaagcagg aataaaacca    2460 gaggatgtta atgaagtcat tttaggaaat gttcttcaag caggtttagg acagaatcca    2520
gcaagacagg catctttaa agcaggatta ccagttgaaa ttccagctat gactattaat    2580
aaggtttgtg gttcaggact tagaacagtt agcttagcag cacaaattat aaaagcagga    2640
gatgctgacg taataatagc aggtggtatg gaaaatatgt ctagagctcc ttacttagcg    2700
aataacgcta gatggggata tagaatggga aacgctaaat tgttgatga aatgatcact    2760 gacggattgt gggatgcatt taatgattac cacatgggaa taacagcaga aaacatagct    2820
gagagatgga catttcaag agaagaacaa gatgagtttg ctcttgcatc acaaaaaaaa    2880
gctgaagaag ctataaaatc aggtcaattt aaagatgaaa tagttcctgt agtaattaaa    2940
ggcagaaagg gagaaactgt agttgataca gatgagcacc ctagatttgg atcaactata    3000
gaaggacttg caaaattaaa acctgccttc aaaaaagatg gaacagttac agctggtaat    3060
gcatcaggat taaatgactg tgcagcagta cttgtaatca tgagtgcaga aaaagctaaa    3120
gagcttggag taaaccact tgctaagata gtttcttatg gttcagcagg agttgaccca    3180
gcaataatgg gatatggacc tttctatgca acaaagcag ctattgaaaa agcaggttgg    3240
acagttgatg aattagattt aatagaatca atgaagctt ttgcagctca agtttagca     3300 gtagcaaaag atttaaaatt tgatatgaat aaagtaaatg taaatggagg agctattgcc    3360
cttggtcatc caattggagc atcaggtgca agaatactcg ttactcttgt acacgcaatg    3420
caaaaaagag atgcaaaaaa aggcttagca actttatgta taggtggcgg acaaggaaca    3480
gcaatattgc tagaaagtg ctaggaattc gagctcggta ccagggagat attaaaatga    3540
```

```
ataaattagt aaaattaaca gatttaaagc gcattttcaa agatggcatg acaattatgg    3600
ttgggggttt tttagattgt ggaactcctg aaaatattat agatatgcta gttgatttaa    3660
atataaaaaa tctgactatt ataagcaatg atacagcttt tcctaataaa ggaataggaa    3720
aacttattgt aaatggtcaa gtttctaaag taattgcttc acatattgga actaatcctg    3780
aaactggaaa aaaatgagc tctggagaac ttaaagttga gctttcccca caaggaacac    3840
tgattgaaag aattcgtgca gctggatctg gactcggagg tgtattaact ccaactggac    3900
ttggaactat cgttgaagaa ggtaagaaaa aagttactat cgatggcaaa gaatatctat    3960
tagaacttcc tttatctgct gatgtttcat taataaaagg tagcattgta gatgaatttg    4020
gaaatacctt ctatagggct gctactaaaa atttcaatcc atatatggca atggctgcaa    4080
aaacagttat agttgaagca gaaaatttag ttaaatgtga agatttaaaa agagatgcca    4140
taatgactcc tggcgtatta gtagattata tcgttaagga ggcggcttaa ttgattgtag    4200
ataaagtttt agcaaaagag ataattgcca aagagttgc aaaagaacta aaaaaagacc    4260
aactcgtaaa ccttggaata ggacttccaa ctttagtagc aaattatgta ccaaaagaaa    4320
tgaacattac ttttgaatca gaaaatggca tggttggtat ggcacaaatg gcatcatcag    4380
gtgaaaatga cccagatata ataaatgctg gcggggaata tgtaacatta ttacctcaag    4440
gttcattttt tgatagttca atgtctttcg cactaatacg aggaggacat gttgatgttg    4500
ctgttcttgg tgctctagaa gttgatgaaa aaggtaattt agctaactgg attgttccaa    4560
ataaaattgt cccaggtatg ggtggcgcta tggatttagc aataggcgca aaaaaaataa    4620
tagtggcaat gcaacataca ggaaaaagta aacctaaaat cgttaaaaaa tgtactctcc    4680
cacttactgc taaggctcaa gtggatttaa ttgtcacaga actttgtgta attgatgtaa    4740
caaatgacgg cttactttta aaagaaattc ataaagatac aactattgat gaaattaaat    4800
ttttaacaga tgcagattta attattccag ataacttaaa gattatggat atatgaatca    4860
ttctatttta aatatataac tttaaaaatc ttatgtatta aaaactaaga aaagaggttg    4920
attgttttat gttagaaagt gaagtatcta aacaaattac aactccactt gctgctccag    4980
cgtttcctag aggaccatat aggtttcaca atagagaata tctaaacatt atttatcgaa    5040
ctgatttaga tgctcttcga aaaatagtac cagagccact tgaattagat agagcatatg    5100
ttagatttga aatgatggct atgcctgata caaccggact aggctcatat acagaatgtg    5160
gtcaagctat tccagtaaaa tataatggtg ttaagggtga ctacttgcat atgatgtatc    5220
tagataatga acctgctatt gctgttggaa gagaaagtag cgcttatcca aaaaagcttg    5280
gctatccaaa gctatttgtt gattcagata ctttagttgg gacacttaaa tatggtacat    5340
taccagtagc tactgcaaca atgggatata agcacgagcc tctagatctt aaagaagcct    5400
atgctcaaat tgcaagaccc aattttatgc taaaaatcat tcaaggttac gatggtaagc    5460
caagaatttg tgaactaata tgtgcagaaa atactgatat aactattcac ggtgcttgga    5520
ctggaagtgc acgtctacaa ttatttagcc atgcactagc tcctcttgct gatttacctg    5580
tattagagat tgtatcagca tctcatatcc tcacagattt aactcttgga acacctaagg    5640
ttgtacatga ttatctttca gtaaaataaa agcaatatag aggatccagg aggaacaaag    5700
atgagtatac cagaaacaca aaaagcaatt atatttatg agtcaaatgg aaaattagag    5760
cataaagata tacctgtacc aaaaccaaaa ccaaacgaac ttcttataaa tgttaagtat    5820
tctggtgttt gtcatactga tcttcatgca tggcatggtg attggcctct tccaactaaa    5880
```

```
ttacctcttg taggtggtca tgaaggtgct ggtgtagttg taggtatggg tgaaaatgtt    5940
aaaggttgga aaataggtga ttatgctgga attaaatggc ttaatggatc ttgtatggca    6000
tgcgagtatt gtgaattagg aaatgaaagt aattgtccac atgctgactt aagtggttat    6060
actcatgatg gatcttttca agaatatgct actgcagatg cagttcaggc tgcacacatt    6120
ccacagggaa ctgatcttgc tgaagtagct cctatattat gcgctggaat tacagtatac    6180
aaagcattaa aaagtgctaa tcttagagca ggacactggg cagctataag tggtgctgca    6240
ggtggtttag gatctttagc agttcaatat gctaaagcta tgggatatag agtattagga    6300
atagacggtg gtccaggaaa agaagagtta tttacatcat taggtggtga agttttata     6360
gatttcacaa aggaaaaaga tattgtttca gctgtagtaa aggcaactaa tggtggtgca    6420
cacggaatta taaatgtttc agtatctgaa gcagcaatag aagcaagtac tagatattgt    6480
agagcaaacg gaacagtagt tttagttgga cttccagctg gtgcaaagtg ttcatctgac    6540
gtatttaacc atgtagtaaa gagtatttca atagttggat cttacgtagg taatagagct    6600
gatacaagag aagctttaga tttctttgca agaggtttag ttaagagtcc tataaaagta    6660
gtaggacttt catcacttcc tgaaatttat gaaaagatgg aaaagggaca aatagctggt    6720
agatatgttg tagatacaag taaataaggc catggagatc tcgaggcctg cagacatgca    6780
agcttggcac tggccgtcgt tttacaacgt cgtgactggg aaaaccctgg cgttacccaa    6840
cttaatcgcc ttgcagcaca tccccctttc gccagctggc gtaatagcga agaggcccgc    6900
accgatcgcc cttcccaaca gttgcgcagc ctgaatggcg aatggcgcta gcataaaaat    6960
aagaagcctg catttgcagg cttcttattt ttatggcgcg ccgccattat ttttttgaac    7020
aattgacaat tcatttctta ttttttatta gtgatagtc aaaaggcata acagtgctga    7080
atagaaagaa atttacagaa aagaaaatta tagaatttag tatgattaat tatactcatt    7140
tatgaatgtt taattgaata caaaaaaaaa tacttgttat gtattcaatt acgggttaaa    7200
atatagacaa gttgaaaaat ttaataaaaa ataagtcct cagctcttat atattaagct    7260
accaacttag tatataagcc aaaacttaaa tgtgctacca acacatcaag ccgttagaga    7320
actctatcta tagcaatatt tcaaatgtac cgacatacaa gagaaacatt aactatatat    7380
attcaattta tgagattatc ttaacagata taaatgtaaa ttgcaataag taagatttag    7440
aagtttatag cctttgtgta ttggaagcag tacgcaaagg cttttttatt tgataaaaat    7500
tagaagtata tttatttttt cataattaat ttatgaaaat gaaggggggt gagcaaagtg    7560
acagaggaaa gcagtatctt atcaaataac aaggtattag caatatcatt attgacttta    7620
gcagtaaaca ttatgacttt tatagtgctt gtagctaagt agtacgaaag ggggagcttt    7680
aaaaagctcc ttggaataca tagaattcat aaattaattt atgaaaagaa gggcgtatat    7740
gaaaacttgt aaaaattgca aagagtttat taaagatact gaaatatgca aaatacattc    7800
gttgatgatt catgataaaa cagtagcaac ctattgcagt aaatacaatg agtcaagatg    7860
tttacataaa gggaaagtcc aatgtattaa ttgttcaaag atgaaccgat atggatggtg    7920
tgccataaaa atgagatgtt ttacagagga agaacagaaa aagaacgta catgcattaa    7980
atattatgca aggagcttta aaaagctca tgtaagaag agtaaaaaga aaaataatt     8040
tatttattaa tttaatattg agagtgccga cacagtatgc actaaaaaat atatctgtgg    8100
tgtagtgagc cgatacaaaa ggatagtcac tcgcattttc ataatacatc ttatgttatg    8160
attatgtgtc ggtgggactt cacgacgaaa acccacaata aaaaaagagt tcggggtagg    8220
gttaagcata gttgaggcaa ctaaacaatc aagctaggat atgcagtagc agaccgtaag    8280
```

-continued

| | |
|---|---|
| gtcgttgttt aggtgtgttg taatacatac gctattaaga tgtaaaaata cggataccaa | 8340 |
| tgaagggaaa agtataattt ttggatgtag tttgtttgtt catctatggg caaactacgt | 8400 |
| ccaaagccgt ttccaaatct gctaaaaagt atatcctttc taaaatcaaa gtcaagtatg | 8460 |
| aaatcataaa taaagtttaa ttttgaagtt attatgatat tatgtttttc tattaaaata | 8520 |
| aattaagtat atagaatagt ttaataatag tatatactta atgtgataag tgtctgacag | 8580 |
| tgtcacagaa aggatgattg ttatggatta taagcggccg g | 8621 |

<210> SEQ ID NO 99
<211> LENGTH: 37
<212> TYPE: DNA
<213> ORGANISM: Artificial sequence
<220> FEATURE:
<223> OTHER INFORMATION: synthetic primer

<400> SEQUENCE: 99

| | |
|---|---|
| atattggatc cacagctatg accgcggccg caatatg | 37 |

<210> SEQ ID NO 100
<211> LENGTH: 39
<212> TYPE: DNA
<213> ORGANISM: Artificial sequence
<220> FEATURE:
<223> OTHER INFORMATION: synthetic primer

<400> SEQUENCE: 100

| | |
|---|---|
| agcgtccatg gccttattta cttgtatcta caacatatc | 39 |

<210> SEQ ID NO 101
<211> LENGTH: 10803
<212> TYPE: DNA
<213> ORGANISM: Artificial sequence
<220> FEATURE:
<223> OTHER INFORMATION: synthetic plasmid

<400> SEQUENCE: 101

| | |
|---|---|
| ccagtgggca agttgaaaaa ttcacaaaaa tgtggtataa tatctttgtt cattagagcg | 60 |
| ataaacttga atttgagagg gaacttagat ggtatttgaa aaaattgata aaaatagttg | 120 |
| gaacagaaaa gagtattttg accactactt tgcaagtgta ccttgtacct acagcatgac | 180 |
| cgttaaagtg gatatcacac aaataaagga aagggaatg aaactatatc ctgcaatgct | 240 |
| ttattatatt gcaatgattg taaaccgcca ttcagagttt aggacggcaa tcaatcaaga | 300 |
| tggtgaattg gggatatatg atgagatgat accaagctat acaatatttc acaatgatac | 360 |
| tgaaacattt tccagccttt ggactgagtg taagtctgac tttaaatcat ttttagcaga | 420 |
| ttatgaaagt gatacgcaac ggtatggaaa caatcataga atggaaggaa agccaaatgc | 480 |
| tccggaaaac atttttaatg tatctatgat accgtggtca accttcgatg gctttaatct | 540 |
| gaatttgcag aaaggatatg attatttgat tcctatttt actatgggga atattataa | 600 |
| agaagataac aaaattatac ttcctttggc aattcaagtt catcacgcag tatgtgacgg | 660 |
| atttcacatt tgccgttttg taaacgaatt gcaggaattg ataaatagtt aacttcaggt | 720 |
| ttgtctgtaa ctaaaaacaa gtatttaagc aaaaacatcg tagaaatacg gtgttttttg | 780 |
| ttaccctaag tttaaactcc tttttgataa tctcatgacc aaaatcccct aacgtgagtt | 840 |
| ttcgttccac tgagcgtcag accccgtaga aagatcaaa ggatcttctt gagatccttt | 900 |
| ttttctgcgc gtaatctgct gcttgcaaac aaaaaaacca ccgctaccag cggtggtttg | 960 |

```
tttgccggat caagagctac caactctttt tccgaaggta actggcttca gcagagcgca    1020
gataccaaat actgttcttc tagtgtagcc gtagttaggc caccacttca agaactctgt    1080
agcaccgcct acatacctcg ctctgctaat cctgttacca gtggctgctg ccagtggcga    1140
taagtcgtgt cttaccgggt tggactcaag acgatagtta ccggataagg cgcagcggtc    1200
gggctgaacg gggggttcgt gcacacagcc cagcttggag cgaacgacct acaccgaact    1260
gagataccta cagcgtgagc tatgagaaag cgccacgctt cccgaaggga gaaaggcgga    1320
caggtatccg gtaagcggca gggtcggaac aggagagcgc acgagggagc ttccaggggg    1380
aaacgcctgg tatctttata gtcctgtcgg gtttcgccac ctctgacttg agcgtcgatt    1440
tttgtgatgc tcgtcagggg ggcggagcct atggaaaaac gccagcaacg cggcctttttt   1500
acggttcctg gccttttgct ggcctttgc tcacatgttc tttcctgcgt tatcccctga    1560
ttctgtggat aaccgtatta ccgcctttga gtgagctgat accgctcgcc gcagccgaac    1620
gaccgagcgc agcgagtcag tgagcgagga agcggaagag cgcccaatac gcagggcccc    1680
ctgcaggata aaaaaattgt agataaattt tataaaatag ttttatctac aattttttta    1740
tcaggaaaca gctatgaccg cggccgcaga tagtcataat agttccagaa tagttcaatt    1800
tagaaattag actaaacttc aaaatgtttg ttaaatatat accaaactag tatagatatt    1860
ttttaaatac tggacttaaa cagtagtaat ttgcctaaaa aatttttca attttttta    1920
aaaaatcctt ttcaagttgt acattgttat ggtaatatgt aattgaagaa gttatgtagt    1980
aatattgtaa acgtttcttg attttttttac atccatgtag tgcttaaaaa accaaaatat    2040
gtcacatgca attgtatatt tcaaataaca atatttattt tctcgttaaa ttcacaaata    2100
atttattaat aatatcaata accaagatta tacttaaatg gatgtttatt ttttaacact    2160
tttatagtaa atatatttat tttatgtagt aaaaaggtta taattataat tgtatttatt    2220
acaattaatt aaaataaaaa atagggtttt aggtaaaatt aagttatttt aagaagtaat    2280
tacaataaaa attgaagtta tttctttaag gagggaatta ttcatatgaa agaagttgta    2340
atagctagtg cagtaagaac agcgattgga tcttatggaa agtctcttaa ggatgtacca    2400
gcagtagatt taggagctac agctataaag gaagcagtta aaaagcagg aataaaacca    2460
gaggatgtta atgaagtcat tttaggaaat gttcttcaag caggtttagg acagaatcca    2520
gcaagacagg catcttttaa agcaggatta ccagttgaaa ttccagctat gactattaat    2580
aaggtttgtg gttcaggact agaacagtt agcttagcag cacaaattat aaaagcagga    2640
gatgctgacg taataatagc aggtggtatg gaaaatatgt ctagagctcc ttacttagcg    2700
aataacgcta gatgggata tagaatggga aacgctaaat ttgttgatga atgatcact    2760
gacggattgt gggatgcatt taatgattac cacatgggaa taacagcaga aaacatagct    2820
gagagatgga acatttcaag agaagaacaa gatgagtttg ctcttgcatc acaaaaaaaa    2880
gctgaagaag ctataaaatc aggtcaattt aaagatgaaa tagttcctgt agtaattaaa    2940
ggcagaaagg gagaaactgt agttgataca gatgagcacc ctagatttgg atcaactata    3000
gaaggacttg caaaattaaa acctgccttc aaaaagatg gaacagttac agctggtaat    3060
gcatcaggat taaatgactg tgcagcagta cttgtaatca tgagtgcaga aaaagctaaa    3120
gagcttggag taaaccact tgctaagata gtttcttatg gttcagcagg agttgaccca    3180
gcaataatgg gatatggacc tttctatgca acaaaagcag ctattgaaaa agcaggttgg    3240
acagttgatg aattagattt aatagaatca atgaagcttt tgcagctcaa agtttagca    3300
gtagcaaaag atttaaaatt tgatatgaat aaagtaaatg taaatggagg agctattgcc    3360
```

-continued

```
cttggtcatc caattggagc atcaggtgca agaatactcg ttactcttgt acacgcaatg    3420
caaaaaagag atgcaaaaaa aggcttagca actttatgta taggtggcgg acaaggaaca    3480
gcaatattgc tagaaaagtg ctaggaattc gagctcggta ccagggagat attaaaatga    3540
ataaattagt aaaattaaca gatttaaagc gcattttcaa agatggcatg acaattatgg    3600
ttggggtttt tttagattgt ggaactcctg aaaatattat agatatgcta gttgatttaa    3660
atataaaaaa tctgactatt ataagcaatg atacagcttt tcctaataaa ggaataggaa    3720
aacttattgt aaatggtcaa gtttctaaag taattgcttc acatattgga actaatcctg    3780
aaactgaaaa aaaaatgagc tctggagaac ttaaagttga gctttcccca caaggaacac    3840
tgattgaaag aattcgtgca gctggatctg gactcggagg tgtattaact ccaactggac    3900
ttggaactat cgttgaagaa ggtaagaaaa aagttactat cgatggcaaa gaatatctat    3960
tagaacttcc tttatctgct gatgtttcat aataaaaagg tagcattgta gatgaatttg    4020
gaaataccct ctatagggct gctactaaaa atttcaatcc atatatgcca atggctgcaa    4080
aaacagttat agttgaagca gaaaatttag ttaaatgtga agatttaaaa agagatgcca    4140
taatgactcc tggcgtatta gtagattata tcgttaagga ggcggcttaa ttgattgtag    4200
ataaagtttt agcaaaagag ataattgcca aaagagttgc aaaagaacta aaaaaagacc    4260
aactcgtaaa ccttggaata ggacttccaa ctttagtagc aaattatgta ccaaaagaaa    4320
tgaacattac ttttgaatca gaaaatggca tggttggtat ggcacaaatg gcatcatcag    4380
gtgaaaatga cccagatata ataaatgctg gcgggaata tgtaacatta ttacctcaag    4440
gttcattttt tgatagttca atgtctttcg cactaatacg aggaggacat gttgatgttg    4500
ctgttcttgg tgctctagaa gttgatgaaa aaggtaattt agctaactgg attgttccaa    4560
ataaaattgt cccaggtatg ggtggcgcta tggatttagc aataggcgca aaaaaaataa    4620
tagtggcaat gcaacataca ggaaaaagta aacctaaaat cgttaaaaaa tgtactctcc    4680
cacttactgc taaggctcaa gtggatttaa ttgtcacaga actttgtgta attgatgtaa    4740
caaatgacgg cttactttta aaagaaattc ataaagatac aactattgat gaaattaaat    4800
ttttaacaga tgcagattta attattccag ataacttaaa gattatggat atatgaatca    4860
ttctatttta aatatataac tttaaaaatc ttatgtatta aaaactaaga aaagaggttg    4920
attgttttat gttagaaagt gaagtatcta acaaattac aactccactt gctgctccag    4980
cgtttcctag aggaccatat aggtttcaca atagagaata tctaaacatt atttatcgaa    5040
ctgatttaga tgctcttcga aaaatagtac cagagccact tgaattagat agagcatatg    5100
ttagatttga aatgatggct atgcctgata caaccggact aggctcatat acagaatgtg    5160
gtcaagctat tccagtaaaa tataatggtg ttaagggtga ctacttgcat atgatgtatc    5220
tagataatga acctgctatt gctgttggaa gagaaagtag cgcttatcca aaaaagcttg    5280
gctatccaaa gctatttgtt gattcagata ctttagttgg gacacttaaa tatggtacat    5340
taccagtagc tactgcaaca atgggatata agcacgagcc tctagatctt aaagaagcct    5400
atgctcaaat tgcaagaccc aatttttatgc taaaaatcat tcaaggttac gatggtaagc    5460
caagaatttg tgaactaata tgtgcagaaa atactgatat aactattcac ggtgcttgga    5520
ctggaagtgc acgtctacaa ttatttagcc atgcactagc tcctcttgct gatttacctg    5580
tattagagat tgtatcagca tctcatatcc tcacagattt aactcttgga acacctaagg    5640
ttgtacatga ttatctttca gtaaaataaa agcaatatag aggatccaca gctatgaccg    5700
```

| | | | | | |
|---|---|---|---|---|---|
| cggccgcaat | atgatattta | tgtccattgt | gaaagggatt | atattcaact | attattccag | 5760 |
| ttacgttcat | agaaattttc | ctttctaaaa | tattttattc | catgtcaaga | actctgttta | 5820 |
| tttcattaaa | gaactataag | tacaaagtat | aaggcatttg | aaaaaatagg | ctagtatatt | 5880 |
| gattgattat | ttattttaaa | atgcctaagt | gaaatatata | catattataa | caataaaata | 5940 |
| agtattagtg | taggatttt | aaatagagta | tctatttca | gattaaattt | ttgattattt | 6000 |
| gatttacatt | atataatatt | gagtaaagta | ttgactagca | aaattttttg | atactttaat | 6060 |
| ttgtgaaatt | tcttatcaaa | agttatattt | ttgaataatt | tttattgaaa | aatacaacta | 6120 |
| aaaaggatta | tagtataagt | gtgtgtaatt | ttgtgttaaa | tttaaaggga | ggaaatgaac | 6180 |
| atgaaacata | tgtatacagt | tggtgattat | ttacttgata | gattacatga | acttggaata | 6240 |
| gaagaaattt | ttggtgtacc | aggtgattac | aatcttcaat | tcttagatca | aataatatca | 6300 |
| cataaggata | tgaaatgggt | tggtaatgct | aatgaattaa | atgcatcata | tatggcagac | 6360 |
| ggatatgcaa | gaactaaaaa | ggcagcagca | tttcttacta | catttggtgt | tggtgaatta | 6420 |
| agtgcagtaa | atgattagc | tggaagttac | gcagaaaact | taccagttgt | tgaaatagtt | 6480 |
| ggatctccta | ctagtaaagt | acaaaatgaa | ggtaaatttg | tacatcacac | tcttgcagat | 6540 |
| ggtgatttta | agcattttat | gaaaatgcat | gaacctgtta | cagctgcaag | aacacttctt | 6600 |
| acagctgaaa | acgctactgt | agaaaattgat | agagttttat | ctgctttact | taaagaaaga | 6660 |
| aagccagtat | atattaacct | tccagtagat | gtagcagcag | caaaagctga | gaaaccttca | 6720 |
| ttaccactta | aaaaggaaaa | ttcaacatca | aatacatctg | atcaagagat | attaaataaa | 6780 |
| attcaggaaa | gtcttaaaaa | tgcaagaaaa | cctatagtaa | taactggaca | tgaaataatt | 6840 |
| agttttggat | tagaaaagac | agttacacag | tttataagta | aaactaagct | tccaattaca | 6900 |
| actttaaatt | ttggaaagag | ttcagtagat | gaggcacttc | catcattctt | aggaatttat | 6960 |
| aatggaacat | tatctgaacc | taatcttaaa | gaatttgtag | agagtgctga | ttttatatta | 7020 |
| atgttaggtg | taaaacttac | tgatagtagt | actggtgcat | ttactcatca | tcttaacgaa | 7080 |
| aataagatga | tatcattaaa | tatagacgaa | ggtaaaatat | tcaatgaaag | aatacagaac | 7140 |
| tttgattttg | aatcacttat | atcatcatta | cttgatttat | cagagataga | atacaaagga | 7200 |
| aaatatatag | ataaaaagca | agaagatttt | gttccatcta | atgctcttct | ttctcaagat | 7260 |
| agactttggc | aagcagttga | gaatcttaca | cagtctaatg | aaactatagt | tgctgagcaa | 7320 |
| ggaacatcat | ttttcggtgc | atcaagtata | tttttaaaat | ctaaaagtca | ctttattgga | 7380 |
| caacctcttt | ggggttctat | tggatatact | tttccagcag | ctttaggaag | tcaaatagct | 7440 |
| gataaagaaa | gtagacattt | attatttatt | ggtgacggtt | cacttcagct | tacagtacaa | 7500 |
| gaattaggat | tagctataag | agagaagata | aatcctattt | gtttcataat | aaacaatgat | 7560 |
| ggatatactg | tagaaagaga | aattcacgga | ccaaatcagt | catataatga | tattccaatg | 7620 |
| tggaattatt | caaagttacc | tgaatctttc | ggtgctactg | aagatagagt | agtttctaaa | 7680 |
| attgttagaa | cagagaacga | atttgtatct | gttatgaaag | aagctcaggc | tgaccctaat | 7740 |
| agaatgtatt | ggattgaatt | aattttagca | aaagaaggtg | ctcctaaagt | acttaagaaa | 7800 |
| atgggaaaat | tatttgcaga | acaaaataag | tcataagaat | tcccataata | aagaaagaat | 7860 |
| tttaaataaa | ggaggaacaa | agatgagtat | accagaaaca | caaaaagcaa | ttatatttta | 7920 |
| tgagtcaaat | ggaaaattag | agcataaaga | tatacctgta | ccaaaaccaa | aaccaaacga | 7980 |
| acttcttata | aatgttaagt | attctggtgt | ttgtcatact | gatcttcatg | catggcatgg | 8040 |
| tgattggcct | cttccaacta | aattacctct | tgtaggtggt | catgaaggtg | ctggtgtagt | 8100 |

```
tgtaggtatg ggtgaaaatg ttaaaggttg gaaaataggt gattatgctg gaattaaatg    8160
gcttaatgga tcttgtatgg catgcgagta ttgtgaatta ggaaatgaaa gtaattgtcc    8220
acatgctgac ttaagtggtt atactcatga tggatctttt caagaatatg ctactgcaga    8280
tgcagttcag gctgcacaca ttccacaggg aactgatctt gctgaagtag ctcctatatt    8340
atgcgctgga attacagtat acaaagcatt aaaaagtgct aatcttagag caggacactg    8400
ggcagctata agtggtgctg caggtggttt aggatcttta gcagttcaat atgctaaagc    8460
tatgggatat agagtattag gaatagacgg tggtccagga aaagaagagt tatttacatc    8520
attaggtggt gaagttttta tagatttcac aaaggaaaaa gatattgttt cagctgtagt    8580
aaaggcaact aatggtggtg cacacggaat tataaatgtt tcagtatctg aagcagcaat    8640
agaagcaagt actagatatt gtagagcaaa cggaacagta gttttagttg gacttccagc    8700
tggtgcaaag tgttcatctg acgtatttaa ccatgtagta aagagtattt caatagttgg    8760
atcttacgta ggtaatagag ctgatacaag agaagcttta gatttctttg caagaggttt    8820
agttaagagt cctataaaag tagtaggact ttcatcactt cctgaaattt atgaaaagat    8880
ggaaaaggga caaatagctg gtagatatgt tgtagataca agtaaataag gccatggaga    8940
tctcgaggcc tgcagacatg caagcttggc actggccgtc gttttacaac gtcgtgactg    9000
ggaaaaccct ggcgttaccc aacttaatcg ccttgcagca catccccctt tcgccagctg    9060
gcgtaatagc gaagaggccc gcaccgatcg cccttcccaa cagttgcgca gcctgaatgg    9120
cgaatggcgc tagcataaaa ataagaagcc tgcatttgca ggcttcttat ttttatggcg    9180
cgccgccatt attttttga acaattgaca attcatttct tattttttat taagtgatag    9240
tcaaaaggca taacagtgct gaatagaaag aaatttacag aaaagaaaat tatagaattt    9300
agtatgatta attatactca tttatgaatg tttaattgaa tacaaaaaaa aatacttgtt    9360
atgtattcaa ttacgggtta aaatatagac aagttgaaaa atttaataaa aaataagtc     9420
ctcagctctt atatattaag ctaccaactt agtatataag ccaaaactta aatgtgctac    9480
caacacatca agccgttaga gaactctatc tatagcaata tttcaaatgt accgacatac    9540
aagagaaaca ttaactatat atattcaatt tatgagatta tcttaacaga tataaatgta    9600
aattgcaata agtaagattt agaagtttat agcctttgtg tattggaagc agtacgcaaa    9660
ggctttttta tttgataaaa attagaagta tatttatttt ttcataatta atttatgaaa    9720
atgaaagggg gtgagcaaag tgacagagga aagcagtatc ttatcaaata acaaggtatt    9780
agcaatatca ttattgactt tagcagtaaa cattatgact tttatagtgc ttgtagctaa    9840
gtagtacgaa aggggagct ttaaaaagct ccttggaata catagaattc ataaattaat    9900
ttatgaaaag aagggcgtat atgaaaactt gtaaaattg caaagagttt attaaagata    9960
ctgaaatatg caaatacat tcgttgatga ttcatgataa aacagtagca acctattgca    10020
gtaaatacaa tgagtcaaga tgtttacata aaggaaagt ccaatgtatt aattgttcaa    10080
agatgaaccg atatggatgg tgtgccataa aaatgagatg ttttacagag gaagaacaga    10140
aaaaagaacg tacatgcatt aaatattatg caaggagctt taaaaaagct catgtaaaga    10200
agagtaaaaa gaaaaaataa tttatttatt aatttaatat tgagagtgcc gacacagtat    10260
gcactaaaaa atatatctgt ggtgtagtga gccgatacaa aaggatagtc actcgcattt    10320
tcataataca tcttatgtta tgattatgtg tcggtgggac ttcacgacga aacccacaa    10380
taaaaaaga gttcggggta gggttaagca tagttgaggc aactaaacaa tcaagctagg    10440
```

```
atatgcagta gcagaccgta aggtcgttgt ttaggtgtgt tgtaatacat acgctattaa    10500
gatgtaaaaa tacggatacc aatgaaggga aaagtataat ttttggatgt agtttgtttg    10560
ttcatctatg ggcaaactac gtccaaagcc gtttccaaat ctgctaaaaa gtatatcctt    10620
tctaaaatca aagtcaagta tgaaatcata aataaagttt aattttgaag ttattatgat    10680
attatgtttt tctattaaaa taaattaagt atatagaata gtttaataat agtatatact    10740
taatgtgata agtgtctgac agtgtcacag aaaggatgat tgttatggat tataagcggc    10800
cgg                                                                  10803
```

RECOMBINANT MICROORGANISMS AND USES THEREFOR

CROSS REFERENCE TO RELATED APPLICATIONS

This application is a continuation of U.S. patent application Ser. No. 13/403,972 filed Feb. 23, 2012, which claims the benefit of U.S. Patent Application No. 61/446,832 filed Feb. 25, 2011, the entirety of which are incorporated herein by reference.

FIELD

The present invention relates to methods for the production of acetone, isopropanol and/or a precursor of acetone and/or isopropanol by microbial fermentation of substrates comprising carbon monoxide and genetically modified micro-organisms of use in such methods.

BACKGROUND

Some microorganisms such as *Clostridium acetobutylicum* or *Clostridium beijerinckii* are known to produce acetone or isopropanol as major by-products during butanol fermentation (ABE or IBE fermentation) [George H A, Johnson J L, Moore W E C, Holdeman L V, Chen J S: Acetone, isopropanol, and butanol production by *Clostridium beijerinckii* (syn. *Clostridium butylicum*) and *Clostridium aurantibutyricum*. Appl Environ Microbiol 45: 1160-1163]. However, all these organisms rely on sugar or starch based substrates. Acetogenic organisms such as the closely related microorganisms *Clostridium autoethanogenum*, *C. ljungdahlii*, and *C. ragsdalei* are able to grow chemoautotrophically on CO or $CO_2/H_2$ containing gases as sole energy and carbon source and synthesize products such as acetate, ethanol, or 2,3-butanediol, but neither acetone nor isopropanol [Munasinghe P C, Khanal S K: Biomass-derived syngas fermentation into biofuels: Opportunities and challenges. Bioresource Technol 2010, 5013-22].

Recently, production of isopropanol was reported in a study on *Clostridium ragsdalei* (*Clostridium* strain P11) in a 100-L pilot scale fermentor from switchgrass derived syngas [Kundiyana D K, Huhnke R L, Wilkins M R: Syngas fermentation in a 100-L pilot scale fermentor: Design and process considerations. J Biosci Bioeng 2010, 109: 492-498]. However, a related study from the same lab showed that this was due to a contamination in the used syngas since it was passed through a scrubbing mixture containing 20% acetone [Ramachandriya K D: Effect of biomass generated producer gas, methane and physical parameters on producer gas fermentations by *Clostridium* strain P11. Masters thesis, Oklahoma State University 2009]. The authors also noted that the production of isopropanol may be the result of reduction of propionic acid rather than acetone. Experiments carried out by the inventors of the present invention with *Clostridium ragsdalei* (*Clostridium* strain P11) and also *C. autoethanogenum* and *C. ljungdahlii* have never shown the production of acetone, isopropanol, or propionic acid.

The cost of many carbohydrate feed stocks suitable for the production of chemical products such as acetone and isopropanol is influenced by their value as human food or animal feed, and the cultivation of starch or sucrose-producing crops for such production is not economically sustainable in all geographies. Therefore, it is of interest to develop technologies to convert lower cost and/or more abundant carbon resources into useful chemical products such as acetone and isopropanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

It is an object of the invention to overcome one or more of the disadvantages of the prior art, or to at least to provide the public with a useful choice.

SUMMARY OF INVENTION

The invention generally provides, inter alia, methods for the production of acetone, isopropanol and/or precursors of acetone and/or isopropanol by microbial fermentation of substrates comprising CO, genetically modified microorganisms of use in such methods, nucleic acids suitable for preparation of genetically modified microorganisms and a novel alcohol dehydrogenase and nucleic acids encoding same.

In a first aspect, the invention provides a carboxydotrophic acetogenic recombinant microorganism capable of producing acetone, isopropanol and/or a precursor of acetone and/or isopropanol by fermentation of a substrate comprising CO.

In one particular embodiment, the microorganism is adapted to express one or more enzymes in the isopropanol biosynthesis pathway which are not naturally present in a parental microorganism from which the recombinant microorganism is derived. In another embodiment, the microorganism is adapted to over-express one or more enzymes in the isopropanol biosynthesis pathway which are naturally present in a parental microorganism from which the recombinant microorganism is derived.

In one particular embodiment, the microorganism is adapted to express one or more enzymes in the acetone biosynthesis pathway which are not naturally present in a parental microorganism from which the recombinant microorganism is derived. In another embodiment, the microorganism is adapted to over-express one or more enzymes in the acetone biosynthesis pathway which are naturally present in a parental microorganism from which the recombinant microorganism is derived.

In one particular embodiment, the microorganism is adapted to express one or more enzymes involved in the conversion of acetone to isopropanol which are not naturally present in a parental microorganism from which the recombinant microorganism is derived. In another embodiment, the microorganism is adapted to over-express one or more enzymes involved in the conversion of acetone to isopropanol which are naturally present in a parental microorganism from which the recombinant microorganism is derived.

In one embodiment, the parental microorganism is capable of fermenting a substrate comprising CO to produce acetone but not of converting acetone to isopropanol and the recombinant microorganism is adapted to express one or more enzymes involved in the conversion of acetone to isopropanol.

In another embodiment, the parental microorganism is capable of converting acetone to isopropanol but is not capable of fermenting a substrate comprising CO to produce acetone and the recombinant microorganism is adapted to express one or more enzymes in the acetone biosynthesis pathway.

In one embodiment, the parental microorganism is not capable of fermenting a substrate comprising CO to produce acetone and isopropanol and the recombinant microorganism is adapted to express one or more enzymes in the acetone biosynthesis pathway and one or more enzymes involved in the conversion of acetone to isopropanol.

In one embodiment the one or more enzymes in the isopropanol and/or acetone biosynthesis pathway are chosen from the group consisting:

Acetyl-Coenzyme A acetyltransferase (Thiolase; ThlA; E.C. 2.3.1.9);

Acetoacetyl-CoA:Acetate Coenzyme A transferase A (CoA transferase; CtfA; EC 2.8.3.9);

Acetoacetyl-CoA:Acetate Coenzyme A transferase B (CoA transferase; CtfB; EC 2.8.3.9);

Acetoacetate decarboxylase (Adc; EC 4.1.1.4);

Alpha-ketoisovalerate decarboxylase (decarboxylase; KivD; EC4.1.1.74); and,

A functionally equivalent variant of any one or more thereof.

In one embodiment, the Acetyl-Coenzyme A acetyltransferase (Thiolase; ThlA) is that derived from *C. acetobutylicum*.

In one embodiment, the enzymes Acetoacetyl-CoA:Acetate Coenzyme A transferase A (CoA transferase; CtfA), Acetoacetyl-CoA:Acetate Coenzyme A transferase B (CoA transferase; CtfB) and Acetoacetate decarboxylase (Adc) are derived from *C. beijerinckii*.

In one embodiment, the Alpha-ketoisovalerate decarboxylase (decarboxylase; KivD) is that derived from *Lactococcus lactis*.

In one embodiment, the one or more enzyme involved in the conversion of acetone to isopropanol are chosen from the group consisting:

Alcohol Dehydrogenase (Adh; EC 1.1.1.2);
Alcohol dehydrogenase (Adh2; EC 1.1.1.1) and,
A functionally equivalent variant thereof.

In one embodiment, the Alcohol Dehydrogenase (Adh) is derived from *C. autoethanogenum, C. ljungdahlii*, and/or *C. ragsdalei*. In one embodiment, the alcohol dehydrogenase has the amino acid sequence of SEQ_ID NO. 1, or it is a functionally equivalent variant thereof. In one embodiment, the functionally equivalent variant has at least approximately 88%, 89%, 90%, 91%, 92%, 93%, 94%, 95%, 96%, 97%, 98% or 99% sequence identity to SEQ_ID NO. 1.

In one embodiment, the Alcohol Dehydrogenase (Adh2) is derived from *S. cerevisiae*.

In one embodiment, the microorganism comprises one or more exogenous nucleic acids adapted to increase expression of one or more nucleic acids native to the parental microorganism and which one or more nucleic acids encode one or more of the enzymes referred to herein before.

In one embodiment, the one or more exogenous nucleic acid adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters. In one embodiment, the promoter has the sequence of SEQ_ID No. 22 or SEQ ID no. 77, or is a functionally equivalent variant thereof.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two of the enzymes. In other embodiments, the microorganism comprises one or more exogenous nucleic acid encoding and adapted to express 3, 4, 5 or 6 of the enzymes.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), and Acetoacetate decarboxylase (Adc; EC 4.1.1.4) or a functionally equivalent variant of any one or more thereof.

In one particular embodiment, the microorganism comprises one or more exogenous nucleic acids encoding Alcohol Dehydrogenase (Adh; EC 1.1.1.2) or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), and Alcohol Dehydrogenase (Adh; EC 1.1.1.2), or a functionally equivalent variant of any one or more thereof.

In one particular embodiment, the microorganism comprises one or more exogenous nucleic acids encoding each of Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), and Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding Alpha-ketoisovalerate decarboxylase (decarboxylase; KivD; EC4.1.1.74), or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), and Alcohol dehydrogenase (Adh2; EC 1.1.1.1), or a functionally equivalent variant of any one or more thereof.

In another particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one embodiment, the nucleic acid encoding Acetyl-Coenzyme A acetyltransferase (Thiolase; ThlA) comprises the sequence SEQ_ID NO. 18, or a functionally equivalent variant thereof. In one embodiment, the nucleic acid encoding Acetoacetyl-CoA:Acetate Coenzyme A transferase A (CoA transferase; CtfA) comprises the sequence SEQ_ID NO. 19, or a functionally equivalent variant thereof. In one embodiment, the nucleic acid encoding Acetoacetyl-CoA: Acetate Coenzyme A transferase B (CoA transferase; CtfB) comprises the sequence SEQ_ID NO. 20, or a functionally equivalent variant thereof. In one embodiment, the nucleic acid encoding Acetoacetate decarboxylase (Adc) comprises the sequence SEQ_ID NO. 21, or a functionally equivalent variant thereof. In one embodiment, the nucleic acid encoding Alpha-ketoisovalerate decarboxylase (decarboxylase; KivD) comprises the sequence SEQ_ID NO. 71, or a functionally equivalent variant thereof. In one embodiment, the nucleic acid encoding Alcohol Dehydrogenase (Adh) comprises the sequence SEQ_ID NO. 2, SEQ_ID NO. 3, or SEQ_ID NO. 4, or a functionally equivalent variant of any one thereof. In one embodiment, the functionally equivalent variant of the nucleic acid encoding alcohol dehydrogenase (Adh) has at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4. In one embodiment, the nucleic acid encoding Alcohol dehydrogenase (Adh2) comprises the sequence SEQ_ID NO. 75, or a functionally equivalent variant thereof.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid. In one particular embodiment, the expression plasmid has the nucleotide sequence SEQ_ID No. 46, 48, 83, 84, 95, 98 or 101.

In one embodiment, the parental microorganism is selected from the group of carboxydotrophic acetogenic bacteria selected from the group comprising *Clostridium autoethanogenum, Clostridium ljungdahlii, Clostridium ragsdalei, Clostridium carboxidivorans, Clostridium drakei, Clostridium scatologenes, Butyribacterium limosum, Butyribacterium methylotrophicum, Acetobacterium woodii, Alkalibaculum bacchii, Blautia producta, Eubacterium limosum, Moorella thermoacetica, Moorella thermoautotrophica, Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding ThlA, CtfA, CtfB, Adc, KivD, Adh and Adh2. In one particular embodiment, the parental microorganism lacks a gene encoding Adh. In another particular embodiment, the parental microorganism lacks each of the genes encoding ThlA, CtfA, CtfB, and Adc and KivD.

In second aspect, the invention provides an Alcohol Dehydrogenase (Adh) having the amino acid sequence of SEQ_ID NO. 1, or a functionally equivalent variant of any one thereof.

In one particular embodiment, the functionally equivalent variant of the Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In a third aspect, the invention provides a nucleic acid encoding Adh of SEQ_ID NO. 1 or a functionally equivalent variant thereof.

In a fourth aspect, the invention provides a nucleic acid having the sequence chosen from the group consisting:
SEQ_ID NO. 2
SEQ_ID NO. 3
SEQ_ID NO. 4; and,
A functionally equivalent variant of any one thereof.

In one particular embodiment, a functionally equivalent variant of SEQ_ID NO. 2, 3 or 4 is a nucleic acid at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

In a fifth aspect, the invention provides a nucleic acid capable of hybridising to at least a portion of the nucleic acid SEQ_ID NO. 2, 3 or 4, a nucleic acid complementary to any one thereof, or a functionally equivalent variant of any one thereof.

In a sixth aspect, the invention provides a nucleic acid chosen from the group consisting: SEQ_ID NO. 5; SEQ_ID NO. 6; SEQ_ID NO. 7; SEQ_ID NO. 8; SEQ_ID NO. 9; SEQ_ID NO. 10; SEQ_ID NO. 11; SEQ_ID NO. 12; SEQ_ID NO. 13; SEQ_ID NO. 14; SEQ_ID NO. 15; SEQ_ID NO. 16; SEQ_ID NO. 17; SEQ_ID NO. 18; SEQ_ID NO. 23; SEQ_ID NO. 24; SEQ_ID NO. 25; SEQ_ID NO. 26; SEQ_ID NO. 27; SEQ_ID NO. 28; SEQ_ID NO. 29; SEQ_ID NO. 30; SEQ_ID NO. 31; SEQ_ID NO. 32; SEQ_ID NO. 33; SEQ_ID NO. 64; SEQ_ID NO. 65; SEQ_ID NO. 66; SEQ_ID NO. 67; SEQ_ID NO. 68; SEQ_ID NO. 69; SEQ_ID NO. 70; SEQ_ID NO. 71; SEQ_ID NO. 85; SEQ_ID NO. 86; SEQ_ID NO. 87; SEQ_ID NO. 88; SEQ_ID NO. 89; SEQ_ID NO. 90; SEQ_ID NO. 91; SEQ_ID NO. 92; SEQ_ID NO. 93; SEQ_ID NO. 94; SEQ_ID NO. 96; SEQ_ID NO. 97; SEQ_ID NO. 99; SEQ_ID NO. 100.

In a seventh aspect, the invention provides a nucleic acid encoding one or more enzymes which when expressed in a microorganism allows the microorganism to produce acetone, isopropanol and/or a precursor of acetone and/or isopropanol by fermentation of substrate comprising CO.

In one embodiment, the nucleic acid encodes two or more enzymes which when expressed in a microorganism allows the microorganism to produce acetone, isopropanol and/or a precursor of acetone and/or isopropanol by fermentation of substrate comprising CO.

In one embodiment, the nucleic acids of the invention encode 3, 4, 5 or 6 such enzymes.

In one embodiment, the enzymes are chosen from Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), Alcohol dehydrogenase (Adh2), Alcohol Dehydrogenase (Adh) and a functionally equivalent variant of any one or more thereof.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Acetoacetate decarboxylase (Adc) or a functionally equivalent variant of any one or more thereof, in any order.

In one embodiment, the nucleic acid comprises nucleic acid sequences encoding Alcohol Dehydrogenase (Adh) or a functionally equivalent variant thereof.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol Dehydrogenase (Adh) or a functionally equivalent variant of any one or more thereof, in any order.

In one embodiment, the nucleic acid comprises nucleic acid sequences encoding each of Alpha-ketoisovalerate decarboxylase (decarboxylase; KivD), Alcohol dehydrogenase (Adh2), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Alpha-ketoisovalerate decarboxylase (decarboxylase; KivD), or a functionally equivalent variant of any one or more thereof, in any order.

In one embodiment, the nucleic acid comprises nucleic acid sequences encoding each of Alpha-ketoisovalerate decarboxylase (decarboxylase; KivD), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alcohol dehydrogenase (Adh2), or a functionally equivalent variant of any one or more thereof, in any order.

In one embodiment, the nucleic acid comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), Alcohol dehydrogenase (Adh2), or a functionally equivalent variant of any one or more thereof, in any order.

In one embodiment, the nucleic acid encodes Acetyl-Coenzyme A acetyltransferase (Thiolase; ThlA) having the sequence of SEQ_ID NO. 42 or a functionally equivalent variant thereof.

In one embodiment, the nucleic acid encodes Acetoacetyl-CoA:Acetate Coenzyme A transferase A (CoA transferase; CtfA) having the sequence of SEQ_ID NO. 43 or a functionally equivalent variant thereof.

In one embodiment, the nucleic acid encodes Acetoacetyl-CoA:Acetate Coenzyme A transferase B (CoA transferase; CtfB) having the sequence of SEQ_ID NO 43 and SEQ_ID NO 44, or a functionally equivalent variant thereof.

In one embodiment, the nucleic acid encodes Acetoacetate decarboxylase (Adc) having the sequence of SEQ ID No. 45, or a functionally equivalent variant thereof.

In one embodiment, the nucleic acid encodes Alcohol Dehydrogenase (Adh) having the sequence of SEQ_ID NO 38 and SEQ_ID NO 40. In one particular embodiment, the nucleic acid encodes Alcohol Dehydrogenase (Adh) having the sequence of SEQ_ID NO. 1, or a functionally equivalent variant thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In one embodiment, the nucleic acid encodes Alpha-ketoisovalerate decarboxylase (decarboxylase; KivD) having the sequence of SEQ ID No. 73, or a functionally equivalent variant thereof.

In one embodiment, the nucleic acid encodes Alcohol dehydrogenase (Adh2) having the sequence of SEQ ID No. 75, or a functionally equivalent variant thereof.

In one embodiment, the nucleic acid sequence encoding Acetyl-Coenzyme A acetyltransferase (Thiolase; ThlA) comprises SEQ_ID NO. 18, or is a functionally equivalent variant thereof.

In one embodiment, the nucleic acid sequence encoding Acetoacetyl-CoA:Acetate Coenzyme A transferase A (CoA transferase; CtfA) comprises SEQ_ID NO. 19, or is a functionally equivalent variant thereof.

In one embodiment, the nucleic acid sequence encoding Acetoacetyl-CoA:Acetate Coenzyme A transferase B (CoA transferase; CtfB) comprises SEQ_ID NO. 20, or is a functionally equivalent variant thereof.

In one embodiment, the nucleic acid sequence encoding Acetoacetate decarboxylase (Adc) comprises SEQ_ID NO. 21, or is a functionally equivalent variant thereof.

In one embodiment, the nucleic acid sequence encoding Alcohol Dehydrogenase (Adh) comprises SEQ_ID NO. 39 or 41. In one particular embodiment, the nucleic acid sequence encoding Alcohol Dehydrogenase (Adh) comprises SEQ_ID NO. 2, SEQ_ID NO. 3, or SEQ_ID NO. 4, or is a functionally equivalent variant of any one thereof. In one embodiment, the functionally equivalent variant of SEQ_ID NO. 2, SEQ_ID NO. 3, or SEQ_ID NO. 4 has at least approximately 83%, 84%, 85%, 86%, 88%, 89%, 90%, 91%, 92%, 93%, 94%, 95%, 96%, 97%, 98% or 99% sequence identity to SEQ_ID NO. 2, 3 or 4.

In one embodiment, the nucleic acid sequence encoding Alpha-ketoisovalerate decarboxylase (decarboxylase; KivD) comprises SEQ_ID NO. 72 or 76, or is a functionally equivalent variant thereof.

In one embodiment, the nucleic acid sequence encoding Alcohol dehydrogenase (Adh2) comprises SEQ_ID NO. 74 or 77, or is a functionally equivalent variant thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*. In one particular embodiment, the promoter has the sequence of SEQ_ID NO. 22, SEQ_ID NO. 79, or is a functionally equivalent variant thereof.

In an eighth aspect, the invention provides a nucleic acid construct or vector comprising one or more nucleic acid of the seventh aspect.

In one particular embodiment, the nucleic acid construct or vector is an expression construct or vector. In one particular embodiment, the expression construct or vector is a plasmid. In one particular embodiment, the expression plasmid has the nucleotide sequence SEQ_ID No. 46, 47, 48, 83, 84, 95, 98 or 101.

In a ninth aspect, the invention provides host organisms comprising any one or more of the nucleic acids of the seventh aspect or vectors or constructs of the eighth aspect.

In a tenth aspect, the invention provides a composition comprising an expression constructor vector as referred to in the eighth aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In an eleventh aspect, the invention provides a method of producing a recombinant microorganism of the invention comprising:
  a) introduction into a shuttle microorganism of (i) an expression construct/vector of the eighth aspect of the invention and (ii) a methylation construct/vector comprising a methyltransferase gene;
  b) expression of the methyltransferase gene;
  c) isolation of one or more constructs/vectors from the shuttle microorganism; and,
  d) introduction of at least the expression construct/vector into a destination microorganism.

In one embodiment, both the methyltransferase gene of step B is expressed constitutively. In another embodiment, expression of the methyltransferase gene of step B is induced.

In one embodiment, both the methylation construct/vector and the expression construct/vector are isolated in step C. In another embodiment, only the expression construct/vector is isolated in step C.

In one embodiment, only the expression construct/vector is introduced into the destination microorganism. In another embodiment, both the expression construct/vector and the methylation construct/vector are introduced into the destination microorganism.

In a related aspect, the invention provides a method of producing a recombinant microorganism of the invention comprising:
  a. methylation of an expression construct/vector of the eighth aspect of the invention in vitro by a methyltransferase;
  b. introduction of the expression construct/vector into a destination microorganism.

In a further related aspect, the invention provides a method of producing a recombinant microorganism of the invention comprising:
  a. introduction into the genome of a shuttle microorganism of a methyltransferase gene
  b. introduction of an expression construct/vector of the eighth aspect of the invention into the shuttle microorganism
  c. isolation of one or more constructs/vectors from the shuttle microorganism; and,
  d. introduction of at least the expression construct/vector into a destination microorganism.

In a twelfth aspect, the invention provides a method for the production of acetone, isopropanol, and/or a precursor of acetone and/or isopropanol by microbial fermentation comprising fermenting a substrate comprising CO using a recombinant microorganism of the first aspect of the invention.

In one embodiment the method comprises the steps of:
  (a) providing a substrate comprising CO to a bioreactor containing a culture of one or more microorganism of the first aspect of the invention; and
  (b) anaerobically fermenting the culture in the bioreactor to produce acetone, isopropanol, and/or a precursor of acetone and/or isopropanol.

In one embodiment the method comprises the steps of:
  (a) capturing CO-containing gas produced as a result of the industrial process, before the gas is released into the atmosphere;
  (b) the anaerobic fermentation of the CO-containing gas to produce acetone, isopropanol, and/or a precursor acetone and/or isopropanol by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering one or more of acetone, isopropanol, and/or a precursor of acetone and/or isopropanol from the fermentation broth, the fermentation broth.

In a thirteenth aspect, the invention provides one or more of acetone, isopropanol, and a precursor of acetone and/or isopropanol when produced by the method of the sixth aspect.

In another aspect, the invention provides a method for the production of a microorganism of the first aspect of the invention comprising transforming a carboxydotrophic acetogenic parental microorganism with one or more exogenous nucleic acid such that the microorganism is capable of producing acetone, isopropanol and/or a precursor of acetone and/or isopropanol by fermentation of a substrate comprising CO, wherein the parental microorganism is not capable of producing acetone, isopropanol and/or a precursor thereof by fermentation of a substrate comprising CO.

In one particular embodiment, a parental microorganism is transformed with one or more exogenous nucleic acid adapted to express one or more enzymes in the isopropanol biosynthesis pathway which are not naturally present in the parental microorganism. In another embodiment, a parental microorganism is transformed with one or more nucleic acid adapted to over-express one or more enzymes in the isopropanol biosynthesis pathway which are naturally present in the parental microorganism.

In one particular embodiment, a parental microorganism is transformed with one or more exogenous nucleic acids adapted to express one or more enzymes in the acetone biosynthesis pathway which are not naturally present in the parental microorganism. In another embodiment, a parental microorganism is transformed with one or more exogenous nucleic acids adapted to over-express one or more enzymes in the acetone biosynthesis pathway which are naturally present in the parental microorganism.

In one particular embodiment, a parental microorganism is transformed with one or more nucleic acid adapted to express one or more enzymes involved in the conversion of acetone to isopropanol which are not naturally present in the parental microorganism. In another embodiment, a parental microorganism is transformed with one or more nucleic acids adapted to over-express one or more enzymes involved in the conversion of acetone to isopropanol which are naturally present in the parental microorganism.

In certain embodiments, the one or more enzymes are as herein before described.

In another aspect, the invention provides a recombinant microorganism capable of producing acetone and comprising one or more exogenous nucleic acid encoding one or more enzyme adapted to convert acetoactate to acetone, wherein the recombinant microorganism is derived from a parental microorganism which is capable of producing acetolactate but not acetone. In one embodiment, one or more enzyme comprises KivD or a functionally equivalent variant thereof.

In another aspect, the invention provides a recombinant microorganism capable of producing acetone and comprising one or more exogenous nucleic acid encoding each of the enzymes thlA, ctfA, ctfB and kivD or a functionally equivalent variant of any one or more thereof, wherein the recombinant microorganism is derived from a parental microorganism which is not capable of producing acetolactate, acetoacetyl-CoA and acetone.

In another aspect, the invention provides a recombinant microorganism capable of producing acetone and comprising one or more exogenous nucleic acid encoding each of the enzymes ctfA, ctfB and kivD or a functionally equivalent variant of any one or more thereof, wherein the recombinant microorganism is derived from a parental microorganism which is not capable of producing acetolactate and acetone.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIG. 14 shows SEQ_ID NO 1: Amino acid sequence of novel alcohol dehydrogenase from *C. autoethanogeum, C. ljungdahlii* and *C. ragsdalei.*

FIG. 15 shows SEQ_ID NO 2: Nucleic acid sequence of novel alcohol dehydrogenase gene from *C. autoethanogeum.*

FIG. 16 shows SEQ_ID NO 3: Nucleic acid sequence of novel alcohol dehydrogenase gene from *C. ljungdahlii.*

FIG. 17 shows SEQ_ID NO 4: Nucleic acid sequence of novel alcohol dehydrogenase gene from *C. ragsdalei.*

FIG. 18 shows SEQ_ID NO 18: Nucleic acid sequence of Thiolase gene (thlA) from *C. acetobutylicum* ATCC824.

FIG. 19 shows SEQ_ID NO 19: Nucleic acid sequence of Acetoacetyl-CoA:acetate Coenzyme A transferase A (ctfA) gene from *C. beijerinckii* NCIMB8052.

FIG. 20 shows SEQ_ID NO 20: Nucleic acid sequence of Acetoacetyl-CoA:acetate Coenzyme A transferase B (ctfB) gene from *C. beijerinckii* NCIMB8052.

FIG. 21 shows SEQ_ID NO 21: Nucleic acid sequence of Acetoacetate decarboxylase (adc) gene from *C. beijerinckii* NCIMB8052.

FIG. 22 shows SEQ_ID NO 22: Nucleic acid sequence of Wood-Ljungdahl cluster promoter ($P_{WL}$) from *C. autoethanogenum.*

FIG. 23 shows SEQ_ID NO 34: Amino acid sequence of designed Type II methyltransferase gene.

FIG. 24 shows SEQ_ID NO 35: Nucleic acid sequence of designed Type II methyltransferase gene.

FIG. 25 shows SEQ_ID NO 38: Amino acid sequence of NADP-dependent alcohol dehydrogenase from *Clostridium beijerinckii* NRRL B-593.

FIG. 26 shows SEQ_ID NO 39: Nucleic acid sequence of NADP-dependent alcohol dehydrogenase from *Clostridium beijerinckii* NRRL B-593.

FIG. 27 shows SEQ_ID NO 40: Amino acid sequence of NADP-dependent alcohol dehydrogenase from *Thermoanaerobacter brockii* ATCC 53556.

FIG. 28 shows SEQ_ID NO 41: Nucleic acid sequence of alcohol dehydrogenase from *Thermoanaerobacter brockii.*

FIG. 29 shows SEQ_ID NO 42: Amino acid sequence of Thiolase ThlA from *C. acetobutylicum* ATCC824.

FIG. 30 shows SEQ_ID NO 43: Amino acid sequence of Acetoacetyl-CoA:acetate Coenzyme A transferase A CtfA from *C. beijerinckii* NCIMB8052.

FIG. 31 shows SEQ_ID NO 44: Amino acid sequence of Acetoacetyl-CoA:acetate Coenzyme A transferase A CtfB from *C. beijerinckii* NCIMB8052.

FIG. 32 shows SEQ_ID NO 45: Amino acid sequence of Acetoacetate decarboxylase Adc from *C. beijerinckii* NCIMB8052.

FIG. 33 shows SEQ_ID NO 46: Nucleic acid sequence of expression plasmid containing novel alcohol dehydrogenase pMTL85147-thlA-ctfAB-adc.

FIG. 34 shows SEQ_ID NO 47: Nucleic acid sequence of Acetoacetyl-CoA:acetate Coenzyme A transferase A (ctfA), acetoacetyl-CoA:acetate Coenzyme A transferase B (ctfB), and acetoacetate decarboxylase (adc) operon of *C. beijerinckii*.

FIG. 35 shows SEQ_ID NO 48: Nucleic acid sequence of expression plasmid containing novel alcohol dehydrogenase pMTL85147-thlA-ctfAB-adc-adh.

FIG. 36 shows SEQ_ID NO 49: Nucleic acid sequence of designed methylation plasmid.

FIG. 37 shows SEQ_ID NO 50: Nucleic acid sequence of lac promoter.

FIG. 38 shows SEQ_ID NO 51: Nucleic acid sequence of *Clostridium autoethanogenum* $F_1F_o$ ATPase operon promoter region.

FIG. 39 shows SEQ_ID NO 52: Nucleic acid sequence of *Clostridium autoethanogenum* Rnf complex operon promoter region.

FIG. 40 shows SEQ_ID NO 53: Nucleic acid sequence of *Clostridium autoethanogenum* Pyruvate:ferredoxin oxidoreductase promoter region.

FIG. 41 shows the sequencing results of expression plasmid containing novel alcohol dehydrogenase pMTL85147-thlA-ctfA-ctfB-adc-adh.

FIG. 42 shows the results of acetone and isopropanol production with *E. coli* XL-1 Blue MRF' Kan carrying control plasmid (pMTL85147), acetone expression plasmid (pMTL85147-thlA-ctfA-ctfB-adc), and acetone expression plasmid including the novel alcohol dehydrogaenase (pMTL85147-thlA-ctfA-ctfB-adc-adh).

FIG. 44 shows SEQ_ID NO 56: Nucleic acid sequence of Wood-Ljungdahl cluster promoter ($P_{WL}$) from *C. ljungdahlii*.

FIG. 45 shows SEQ_ID NO 57: Nucleic acid sequence of Wood-Ljungdahl cluster promoter ($P_{WL}$) from *C. ragsdalei*.

FIG. 46 shows SEQ_ID NO 58: Nucleic acid sequence of *Clostridium ljungdahlii* $F_1F_o$ ATPase operon promoter region.

FIG. 47 shows SEQ_ID NO 59: Nucleic acid sequence of *Clostridium ragsdalei* $F_1F_o$ ATPase operon promoter region.

FIG. 48 shows SEQ_ID NO 60: Nucleic acid sequence of *Clostridium ljungdahlii* Rnf complex operon promoter region.

FIG. 49 shows SEQ_ID NO 61: Nucleic acid sequence of *Clostridium ragsdalei* Rnf complex operon promoter region.

FIG. 50 shows SEQ_ID NO 62: Nucleic acid sequence of *Clostridium ljungdahlii* Pyruvate:ferredoxin oxidoreductase promoter region.

FIG. 51 shows SEQ_ID NO 63: Nucleic acid sequence of *Clostridium ragsdalei* Pyruvate:ferredoxin oxidoreductase promoter region.

FIG. 54 shows SEQ_ID No. 73: Amino acid sequence of alpha-ketoisovalerate decarboxylase KivD from *Lactococcus lactis* KF147 and SEQ_ID No. 72 Nucleic acid sequence of Alpha-ketoacid decarboxylase (kivd).

FIG. 55 shows Seq. ID No. 76: Codon optimized sequence of Alpha-ketoacid decarboxylase (kivd), SEQ_ID No. 75: Amino acid sequence of alcohol dehydrogenase Adh2 from *Saccharomyces cerevisiae* and SEQ_ID No. 74 Nucleic acid sequence of Alcohol dehydrogenase (adh2)

FIG. 56 shows Seq. ID No. 78: Synthetic operon of codon optimized Alpha-ketoacid decarboxylase (kivd) and Alcohol dehydrogenase (Adh2) including spacer sequence with ribosomal binding site, flanked by NdeI and KpnI and Seq. ID No. 77: Codon optimized sequence of Alcohol dehydrogenase (Adh2).

FIG. 57 shows SEQ_ID No. 82: Nucleic acid sequence of *E. coli*-*Clostridium* shuttle vector pMTL 85245 and SEQ_ID No. 79: Nucleic acid sequence of Phosphotransacetylase Acetate kinase promoter from *C. autoethanogenum*, FIG. 58 shows SEQ_ID No. 83: Nucleic acid sequence of expression plasmid pMTL85245-kivd-adh2

FIG. 59 shows SEQ_ID No. 84 Nucleic acid sequence of expression plasmid pMTL85245-kivd FIG. 60 shows SEQ_ID No. 93: Nucleic acid sequence of expression plasmid pMTL85245-P-thl-ctfAB-P-kivd FIG. 61 shows SEQ_ID No. 98 Nucleic acid sequence of expression plasmid pMTL83147-thlA-ctfAB-adc-adh2.

FIG. 62 shows SEQ_ID No. 101 Nucleic acid sequence of expression plasmid pMTL83147-thlA-ctfAB-adc-P-kivd-adh2.

DSM23693+pMTL83147-thlA-ctfAB-adc-P-kivd-adh2 from CO-containing steel mill gas.

Figure 73:
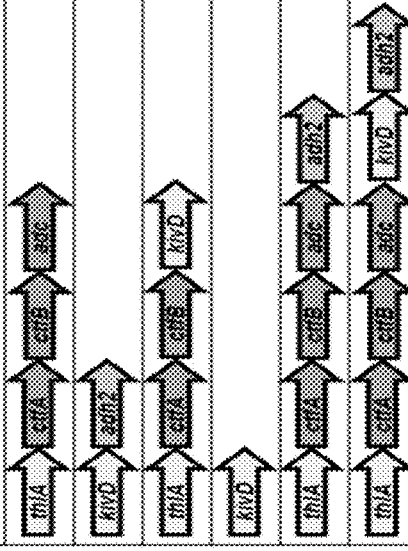

FIG. 73 shows tested gene combinations of Clostridial pathway genes and codon-optimized Alpha-ketoacid decarboxylase Kivd from *L lactis* and Alcohol dehydrogenase Adh2 from *S. cerevisiae* heterologously expressed in *E. coli* and *C. autoethanogenum*.

Figure 74:
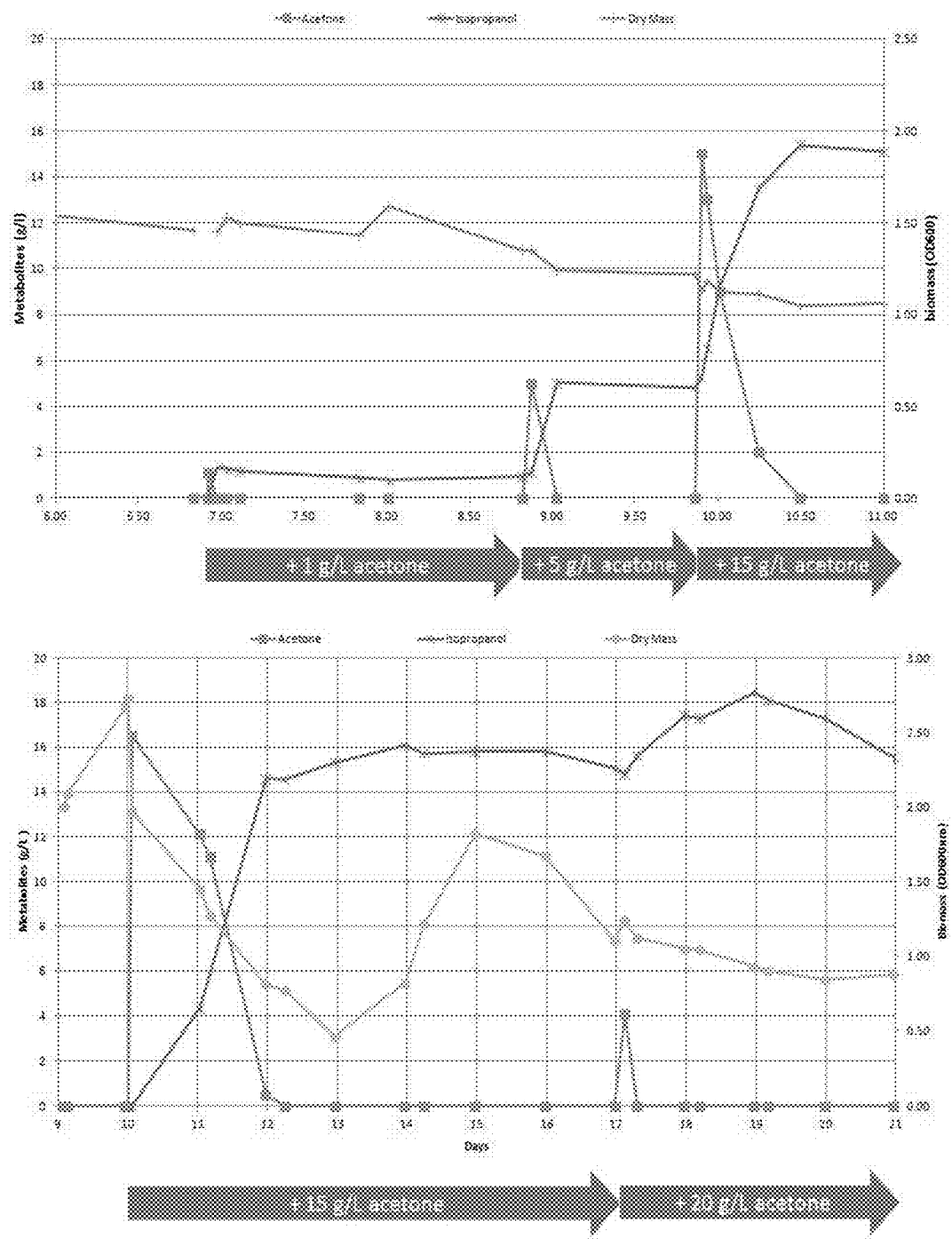

FIG. 74 shows complete conversion of acetone to isopropanol at high concentrations and rates when fed into a stable continuous culture of *C. autoethanogenum* DSM23693 with CO-containing steel mill gas as substrate.

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The production of acetone and/or isopropanol by microbial fermentation of substrates comprising CO has not previously been reported. The inventors of the present invention have now demonstrated (inter alia), through genetic modification, the production of acetone and isopropanol in species of carboxydotrophic acetogenic bacteria capable of using CO as a carbon and energy source. The inventors have also surprisingly been able to demonstrate the natural enzymatic conversion of acetone to isopropanol in presence of CO-containing gases by closely related carboxydotrophic acetogenic species *C. autoethanogenum*, *C. ljungdahlii*, and *C. ragsdalei*. A novel alcohol dehydrogenase was identified, which was shown to be expressed constitutively at a high level during a normal fermentation run with *C. autoethanogenum* and is able to convert acetone to isopropanol at high concentrations and ratios. The inventors have also found two genes that surprisingly confer activity towards acetone and isopropanol in *C. autoethanogenum*. These genes, an alpha-ketoacid decarboxylase (Kivd) from *Lactococcus lactis* and an alcohol dehydrogenase (Adh2) from *Saccharomyces cerevisiae* haven't been reported to confer activity towards acetone or isopropanol or any of it's precursors, rather converting amino acid precursors into branched chain alcohols. The inventors demonstrated production of acetone and isopropanol from CO in *C. autoethanogenum* using several different gene and enzyme combinations.

Accordingly, the invention provides, for example, methods for the production of acetone, isopropanol and/or precursors of acetone and/or isopropanol by microbial fermentation of substrates comprising CO, genetically modified microorganisms of use in such methods, nucleic acids suitable for preparation of genetically modified microorganisms and novel alcohol dehydrogenases and nucleic acids encoding same.

As referred to herein, a "fermentation broth" is a culture medium comprising at least a nutrient media and bacterial cells.

As referred to herein, a shuttle microorganism is a microorganism in which a methyltransferase enzyme is expressed and is distinct from the destination microorganism.

As referred to herein, a destination microorganism is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated acetone and/or isopropanol concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

It should be appreciated that the invention may be practiced using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. saccharobutylicum* and *C. saccharoperbutylacetonicum*, details of which are publicly available on websites such as Genbank or NCBI. In the case of genes derived from *Saccharomyces cerevisiae* and *Lactococcus lactics*, homologous genes may be found, for example, in *Staphylococcus epidermidis* (for example, NP_765765.1, EGG67352.1, ZP_04826144.1, ZP_04797999.1), *Bacillus cereus* (for example, ZP_04273468.1, ZP_04317620.1) and *Bacillus thuringiensis* (for example, YP_003664720.1). The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practiced using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined in Wiesenborn et al [Thiolase from *Clostridium acetobutylicum* ATCC 824 and Its Role in the Synthesis of Acids and Solvents. *Appl Environ Microbiol.* 1988, 54: 2717-2722], Wiesenborn et al [Coenzyme A transferase from *Clostridium acetobutylicum* ATCC 824 and its role in the uptake of acids. *Appl Environ Microbiol.* 1989, 55:323-

9.], Peterson and Bennet [Purification of acetoacetate decarboxylase from *Clostridium acetobutylicum* ATCC 824 and cloning of the acetoacetate decarboxylase gene in *Escherichia coli. Appl Environ Microbiol.* 1990 56: 3491-3498], Ismail et al. [Purification and characterization of a primary-secondary alcohol dehydrogenase from two strains of *Clostridium beijerinckii. J Bacteriol* 1993, 175: 5097-5105], de la Plaza et al [Biochemical and molecular characterization of a-ketoisovalerate decarboxylase, an enzyme involved in the formation of aldehydes from amino acids by *Lactococcus lactis*. FEMS Microbiol Lett. 2004 238: 367-374] or Khorkin et al [NADP-dependent bacterial alcohol dehydrogenases: crystal structure, cofactor-binding and cofactor specificity of the ADHs of *Clostridium beijerinckii* and *Thermoanaerobacter brockii. J Mol Biol.* 1998, 22: 278(5): 967-981] may be used to assess enzyme activity.

"Over-express", "over expression" and like terms and phrases when used in relation to the invention should be taken broadly to include any increase in expression of one or more protein as compared to the expression level of the protein of a parental microorganism under the same conditions. It should not be taken to mean that the protein is expressed at any particular level.

A "parental microorganism" is a microorganism used to generate a recombinant microorganism of the invention. The parental microorganism may be one that occurs in nature (i.e. a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

Figure 4:
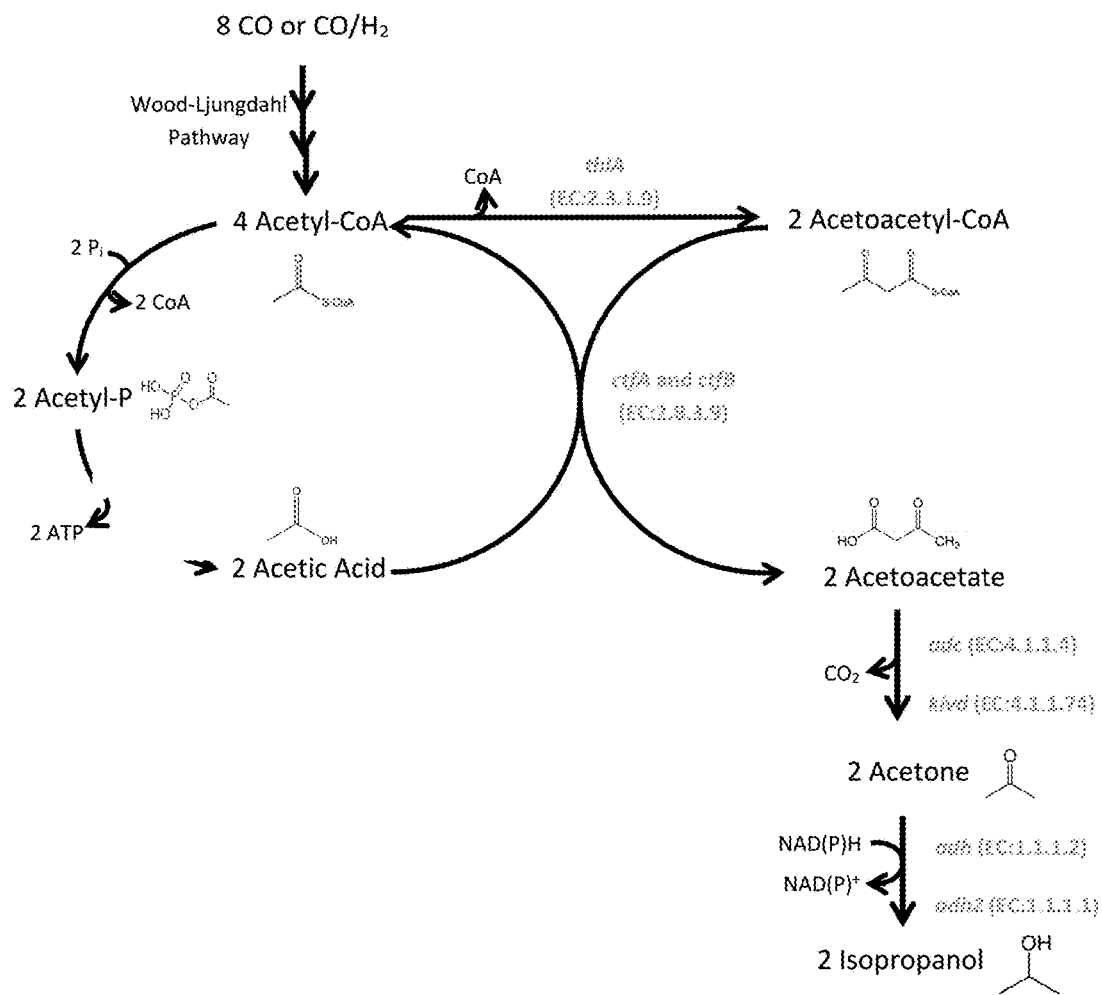
FIG. 4 shows the pathway for production of acetone and isopropanol from CO or $CO/H_2$ containing gases in engineered *C. autoethanogenum* and *C. ljungdahlii* carrying plasmid pMTL85147-thlA-ctfA-ctfB-adc.

The "isopropanol biosynthesis pathway" is the enzymatic pathway allowing for metabolism of CO or CO/$H_2$ to isopropanol, as outlined, for example, in FIG. 4.

The "acetone biosynthesis pathway" is the enzymatic pathway allowing for metabolism of CO or CO/$H_2$ to acetone, as outlined, for example, in FIG. 4.

A "precursor" of acetone includes Acetyl-CoA, Acetoacetyl-CoA, Acetoacetate, Acetyl-Phosphate and Acetic Acid.

A "precursor" of isopropanol includes Acetyl-CoA, Acetoacetyl-CoA, Acetoacetate, Acetone, Acetyl-Phosphate and Acetic Acid.

Reference to "alcohol dehydrogenases" should be taken to include alcohol dehydrogenases which are capable of catalysing the conversion of ketones (such as acetone) to secondary alcohols (such as isopropanol), or vice versa. Such alcohol dehydrogenases include secondary alcohol dehydrogenases and primary alcohol dehydrogenases. A "secondary alcohol dehydrogenase" is one which can convert ketones (such as acetone) to secondary alcohols (such as isopropanol), or vice versa. A "primary alcohol dehydrogenase" is one which can convert aldehydes to primary alcohols, or vice versa; however, a number of primary alcohol dehydrogenases are also capable of catalysing the conversion of ketones to secondary alcohols, or vice versa. These alcohol dehydrogenases may also be referred to as "primary-secondary alcohol dehydrogenases".

As discussed herein before, the invention provides a recombinant microorganism capable of producing acetone, isopropanol and/or a precursor of acetone and/or isopropanol by fermentation of a substrate comprising CO.

In one particular embodiment, the microorganism is adapted to express one or more enzymes in the isopropanol biosynthesis pathway which are not naturally present in the parental microorganism. In another embodiment, the microorganism is adapted to over-express one or more enzymes in the isopropanol biosynthesis pathway which are naturally present in the parental microorganism.

In one particular embodiment, the microorganism is adapted to express one or more enzymes in the acetone biosynthesis pathway which are not naturally present in the parental microorganism. In another embodiment, the microorganism is adapted to over-express one or more enzymes in the acetone biosynthesis pathway which are naturally present in the parental microorganism.

In one particular embodiment, the microorganism is adapted to express one or more enzymes involved in the conversion of acetone to isopropanol which are not naturally present in the parental microorganism. In another embodiment, the microorganism is adapted to over-express one or more enzymes involved in the conversion of acetone to isopropanol which are naturally present in the parental microorganism.

In one embodiment, the parental microorganism is capable of fermenting a substrate comprising CO to produce acetone but not of converting acetone to isopropanol and the recombinant microorganism is adapted to express one or more enzymes involved in the conversion of acetone to isopropanol.

In another embodiment, the parental microorganism is capable of converting acetone to isopropanol but is not capable of fermenting a substrate comprising CO to produce acetone and the recombinant microorganism is adapted to express one or more enzymes in the acetone biosynthesis pathway.

In one embodiment, the parental microorganism is not capable of fermenting a substrate comprising CO to produce acetone and isopropanol and the recombinant microorganism is adapted to express one or more enzymes in the acetone biosynthesis pathway and one or more enzymes involved in the conversion of acetone to isopropanol.

The microorganism may be adapted to express or over-express the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In certain embodiments, the parental microorganism may be transformed to provide a combination of increased or over-expression of one or more genes native to the parental microorganism and introduction of one or more genes not native to the parental microorganism. For example, one or more genes encoding an enzyme in the acetone biosynthesis pathway may be native to the parental microorganism but it may not include one or more gene encoding an enzyme involved in the conversion of acetone to isopropanol, or vice versa. The microorganism could be engineered to over-express the one or more native genes encoding an enzyme in the acetone biosynthesis pathway and to introduce a gene encoding an enzyme involved in conversion of acetone to isopropanol, or vice versa. Similarly, the microorganism could be engineered to over-express one or more enzymes in the acetone biosynthesis pathway (and/or the conversion of acetone to isopropanol) and to introduce one or more genes encoding an enzyme involved in the same pathway. Skilled persons will appreciate various other combinations of use in the invention.

In one embodiment the one or more enzymes in the acetone biosynthesis pathway are chosen from the group consisting:

Acetyl-Coenzyme A acetyltransferase (Thiolase; ThlA; E.C. 2.3.1.9);

Acetoacetyl-CoA:Acetate Coenzyme A transferase A (CoA transferase; CtfA; EC 2.8.3.9);

Acetoacetyl-CoA:Acetate Coenzyme A transferase B (CoA transferase; CtfB; EC 2.8.3.9);

Acetoacetate decarboxylase (Adc; EC 4.1.1.4);

Alpha-ketoisovalerate decarboxylase (decarboxylase; KivD; EC4.1.1.74); and,

A functionally equivalent variant of any one or more thereof.

By way of example only, sequence information for each of the peptides in provided in table 6 or table 18 herein after.

The enzymes used in the microorganisms of the invention may be derived from any appropriate source, including different genera and species of bacteria, or other organisms. However, in one embodiment, the Acetyl-Coenzyme A acetyltransferase (Thiolase; ThlA) is that derived from *C. acetobutylicum*. In one embodiment, the Acetyl-Coenzyme A acetyltransferase has the amino acid sequence exemplified in table 6 herein after, or it is a functionally equivalent variant thereof.

In one embodiment, the enzymes Acetoacetyl-CoA:Acetate Coenzyme A transferase A (CoA transferase; CtfA), Acetoacetyl-CoA:Acetate Coenzyme A transferase B (CoA transferase; CtfB) and Acetoacetate decarboxylase (Adc) are derived from *C. Beijerinckii*.

In one embodiment, the enzymes alpha-ketoisovalerate decarboxylase (decarboxylase; KivD) is that derived from *L. lactis*.

In one embodiment, each enzyme has the amino acid sequence exemplified in table 6 or 18 herein after, or it is a functionally equivalent variant thereof.

In one embodiment, the one or more enzyme involved in the conversion of acetone to isopropanol are chosen from the group consisting:

Alcohol Dehydrogenase (Adh; EC 1.1.1.2);

Alcohol dehydrogenase (Adh2; EC 1.1.1.1); and,

A functionally equivalent variant thereof.

Again, the alcohol dehydrogenase enzyme used in the invention may be derived from any appropriate source, including different genera and species of bacteria (for example, the species of bacteria exemplified in table 13 herein after. However, in one particular embodiment, the Alcohol Dehydrogenase (Adh) is derived from *C. autoethanogenum*, *C. ljungdahlii*, and/or *C. ragsdalei*. In one embodiment, the alcohol dehydrogenase has the amino acid sequence of SEQ_ID NO. 1 or it is a functionally equivalent variant thereof. In one embodiment, the functionally equivalent variant has at least approximately 88%, 89%, 90%, 91%, 92%, 93%, 94%, 95%, 96%, 97%, 98% or 99% sequence identity to SEQ_ID NO. 1.

In one embodiment, the Alcohol Dehydrogenase (Adh2) is derived from *S. cerevisiae*.

In one embodiment, the microorganism comprises one or more exogenous nucleic acids adapted to increase expression of one or more nucleic acids native to the parental microorganism and which one or more nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. In one embodiment, the promoter has the sequence of SEQ_ID No. 22 or 77, or is a functionally equivalent variant thereof. In another embodiment, a Wood-Ljungdahl cluster promoter ($P_{WL}$) (SEQ ID No. 56 or 57), the promoter region of $F_1F_o$-ATPase operon (SEQ_ID NO 51, 58 or 59), Rnf complex operon promoter region (SEQ_ID NO 52, 60 or 61), or Pyruvate:ferredoxin oxidoreductase (SEQ_ID NO 53, 62 or 63) promoter region could be used. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two of the enzymes. In other embodiments, the microorganism comprises one or more exogenous nucleic acid encoding and adapted to express 3, 4, 5, or 6 of the enzymes.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), and Acetoacetate decarboxylase (Adc; EC 4.1.1.4) or a functionally equivalent variant of any one or more thereof.

In one particular embodiment, the microorganism comprises one or more exogenous nucleic acids encoding Alcohol Dehydrogenase (Adh; EC 1.1.1.2) or a functionally equivalent variant thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), and Alcohol Dehydrogenase (Adh; EC 1.1.1.2), or a functionally equivalent variant of any one or more thereof.

In one particular embodiment, the microorganism comprises one or more exogenous nucleic acids encoding each of Alpha-ketoisovalerate decarboxylase (decarboxylase;

KivD; EC4.1.1.74), and Alcohol dehydrogenase (Adh2; EC 1.1.1.1), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), and Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding Alpha-ketoisovalerate decarboxylase (decarboxylase; KivD; EC4.1.1.74), or a functionally equivalent variant of any one or more thereof.

In one particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), and Alcohol dehydrogenase (Adh2; EC 1.1.1.1), or a functionally equivalent variant of any one or more thereof.

In another particular embodiment, the microorganism comprises one or more exogenous nucleic acids encoding each of Acetyl-Coenzyme A acetyltransferase (Thiolase; ThlA; E.C. 2.3.1.9), Acetoacetyl-CoA:Acetate Coenzyme A transferase A (CoA transferase; CtfA; EC 2.8.3.9), Acetoacetyl-CoA:Acetate Coenzyme A transferase B (CoA transferase; CtfB; EC 2.8.3.9), Acetoacetate decarboxylase (Adc; EC 4.1.1.4), Alpha-ketoisovalerate decarboxylase (decarboxylase; KivD; EC4.1.1.74), and Alcohol dehydrogenase (Adh2; EC 1.1.1.1), or a functionally equivalent variant of any one or more thereof.

In one embodiment, Acetyl-Coenzyme A acetyltransferase (Thiolase; ThlA) is encoded by a nucleic acid comprising SEQ_ID NO. 18, or a functionally equivalent variant thereof. In one embodiment, the Acetoacetyl-CoA:Acetate Coenzyme A transferase A (CoA transferase; CtfA) is encoded by a nucleic acid comprising SEQ_ID NO. 19, or a functionally equivalent variant thereof. In one embodiment, Acetoacetyl-CoA:Acetate Coenzyme A transferase B (CoA transferase; CtfB) is encoded by a nucleic acid comprising SEQ_ID NO. 20, or a functionally equivalent variant thereof. In one embodiment, Acetoacetate decarboxylase (Adc) is encoded by a nucleic acid comprising SEQ_ID NO. 21, or a functionally equivalent variant thereof. In one embodiment, the alpha-ketoisovalerate decarboxylase (decarboxylase; KivD) is encoded by a nucleic acid comprising SEQ_ID NO. 72 or 76, or a functionally equivalent variant of any one thereof. In one embodiment, the Alcohol Dehydrogenase (Adh) is encoded by a nucleic acid comprising SEQ_ID NO. 2, SEQ_ID NO. 3, or SEQ_ID NO. 4, or a functionally equivalent variant of any one thereof. In one embodiment, the Alcohol Dehydrogenase (Adh2) is encoded by a nucleic acid comprising SEQ_ID NO. 74 or 77, or a functionally equivalent variant of any one thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination. In one particular embodiment, the construct encodes each of ThlA, CtfA, CtfB, and Adc and optionally, Adh. In another embodiment, the one or more exogenous nucleic acids is a nucleic acid construct or vector, in one particular embodiment a plasmid, encoding Adh, and optionally ThlA, CtfA, CtfB, and/or Adc. In one particular embodiment, the construct encodes all of ThlA, CtfA, CtfB, Adc and Adh. The vector may also comprise other combinations of nucleic acids encoding alternative enzyme combinations, as is apparent from the description elsewhere in this document. In one particular embodiment, the vector comprises 1, 2, 3 or 4 of the nucleic acid sequences SEQ_ID NO. 19, 20, 21 and 22 or a functionally equivalent variant of any one thereof, in any order. In another embodiment, the vector comprises SEQ_ID_NO. 2, 3 and/or 4, or a functionally equivalent variant of any one thereof, in any order. In one embodiment, the vector comprises 1, 2, 3, or 4 of sequences SEQ_ID NO. 19, 20, 21 and 22 or a functionally equivalent variant of any one thereof and SEQ_ID_NO. 2, 3 or 4, or a functionally equivalent variant of any one thereof, in any order.

In another embodiment, the vector comprises one or more of SEQ ID No. 72, 76, 74, 77, alone or in combination with one or more of the nucleic acids represented by SEQ ID No. 19, 20, 21, 22, 2, 3, and 4.

The exogenous nucleic acids may remain extra-chromosomal upon transformation of the parent microorganism or may integrate into the genome of the parent microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. In one embodiment, the promoter has the sequence of SEQ_ID No. 22, SEQ ID No. 77, or is a functionally equivalent variant of any one thereof. In another embodiment, a Wood-Ljungdahl cluster promoter ($P_{WL}$) (SEQ ID No. 56 or 57), the promoter region of $F_1F_o$-ATPase operon (SEQ_ID NO 51, 58 or 59), Rnf complex operon promoter region (SEQ_ID NO 52, 60 or 61), or Pyruvate:ferredoxin oxidoreductase (SEQ_ID NO 53, 62 or 63) promoter region could be used. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid. In one particular embodiment, the expression plasmid has the nucleotide sequence SEQ_ID No. 46, 48, 83, 84, 95, 98, or 101.

In one embodiment, the parental microorganism is selected from the group of carboxydotrophic acetogenic bacteria. In certain embodiments the microorganism is selected from the group comprising *Clostridium autoetha-* nogenum, *Clostridium ljungdahlii, Clostridium ragsdalei, Clostridium carboxidivorans, Clostridium drakei, Clostridium scatologenes, Clostridium coskatii, Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii,* and *Thermoanaerobacter kiuvi.*

In one particular embodiment, the parental microorganism is selected from the cluster of ethanologenic, acetogenic Clostridia comprising the species *C. autoethanogenum, C. ljungdahlii,* and *C. ragsdalei* and related isolates. These include but are not limited to strains *C. autoethanogenum* JAI-1$^T$ (DSM10061) [Abrini J, Naveau H, Nyns E-J: *Clostridium autoethanogenum,* sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* O-52 (ATCC 55989) [Gaddy J L, Clausen E C, Ko C-W: Microbial process for the preparation of acetic acid as well as solvent for its extraction from the fermentation broth. US patent, 2002, U.S. Pat. No. 6,368,819], *C. ragsdalei* P11$^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)], or mutated strains such as *C. ljungdahlii* OTA-1 (Tirado-Acevedo O. Production of Bioethanol from Synthesis Gas Using *Clostridium ljungdahlii.* PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 µm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum,* sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum,* sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not.

In one embodiment, the parental strain uses CO as its sole carbon and energy source.

In one embodiment the parental microorganism is *Clostridium autoethanogenum* or *Clostridium ljungdahlii.* In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes encoding ThlA, CtfA, CtfB, Adc, KivD, Adh and Adh2. In one particular embodiment, the parental microorganism lacks a gene encoding Adh. In another particular embodiment, the parental microorganism lacks each of the genes encoding ThlA, CtfA, CtfB, Adc, and KivD.

The inventors have identified a novel Adh protein. Accordingly, the invention provides an Alcohol Dehydrogenase (Adh) having the amino acid sequence of SEQ_ID NO. 1, or a functionally equivalent variant of any one thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1.

In addition the invention provides a nucleic acid encoding Adh of SEQ_ID NO. 1 or a functionally equivalent variant thereof. Skilled persons will readily appreciate such nucleic acids, having regard to the amino acid sequence provided herein and the genetic code and the degeneracy therein. However, by way of example, nucleic acids encoding Adh of SEQ_ID NO. 1 include the nucleic acids of SEQ_ID NO. 2, 3 or 4, or functionally equivalent variants thereof. In one particular embodiment, a functionally equivalent variant of SEQ_ID NO. 2, 3 or 4 is a nucleic acid having at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

The invention also provides nucleic acids which are capable of hybridising to at least a portion of the nucleic acid SEQ_ID NO. 2, 3 or 4, a nucleic acid complementary to any one thereof, or a functionally equivalent variant of any one thereof. Such nucleic acids will preferably hybridise to the nucleic acid of SEQ_ID NO. 2, 3 or 4, a nucleic acid complementary to any one thereof, or a functionally equivalent variant of any one thereof, under stringent hybridisation conditions. "Stringent hybridisation conditions" means that the nucleic acid is capable of hybridising to a target template under standard hybridisation conditions such as those described in Sambrook et al, Molecular Cloning: A Laboratory Manual (1989), Cold Spring Harbor Laboratory Press, New York, USA. It will be appreciated that the minimal size of such nucleic acids is a size which is capable of forming a stable hybrid between a given nucleic acid and the complementary sequence to which it is designed to hybridise. Accordingly, the size is dependent on the nucleic acid composition and percent homology between the nucleic acid and its complementary sequence, as well as the hybridisation conditions which are utilised (for example, temperature and salt concentrations). In one embodiment, the nucleic acid is at least 10 nucleotides in length, at least 15 nucleotides in length, at least, 20 nucleotides in length, at least 25 nucleotides in length, or at least 30 nucleotides in length.

The inventor's have also identified a number of novel nucleic acids useful as probes and primers, as detailed herein after in the examples section. For example, SEQ_ID NO. 5; SEQ_ID NO. 6; SEQ_ID NO. 7; SEQ_ID NO. 8; SEQ_ID NO. 9; SEQ_ID NO. 10; SEQ_ID NO. 11; SEQ_ID NO. 12; SEQ_ID NO. 13; SEQ_ID NO. 14; SEQ_ID NO. 15; SEQ_ID NO. 16; SEQ_ID NO. 17; SEQ_ID NO. 18; SEQ_ID NO. 23; SEQ_ID NO. 24; SEQ_ID NO. 25; SEQ_ID NO. 26; SEQ_ID NO. 27; SEQ_ID NO. 28; SEQ_ID NO. 29; SEQ_ID NO. 30; SEQ_ID NO. 31; SEQ_ID NO. 32; SEQ_ID NO. 33; SEQ_ID NO. 64; SEQ_ID NO. 65; SEQ_ID NO. 66; SEQ_ID NO. 67; SEQ_ID NO. 68; SEQ_ID NO. 69; SEQ_ID NO. 70; SEQ_ID NO. 71; SEQ_ID NO. 85; SEQ_ID NO. 86; SEQ_ID NO. 87; SEQ_ID NO. 88; SEQ_ID NO. 89; SEQ_ID NO. 90; SEQ_ID NO. 91; SEQ_ID NO. 92; SEQ_ID NO. 93; SEQ_ID NO. 94; SEQ_ID NO. 96; SEQ_ID NO. 97; SEQ_ID NO. 99; SEQ_ID NO. 100.

The invention also provides nucleic acids and nucleic acid constructs of use in generating a recombinant microorganism of the invention.

In one embodiment, the nucleic acids comprises sequences encoding one or more of the enzymes which when expressed in a microorganism allows the microorganism to produce acetone, isopropanol and/or a precursor of acetone and/or isopropanol by fermentation of substrate comprising CO. In one particular embodiment, the invention provides a nucleic acid encoding two or more enzymes which when expressed in a microorganism allows the microorganism to produce acetone, isopropanol and/or a precursor of acetone and/or isopropanol by fermentation of substrate comprising CO. In one embodiment, the nucleic acids of the invention encode 3, 4, 5 or 6 such enzymes.

In one particular embodiment, the enzymes are chosen from Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), ketoisovalerate decarboxylase (decarboxylase; KivD), Alcohol Dehydrogenase (Adh), Alcohol Dehydrogenase (Adh2), and a functionally equivalent variant of any one or more thereof.

In one embodiment, a nucleic acid of the invention comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Acetoacetate decarboxylase (Adc) or a functionally equivalent variant of any one or more thereof, in any order In one embodiment, a nucleic acid of the invention comprises nucleic acid sequences encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol Dehydrogenase (Adh) or a functionally equivalent variant of any one or more thereof, in any order.

In one embodiment, a nucleic acid of the invention comprises nucleic acid sequences encoding each of Alpha-ketoisovalerate decarboxylase (decarboxylase; KivD), and Alcohol dehydrogenase (Adh2), or a functionally equivalent variant of any one or more thereof, in any order.

In one embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), and Alpha-ketoisovalerate decarboxylase (decarboxylase; KivD), or a functionally equivalent variant of any one or more thereof, in any order.

In one embodiment, a nucleic acid of the invention comprises nucleic acids encoding Alpha-ketoisovalerate decarboxylase (decarboxylase; KivD), or a functionally equivalent variant thereof.

In one one embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase; CtfA), Acetoacetyl-CoA:Acetate Coenzyme A transferase B (CoA transferase; CtfB), Acetoacetate decarboxylase (Adc), and Alcohol dehydrogenase (Adh2), or a functionally equivalent variant of any one or more thereof, in any order.

In another embodiment, a nucleic acid of the invention comprises nucleic acids encoding each of Acetyl-Coenzyme A acetyltransferase (Thiolase; ThlA), Acetoacetyl-CoA:Acetate Coenzyme A transferase A (CoA transferase), Acetoacetyl-CoA:Acetate Coenzyme A transferase B (CoA transferase; CtfB), Acetoacetate decarboxylase (Adc), Alpha-ketoisovalerate decarboxylase (decarboxylase; KivD), and Alcohol dehydrogenase (Adh2), or a functionally equivalent variant of any one or more thereof, in any order.

Exemplary amino acid sequences and nucleic acid sequence encoding each of the above enzymes are provided in GenBank as described elsewhere herein (see, in particular, the examples provided in tables 6 and 18 herein after). However, skilled persons will readily appreciate alternative nucleic acids sequences encoding the enzymes or functionally equivalent variants thereof, having regard to the information contained herein, in GenBank and other databases, and the genetic code.

In one embodiment, Acetyl-Coenzyme A acetyltransferase (Thiolase; ThlA) has the sequence of Seq_ID No. 42 or a functionally equivalent variant thereof. In one embodiment, the Acetoacetyl-CoA:Acetate Coenzyme A transferase A (CoA transferase; CtfA) has the sequence of Seq_ID No. 43, or a functionally equivalent variant thereof. In one embodiment, Acetoacetyl-CoA:Acetate Coenzyme A transferase B (CoA transferase; CtfB) has the sequence of Seq_ID No. 44 or a functionally equivalent variant thereof. In one embodiment, Acetoacetate decarboxylase (Adc) has the sequence of Seq_ID No. 45, or a functionally equivalent variant thereof. In one embodiment, Alpha-ketoisovalerate decarboxylase (decarboxylase; KivD) has the sequence of Seq_ID No. 73, or a functionally equivalent variant thereof. In one embodiment, Alcohol Dehydrogenase (Adh) has the sequence of SEQ_ID NO 38 and SEQ_ID NO 40. In one particular embodiment, the Alcohol Dehydrogenase (Adh) has the sequence of SEQ_ID NO. 1, or a functionally equivalent variant thereof. In one particular embodiment, the functionally equivalent variant of Alcohol Dehydrogenase (Adh) has at least approximately 88%, 89%, 90%, 91%, 92%, 93%, 94%, 95%, 96%, 97%, 98% or 99% sequence identity to SEQ_ID NO. 1. In one embodiment, Alcohol Dehydrogenase (Adh2) has the sequence of SEQ_ID NO 75, or a functionally equivalent variant thereof.

In one embodiment, the nucleic acid sequence encoding Acetyl-Coenzyme A acetyltransferase (Thiolase; ThlA) comprises SEQ_ID NO. 18, or is a functionally equivalent variant thereof. In one embodiment, the nucleic acid sequence encoding Acetoacetyl-CoA:Acetate Coenzyme A transferase A (CoA transferase; CtfA) comprises SEQ_ID NO. 19, or is a functionally equivalent variant thereof. In one embodiment, the nucleic acid sequence encoding Acetoacetyl-CoA:Acetate Coenzyme A transferase B (CoA transferase; CtfB) comprises SEQ_ID NO. 20, or is a functionally equivalent variant thereof. In one embodiment, the nucleic acid sequence encoding Acetoacetate decarboxylase (Adc) comprises SEQ_ID NO. 21, or is a functionally equivalent variant thereof. In one embodiment, the nucleic acid sequence encoding Alpha-ketoisovalerate decarboxylase (decarboxylase; KivD) comprises SEQ_ID NO. 72 or 76, or is a functionally equivalent variant of any one thereof. In one embodiment, the nucleic acid sequence encoding Alcohol Dehydrogenase (Adh2) comprises SEQ_ID NO. 74 or 77, or is a functionally equivalent variant thereof. In one embodiment, the nucleic acid sequence encoding Alcohol Dehydrogenase (Adh) comprises Seq_ID No. 39 or SEQ_ID NO 41, or is a functionally equivalent variant of any one thereof. In one particular embodiment, the nucleic acid sequence encoding Alcohol Dehydrogenase (Adh) comprises SEQ_ID NO. 2, SEQ_ID NO. 3, or SEQ_ID NO. 4, or is a functionally equivalent variant of any one thereof. In one embodiment, the functionally equivalent variant of SEQ_ID NO. 2, SEQ_ID NO. 3, or SEQ_ID NO. 4 has at least approximately 83%, 84%, 85%, 86%, 87%, 88%, 89%, 90%, 91%, 92%, 93%, 94%, 95%, 96%, 97%, 98% or 99% sequence identity to SEQ_ID NO. 2, 3 or 4.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kindase promoter is used. In another embodiment a pyruvate:ferredoxin oxidoreductase promoter, an Rnf complex operon promoter or an ATP synthase operon promoter. In one particular embodiment, the promoter is from *C. autoethanogenum*. In one particular embodiment, the promoter has the sequence of SEQ_ID NO. 22, SEQ ID No 79, or is a functionally equivalent variant of any one thereof. In other embodiments, the promoter has the sequence of SEQ ID No. 56, 57, 51, 58, 59, 52, 60, 61, 53, 62 or 63, or is a functionally equivalent variant of any one thereof.

The nucleic acids of the invention may remain extra-chromosomal upon transformation of a parental microorganism or may be adapted for intergration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid. In one particular embodiment, the expression plasmid has the nucleotide sequence SEQ_ID No. 46, 48, 83, 84, 95, 98 or 101.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

introduction into a shuttle microorganism of (i) of an expression construct/vector as described herein and (ii) a methylation construct/vector comprising a methyltransferase gene;

expression of the methyltransferase gene;

isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter (preferably encoded by SEQ_ID NO 50) and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ_ID No. 34, or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ_ID NO 35, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used. In one particular embodiment, the plasmid has the sequence of SEQ_ID NO. 49.

The invention provides a method for the production of one or more desirable products (acetone, isopropanol, and/or or a precursor of acetone and/or isopropanol) by microbial fermentation comprising fermenting a substrate comprising CO using a recombinant microorganism of the invention. The methods of the invention may be used to reduce the total atmospheric carbon emissions from an industrial process.

Preferably, the fermentation comprises the steps of anaerobically fermenting a substrate in a bioreactor to produce the one or more products using a recombinant microorganism of the invention.

In one embodiment the method comprises the steps of:
(a) providing a substrate comprising CO to a bioreactor containing a culture of one or more microorganism of the invention; and
(b) anaerobically fermenting the culture in the bioreactor to produce the one or more products.

In one embodiment the method comprises the steps of:
(a) capturing CO-containing gas produced as a result of the industrial process, before the gas is released into the atmosphere;
(b) the anaerobic fermentation of the CO-containing gas to produce the one or more products by a culture containing one or more microorganism of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-the one or more product(s) to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce butanol using CO are known in the art. For example, suitable media are described Biebel (2001). In one embodiment of the invention the media is as described in the Examples section herein after.

The fermentation should desirably be carried out under appropriate conditions for the CO-to-the one or more product(s) fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of the one or more products. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-the one or more product(s) conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173, 429 and 5,593,886 and WO 02/08438, and as described in the Examples section herein after.

Acetone, isopropanol, or a mixed stream containing acetone and/or isopropanol and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.
Microorganisms and Growth Conditions

*Acetobacterium woodii* DSM1030, *Clostridium aceticum* DSM1496, *C. autoethanogenum* DSM23693, *C. carboxidivorans* DSM15243, and *C. ljungdahlii* DSM13528 were sourced from DSMZ (The German Collection of Microorganisms and Cell Cultures, Inhoffenstraße 7 B, 38124 Braunschweig, Germany). *C. autoethanogenum* DSM23693 is a derivate of *C. autoethanogenum* DSM10061.

*C. ragsdalei* ATCC BAA-622 were sourced from the American Type Culture Collection, Manassas, Va. 20108, USA.

*C. acetobutylicum* ATCC824, *C. beijerinckii* NRRL-B593, and *C. beijerinckii* NCIMB8052 were obtained from Prof. David Jones (University of Otago) and can also be obtained from public strain collections DSMZ and ATCC under accession numbers ATCC824/DSM792, DSM6423, and ATCC51743 respectively.

*Escherichia coli* DH5α-T1$^R$ was sourced from Invitrogen, Carlsbad, Calif. 92008, USA and *Escherichia coli* XL1-Blue MRF' Kan and ABLE K from Stratagene (Santa Clara, Calif. 95051-7201, USA). *Escherichia coli* JW3350-2 was sourced from The *Coli* Genetic Stock Center (CGSC), New Haven, Conn. 06520-8103.

*E. coli* was cultivated under both aerobic and anaerobic conditions, while all other strains were grown strictly anaerobically in a volume of 50 ml liquid media in serum bottles with fructose (heterotrophic growth) or 30 psi CO-containing steel mill gas (collected from New Zealand Steel site in Glenbrook, NZ; composition: 44% CO, 32% $N_2$, 22% $CO_2$, 2% $H_2$) in the headspace (autotrophic growth).

Media was prepared using standard anaerobic techniques [Hungate R E: A roll tube method for cultivation of strict anaerobes, in Norris J R and Ribbons D W (eds.), Methods in Microbiology, vol. 3B. Academic Press, New York, 1969: 117-132; Wolfe R S: Microbial formation of methane. *Adv Microb Physiol* 1971, 6: 107-146] according to formulations are given in Tab. 2-4. For solid media, 1.2% Bacto agar (BD, Frankton Lakes, N.J. 07417, USA) was added.

All strains were grown at 37° C., except for *A. woodii*, *C. aceticum*, and *C. ragsdalei* which were grown at 30° C.

TABLE 2

PETC medium (*A. woodii*, pH 8.2; *C. aceticum*, pH 7.4; *C. autoethanogenum*, *C. carboxidivorans*, *C. ljungdahlii*, and *C. ragsdalei*, pH 5.6)

| Media component | Concentration per 1.0 L of media |
|---|---|
| $NH_4Cl$ | 1 g |
| KCl | 0.1 g |
| $MgSO_4 \cdot 7H_2O$ | 0.2 g |

TABLE 2-continued

PETC medium (*A. woodii*, pH 8.2; *C. aceticum*, pH 7.4; *C. autoethanogenum*, *C. carboxidivorans*, *C. ljungdahlii*, and *C. ragsdalei*, pH 5.6)

| | |
|---|---|
| NaCl | 0.8 g |
| $KH_2PO_4$ | 0.1 g |
| $CaCl_2$ | 0.02 g |
| Trace metal solution (see below) | 10 ml |
| Wolfe's vitamin solution (see below) | 10 ml |
| Yeast Extract (optional) | 1 g |
| Resazurin (2 g/L stock) | 0.5 ml |
| $NaHCO_3$ | 2 g |
| Reducing agent | 0.006-0.008% (v/v) |
| Fructose (for heterotrophic growth) | 5 g |

| Trace metal solution | per L of stock |
|---|---|
| Nitrilotriacetic Acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |

| Reducing agent stock | per 100 ml of stock |
|---|---|
| NaOH | 0.9 g |
| Cystein•HCl | 4 g |
| $Na_2S$ | 4 g |

TABLE 3

Reinforced Clostridial Medium RCM (*C. acetobutylicum, C. beijerinckii*)

| Media component | Concentration per 1.0 L of media |
|---|---|
| Pancreatic Digest of Casein | 5 g |
| Proteose Peptone No. 3 | 5 g |
| Beef Extract | 10 g |
| Yeast Extract | 3 g |
| Dextrose | 5 g |
| NaCl | 5 g |
| Soluble starch | 1 g |
| Cystein•HCl | 0.5 g |
| Sodium Acetate | 3 g |

TABLE 4

Luria Bertani medium LB (*E. coli*)

| Media component | Concentration per 1.0 L of media |
|---|---|
| Tryptone | 10 g |
| Yeast Extract | 5 g |
| NaCl | 10 g |

TABLE 5

SD-8 minimal media (*E. coli*)

| Media component | Concentration per 1.0 L of media |
|---|---|
| $NH_4Cl$ | 7 g |
| $Na_2HPO_4$ | 7.5 g |
| $K_2SO_4$ | 0.85 g |
| $MgSO_4 \cdot 7H_2O$ | 0.17 g |
| $KH_2PO_4$ | 7.5 g |
| Trace metal solution (see below) | 0.8 ml |

TABLE 5-continued

| SD-8 minimal media (E. coli) | |
| --- | --- |
| Yeast Extract | 5 g |
| Glucose | 2 0 g |

| Trace metal solution | per 100 L of stock |
| --- | --- |
| $MnSO_4 \cdot H_2O$ | 1 g |
| $FeSO_4 \cdot 7H_2O$ | 4 g |
| $CoCl_2 \cdot 6H_2O$ | 0.4 g |
| $ZnSO_4 \cdot 7H_2O$ | 0.2 g |
| $CuCl_2 \cdot 2H_2O$ | 0.1 g |
| $Na_2MoO_4 \cdot 2H_2O$ | 0.2 g |
| $Al_2(SO_4)_3$ | 2.83 g |
| $H_3BO_4$ | 0.5 g |

Fermentations with *C. autoethanogenum* DSM23693 were carried out in 1.5 L bioreactors at 37° C. and CO-containing steel mill gas as sole energy and carbon source as described below. A defined medium was used containing per liter: MgCl, $CaCl_2$ (0.5 mM), KCl (2 mM), $H_3PO_4$ (5 mM), Fe (100 µM), Ni, Zn (5 µM), Mn, B, W, Mo, Se(2 µM) was prepared for culture growth. The media was transferred into the bioreactor and autoclaved at 121° C. for 45 minutes. After autoclaving, the medium was supplemented with Thiamine, Pantothenate (0.05 mg), Biotin (0.02 mg) and reduced with 3 mM Cysteine-HCl. To achieve anaerobicity the reactor vessel was sparged with nitrogen through a 0.2 µm filter. Prior to inoculation, the gas was switched to CO-containing steel mill gas, feeding continuously to the reactor. The gas flow was initially set at 80 ml/min, increasing to 200 ml/min during mid exponential phase, while the agitation was increased from 200 rpm to 350. $Na_2S$ was dosed into the bioreactor at 0.25 ml/hr. Once the OD600 reached 0.5, the bioreactor was switched to a continuous mode at a rate of 1.0 ml/min (Dilution rate 0.96 $d^{-1}$). Media samples were taken to measure the biomass and metabolites and a headspace analysis of the in- and outflowing gas was performed on regular basis.

Analysis of Metabolites

HPLC analysis of acetone, isopropanol and other metabolites was performed using an Agilent 1100 Series HPLC system equipped with a RID operated at 35° C. (Refractive Index Detector) and an Alltech IOA-2000 Organic acid column (150×6.5 mm, particle size 5 µm) kept at 60° C. Slightly acidified water was used (0.005 M $H_2SO_4$) as mobile phase with a flow rate of 0.7 ml/min. To remove proteins and other cell residues, 400 µl samples were mixed with 100 µl of a 2% (w/v) 5-Sulfosalicylic acid and centrifuged at 14,000×g for 3 min to separate precipitated residues. 10 µl of the supernatant were then injected into the HPLC for analyses.

GC analysis of acetone, isopropanol and other metabolites was performed using an Agilent 6890N headspace GC equipped with a Supelco PDMS 100 1 cm fiber, an Alltech EC-1000 (30 m×0.25 mm×0.25 µm) column, and a flame ionization detector (FID). 5 ml samples were transferred into a Hungate tube, heated to 40° C. in a water bath and exposed to the fiber for exactly 5 min. The injector was kept at 250° C. and helium with a constant flow of 1 ml/min was used as carrier gas. The oven program was 40° C. for 5 min, followed by an increase of 10° C./min up to 200° C. The temperature was then further increased to 220° C. with a rate of 50° C./min followed by a 5 min hold this temperature, before the temperature was decreased to 40° C. with a rate of 50° C./min and a final 1 min hold. The FID was kept at 250° C. with 40 ml/min hydrogen, 450 ml/min air and 15 ml/min nitrogen as make up gas.

Headspace Analysis

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Genetic Modification of *C. autoethanogenum* and *C. ljungdahlii* for Acetone Production Using Clostridial Pathway

*C. autoethanogenum* and *C. ljungdahlii* are naturally not able to produce acetone, therefore the acetone biosynthesis pathway occurring in other Clostridial species was introduced into both organisms (FIG. 4). The first step in the Clostridial acetone biosynthesis pathway from acetyl-CoA to acetoacetyl-CoA is catalysed by a acetyl-Coenzyme A acetyltransferase or thiolase. The conversion of acetoacetyl-CoA to acetone is then catalysed by a specialized set of enzymes acetate/butyrate-acetoacetate CoA-transferase complex and acetoacetate decarboxylase, which can be found in few organisms like *C. acetobutylicum* and *C. beijerinckii* (Tab. 6).

TABLE 6

Accession numbers of genes and enzymes involved in acetone and isopropanol formation.

| | *C. acetobutylicum* | | *C. beijerinckii* | |
| --- | --- | --- | --- | --- |
| Description | nucleic acid | amino acid | nucleic acid | Amino acid |
| Thiolase (ThlA) | NC_003030.1; GI: 1119056 | NP_349476.1 | NC_009617; GI: 5294796 | YP_001310706.1 |
| Acetate/Butyrate-acetoacetate CoA-transferase subunit A (CtfA) | NC_001988.2; GI: 1116168 | NP_149326.1 | NC_009617; GI: 5294994 | YP_001310904.1 |
| Acetate/Butyrate-acetoacetate CoA-transferase subunit A CtfB | NC_001988.2; GI: 1116169 | NP_149327.1 | NC_009617; GI: 5294995 | YP_001310905.1 |
| Acetoacetate decarboxylase (Adc) | NC_001988.2; GI: 1116170 | NP_149328.1 | NC_009617; GI: 5294996 | YP_001310906.1 |

Figure 3:
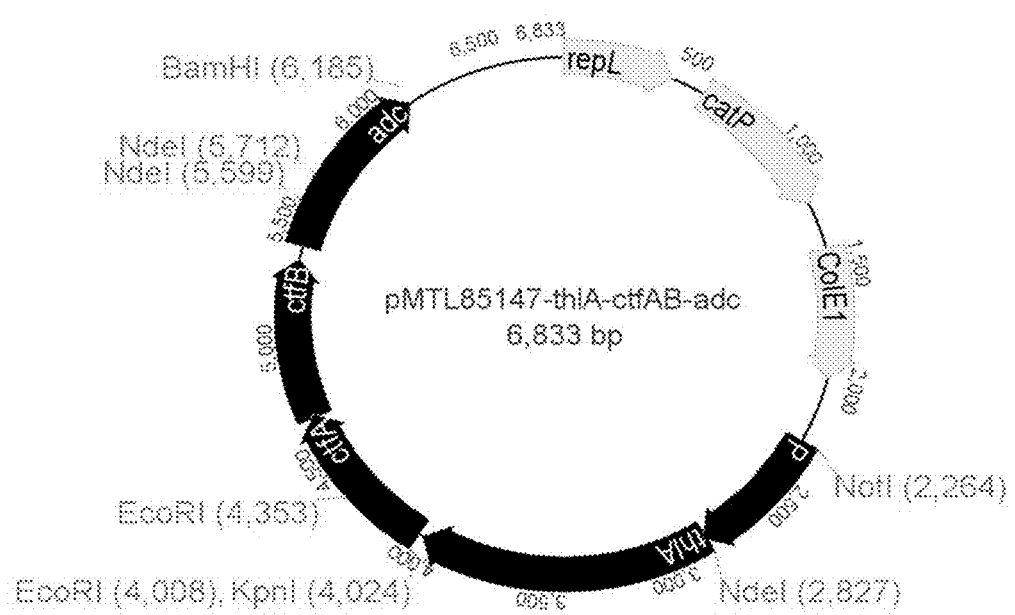
FIG. 3 shows acetone expression plasmid pMTL85147-thlA-ctfA-ctfB-adc.

Whereas the genes of C. acetobutylicum encoding the respective enzymes are split into 2 operons, the genes of C. beijerinckii form a common operon, which the inventor(s) believe offers an advantage. The genes encoding a thiolase from C. acetobutylicum and the operon coding for enzymes acetate/butyrate-acetoacetate CoA-transferase subunit A, acetate/butyrate-acetoacetate CoA-transferase subunit B and acetoacetate decarboxylase were assembled into a synthetic operon under control of a strong, native C. autoethanogenum promoter (FIG. 3). This construct was used to genetically engineer both organism for acetone production. In order to create a recombinant strain, a novel methyltransferase was used to methylate the construct, which was then transformed and expressed in C. autoethanogenum DSM23693 and C. ljungdahlii DSM13528 (described herein after). Production of acetone was shown on different industrial gas streams (steel mill waste gas, syngas).

Construction of Expression Plasmid with Clostridial Acetone Pathway Genes:

Standard Recombinant DNA and molecular cloning techniques were used in this invention [Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987]. DNA sequences of acetone biosynthetic genes are shown in Tab. 7. The Wood-Ljungdahl cluster promoter of C. autoethanogenum (upstream of CO dehydrogenase gene acsA) was used for expression of target genes (Tab. 7).

Genomic DNA from Clostridium acetobutylicum ATCC824, C. beijerinckii NCIMB8052 and C. autoethanogenum DSM10061 was isolated using a modified method by Bertram and Dürre (Conjugal transfer and expression of streptococcal transposons in Clostridium acetobutylicum. Arch Microbiol 1989, 151: 551-557). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 µl lysozyme (~100,000 U) were added and the mixture was incubated at 37° C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A. Then, 100 µl Proteinase K (0.5 U) were added and proteolysis took place for 1-3 h at 37° C. Finally, 600 µl of sodium perchlorate (5 M) were added, followed by a phenol-chloroform extraction and an isopropanol precipitation. DNA quantity and quality was inspected spectrophotometrically.

Acetone biosynthetic genes and the Wood-Ljungdahl cluster promoter were amplified by PCR with oligonucleotides in Tab. 8 using iProof High Fidelity DNA Polymerase (Bio-Rad Laboratories, Hercules, Calif. 94547, USA) and the following program: initial denaturation at 98° C. for 30 seconds, followed by 32 cycles of denaturation (98° C. for 10 seconds), annealing (50-62° C. for 30-120 seconds) and elongation (72° C. for 45 seconds), before a final extension step (72° C. for 10 minutes).

TABLE 7

Sequences used for Clostridial acetone expression plasmid

| Description | Source | SEQ_ID NO. |
| --- | --- | --- |
| Thiolase (thlA) | Clostridium acetobutylicum ATCC 824; NC_003030.1; GI: 1119056 | 18 |
| Acetoacetyl-CoA:acetate Coenzyme A transferase A (ctfA), acetoacetyl-CoA:acetate Coenzyme A transferase B (ctfB), and acetoacetate decarboxylase (adc) operon | Clostridium beijerinckii NCIMB 8052; NC_009617; region: 4,400,524-4,402,656; including GI: 5294994, GI: 5294995, and GI: 5294996 | 47 |
| Wood-Ljungdahl cluster promoter ($P_{WL}$) | Clostridium autoethanogenum DSM10061 | 22 |

TABLE 8

Oligonucleotides used for amplification of acetone biosynthesis genes and promoter region

| Description | Oligonucleotide Name | DNA Sequence (5' to 3') | SEQ_ID NO |
| --- | --- | --- | --- |
| ThlA | ThlA-Cac-NdeI-F | GTTCATATGAAAGAAGTTGTAATAGC | 23 |
| | ThlA-Cac-EcoRI-R | CAAGAATTCCTAGCACTTTTCTAGC | 24 |
| CtfA, CtfB, Adc operon | Ctf-adc-cbei-KpnI-F | CTAGGTACCAGGGAGATATTAAAATG | 25 |
| | Ctf-adc-cbei-BamH1-R | CGTGGATCCTCTATATTGCTTTTATT | 26 |
| $P_{WL}$ | Pwoodlj-NotI-F | AAGCGGCCGCAGATAGTCATAATAGTTCC | 27 |
| | Pwoodlj-NdeI-R | TTCCATATGAATAATTCCCTCCTTAAAGC | 28 |

Figure 5:
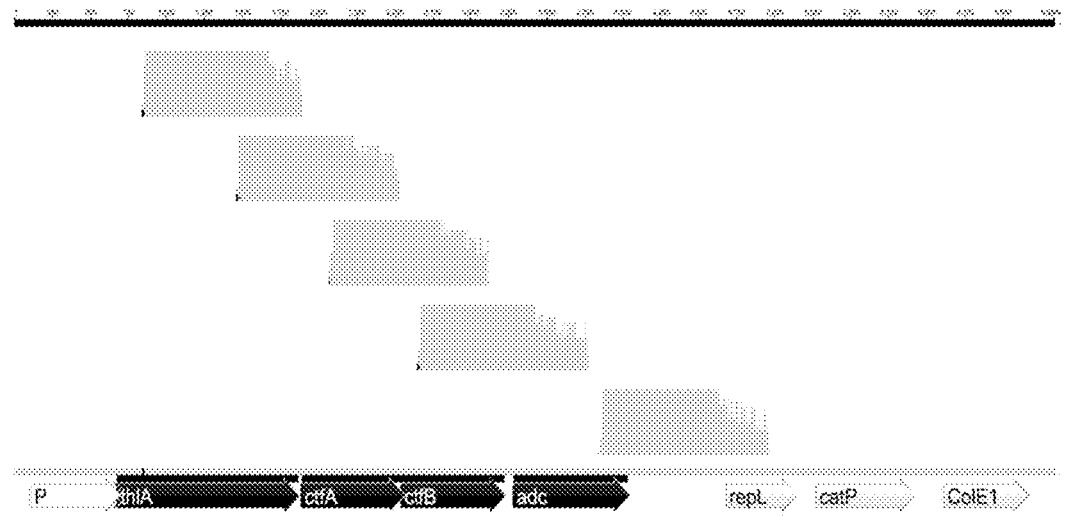
FIG. 5 shows the sequencing results of acetone expression plasmid pMTL85147-thlA-ctfA-ctfB-adc.

The amplified 573 bp promoter region of the Wood-Ljungdahl cluster ($P_{WL}$) was cloned into the *E. coli-Clostridium* shuttle vector pMTL 85141 (FJ797651.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using NotI and NdeI restriction sites and strain DH5α-T1$^R$. The created plasmid pMTL85147 and the 1,194 bp PCR product of the thiolase gene were both cut with NdeI and EcoRI. A ligation was transformed into *E. coli* XL1-Blue MRF' Kan resulting in plasmid pMTL85147-thlA. Subsequently, the amplified 2,177 bp PCR fragment of the ctfA-ctfB-adc operon from *C. beijerinckii* NCIMB 8052 was cloned into this vector using KpnI and BamHI and *E. coli* ABLE K, creating plasmid pMTL85147-thlA-ctfA-ctfB-adc. The insert of the resulting plasmid pMTL85147-thlA-ctfAB-adc was completely sequenced using oligonucleotides given in Tab. 9 and results confirmed that the acetone biosynthesis genes and promoter region were free of mutations (FIG. 5).

Both expression plasmid and methylation plasmid were transformed into same cells of restriction negative *E. coli* XL1-Blue MRF' Kan, which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN GmbH, Hilden, Germany). The resulting mix was used for transformation experiments with *C. autoethanogenum* DSM23693 and *C. ljungdahlii* DSM 13528, but only the abundant (high-copy) expression plasmid has a Gram-(+) replication origin (repL) allowing to replicate in Clostridia.

Transformation of Methylated Acetone Expression Plasmid in *C. autoethanogenum* and *C. ljungdahlii*:

To make competent cells of *C. autoethanogenum* DSM23693 and *C. ljungdahlii* DSM 13528, a 50 ml culture (PETC media (Tab. 2) with steel mill gas and fructose as carbon source; 37° C.) was subcultured to fresh media for 3 consecutive days. These cells were used to inoculate 50 ml

TABLE 9

Oligonucleotides used for sequencing

| Oligonucleotide Name | DNA Sequence (5' to 3') | SEQ_ID NO. |
|---|---|---|
| Seq-ThlA-CtfAB-Adh 3539-4139 | CAGAGGATGTTAATGAAGTC | 29 |
| Seq-ThlA-CtfAB-Adh 4140-4740 | CTGTGCAGCAGTACTTGT | 30 |
| Seq-ThlA-CtfAB-Adh 4741-5341 | GCAATGATACAGCTT | 31 |
| Seq-ThlA-CtfAB-Adh 5342-5942 | AACCTTGGAATAGGACTTC | 32 |
| Seq-ThlA-CtfAB-Adh 6544-7144 | TGTGAACTAATATGTGCAGA | 33 |
| M13 Forward | GTAAAACGACGGCCAG | 56 |
| M13 Reverse | CAGGAAACAGCTATGAC | 57 |

Acetone Production in *E. coli* with Clostridial Acetone Pathway Genes:

To confirm the functionality of the constructed plasmid, a metabolic profile from a 5 ml overnight culture of *E. coli* ABLE K harbouring plasmid pMTL85147-thlA-ctfA-ctfB-adc were obtained using GC and HPLC, confirming acetone production.

To investigate this further, detailed growth experiments were carried out in triplicates with SD-8 minimal media containing 25 μg/ml chloramphenicol and *E. coli* XL-1 Blue MRF' Kan carrying either plasmid pMTL 85147 (negative control) or expression plasmid pMTL 85147-thlA-ctfA-ctfB-adc (FIG. 42). While no acetone production could be observed in the negative control, an average maximum acetone production of 75.05 mg/L with an average dry biomass of 1.44 g/L was measured for the strain carrying the acetone plasmid.

Figure 6:
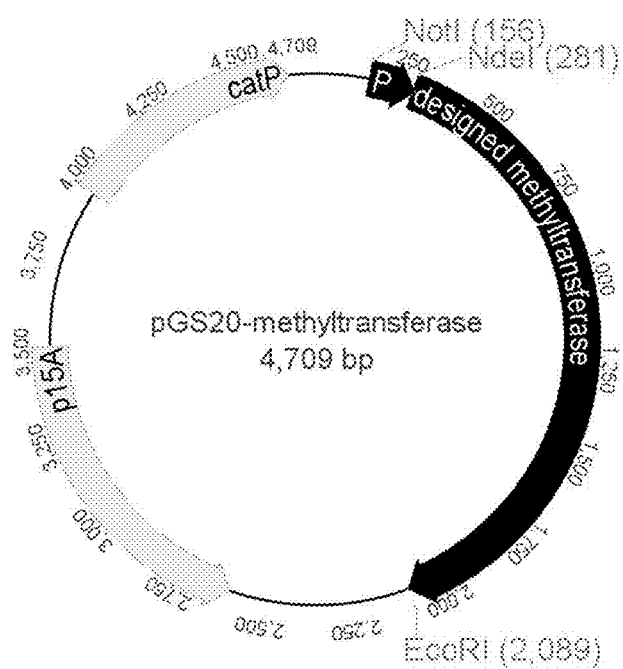
FIG. 6 illustrates the designed methylation plasmid.

Methylation of Expression Plasmid with Clostridial Acetone Pathway Genes:

Methylation of the acetone expression plasmid pMTL85147-thlA-ctfA-ctfB-adc was performed in vivo in *E. coli* using a synthesized hybrid Type II methyltransferase gene (SEQ_ID NO 35) designed from methyltransferase genes from *C. autoethanogenum*, *C. ragsdalei* and *C. ljungdahlii*. The methyltransferase (SEQ_ID NO 34) was synthesized and fused with an inducible lac promoter in vector pGS20 (ATG:biosynthetics GmbH, Merzhausen, Germany) (FIG. 6; SEQ_ID NO 49).

PETC media containing 40 mM DL-threonine at an $OD_{600\ nm}$ of 0.05. When the culture reached an $OD_{600\ nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 500 μl fresh electroporation buffer. This mixture was transferred into a pre-cooled electroporation cuvette with a 0.4 cm electrode gap containing ~1 μg of the methylated plasmid mix. Since an additional Type I restriction system was identified in the genome of *C. ljungdahlii* compared to *C. autoethanogenum*, 5 μl of a Type I restriction inhibitor (EPICENTRE Biotechnologies, Madison, Wis. 53713, USA) were added to the plasmid mix, which increased the transformation efficiency of *C. ljungdahlii* by 2-10 fold. The cells were mixed with plasmid and restriction inhibitor and immediately pulsed using a Gene pulser Xcell electroporation system (Bio-Rad Laboratories, Hercules, Calif. 94547, USA) with the following settings: 2.5 kV, 600Ω, and 25 μF. Time constants were between 3.7-5.1 ms. For regeneration, the culture was transferred in 5 ml special regeneration media (Tab. 10), which increased recovery of the cells, which was monitored at a wavelength of 600 nm using a Spectronic Helios Epsilon Spectrophotometer (Thermo Fisher Scientific Inc., Waltham Mass. 02454, USA) equipped with a tube holder. Once growth was observed (one doubling) the cells were harvested, suspended in 200 μl fresh media and plated on selective PETC plates with 15 μg/ml thiamphenicol (dissolved in 100% (v/v) dimethylfuran (DMF)) and 30 psi steel mill gas in the headspace. 50-200 colonies were visible after 4-6 days, which were used to inoculate 2 ml PETC media containing 15 μg/ml thiamphenicol (in DMF) and fructose and 30 psi steel mill gas as carbon source. When growth occurred, the culture was up-scaled into 5 ml and later 50 ml PETC media containing each 15 μg/ml thiamphenicol (in DMF) and 30 psi steel mill gas in the headspace as sole carbon source.

TABLE 10

Regeneration media

| Media component | Concentration per 1.0 L of media |
| --- | --- |
| $NH_4Cl$ | 1 g |
| KCl | 0.1 g |
| $MgSO_4 \cdot 7H_2O$ | 0.2 g |
| $KH_2PO_4$ | 0.2 g |
| $CaCl_2$ | 0.02 g |
| Trace metal solution (see Tab. 2) | 10 ml |
| Wolfe's vitamin solution (see Tab. 2) | 10 ml |
| Yeast Extract | 2 g |
| Resazurin (2 g/L stock) | 0.5 ml |
| 2-(N-morpholino)ethanesulfonic acid (MES) | 20 g |
| Reducing agent | 0.006-0.008% (v/v) |
| Fructose | 5 g |
| Sodium acetate | 0.25 g |
| $Fe(SO_4)_2(NH_4)_2 \cdot 6H_2O$ | 0.05 g |
| Nitriolotriacetic Acid | 0.05 g |
| pH 5.7 | Adjusted with NaOH |

Figure 7:
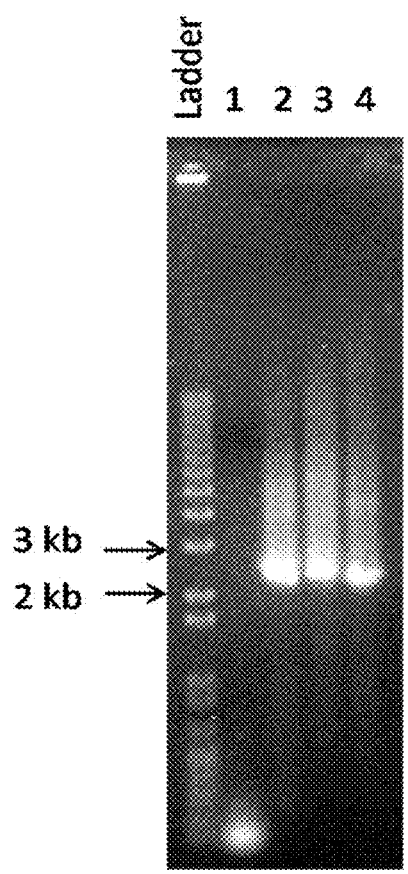
FIG. 7 shows detection of ctfAB-adc (2.2 kb) from PCR of plasmids isolated from transformed *C. autoethanogenum* DSM23693 and *C. ljungdahlii* DSM13528. Ladder=1 KB Plus DNA ladder (Invitrogen); 1=non-template control; 2=plasmid isolated from *C. autoethanogenum;* 3=plasmid isolated from *C. ljungdahlii;* 4=original pMTL85147-thlA-ctfAB-adc (positive control).

Confirmation of Successful Transformation of *C. autoethanogenum* and *C. ljungdahlii* with Acetone Plasmid with Clostridial Acetone Pathway Genes:

To verify the DNA transfer, a plasmid mini prep was performed from 10 ml culture volume using Zyppy plasmid miniprep kit (Zymo Research, Irvine, Calif. 92614, USA). Since the quality of the isolated plasmid wasn't sufficient for a restriction digest due to Clostridial exonuclease activity [Burchhardt G and Dürre P, Isolation and characterization of DNase-deficient mutants of *Clostridium acetobutylicum. Curr Microbiol* 1990, 21: 307-311] with the isolated plasmid as template using primers ctf-adc-cbei-KpnI-F (Seq_ID no 25) and ctf-adc-cbei-BamH1-R (SEQ_ID NO 26) to confirm the presence of the plasmid (FIG. 7). PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 135 seconds), before a final extension step (72° C. for 5 minutes).

To confirm the identity of the clones, genomic DNA was isolated using the protocol given above from 50 ml cultures of each *C. autoethanogenum* DSM23693 and *C. ljungdahlii* DSM13528. A PCR was performed against the 16s rRNA gene using oligonucleotides fD1 (SEQ_ID NO 36: CCGAATTCGTCGACAACAGAGTTTGATCCTG-GCTCAG) and rP2 (SEQ_ID NO 37: CCCGGGATC-CAAGCTTACGGCTACCTTGTTACGACTT) [Weisberg W G, Barns S M, Pelletier B A and Lane D J, 16S ribosomal DNA amplification for phylogenetic study. *J Bacteriol* 1990, 173: 697-703] and iNtRON Maximise Premix PCR kit (Intron Bio Technologies, Sangdaewon Joongwon Seognam Kyunggi, Korea) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes). All sequences obtained had >99.9% identity against the 16s rRNA gene (rrsA) of *C. autoethanogenum* (Y18178, GI:7271109) and respectively *C. ljungdahlii* (CP001666.1; GI:300433347).

Acetone Production from CO and $CO_2/H_2$ with with Clostridial Acetone Pathway Genes in *C. autoethanogenum* and *C. jungdahlii:*

Figure 9:
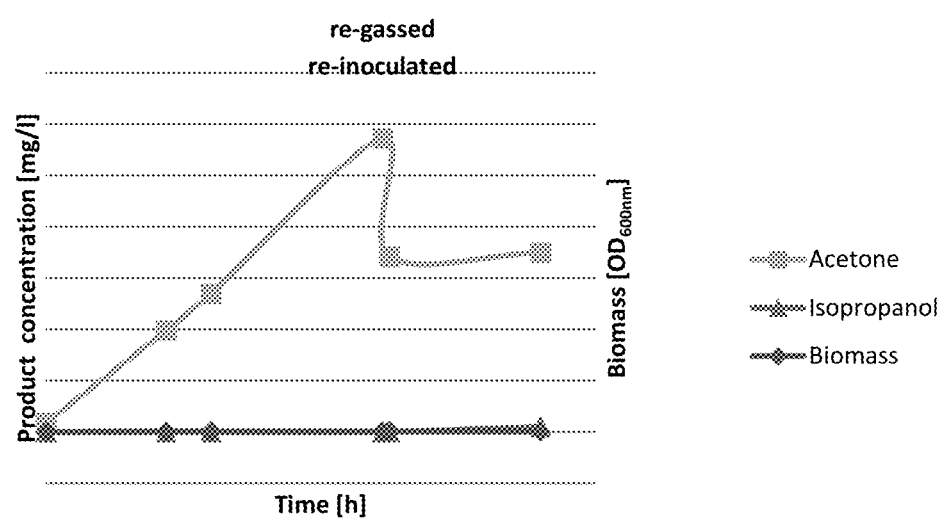
FIG. 9 shows the result of growth experiments with *C. ljungdahlii* DSM13528+pMTL85147-thlA-ctfAB-adc on steel mill gas.
Figure 10:
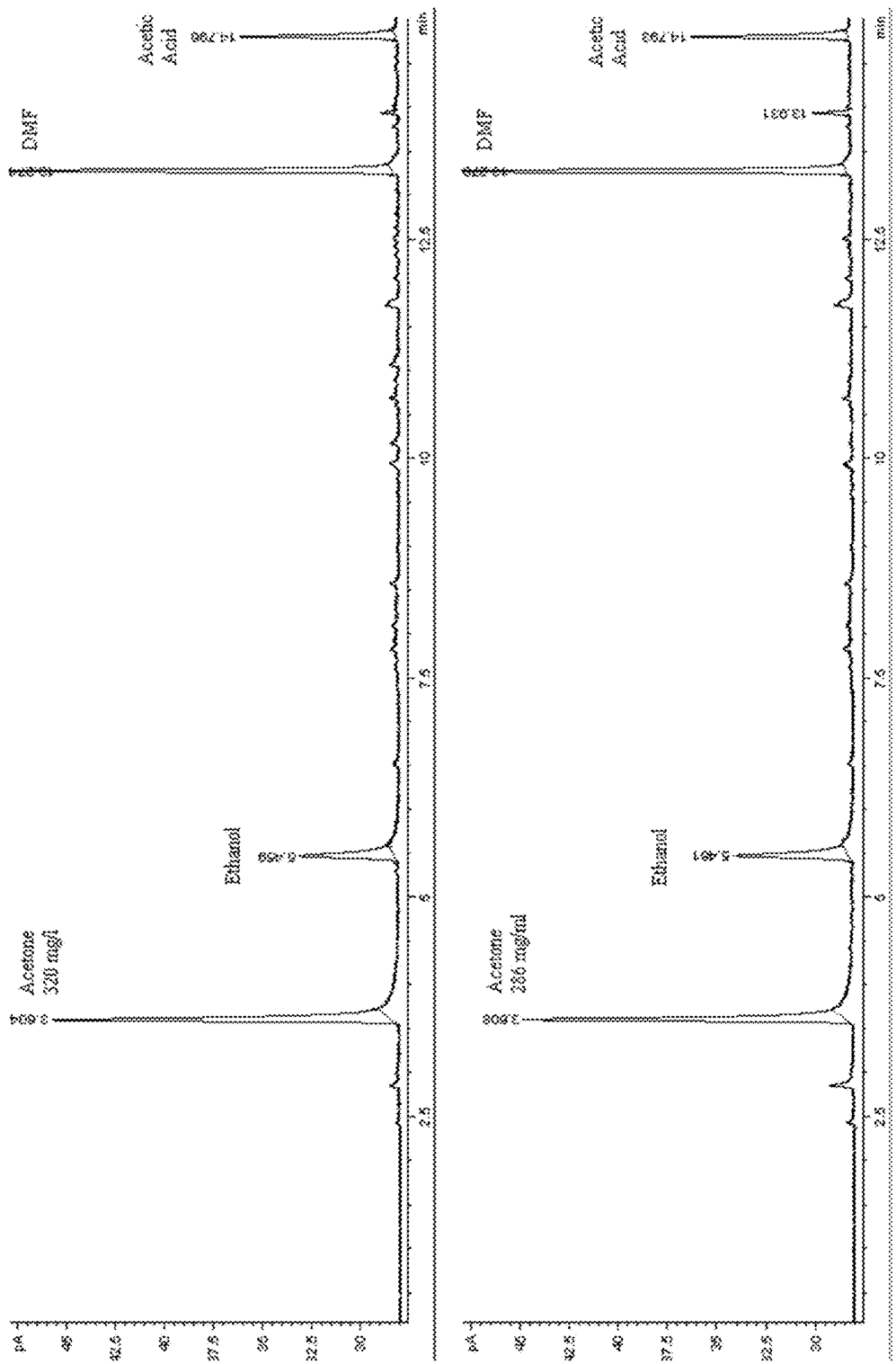
FIG. 10 shows the GC result confirming acetone production with *C. autoethanogenum* DSM13528+pMTL85147-thlA-ctfAB-adc (top) and *C. ljungdahlii* DSM13528+pMTL85147-thlA-ctfAB-adc (bottom) from steel mill gas.
Figure 11:
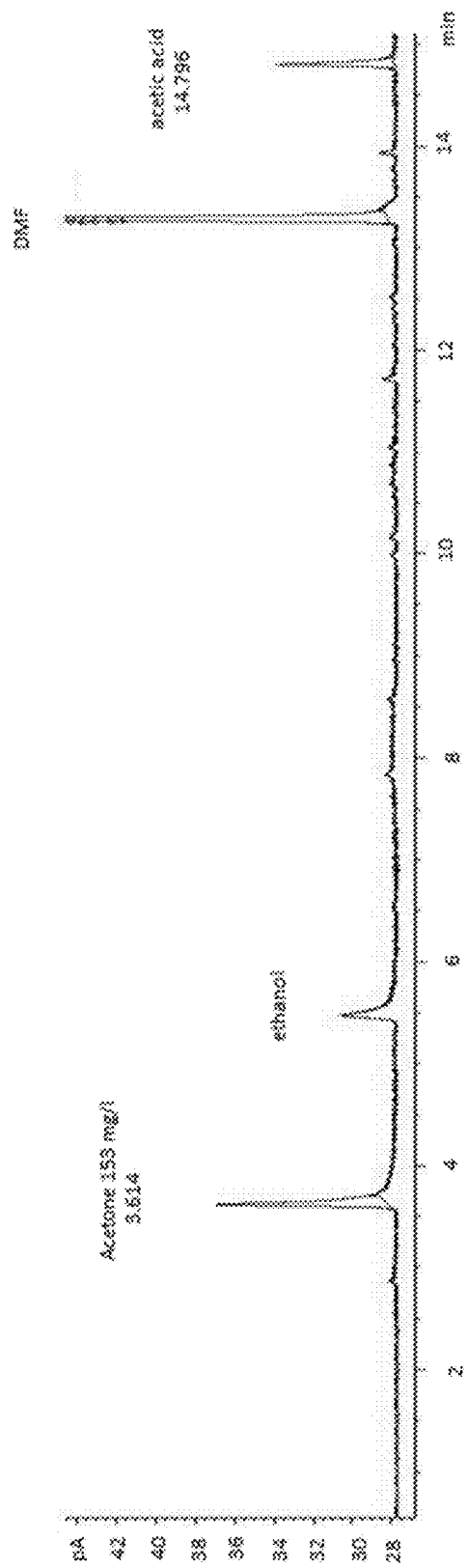
FIG. 11 shows the GC result confirming acetone production with *C. autoethanogenum* DSM23693+pMTL85147-thlA-ctfAB-adc from syngas.

Growth experiments were carried out with transformed *C. autoethanogenum* DSM23693 and *C. ljungdahlii* DSM 13528 carrying plasmid pMTL85147-thlA-ctfAB-adc in 250 ml PETC media (Tab. 2; without fructose and yeast extract) in 1 l Schott bottles with rubber stoppers and 30 psi steel mill gas (collected from New Zealand Steel site in Glenbrook, NZ; composition: 44% CO, 32% $N_2$, 22% $CO_2$, 2% $H_2$) in the headspace as sole energy and carbon source. Acetone production was confirmed with both strains using HPLC and GC analysis. In Schott bottles acetone concentrations of around 0.3 g/l (6.5 mM) after 48 hours were achieved with both, *C. autoethanogenum* DSM23693 (FIGS. 8 and 10) and *C. ljungdahlii* DSM 13528 (FIGS. 9 and 10). Using appropriate conditions, the produced acetone can then be further converted to isopropanol. Acetone production of 153 mg/ml was also demonstrated on 30 psi biomass syngas (Range Fuels Inc., Broomfield, Colo.; composition: 29% CO, 45% $H_2$, 13% $CH_4$, 12% $CO_2$, 1% $N_2$) as sole energy and carbon source in 50 ml PETC media (Tab. 2; without fructose and yeast extract) in serum bottles with *C. autoethanogenum* DSM23693 (FIG. 11).

Figure 52:
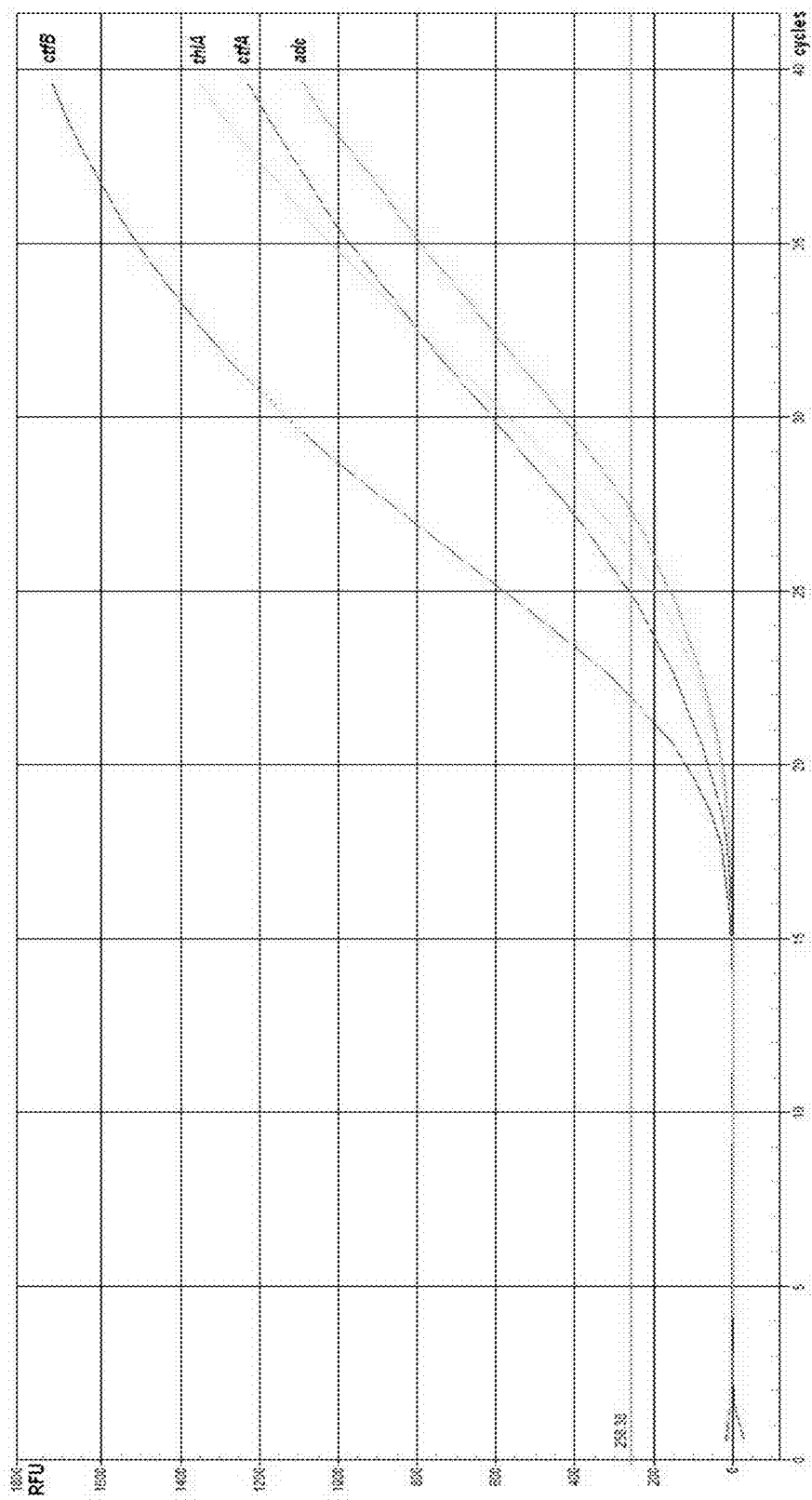
FIG. 52 shows qRT-PCR amplification plot confirming amplification of probes for heterologous genes thlA, ctfA, ctfB, and adc in *Clostridium autoethanogenum* harbouring plasmid pMTL85147-thlA-ctfAB-adc
Figure 53:
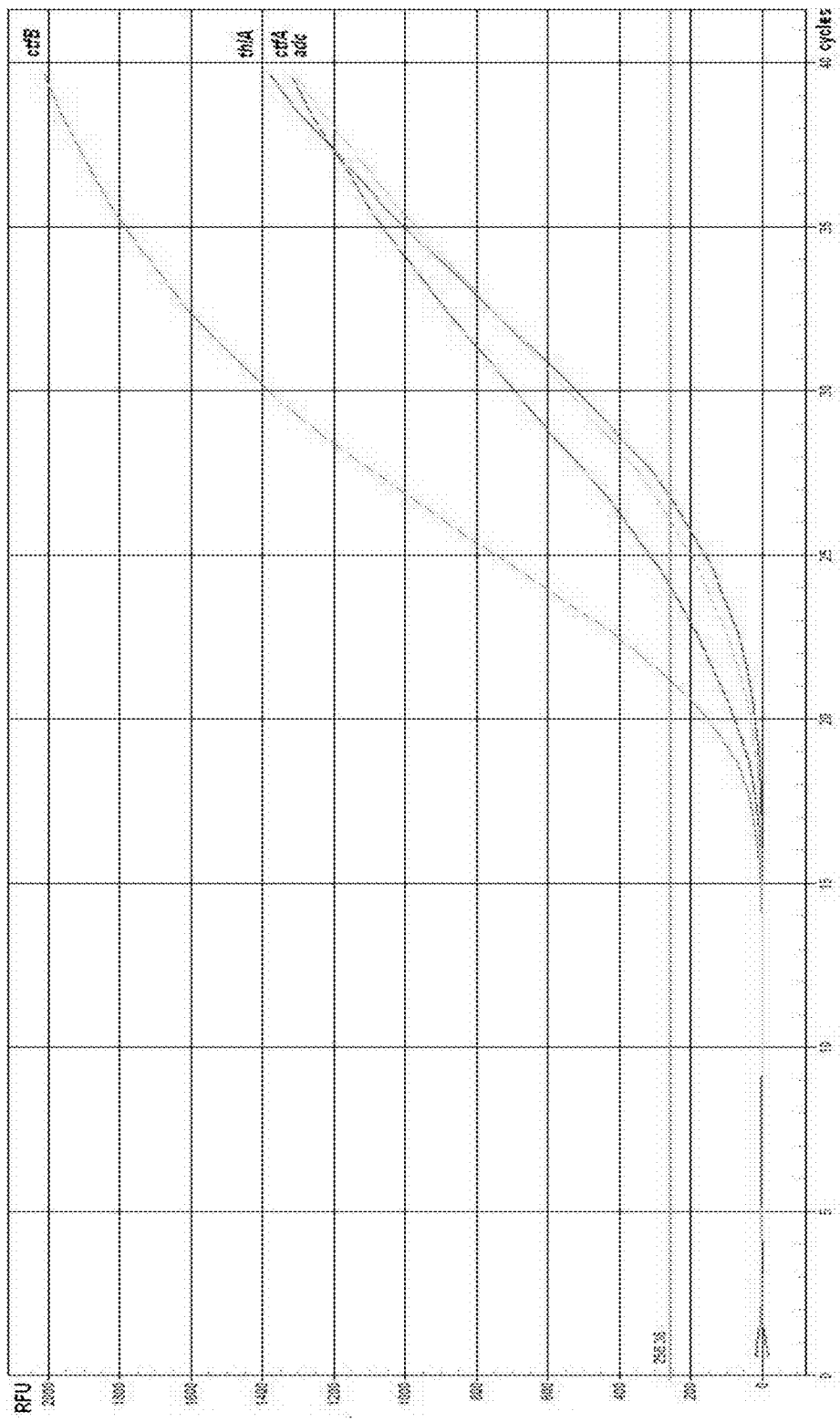
FIG. 53 shows qRT-PCR amplification plot confirming amplification of probes for heterologous genes thlA, ctfA, ctfB, and adc in *Clostridium ljungdahlii* harbouring plasmid pMTL85147-thlA-ctfAB-adc

Expression of Heterologous with Clostridial Acetone Pathway Genes in *C. autoethanogenum:* qRT-PCR experiments were performed to confirm successful expression of introduced genes thlA, ctfA, ctfB, and adc leading to acetone production in *C. autoethanogenum* and *C. ljungdahlii.* Signals for all genes could successfully be detected (FIGS. 52 and 53).

A 50-ml culture of each *C. autoethanogenum* and *C. ljungdahlii* harbouring plasmid pMTL85147-harvested by centrifugation (6,000×g, 5 min, 4° C.), snap frozen in liquid nitrogen and stored at −80° C. until RNA extraction. Total RNA was isolated using PureLink™ RNA Mini Kit (Invitrogen, Carlsbad, Calif., USA) and eluted in 100 μl of RNase-free water. After DNase I treatment (Roche Applied Science, Indianapolis, Ind., USA), the reverse transcription step was then carried out using SuperScript III Reverse Transcriptase Kit (Invitrogen, Carlsbad, Calif., USA). RNA was checked using an Agilent Bioanalyzer 2100 (Agilent Technologies, Santa Clara, Calif., USA), Qubit Fluorometer (Invitrogen, Carlsbad, Calif., USA) and by gel electrophoresis. A non-RT control was performed for every primer pair. All qRT-PCR reactions were performed in duplicates using a MyiQ Single Colour Detection System (Bio-Rad Laboratories, Carlsbad, Calif., USA) in a total reaction volume of 15 μl with 25 ng of cDNA template, 67 nM of each primer (Table 17), and 1× iQ SYBR Green Supermix (Bio-Rad Laboratories, Carlsbad, Calif., USA). The reaction conditions were 95° C. for 3 min, followed by 40 cycles of 95° C. for 15 s, 55° C. for 15 s and 72° C. for 30 s. For detection of primer dimerisation or other artifacts of amplification, a melting-curve analysis was performed immediately after completion of the qPCR (38 cycles of 58° C. to 95° C. at 1° C./s). Two housekeeping genes (Guanylate kinase and formate tetrahydrofolate ligase) were included for each cDNA sample for normalization. Derivation of relative gene expression was conducted using Relative Expression Software Tool (REST©) 2008 V2.0.7 (38). Dilution series of cDNA spanning 4 log units were used to generate standard curves and the resulting amplification efficiencies to calculate concentration of mRNA.

TABLE 17

Oligonucleotides for qRT-PCR

| Target | Oligonucleotide Name | DNA Sequence (5' to 3') | SEQ ID NO. |
|---|---|---|---|
| Guanylate kinase (gnk) | GnK-F | TCAGGACCTTCTGGAACTGG | 5 |
| | GnK-R | ACCTCCCCTTTTCTTGGAGA | 6 |
| Formate tetrahydrofolate ligase (FoT4L) | FoT4L-F | CAGGTTTCGGTGCTGACCTA | 7 |
| | FoT4L-F | AACTCCGCCGTTGTATTTCA | 8 |
| Thiolase A | thlA-RT-F | TTGATGAAATGATCACTGACGGATT | 64 |
| | thlA-RT-R | GAAATGTTCCATCTCTCAGCTATGT | 65 |
| Acetoacetyl-CoA: Acetate CoA-transferase B | ctfB-RT-F | CTAATACGAGGAGGACATGTTGATG | 66 |
| | ctfB-RT-R | CACCCATACCTGGGACAATTTTATT | 67 |
| Acetoacetyl-CoA: Acetate CoA-transferase A | ctfA-RT-F | GGGCTGCTACTAAAAATTTCAATCC | 68 |
| | ctfA-RT-R | CAGGAGTCATTATGGCATCTCTTTT | 69 |
| Acetoacetate decarboxylase | adc-RT-F | TAGTACCAGAGCCACTTGAATTAGA | 70 |
| | adc-RT-R | GGAATAGCTTGACCACATTCTGTAT | 71 |

Conversion of Acetone to Isopropanol by C. autoethanogenum, C. Ljungdahlii, and C. ragsdalei:

Acetone can be further converted to isopropanol by action of an alcohol dehydrogenase. However, only few microorganisms such as C. beijerinckii NRRL-B593 are described to produce isopropanol, and acetone-to-isopropanol converting enzymes are very rare in nature. So far only two secondary alcohol dehydrogenases have been identified and described to date, from C. beijerinckii NRRL-B593 [Ismaiel A A, Zhu C X, Colby G D, Chen J S: Purification and characterization of a primary-secondary alcohol dehydrogenase from two strains of Clostridium beijerinckii. J Bacteriol 1993, 175: 5097-5105] (SEQ_ID NO 38-39) and Thermoanaerobacter brockii [Peretz M and Burstein Y: Amino acid sequence of alcohol dehydrogenase from the thermophilic bacterium Thermoanaerobium brockii. Biochemistry. 1989, 28:6549-6555] (SEQ_ID NO 40-41).

Therefore, a collection of microorganisms—acetogenic bacteria, acetone and isopropanol producing Clostridia and E. coli—were tested for their ability to convert acetone to isopropanol (Tab. 11).

TABLE 11

Addition of acetone to growing cultures of various microorganisms.

| Organism/Sample | Description | Media | Directly after acetone addition | | End of growth | |
|---|---|---|---|---|---|---|
| | | | Acetone [g/l] | Isopropanol [g/l] | Acetone [g/l] | Isopropanol [g/l] |
| Acetobacterium woodii DSM1030 | Acetogenic species | PETC (pH 8.2) | 10.81 | 0 | 10.83 | 0 |
| Clostridium aceticum DSM1496 | | PETC (pH 7.4) | 10.07 | 0 | 10.09 | 0 |
| C. autoethanogenum DSM23693 | | PETC (pH 5.9) | 9.25 | 0 | 1.13 | 8.03 |
| C. carboxidivorans DSM15243 | | | 10.43 | 0 | 10.34 | 0 |
| C. ljungdahlii DSM13528 | | | 10.23 | 0 | 3.73 | 6.54 |
| C. ragsdalei ATCC BAA-622 | | | 11.25 | 0 | 9.94 | 1.34 |
| C. beijerinckii NRRL-B593 | Isopopanol producing species | RCM | 9.96 | 0 | 7.65 | 2.54 |
| C. beijerinckii NCIMB8052 | Acetone producing species | | 10.49 | 0 | 10.59 | 0 |
| C. acetobutylicum ATCC824 | | | 10.80 | 0 | 10.91 | 0 |
| Escherichia coli DH5 (Invitrogen) | | LB + glucose | 11.67 | 0 | 11.71 | 0 |
| Blank media | Control | PETC | 10.51 | 0 | 10.55 | 0 |

All cultures were inoculated to an $OD_{600\ nm}$ of 0.1 in 50 ml appropriate media containing a heterotrophic carbon source and 30 psi steel mill gas. The cultures were allowed to double ($OD_{600\ nm}$=0.2) before acetone was added. A sample was taken and analyzed by HPLC and GC immediately after acetone addition and again at the end of growth (which were followed by measuring the optical density).

Results are summarized in Tab. 11. Blank media was used as negative control.

As expected, isopropanol producing strain C. beijerinckii NRRL-B593 [George H A, Johnson J L, Moore W E C, Holdeman L V, Chen J S: Acetone, isopropanol, and butanol production by Clostridium beijerinckii (syn. Clostridium butylicum) and Clostridium aurantibutyricum. Appl Environ Microbiol 45: 1160-1163] had the ability to reduce externally added acetone to isopropanol by action of its alcohol dehydrogenase. A different strain of C. beijerinckii, NRCIMB8052, which lacks this enzyme wasn't able to convert acetone to isopropanol, as the acetone producing C. acetobutylicum ATCC-824. The same is also true for E. coli.

Surprisingly, three carboxydotrophic acetogenic bacteria C. autoethanogenum, C. ljungdahlii, and C. ragsdalei, which form a subcluster within the Clostridial rRNA Homology Group I, were found to be able to convert acetone to isopropanol as well, while all other acetogenic bacteria tested couldn't utilize acetone (Tab. 11). Conversion of different amounts of acetone to isopropanol by C. autoethanogenum was then tested using different concentrations (Tab. 12).

TABLE 12

Conversion of different concentrations of acetone to isopropanol by cultures of C. autoethanogenum DSM23693.

| Acetone [g/l] added | Acetone [g/l] left at end of growth | Isopropanol [g/l] left at end of growth |
|---|---|---|
| 0 | 0 | 0 |
| 1.66 | 0.22 | 1.48 |
| 9.25 | 1.13 | 8.03 |
| 26.13 | 17.82 | 8.39 |
| 50.01 | 43.30 | 6.95 |

A reactor study with C. autoethanogenum DSM23693 was performed to demonstrate effective conversion of acetone to isopropanol at high rates. The reactor was set-up as described above. Once in continuous mode with stable biomass and metabolite production, acetone was added to both the bioreactor and the feed medium. Acetone was spiked into the reactor to a certain level, which was then obtained by continuous feeding. Initially, 1 g/L acetone was added, once the metabolite concentrations had stabilised, the concentration was increased to 5 g/L, 15 g/l, and in a second experiment to 20 g/L. Even at high concentrations of 20 g/L the culture converted all acetone to isopropanol at high rate demonstrating that the identified primary:secondary alcohol dehydrogenase is highly effective (FIG. 74).

Identification of a Novel Alcohol Dehydrogenase in C. autoethanogenum, C. Ljungdahlii, and C. ragsdalei:

To confirm that the conversion of acetone to isopropanol by C. autoethanogenum is driven enzymatically, enzyme assays were carried out with crude extract of C. autoethanogenum 23693, C. beijerinckii NRRL-B593, and C. carboxidivorans DSM15243 according to Ismaiel et al [Ismaiel A A, Zhu C X, Colby G D, Chen J S: Purification and characterization of a primary-secondary alcohol dehydrogenase from two strains of Clostridium beijerinckii. J Bacteriol 1993, 175: 5097-5105]. Crude extracts were obtained by sonication and lysozyme treatment (100,000 U/ml) of late exponential cultures. Cell debris was removed by centrifugation and protein concentrations was determined using the Pierce BCA protein assay—reducing agent compatible (Thermo Fisher Scientific Inc., Waltham Mass. 02454, USA). The assay mixture (1 ml) contained 50 mM Tris buffer (pH 7.5), 1 mM dithiothreitol (DTT), and 0.2 mM NAD(P)H. The reaction was started by adding 10 mM of the substrate acetone (from a 10-fold dilution in water) and followed spectrophotometrically with a Spectramax M2 (Molecular Devices, Inc., Sunnyvale, Calif. 94089-1136, USA) at a wavelength of 365 nm. $H_2O$ was used as negative control instead of crude extract and respectively acetone. Enzyme activity could be detected with crude extracts of both C. beijerinckii and C. autoethanogenum and NADPH (not with NADH), but not with crude extracts of C. carboxidivorans DSM15243 or $H_2O$ (with both NADPH and NADH). This demonstrates that the conversion of acetone to isopropanol by C. autoethanogenum is driven enzymatically, and as no activity was detected with NADH, the enzyme appears to be NADPH-dependent.

Figure 1:
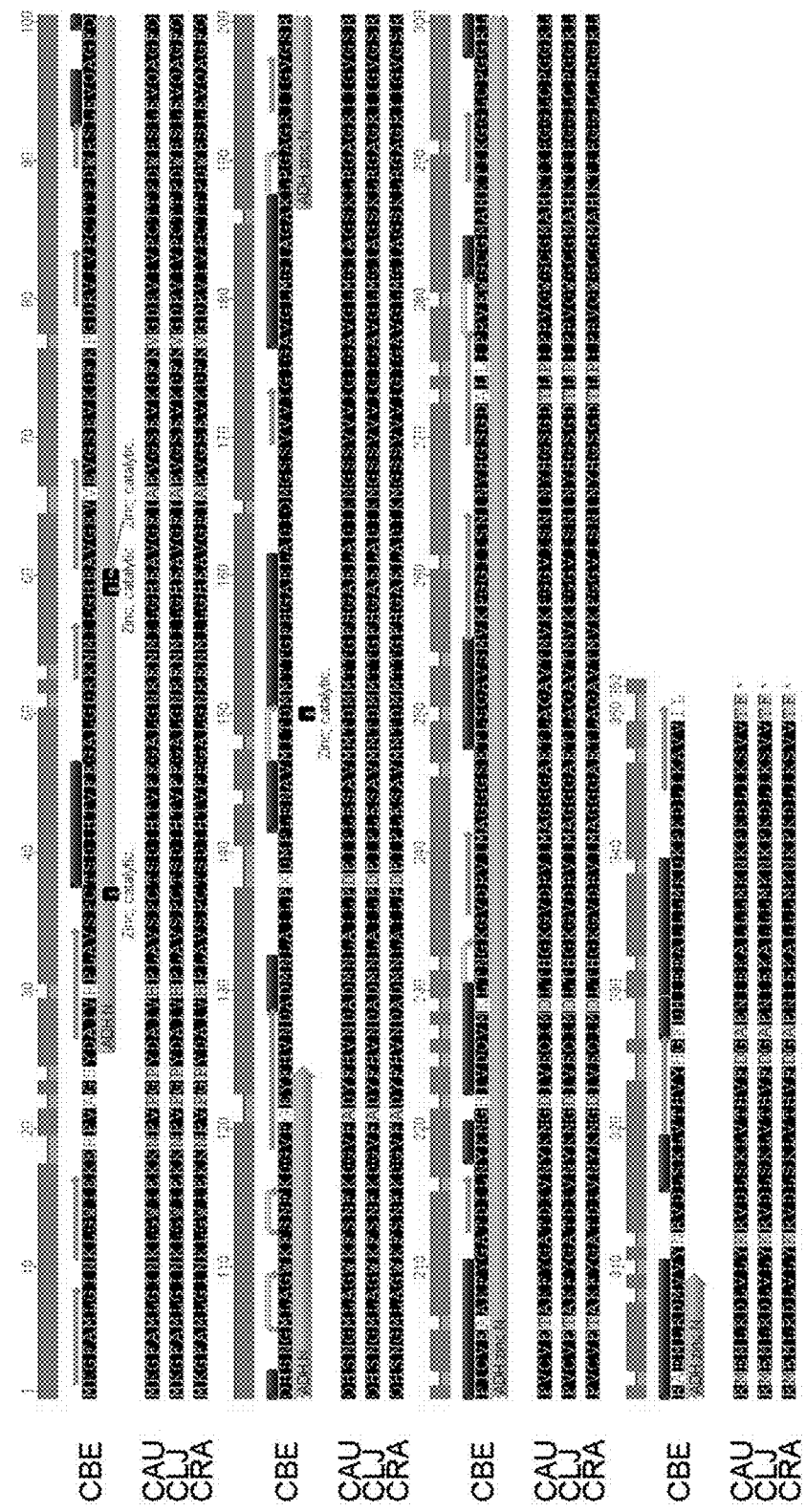
FIG. 1 shows amino acid alignment of novel alcohol dehydrogenase of *C. autoethanogenum* (CAU) (SEQ ID NO: 1), *C. ljungdahlii* (CU) (SEQ ID NO: 1), and *C. ragsdalei* (CRA) (SEQ ID NO: 1) with the secondary alcohol dehydrogenase of *C. beijerinckii* strain NRRL-B593 (SEQ ID NO: 38).

By sequencing and careful analysis, a novel alcohol dehydrogenase gene/enzyme was identified in all three strain, C. autoethanogenum, C. ljungdahlii, and C. ragsdalei (FIG. 1; SEQ_ID NO. 1-4). The amino acid sequence was found to be identical in all three species and share some homology to the primary-secondary alcohol dehydrogenase of C. beijerinckii NRRL-B593 (87%) and T. brockii ATCC 53556 (76%) (Tab. 13). Compared to the well-described secondary alcohol dehydrogenase of C. beijerinckii NRRL-B593 [Ismaiel A A, Zhu C X, Colby G D, Chen J S: Purification and characterization of a primary-secondary alcohol dehydrogenase from two strains of Clostridium beijerinckii. J Bacteriol 1993, 175: 5097-5105], a total of 49 amino acids exchanges were found. 4 amino acids of the catalytic centre of the protein are conserved, however, other amino acids in the catalytic domain are not (FIG. 1). A motif search predicted the novel alcohol dehydrogenase gene/enzyme to be zinc and NAD(P)H dependent. The respective genes coding for the novel alcohol dehydrogenase was found to be 98% identical within the 3 species C. autoethanogenum, C. ljungdahlii, and C. ragsdalei, but only 82% identical to the one from C. beijerinckii and 72% identical to the one from T. brockii (Tab. 14).

TABLE 13

Comparison of amino acid sequences of novel alcohol dehydrogenase and known secondary alcohol dehydrogenases

| Organism | Description | Seq ID | Accession number | Reference | Score | e-Value | Identity |
|---|---|---|---|---|---|---|---|
| C. autoethanogenum | — | SEQ_ID NO. 1 | — | — | 717 bits (1852) | 0 | 351/351 (100%) |
| C. ljungdahlii | zinc-containing alcohol dehydrogenase | SEQ_ID NO. 1 | YP_003780646.1 | — | 717 bits (1852) | 0 | 351/351 (100%) |
| C. ragsdalei | — | SEQ_ID NO. 1 | — | — | 717 bits (1852) | 0 | 351/351 (100%) |

TABLE 13-continued

Comparison of amino acid sequences of novel alcohol dehydrogenase
and known secondary alcohol dehydrogenases

| Organism | Description | Seq ID | Accession number | Reference | Score | e-Value | Identity |
|---|---|---|---|---|---|---|---|
| C. beijerinckii NRRL B-593 | NADP-dependent alcohol dehydrogenase | SEQ_ID NO. 38 | P25984.2 | Ismaiel et al., 1993 | 630 bits (1626) | 7E–179 | 302/351 (87%) |
| T. brockii ATCC 53556 | NADP-dependent alcohol dehydrogenase | SEQ_ID NO. 40 | P14941.1 | Peretz and Burstein, 1989 | 557 bits (1436) | 7E–157 | 264/351 (76%) |

TABLE 14

Comparison of nucleic acid sequences of novel alcohol dehydrogenase
and known secondary alcohol dehydrogenases

| Organism | Description | Seq ID | Accession number | Reference | Score | e-Value | Identity |
|---|---|---|---|---|---|---|---|
| C. autoethanogenum | | SEQ_ID NO. 2 | — | — | 1905 bits (2112) | 0 | 1056/1056 (100%) |
| C. ljungdahlii | zinc-containing alcohol dehydrogenase | SEQ_ID NO. 3 | CP001666.1 | — | 1900 bits (2106) | 0 | 1055/1056 (99%) |
| C. ragsdalei | | SEQ_ID NO. 4 | — | — | 1803 bits (1998) | 0 | 1033/1056 (98%) |
| C. beijerinckii NRRL B-593 | NADP-dependent alcohol dehydrogenase | SEQ_ID NO. 39 | AF157307.2 | — | 558 bits (618) | 0 | 861/1056 (82%) |
| T. brockii | alcohol dehydrogenase | SEQ_ID NO. 41 | X64841.1 | — | 562 bits (622) | 3.00E–155 | 757/1053 (72%) |

Expression Studies of the Novel Alcohol Dehydrogenase from C. autoethanogenum

To identify, if the gene encoding the novel alcohol dehydrogenase is active during a normal fermentation with C. autoethanogenum, as well as identifying potential promoter regions for gene-overexpression, a qRT-PCR study with a over 250 genes was performed.

Samples were taken from a typical 1.5 l fed-batch fermentation run as described above over the whole growth (4 days). The samples were harvested by centrifugation (6,000×g, 5 min, 4° C.) and the cell pellet snap frozen in liquid nitrogen and stored at −80° C. until use. RNA was isolated by thawing the cell pellet on ice and suspending it in 100 μL of lysozyme solution (50,000 U lysozyme, 0.5 μL 10% SDS, 10 mM Tris-HCl, 0.1 mM EDTA; pH 8). After 5 min, 350 μL of lysis buffer (containing 10 μL of 2-mercaptoethanol) was added. The cell suspension was mechanistically disrupted by passing five times through an 18-21 gauge needle. RNA was then isolated using PureLink™ RNA Mini Kit (Invitrogen, Carlsbad, Calif. 92008, USA) and eluted in 100 μL of RNase-free water. The RNA was checked via PCR and gel electrophoresis and quantified spectrophotometrically, and treated with DNase I (Roche) if necessary. The reverse transcription step was carried out using SuperScript III Reverse Transcriptase Kit (Invitrogen, Carlsbad, Calif. 92008, USA). RT-PCR reactions were performed in MyiQ Single Colour Real-Time PCR Detection System (Bio-Rad Laboratories, Hercules, Calif. 94547, USA) in a reaction volume of 15 μL with 25 ng of cDNA template, 67 nM of each primer (Tab. 15), and 1× iQ SYBR Green Supermix (Bio-Rad Laboratories, Hercules, Calif. 94547, USA). Guanylate kinase (GnK) and formate tetrahydrofolate ligase (FoT4L) were used as housekeeping gene and non-template controls were included. The reaction conditions were 95° C. for 3 min, followed by 40 cycles of 95° C. for 15 s, 55° C. for 15 s and 72° C. for 30 s. A melting-curve analysis was performed immediately after completion of the qRT PCR (38 cycles of 58° C. to 95° C. at 1° C./s), for detection of primer dimerisation or other artifacts of amplification. Data on the expression level was computed in the form of threshold cycle ($C_t$) values based on PCR base line subtracted curve fit method as calculated by the Biorad iQ5 2.0 software. The raw $C_t$ values were further analyzed using Relative Expression Software Tool (REST©) 2008 V2.0.7.

TABLE 15

Oligonucleotides for RT-PCR

| Target | Oligonucleotide Name | DNA Sequence (5' to 3') | SEQ ID NO. |
|---|---|---|---|
| Guanylate kinase (gnk) | GnK-F | TCAGGACCTTCTGGAACTGG | 5 |
| | GnK-R | ACCTCCCCTTTTCTTGGAGA | 6 |

TABLE 15-continued

Oligonucleotides for RT-PCR

| Target | Oligonucleotide Name | DNA Sequence (5' to 3') | SEQ ID NO. |
|---|---|---|---|
| Formate tetrahydrofolate ligase (FoT4L) | FoT4L-F | CAGGTTTCGGTGCTGACCTA | 7 |
|  | FoT4L-F | AACTCCGCCGTTGTATTTCA | 8 |
| CO dehydrogenase (acsA) | acsA-F | ACAAGATGGGGTCGAAACAGTTTGG | 9 |
|  | acsA-R | TGGCACTGGACTTACTCTACATGGG | 10 |
| Formyl-THF synthase (fhs) | fhs-F | TATTTCCGAAGATGATATTGAATTGTATGG | 11 |
|  | fhs-R | TCCAGCAGGTGTTGGGTTTATAGC | 12 |
| Formimido-THF cyclodeaminase (fchA) | fchA-F | AGCTGCAACTCCTGGTGGAGGC | 13 |
|  | fchA-R | GCCTTTTACCTTTTCGTCATACTGTGC | 14 |
| Methylene-THF dehydrogenase formyl-THF cyclohydrolase (folD) | folD-F | GCTTACATTAGTAAGAGTTGGAGCAAACG | 15 |
|  | folD-R | ACTTGTCCTGTGATATATCTGCTGGTAGC | 16 |
| alcohol dehydrogenase (adh) | Adh-F | GGTCCTTATGATGCGATTGTACATCC | 17 |
|  | Adh-R | GCTATTTCACCTACAGCTTCATGGCC | 18 |

Figure 2:
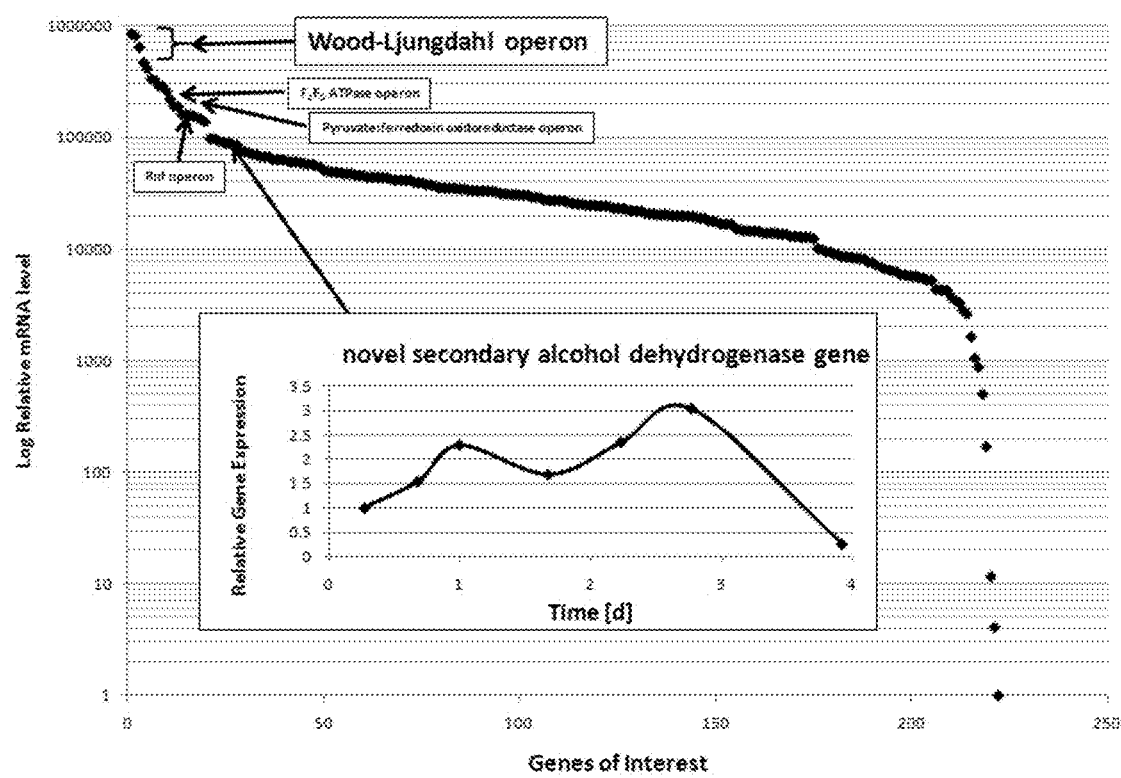
FIG. 2 show expression of novel alcohol dehydrogenase gene of *Clostridium autoethanogenum* DSM23693 during a typical fermentation run, as well as expression of genes controlled by Wood-Ljungdahl operon promoter, $F_1F_o$ ATPase operon promoter, Rnf complex operon promoter, and Pyruvate:ferredoxin oxidoreductase promoter. mRNA levels of more than 200 genes of interest were compared.

The result of the qRT-PCR study showed, that the gene for the novel alcohol dehydrogenase is expressed over the whole growth on a relatively constant level and only ceases at end of growth (FIG. 2). Compared to over 200 genes chosen from every part of the metabolism, the alcohol dehydrogenase gene belongs to the top 50 expressed genes. The highest gene expression of all genes analyzed showed the genes of the Wood-Ljungdahl operon, with an mRNA level of more than 10-fold higher than the alcohol dehydrogenase gene (FIG. 2). The respective promoter (SEQ_ID NO 22) region is therefore ideal to over-express genes, such as the genes for acetone biosynthesis enzymes and an alcohol dehydrogenase gene, although in the case of over-expression of an alcohol dehydrogenase gene native to the microorganisms it may require additional genetic modification to ensure sufficient co-factor availability. This could include, for example, (over-)expression of further genes to increase the NADPH pool such as transhydrogenase, elimination of competing NADPH consuming reactions, or protein engineering to change the co-factor requirement to NADH. Other useful promoter regions identified for gene over-expression include the promoter region of $F_1F_o$-ATPase operon (SEQ_ID NO 51), Rnf complex operon (SEQ_ID NO 52), and Pyruvate:ferredoxin oxidoreductase (SEQ_ID NO 53).

Figure 8:
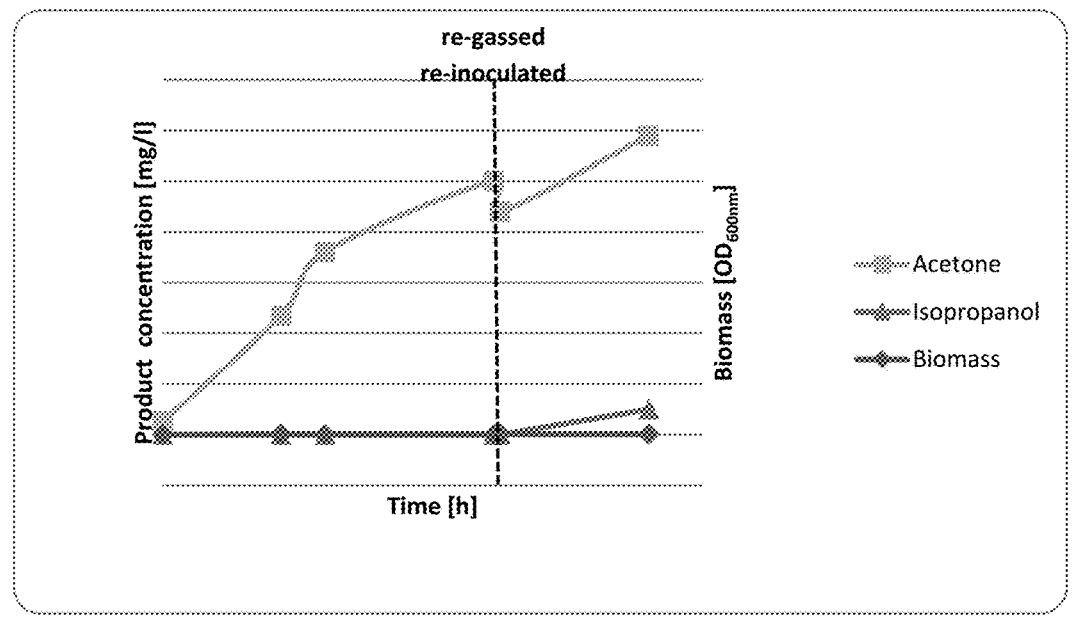
FIG. 8 shows the result of growth experiments with *C. autoethanogenum* DSM23693+pMTL85147-thlA-ctfAB-adc on steel mill gas.

Isopropanol Production from CO and $CO_2/H_2$ by *C. autoethanogenum* and *C. ljungdahlii* with Expression Plasmid Containing Clostridial Acetone Genes The 250 ml Schott bottle cultures of recombinant strains of *C. autoethanogenum* DSM23693 and *C. ljungdahlii* DSM 13528 carrying acetone expression plasmid pMTL85147-thlA-ctfAB-adc were shown to produce acetone, but no isopropanol could be detected (FIG. 8+9). This might be due to the lack of reducing power at end of growth, due to the given static conditions in Schott bottles, where CO gets depleted from the headspace and is not constantly fed like in a fed-batch or continuous fermentation process. Reducing equivalents such as NAD(P)H or ferredoxin gets generated from CO, but are also consumed for ethanol production, which already occurs during exponential and early stationary growth. At this point is the concentration of produced acetone, which is needed as precursor for isopropanol production, is still relatively low.

Therefore, both cultures were re-gassed with 30 psi fresh steel-mill gas after 48 h of growth and also re-inoculated. While biomass didn't increase much further, some of the produced acetone got converted into isopropanol within 24 hours (Tab. 16).

TABLE 16

Conversion of acetone to isopropanol by cultures of *C. autoethanogenum* DSM23693 and *C. ljungdahlii* DSM 13528

| | Acetone [mg/l] | | Isopropanol [mg/l] | |
|---|---|---|---|---|
| Organism | After 48 h | After 72 hours | After 48 h | After 72 hours |
| *C. autoethanogenum* + pMTL85147-thlA-ctfAB-adc | 220 | 295 | 0 | 25 |
| *C. ljungdahlii* + pMTL85147-thlA-ctfAB-adc | 171 | 175 | 0 | 5 |

In a fermentation system with constant supply of CO, sufficient reducing power is present for continuous production of isopropanol from CO or $CO/H_2$ and both acetone and isopropanol were produced in a respective fermentation run with *C. autoethanogenum* DSM23693 carrying acetone expression plasmid pMTL85147-thlA-ctfAB-adc.

Cloning of Novel Alcohol Dehydrogenase

The novel alcohol dehydrogenase was cloned into the acetone expression plasmid and put under control of the Wood-Ljungdahl promoter for gene over-expression and test of functionality in *E. coli*.

Figure 43:
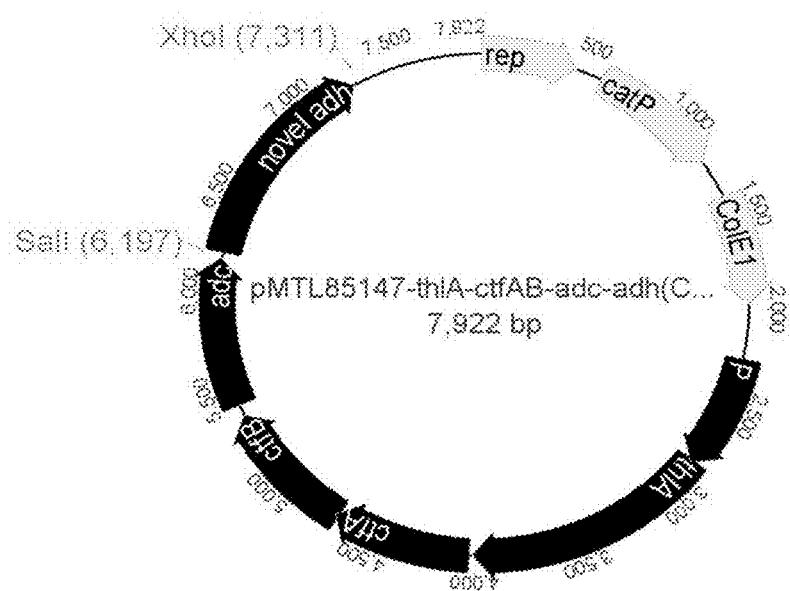
FIG. 43 shows expression plasmid containing novel alcohol dehydrogenase pMTL85147-thlA-ctfA-ctfB-adc-adh.

Alcohol dehydrogenase was amplified from isolated *C. autoethanogenum* DSM10061 chromosomal DNA using oligonucleotides SecAdh-SalI-F (SEQ_ID NO 54: TATTT-GTCGACTTAGGAGGTTCTATTATGAAAGG) and SecAdh-XhoI-R (SEQ_ID NO 55: AAAACTCGAGACATTTTTTTAATGCGACAG). The 1129 bp PCR fragment was cloned into plasmid pMTL85147-thlA-ctfAB-adc using SalI and XhoI and *E. coli* XL-1 Blue MRF' Kan. The resulting plasmid pMTL85147-thlA-ctfA-ctfB-adc-adh (SEQ_ID NO 48; FIG. 43) was completely sequenced using oligonucleotides given in Tab. 9 and results confirmed that the isopropanol biosynthesis genes and promoter region were free of mutations (FIG. 41).

Production of Isopropanol with Novel Alcohol Dehydrogenase from C. autoethanogenum in E. coli To further test the functionality of the novel alcohol dehydrogenase from C. autoethanogenum, growth experiments were carried out using E. coli XL-1 Blue MRF' Kan expressing only the acetone biosynthesis genes (carrying plasmid pMTL 85147-thlA-ctfA-ctfB-adc) and expressing the acetone biosynthesis genes plus the novel alcohol dehydrogenase (carrying plasmid pMTL85147-thlA-ctfA-ctfB-adc-adh) in 100 ml SD-8 minimal media with chloramphenicol (FIG. 42).

While no isopropanol could be detected with the strain carrying the acetone plasmid, an average maximum of 32.7 mg/L isopropanol was measured with the strain additionally expressing the novel alcohol dehydrogenase from C. autoethanogenum.

Identification of Genes from Lactococcus lactis and Saccharomyces cerevisiae that Confer Novel Activity Towards Acetone or Isopropanol in C. autoethanogenum In addition to the Clostridial acetone and isopropanol pathway, two enzymes an Alpha-ketoisovalerate decarboxylase (KivD) from Lactococcus lactis and an Alcohol dehydrogenase (Adh2) from Saccharomyces cerevisiae (Tab. 18) were identified that confer activity towards acetone and isopropanol production in C. autoethanogenum. Those two enzymes haven't been reported to be involved in acetone or isopropanol production or have catalytic functions on any of the precursors in the Clostridial acetone and isopropanol pathway. Heterologous expression of these proteins in E. coli (Atsumi et al., 2008. Non-fermentative pathways for synthesis of branched-chain higher alcohols as biofuels. Nature, 451: 86-90) or other organisms like Corynebacterium glutamicum (Blombach et al., 2011. Corynebacterium glutamicum tailored for efficient Isobutanol production. Appl. Environ. Microbiol. 77: 3300-10) or Clostridium cellulolyticum (Higashide W., et al. 2011. Metabolic Engineering of Clostridium cellulolyticum for Production of Isobutanol from Cellulose. Appl. Environ. Microbiol. 77: 2727-33) led to production of branched-chain higher alcohols like isobutanol, 1-butanol, 2-methyl-1-butanol, 3-methyl-1-butanol and 2-phenylethanol from amino acid precursors, but neither acetone nor isobutanol was reported. Expression of codon-optimized Alpha-ketoisovalerate decarboxylase (KivD) from Lactococcus lactis alone or a combination of codon optimized Alpha-ketoisovalerate decarboxylase (KivD) from Lactococcus lactis and an Alcohol dehydrogenase (Adh2) from Saccharomyces cerevisiae in C. autoethanogenum however, led surprisingly to production of acetone and isopropanol.

TABLE 18

Sequences from Lactococcus lactis and Saccharomyces cerevisiae that confer novel activity towards acetone or isopropanol in C. autoethanogenum

| | L. lactis | |
| --- | --- | --- |
| Description | nucleic acid | amino acid |
| Alpha-ketoisovalerate decarboxylase (KivD) | SEQ_ID No. 72 AJ746364 | SEQ_ID No. 73; YP_003353820.1 |
| | S. cerevisiae nucleic acid | amino acid |

TABLE 18-continued

Sequences from Lactococcus lactis and Saccharomyces cerevisiae that confer novel activity towards acetone or isopropanol in C. autoethanogenum

| | L. lactis | |
| --- | --- | --- |
| Description | nucleic acid | amino acid |
| Alcohol dehydrogenase (Adh2) | SEQ_ID No. 74 NC_001145.2, GeneID: 855349 | SEQ_ID No. 75; AAA34408.1 |

Construction of Expression Plasmid with Alpha-Ketoisovalerate Decarboxylase (KivD) from Lactococcus lactis and Alcohol Dehydrogenase (Adh2) from Saccharomyces cerevisiae The Alpha-ketoisovalerate decarboxylase (decarboxylase; KivD) from L. lactis, and Alcohol dehydrogenase (Adh2) from S. cerevisiae (Tab. 18) were codon-optimised by ATG: Biosynthetics GmbH (Merzhausen, Germany) and flanked by NdeI and KpnI restriction sites for further sub-cloning. The Phosphiotransacetylase/Acetate kinase operon promoter of C. autoethanogenum was used for expression of target genes. All DNA sequences used are given in Tab. 19.

TABLE 19

Sequences used for expression plasmid with Alpha-ketoisovalerate decarboxylase (KivD) from Lactococcus lactis and Alcohol dehydrogenase (Adh2) from Saccharomyces cerevisiae

| Description | Source | SEQ_ID NO. |
| --- | --- | --- |
| Alpha-ketoisovalerate decarboxylase (KivD) and Alcohol dehydrogenase (Adh2) | Codon optimized | 76-78 |
| Phosphotransacetylase/Acetate kinase operon promoter region | Clostridium autoethanogenum DSM10061 | 79 |

The promoter region of the phosphotransacetylase-acetate kinase operon ($P_{pta-ack}$) was amplified using primers Ppta-ack-NotI-F (Seq. ID. No. 80: GAGCGGCCGCAATATGA-TATTTATGTCC) and Ppta-ack-NdeI-R (Seq. ID. No. 81: TTCCATATGTTTCATGTTCATTTCCTCC) and cloned into the E. coli-Clostridium shuttle vector pMTL 85141 (FJ797651.1; Nigel Minton, University of Nottingham, UK) [Heap J T, Pennington O J, Cartman S T, Minton N P. A modular system for Clostridium shuttle plasmids. J Microbiol Methods. 2009, 78: 79-85] using NotI and NdeI restriction sites and strain XL1-Blue MRF' Kan.

The antibiotic resistance gene in the created plasmid pMTL85145 was subsequently replaced with an erythromycin resistance gene from pMTL 82254 (FJ797646.1; Nigel Minton, University of Nottingham, UK) [Heap J T, Pennington O J, Cartman S T, Minton N P. A modular system for Clostridium shuttle plasmids. J Microbiol Methods. 2009, 78: 79-85] using FseI and PmeI restriction sites and strain XL1-Blue MRF' Kan.

Figure 63:
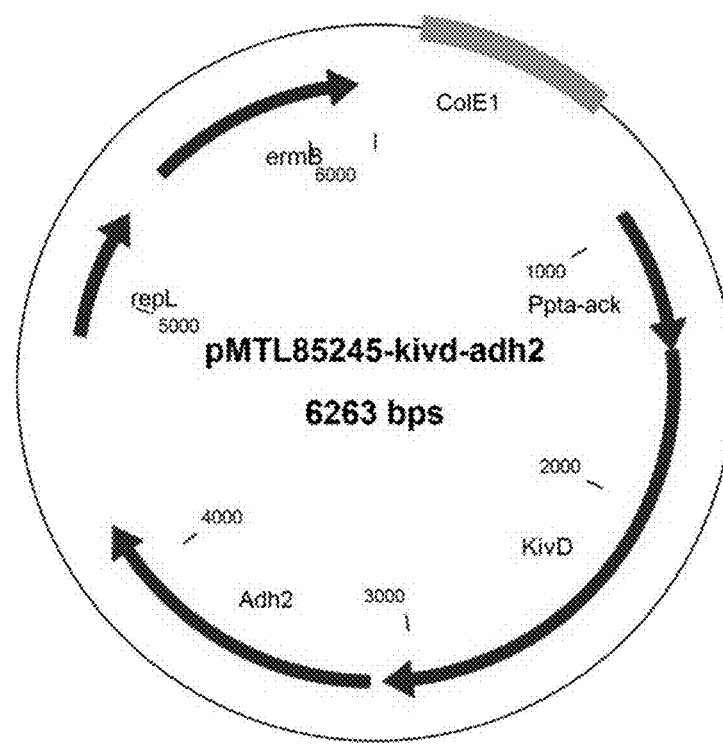
FIG. 63 shows acetone expression plasmid pMTL85245-kivd-adh2

The created plasmid pMTL85245 (Seq. ID. No. 80) and the 2746 bp codon-optimised product of the decarboxylase and alcohol dehydrogenase (Adh2) gene cluster were both cut with NdeI and KpnI. A ligation was transformed into E. coli XL1-Blue MRF' Kan resulting in plasmid pMTL85245-kivd-adh2 (Seq. ID. No. 83; FIG. 63). The insert of the resulting plasmid pMTL85245-kivd-adh was completely sequenced using oligonucleotides given in Tab. 20 and results confirmed that genes and promoter region were free of mutations.

Figure 64:
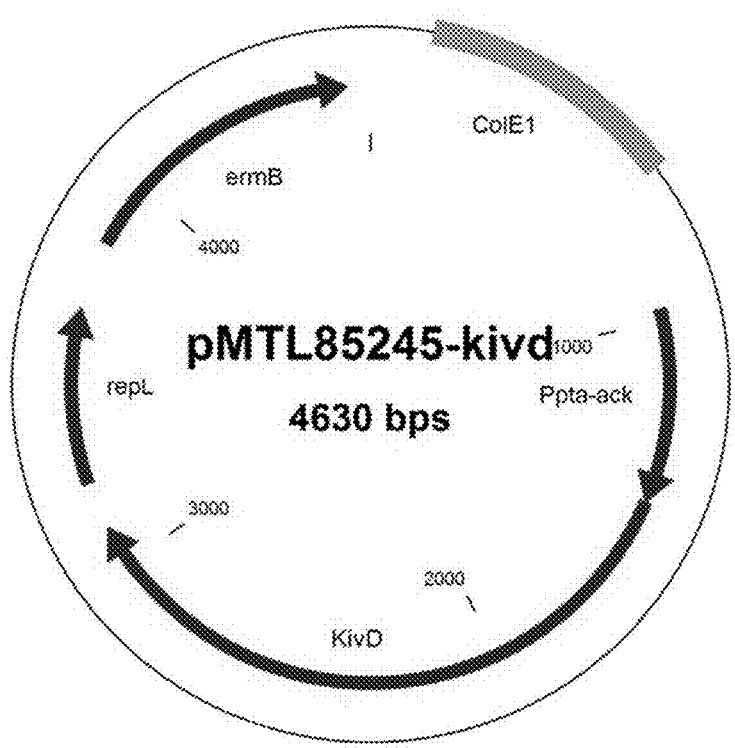
FIG. 64 shows acetone expression plasmid pMTL85245-kivd

The kivD gene alone was amplified using primer pair M13 Reverse (Seq. ID. 57: CAGGAAACAGCTATGAC) and Adh_seqR1 (Seq. ID. 85; Tab. 16). The 2635 bp PCR fragment of KivD was cloned into the E. coli-Clostridium shuttle vector pMTL 85245 using NdeI and EcoRI restriction sites and strain E. coli XL1-Blue MRF' Kan, creating plasmid pMTL85245-kivd (Seq. ID No. 84; FIG. 64). The insert of the resulting plasmid pMTL85245-kivd was completely sequenced using oligonucleotides given in Tab. 20 and results confirmed that the acetone biosynthesis gene was free of mutations.

Construction of Expression Plasmids with Different Gene Combinations

Based on the constructed expression plasmids pMTL85147-thlA-ctfA-ctfB-adc, pMTL85245-kivd-adh2 and pMTL85245-kivd, new combinations were constructed.

A 3122 bp $P_{WL}$-thlA-ctfAB fragment was amplified from plasmid pMTL85147-thlA-ctfA-ctfB-adc using oligonucleotides P-thl-ctfAB_F2 (Seq. ID. No. 93: ATCTTCTGCA-GGGCCGCAGATAGTCATAATAGTTCCAG) and P-thl-ctfAB_R2 (Seq. ID. No. 94: AGGGTGCGGCCGCGATTCATATATCCATAATCTT-

TABLE 20

| Oligonucleotides used for sequencing | | |
|---|---|---|
| Adh_seqR1 | TCAGTTCCCTGTGGAATGTGTGC | Seq. ID. No. 85 |
| Kivd_seqR2 | TCAGTAGCACCGAAAGATTCAG | Seq. ID. No. 86 |
| Kivd_seqR3 | AGTGCCTCATCTACTGAACTC | Seq. ID. No. 87 |
| -ori_F | ATTAGTTTAAACACGCCAGCAACGCGGCCTTTTTAC | Seq. ID. No. 88 |
| ctfAB_seqR1 | TCCTATTCCAAGGTTTACGAGTTGGTC | Seq. ID. No. 89 |
| ctfAB_seqR2 | ACCCCCAACCATAATTGTCATGCCATC | Seq. ID. No. 90 |
| ctfAB_seqR3 | TGCAAGAGCAAACTCATCTTGTTCTTC | Seq. ID. No. 91 |
| P-thl-ctfAB_R2 | AGGGTGCGGCCGCGATTCATATATCCATAATCTTTAAGTTATC | Seq. ID. No. 92 |

Figure 65:
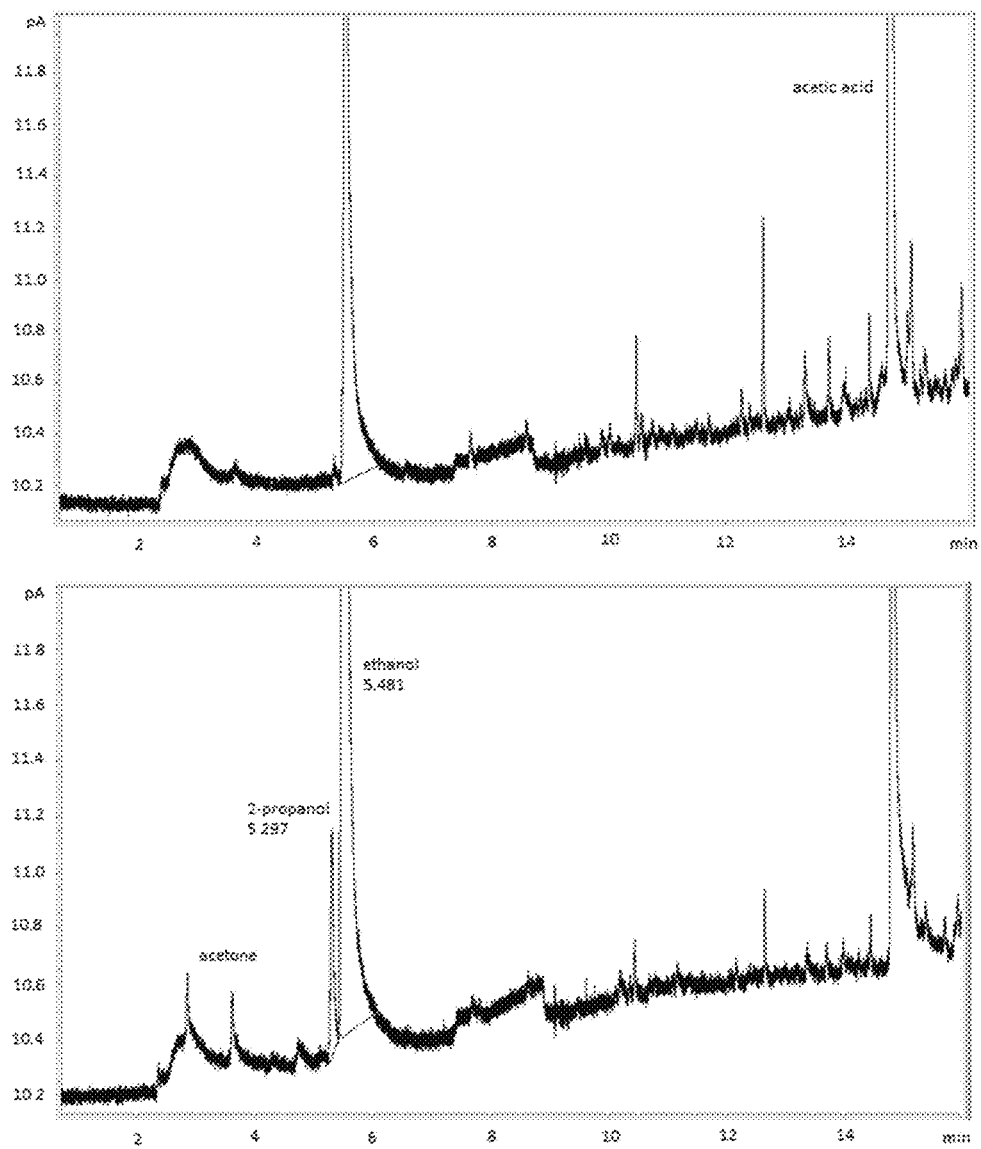
FIG. 65 shows the GC result confirming acetone and isopropanol production with *C. autoethanogenum* DSM23693 as a control strain (top) and *C. autoethanogenum* DSM23693+pMTL85245-kivd-adh2 (bottom) from CO-containing steel mill gas.
Figure 66:
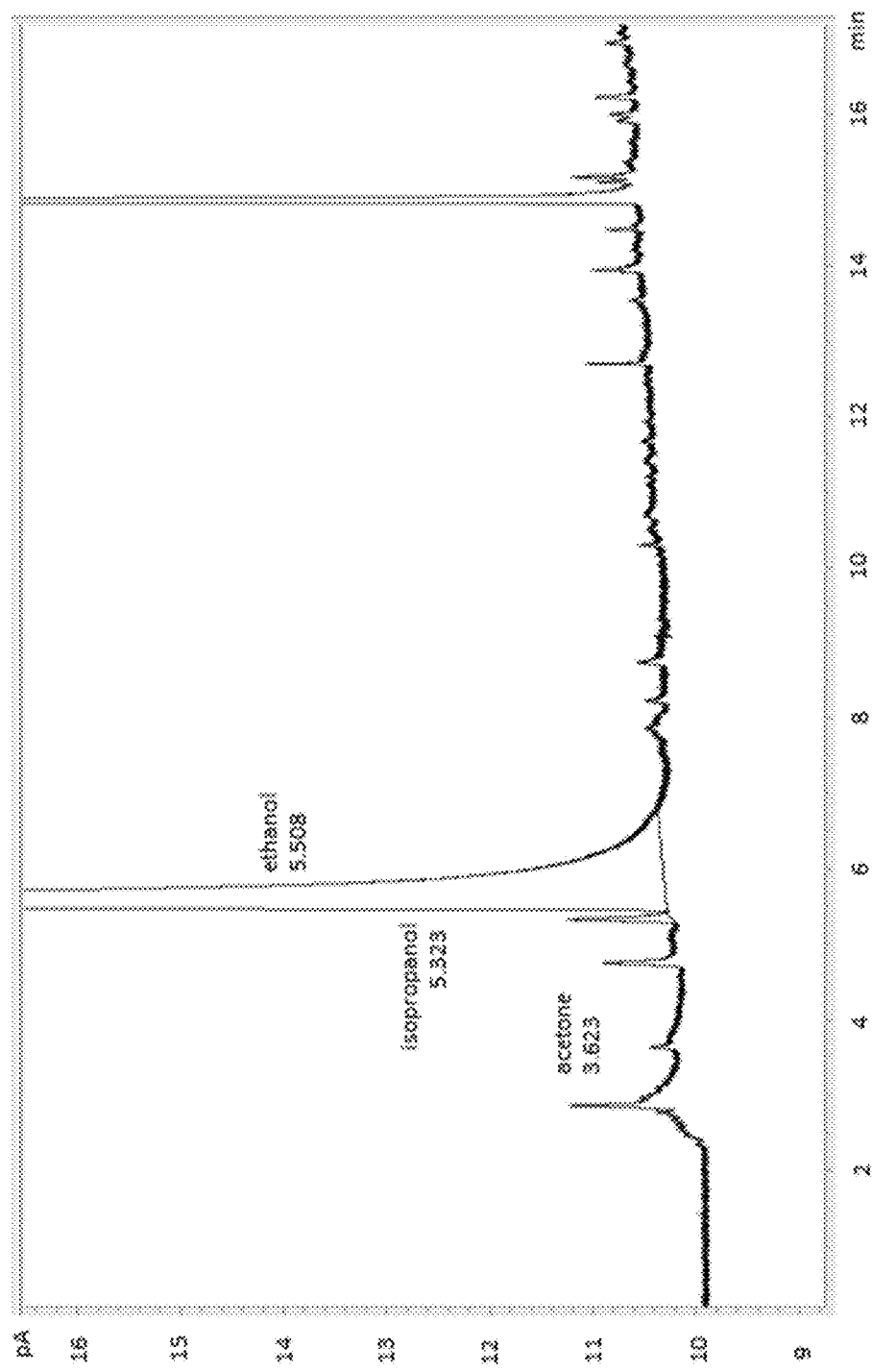
FIG. 66 shows the GC result confirming acetone and isopropanol production with *C. autoethanogenum* DSM23693+pMTL85245-kivd from CO-containing steel mill gas.

Expression of Codon-Optimized Genes for Alpha-Ketoisovalerate Decarboxylase (KivD) from Lactococcus lactis and Alcohol Dehydrogenase (Adh2) from Saccharomyces cerevisiae in C. autoethanogenum for Production of Acetone and Isopropanol Constructed expression plasmids pMTL85245-kivd-adh2 and pMTL85245-kivd were transformed into E. coli strain JW3350-2 and prepared for transformation in C. autoethanogenum DSM23693, which was performed as described above. While in E. coli harbouring the two plasmids, neither acetone nor isopropanol could be detected (but higher branched-chain alcohols such as isobutanol as described in the literature), in C. autoethanogenum, both acetone and isopropanol could be detected. In serum bottle experiments, highest isopropanol concentrations from CO-containing steel mill gas were 0.050-0.064 g/L for both expression plasmids (FIGS. 65 and 66).

Production of Acetone and Isopropanol with a Combination of Clostridial Pathway Genes and Alpha-Ketoisovalerate Decarboxylase (KivD) from Lactococcus lactis and Alcohol Dehydrogenase (Adh2) from Saccharomyces cerevisiae Without wanting to be bound by any particular theory, the inventors believe that the codon-optimized alpha-ketoacid decarboxylase Kivd from Lactococcus lactis has activity converting acetoacetate to acetone, as the Clostridial acetoacetate decarboxylase, while the codon-optimized alcohol dehydrogenase Adh2 from Saccharomyces cerevisiae have activity converting acetone to isopropanol as the novel primary:secondary alcohol dehydrogenase identified or the primary:secondary alcohol dehydrogenase from Clostridium beijkerickii. To test this hypothesis several combinations of Clostridial acetone/isopropanol pathway genes and the alpha-ketoacid decarboxylase Kivd from Lactococcus lactis and alcohol dehydrogenase Adh2 from Saccharomyces cerevisiae have been created and tested within E. coli and C. autoethanogenum demonstrating production of acetone and isopropanol.

Figure 67:
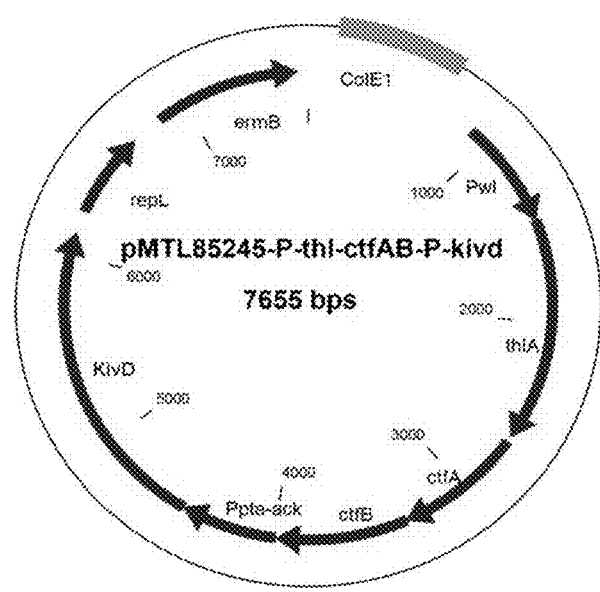
FIG. 67 shows acetone expression plasmid pMTL85147-thlA-ctfA-ctfB-adc-P-kivd

TAAGTTATC). The amplified fragment was cloned into plasmid pMTL 85245-kivd using PstI and NotI restriction sites and strain E. coli XL1-Blue MRF' Kan, creating plasmid pMTL85245-$P_{WL}$-thlA-ctfAB-kivd (Seq. ID. No. 95; FIG. 67). The insert of the resulting plasmid pMTL85245-$P_{WL}$-thlA-ctfAB-kivd was completely sequenced using oligonucleotides given in Tab. 9 and 20 and confirmed that the plasmid was free of mutations.

Figure 68:
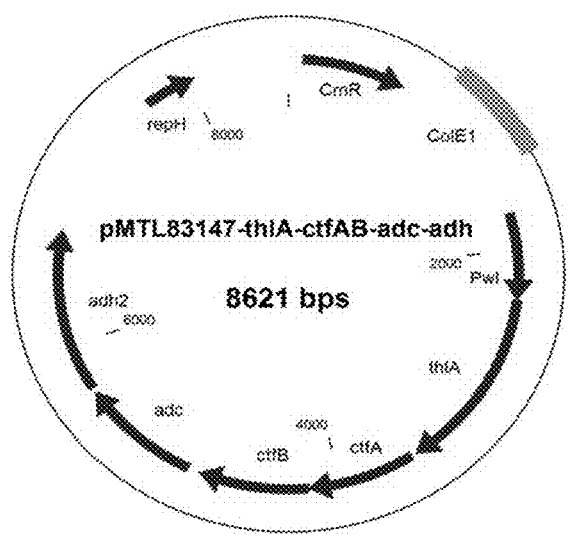
FIG. 68 shows acetone expression plasmid pMTL83147-thlA-ctfA-ctfB-adc-adh

The Adh2 gene was amplified from plasmid pMTL85245-kivd-adh2 using primer pair adh_F (Seq. ID. No. 96: ACGT-TGGATCCAGGAGGAACAAAGATGAGTATACC) and P-kivd-adh_R (Seq. ID. No. 97: AGCGTCCATGGCCTT-ATTTACTTGTATCTACAACATATC). The 1084 bp PCR fragment was cloned into the plasmid pMTL85147-thlA-ctfAB-adc using BamHI and NcoI restriction sites and strain E. coli XL1-Blue MRF' Kan, creating plasmid pMTL85147-thlA-ctfAB-adc-adh2 (Seq. ID. No. 98; FIG. 68). The created plasmid pMTL85147-thlA-ctfAB-adc-adh2 and a 1625 bp fragment of the repL gene from pMTL83151 (FJ797647.1; Nigel Minton, University of Nottingham, UK) [Heap J T, Pennington O J, Cartman S T, Minton N P. A modular system for Clostridium shuttle plasmids. J Microbiol Methods. 2009, 78: 79-85] were both cut with FseI and AscI. A ligation was performed resulting in plasmid pMTL83147-thlA-ctfAB-adc-adh2. The insert of the resulting plasmid pMTL83147-thlA-ctfAB-adc-adh2 was completely sequenced using oligonucleotides given in Tab. 9 and 20 and results confirmed that the fragment was mutation free.

Figure 69:
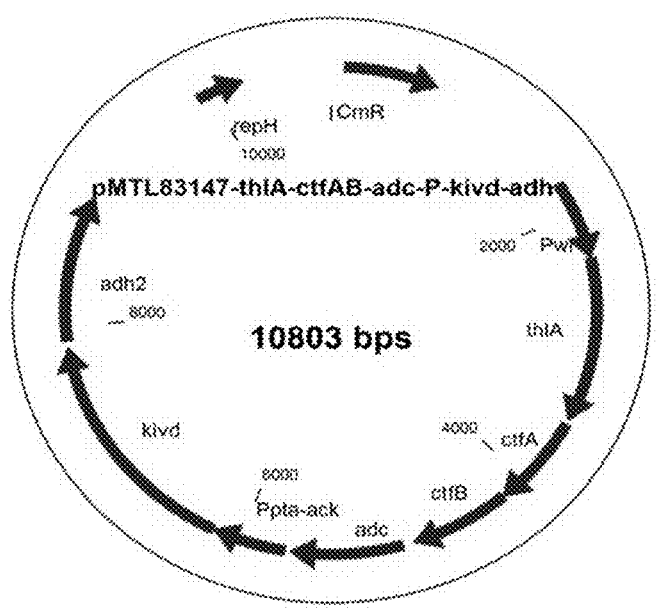
FIG. 69 shows acetone expression plasmid pMTL83147-thlA-ctfA-ctfB-adc-P-kivd-adh

Oligonucleotides P-kivd-adh_F (Seq. ID. No. 99: ATAT-TGGATCCACAGCTATGACCGCGGCCGCAATATG) and P-kivd-adh_R (Seq. ID. No. 100: AGCGTCCATGGCCTT-ATTTACTTGTATCTACAACATATC) were used to amplify a 3266 bp PCR fragment of $P_{pta-ack}$-kivd-adh2 from plasmid pMTL85245-kivd-adh2, which was then cloned into the plasmid pMTL85147-thlA-ctfAB-adc using BamHI and NcoI restriction sites and strain E. coli XL1-Blue MRF' Kan, creating plasmid pMTL83147-thlA-ctfAB-adc-P$_{pta-ack}$-kivd-adh2 (Seq. ID. 101; FIG. 69). The created plasmid pMTL83147-thlA-ctfAB-adc-P$_{pta-ack}$-kivd-adh2 and a 1625 bp fragment of the repL gene from pMTL83151 (FJ797647.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] were both cut with FseI and AscI. A ligation was performed resulting in plasmid pMTL83147-thlA-ctfAB-adc-P$_{pta-ack}$-kivd-adh2. The insert of the resulting plasmid pMTL83147-thlA-ctfAB-adc-P$_{pta-ack}$-kivd-adh2 was completely sequenced using oligonucleotides given in Tab. 9 and results confirmed that the plasmid was free of mutations.

Production of Acetone and Isopropanol in *C. autoethanogenum* Using Different Gene Combinations Methylation of the newly constructed expression plasmids pMTL85147-thlA-ctfA-ctfB-adc, pMTL83147-thlA-ctfAB-adc-adh2 and pMTL83147-thlA-ctfAB-adc-P$_{pta-ack}$-kivd-adh2 were performed in vivo in *E. coli* using a synthesized hybrid Type II methyltransferase gene (SEQ_ID NO 35) designed from methyltransferase genes from *C. autoethanogenum*, *C. ragsdalei* and *C. ljungdahlii* and transformed into *C. autoethanogenum* DSM23693 as described above.

All plasmid construct were tested in *E. coli* and *C. autoethanogenum* DSM23693 using serum bottle experiments with sugar (*E. coli*) or CO-containing steel mill gas (*C. autoethanogenum*) as sole substrate. With all combinations tested, acetone and isopropanol production was measured when expressed heterologously in *C. autoethanogenum*, while in *E. coli* acetone production only occurred with few combinations and an alcohol dehydrogenase gene was needed for isopropanol production (Tab. 21). The results presented show that both, in *E. coli* as well as *C. autoethanogenum*, the codon-optimized Alpha-ketoacid decarboxylase Kivd from *Lactococcus lactis* is able to replace the Clostridial acetoacetate decarboxylase and catalyse the conversion of acetoacetate to acetone (FIG. 4). In *C. autoethanogenum*, acetone and isopropanol production even occurred with expressing the decarboxylase as only heterologous gene, indicating CoA-transferase activity. FIG. 4 illustrates the proposed pathway and Tab. 21 of acetone and isopropanol formation from CO and FIG. 73 gives an overview of combinations of Clostridial pathway genes and codon-optimized genes for Alpha-ketoacid decarboxylase Kivd from *L lactis* and Alcohol dehydrogenase Adh2 from *S. cerevisiae* tested in *E. coli* and *C. autoethanogenum*.

Figure 70:
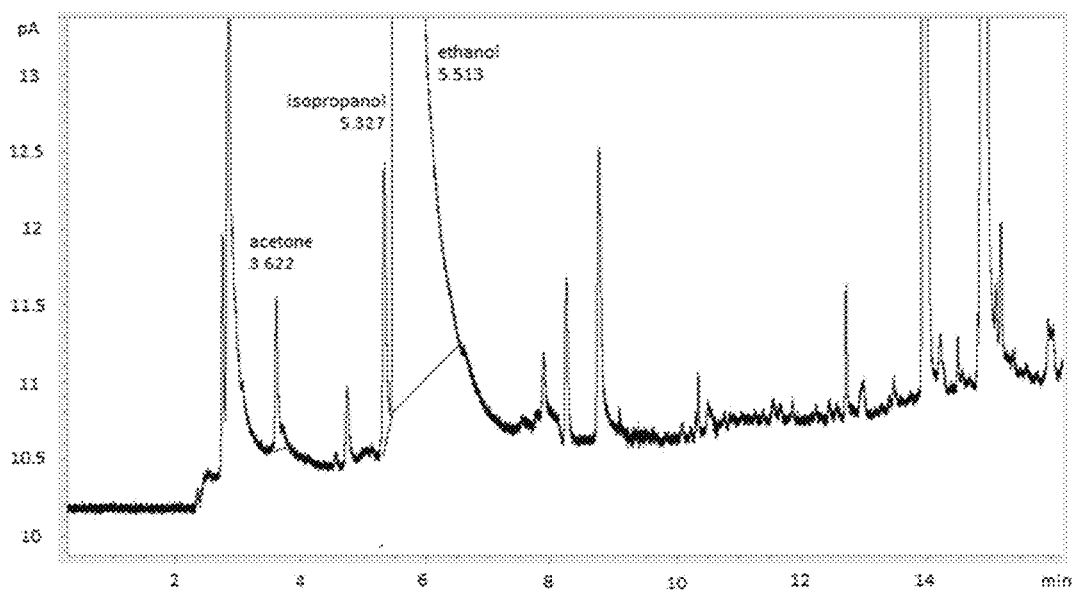
FIG. 70 shows the GC result confirming acetone and isopropanol production with *C. autoethanogenum* DSM23693 (top) and *C. autoethanogenum* DSM23693+pMTL85245-Pwl-thlA-ctfAB-kivd from CO-containing steel mill gas.
Figure 71:
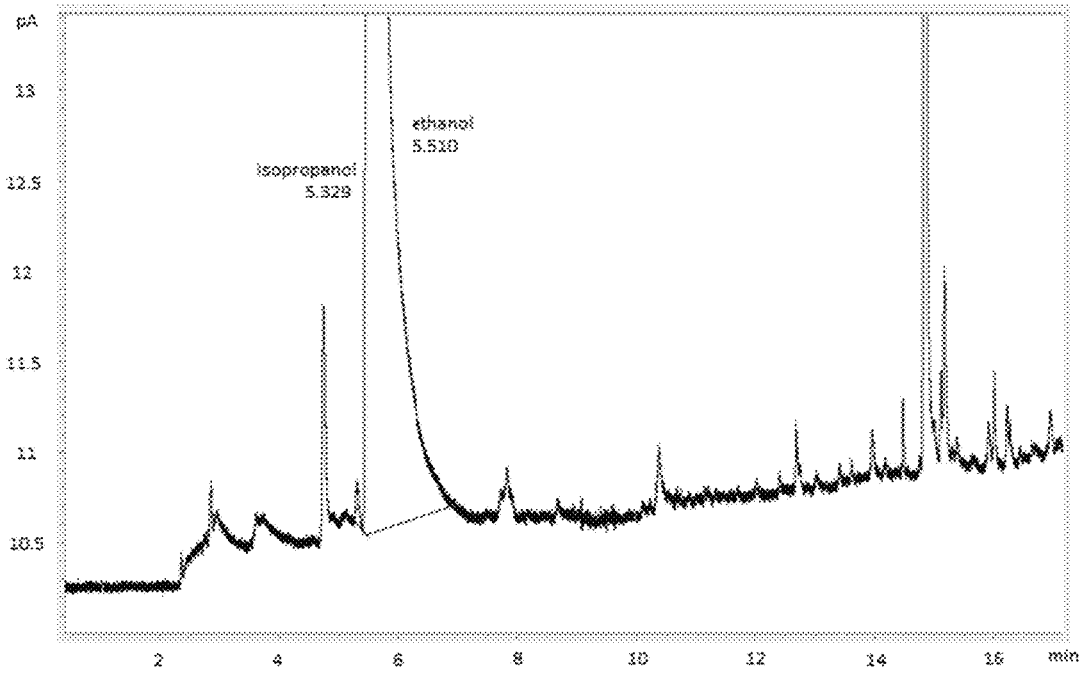
FIG. 71 shows shows the GC result confirming acetone and isopropanol production with *C. autoethanogenum* DSM23693+pMTL83147-thlA-ctfAB-adc-adh2 from CO-containing steel mill gas.
Figure 72:
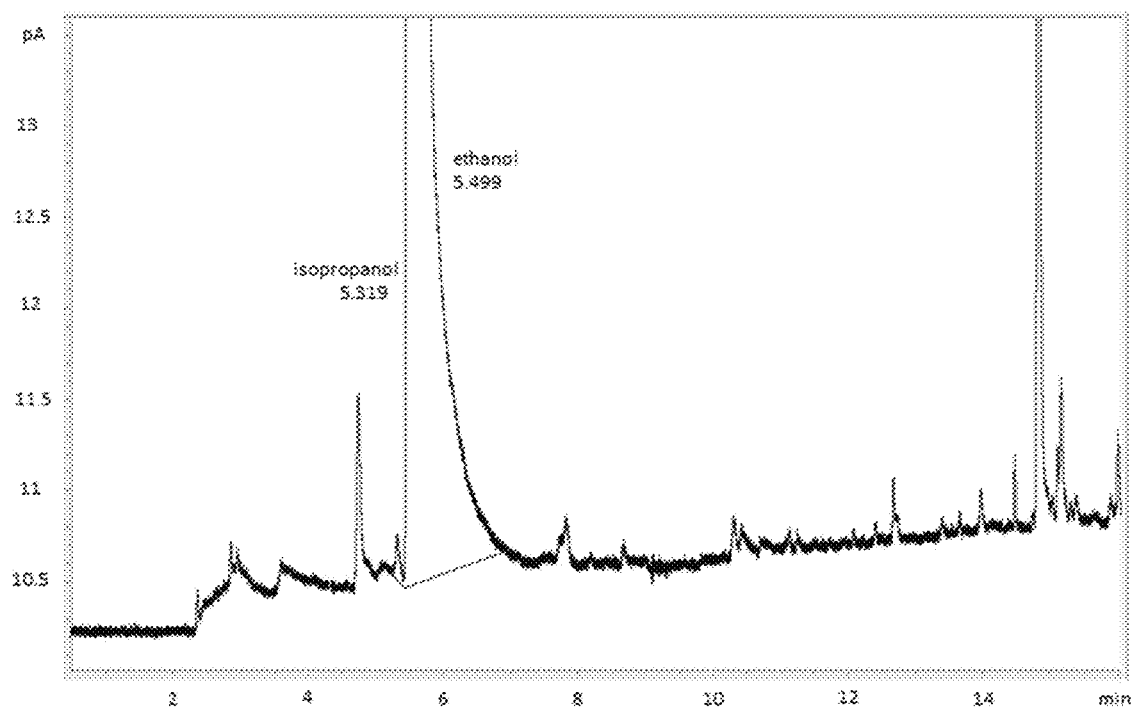
FIG. 72 shows the GC result confirming acetone and isopropanol production with *C. autoethanogenum*

Production of acetone and isopropanol with *C. autoethanogenum* DSM23693 and plasmids pMTL85245-P$_{WL}$-thlA-ctfAB-kivd, pMTL83147-thlA-ctfAB-adc-adh2 and pMTL83147-thlA-ctfAB-adc-P$_{pta-ack}$-kivd-adh2 from CO-containing steel mill gas is shown in FIGS. 70, 71, and 72 respectively.

TABLE 21

Acetone and isopropanol produced from various combinations of genes

| | Organism | Substrate | Acetone (g/L) | Isopropanol (g/L) |
|---|---|---|---|---|
| Clostridia genes | | | | |
| pMTL85147-thlA-ctfAB-adc | *E. coli* | Sugar | 0.200 | N/A |
| | *C. autoethanogenum* | CO | 0.300 | 0.025 |
| | *C. ljungdahlii* | CO | 0.180 | 0.005 |
| pMTL85147-thlA-ctfAB-adc-sadh (*C. beijerinckii*) | *E. coli* | Sugar | 0.080 | 0.070 |
| pMTL85147-thlA-ctfAB-adc-sadh (*C. autoethanogenum*) | *E. coli* | Sugar | 0.060 | 0.080 |
| Novel genes | | | | |
| pMTL85245-kivd-adh2 | *E. coli* | Sugar | N/A | N/A |
| | *C. autoethanogenum* | CO | Detected by GC qualitatively | 0.050 |
| pMTL85245-kivd | *E. coli* | Sugar | N/A | N/A |
| | *C. autoethanogenum* | CO | Detected by GC qualitatively | 0.064 |
| Combination of Clostridia and novel genes | | | | |
| pMTL85147-thlA-ctfAB-adc-kivd | *E. coli* | Sugar | Detected by GC qualitatively | N/A |
| | *C. autoethanogenum* | CO | Detected by GC qualitatively | 0.091 |
| pMTL83147-thlA-ctfAB-adc-adh2 | *E. coli* | Sugar | 0.040 | N/A |
| | *C. autoethanogenum* | CO | Detected by GC qualitatively | 0.648 |
| pMTL83147-thlA-ctfAB-adc-P-kivd-adh2 | *E. coli* | Sugar | 0.076 | N/A |
| | *C. autoethanogenum* | CO | Detected by GC qualitatively | 0.043 |

Tolerance to Acetone and Isopropanol and Detoxification of Acetate in Acetogens

Figure 12:
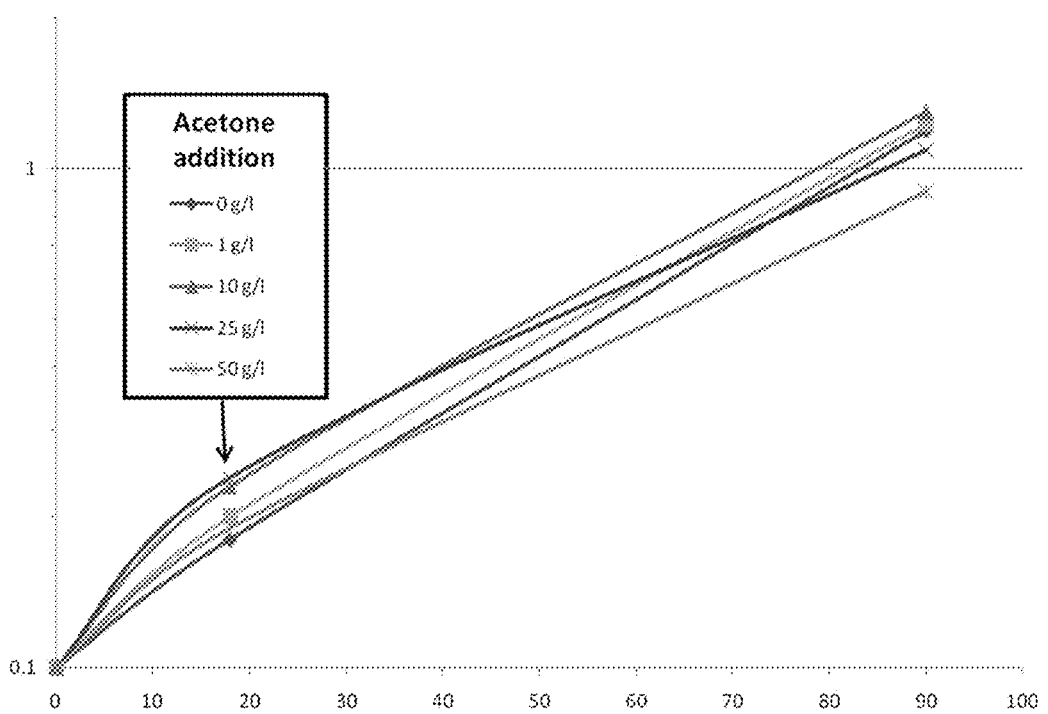
FIG. 12 shows the toxicity of acetone on cultures of *C. autoethanogenum* DSM23693.
Figure 13:
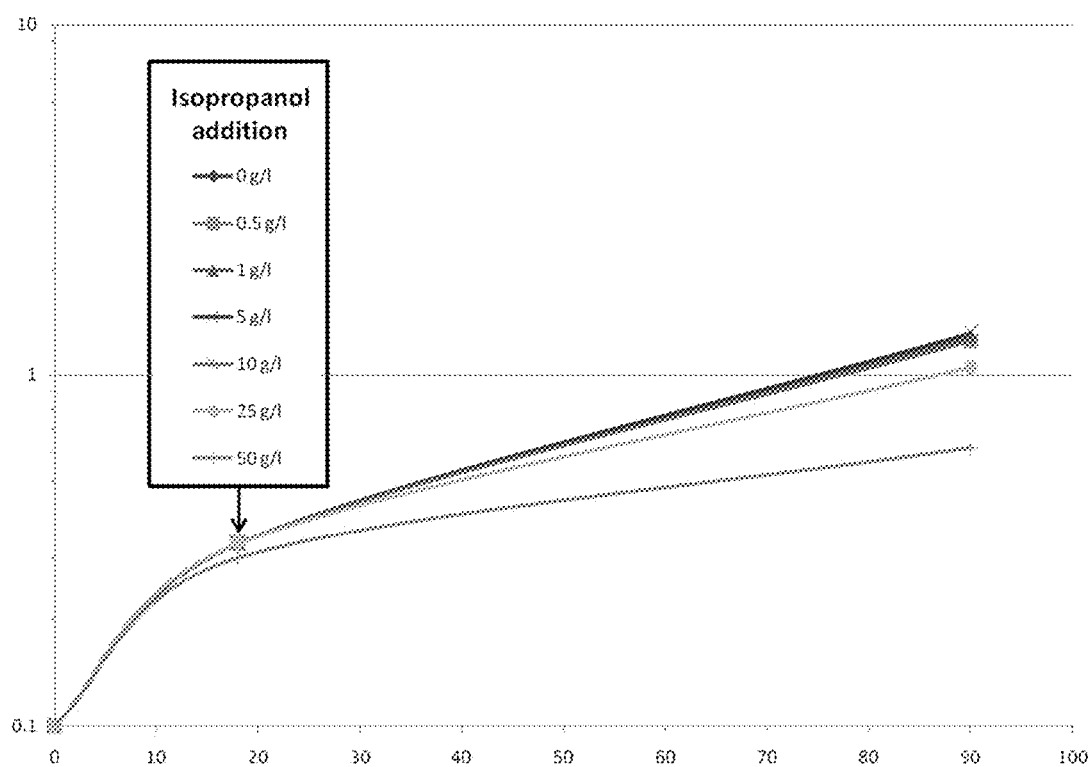
FIG. 13 shows the toxicity of isopropanol on cultures of *C. autoethanogenum* DSM23693.

Several metabolites such as alcohols (ethanol and butanol) or acids (acetic acid and butyric acid) are known to be toxic for bacteria in high concentrations and thus limit their biotechnological production [Alsaker K V, Parades C, Papoutsakis E T: Metabolite stress and tolerance in the production of biofuels and chemicals—systems analysis of butanol, butyrate, and Acetate Stresses in the Anaerobe *Clostridium acetobutylicum*. Biotechnol Bioeng, 2009, 105: 1131-1147]. To see if acetone and isopropanol have a toxic effect on cultures, growth experiments were carried out in 50 ml PETC media (Tab. 2) in serum bottles, adding different concentrations of acetone (FIG. 12) and isopropanol (FIG. 13) to growing cultures of *Clostridium autoethanogenum* DSM23693. Cell growth was visible in presence of concentrations as high as 5% acetone or isopropanol (with only slight inhibition of growth rate).

A high concentration of free or undissociated acetic acid on the other hand is known to be detrimental for most anaerobic bacteria (including acetogenic bacteria) due to the deleterious effect on the membrane gradient [Warnecke T, Gill R T: Organic acid toxicity, tolerance, and production in *Escherichia coli* biorefining applications. Microb Cell Fact, 2005, 4: 25; Köpke M, Dürre P: Biochemical production of biobutanol, in Luque R, Campelo J, Clark J H (Eds.): Handbook of biofuel production—Processes and technologies, Woodhead Publishing, Camebridge, 2010: 221-257]. Acetogenic bacteria however, need to produce acetic acid to gain ATP from substrate level phosphorylation [Drake H L, Küsel K, Matthies C: Acetogenic Prokaryotes. In Dworkin M, Falkow S, Rosenberg E, Schleifer K H, Stackebrandt E (eds.): The Prokaryotes, 3$^{rd}$ Edition, Volume 2, Springer, New York, 2006: 354-420] and thus all known acetogenic species produce acetic acid [Drake H L, Küsel K, Matthies C: Acetogenic Prokaryotes. In Dworkin M, Falkow S, Rosenberg E, Schleifer K H, Stackebrandt E (eds.): The Prokaryotes, 3$^{rd}$ Edition, Volume 2, Springer, New York, 2006: 354-420]. Conversion of acetic acid to other products such as ethanol via aldehyde ferredoxin oxidoreductase (AOR) or back to acetyl-CoA via phosphotransacetylase/acetate kinase (Pta/Ack) or AMP-dependent acetyl-CoA synthase (Acs) is unfavourable, since it requires energy in the form of reduced ferredoxin or ATP [Wolfe A J: The acetate switch. Microbiol Mol Biol Rev, 2005, 69: 12-50]. This invention presents a novel mode of acetic acid detoxification in acetogenic bacteria, which is free of energy requirement. Acetic acid can get recycled back to acetyl-CoA via a Acetoacetyl-CoA:Acetate/Butyrate Coenzyme A transferase system consisting of Acetyl-Coenzyme A acetyl-transferase, Acetoacetyl-CoA:Acetate/Butyrate Coenzyme A transferase A, Acetoacetyl-CoA:Acetate/Butyrate Coenzyme A transferase B. This reaction drives the conversion of Acetoacetyl-CoA to Acetoacetate, which can then get decarboxylated to acetone and reduced to isopropanol (FIG. 4).

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

---

The invention claimed is:

1. A method of producing acetone comprising culturing a recombinant microorganism in the presence of a gaseous substrate comprising one or more of CO, $CO_2$, and $H_2$ to produce acetone, wherein the recombinant microorganism comprises an exogenous thiolase (EC 2.3.1.9), an exogenous CoA transferase (EC 2.8.3.9), and an exogenous decarboxylase (EC 4.1.1.4 or EC 4.1.1.74), wherein the recombinant microorganism is derived from a parental microorganism selected from the group consisting of *Clostridium autoethanogenum*, *Clostridium ljungdahlii*, and *Clostridium ragsdalei*.

2. The method of claim 1, wherein the recombinant microorganism is a carboxydotrophic and acetogenic bacterium.

3. The method of claim 1, wherein the recombinant microorganism is derived from a parental microorganism that does not produce acetone.

4. The method of claim 1, wherein the parental microorganism is a microorganism that occurs in nature or a microorganism that has been previously modified.

5. The method of claim 1, wherein the recombinant microorganism is derived from a parental microorganism that lacks a gene encoding alcohol dehydrogenase.

6. The method of claim 1, wherein the thiolase is *Clostridium acetobutylicum* ThlA or *Clostridium beijerinckii* ThlA.

7. The method of claim 1, wherein the CoA transferase is *Clostridium acetobutylicum* CtfA and CtfB or *Clostridium beijerinckii* CtfA and CtfB.

8. The method of claim 1, wherein the decarboxylase is acetoacetate decarboxylase (EC 4.1.1.4).

9. The method of claim 8, wherein the acetoacetate decarboxylase is *Clostridium acetobutylicum* Adc or *Clostridium beijerinckii* Adc.

10. The method of claim 1, wherein the decarboxylase is alpha-ketoisovalerate decarboxylase (EC 4.1.1.74).

11. The method of claim 10, wherein the alpha-ketoisovalerate decarboxylase is *Lactococcus lactis* KivD.

12. The method of claim 1, wherein the gaseous substrate comprises 20-70% CO.

13. The method of claim 1, wherein the gaseous substrate is derived from an industrial process selected from the group consisting of ferrous metal products manufacturing, non-ferrous products manufacturing, petroleum refining, coal gasification, biomass gasification, electric power production, carbon black production, and coke manufacturing.

14. The method of claim 1, wherein the gaseous substrate is syngas.

* * * * *